(12) United States Patent
Pfau et al.

(10) Patent No.: US 8,921,405 B2
(45) Date of Patent: Dec. 30, 2014

(54) COMPOUNDS

(71) Applicants: Roland Pfau, Biberach an der Riss (DE); Kirsten Arndt, Ravensburg (DE); Henri Doods, Warthausen (DE); Klaus Klinder, Oggelshausen (DE); Raimund Kuelzer, Mittelbiberach (DE); Dimitrijs Lubriks, Riga (LV); Juergen Mack, Biberach an der Riss (DE); Benjamin Pelcman, Uppsala (SE); Henning Priepke, Warthausen (DE); Robert Roenn, Uppsala (SE); Dirk Stenkamp, Biberach an der Riss (DE); Edgars Suna, Riga (LV)

(72) Inventors: Roland Pfau, Biberach an der Riss (DE); Kirsten Arndt, Ravensburg (DE); Henri Doods, Warthausen (DE); Klaus Klinder, Oggelshausen (DE); Raimund Kuelzer, Mittelbiberach (DE); Dimitrijs Lubriks, Riga (LV); Juergen Mack, Biberach an der Riss (DE); Benjamin Pelcman, Uppsala (SE); Henning Priepke, Warthausen (DE); Robert Roenn, Uppsala (SE); Dirk Stenkamp, Biberach an der Riss (DE); Edgars Suna, Riga (LV)

(73) Assignee: Orexo AB, Stockholm (SE)

( * ) Notice: Subject to any disclaimer, the term of this patent is extended or adjusted under 35 U.S.C. 154(b) by 0 days.

(21) Appl. No.: 13/942,077

(22) Filed: Jul. 15, 2013

(65) Prior Publication Data

US 2013/0303571 A1 Nov. 14, 2013

Related U.S. Application Data

(63) Continuation of application No. 13/441,085, filed on Apr. 6, 2012, now abandoned, which is a continuation of application No. 12/717,407, filed on Mar. 4, 2010, now abandoned.

(30) Foreign Application Priority Data

Mar. 5, 2009 (EP) .................................. 09154414
Dec. 17, 2009 (EP) .................................. 09179618

(51) Int. Cl.
| | |
|---|---|
| *A61K 31/4168* | (2006.01) |
| *C07D 235/30* | (2006.01) |
| *C07D 403/12* | (2006.01) |
| *C07D 401/12* | (2006.01) |
| *C07D 409/12* | (2006.01) |
| *C07D 405/12* | (2006.01) |

(52) U.S. Cl.
CPC ............ *C07D 235/30* (2013.01); *C07D 403/12* (2013.01); *C07D 401/12* (2013.01); *C07D 409/12* (2013.01); *C07D 405/12* (2013.01)

USPC ........................................ 514/395; 548/307.4

(58) Field of Classification Search
USPC ........................................ 548/307.4; 514/395
See application file for complete search history.

(56) References Cited

U.S. PATENT DOCUMENTS

| 6,608,084 B1 | 8/2003 | Bourzat et al. |
| 2004/0198768 A1 | 10/2004 | Park Choo et al. |
| 2006/0287344 A1 | 12/2006 | Albers et al. |
| 2007/0060598 A1 | 3/2007 | Albers et al. |
| 2010/0004301 A1 | 1/2010 | Pelcman et al. |

(Continued)

FOREIGN PATENT DOCUMENTS

| EP | 0034743 A1 | 9/1981 |
| EP | 0295656 A1 | 12/1988 |

(Continued)

OTHER PUBLICATIONS

Cancer [online], [retrieved on Jul. 6, 2007]. Retrieved from the internet, URL http://en.wikipedia.orglwikilCancer.

(Continued)

*Primary Examiner* — Shawquia Young

(57) ABSTRACT

The present invention relates to compounds of general formula I

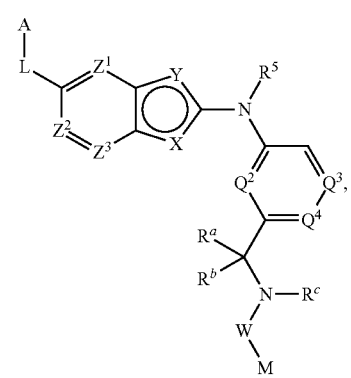

in which A, L, M, $Q^2$, $Q^3$, $Q^4$, $R^1$, $R^5$, $R^a$, $R^b$, $R^c$, W, X, Y, $Z^1$, $Z^2$, $Z^3$ are defined in the description, the salts thereof, particularly the physiologically acceptable salts thereof. The compounds are of potential utility in the treatment and/or prevention of inflammatory diseases and associated conditions, in particular, in the treatment and/or prevention of pain. The invention also relates to the use of such compounds as medicaments, to pharmaceutical compositions containing them, and to their preparation.

18 Claims, No Drawings

(56) References Cited

U.S. PATENT DOCUMENTS

| | | |
|---|---|---|
| 2010/0256188 A1 | 10/2010 | Pfau et al. |
| 2011/0275656 A1 | 11/2011 | Pfau et al. |
| 2011/0312935 A1 | 12/2011 | Pfau et al. |
| 2012/0115902 A1 | 5/2012 | Pfau et al. |
| 2012/0122930 A1 | 5/2012 | Pfau et al. |
| 2012/0149676 A1 | 6/2012 | Priepke et al. |
| 2012/0196897 A1 | 8/2012 | Pfau et al. |
| 2012/0208839 A1 | 8/2012 | Priepke et al. |
| 2012/0214786 A1 | 8/2012 | Priepke et al. |
| 2012/0309738 A1 | 12/2012 | Priepke et al. |
| 2012/0309755 A1 | 12/2012 | Priepke et al. |

FOREIGN PATENT DOCUMENTS

| | | | |
|---|---|---|---|
| EP | 0419210 | A1 | 3/1991 |
| EP | 1069124 | A1 | 1/2001 |
| FR | 2851563 | A1 | 8/2004 |
| FR | 2852957 | A1 | 10/2004 |
| WO | 0015612 | A1 | 3/2000 |
| WO | 0049005 | A1 | 8/2000 |
| WO | 0061580 | A1 | 10/2000 |
| WO | 0068213 | A1 | 11/2000 |
| WO | 0125238 | A2 | 4/2001 |
| WO | 03053939 | A1 | 7/2003 |
| WO | 03074515 | A1 | 9/2003 |
| WO | 03082272 | A1 | 10/2003 |
| WO | 2004005323 | A2 | 1/2004 |
| WO | 2004035740 | A2 | 4/2004 |
| WO | 2004072068 | A1 | 8/2004 |
| WO | 2004085425 | A1 | 10/2004 |
| WO | 2004089951 | A1 | 10/2004 |
| WO | 2005044793 | A2 | 5/2005 |
| WO | 2005070906 | A1 | 8/2005 |
| WO | 2005070920 | A1 | 8/2005 |
| WO | 2005123674 | A1 | 12/2005 |
| WO | 2006077366 | A1 | 7/2006 |
| WO | 2006090167 | A2 | 8/2006 |
| WO | 2007095124 | A2 | 8/2007 |
| WO | 2007127382 | A2 | 11/2007 |
| WO | 2008009924 | A2 | 1/2008 |
| WO | 2008035956 | A1 | 3/2008 |
| WO | 2008071944 | A1 | 6/2008 |
| WO | 2008129276 | A1 | 10/2008 |
| WO | 2010034796 | A1 | 4/2010 |
| WO | 2010034797 | A1 | 4/2010 |
| WO | 2010034798 | A1 | 4/2010 |
| WO | 2010034799 | A1 | 4/2010 |
| WO | 2010100249 | A1 | 9/2010 |

OTHER PUBLICATIONS

Cancer [online], [retrieved on Jul. 6, 2007]. Retrieved from the internet, URL http://www.nlm.nih.gov/medlineplus/cancer.html>.

D.J. Gale et al., The Amidomethylation of Some N,N-Dialkylanilines; Aust.J. Chem.; pp. 2447-2458; vol. 28; 1975.

European Search Report, for corresponding application No. EP 08 16 5120; date of mailing: May 6, 2009.

Golub et al., Science (1999), vol. 286, 531-537.

Lala et al., Cancer and Metastasis reviews (1998), 17 (1), 91-106.

R.D. Carpenter et al., Carbodiimide-based benzinidazole library method, Journal of Combinatorial Chemistry, Oct. 27, 2006, pp. 907-914, vol. 8, No. 6.

Samuelsson et al., Pharmacology Review, vol. 59, No. 3, pp. 207-224, 2007.

Silverman et al., The Organic Chemistry of Drug Design and Drug Action, Chapter 2: Drug Discovery, Design, and Development, Academic Press, p. 5-51, 1992.

COMPOUNDS

FIELD OF THE INVENTION

This invention relates to novel compounds, which are inhibitors of the microsomal prostaglandin $E_2$ synthase-1 (mPGES-1), pharmaceutical compositions containing them, and their use as medicaments for the treatment and/or prevention of inflammatory diseases and associated conditions.

BACKGROUND OF THE INVENTION

There are many acute and chronic diseases/disorders that are inflammatory in their nature including but not limited to rheumatoid diseases e.g. rheumatoid arthritis, osteoarthritis, diseases of the visceral system e.g. inflammatory bowel syndrome, autoimmune diseases, e.g. lupus erythematodes, lung diseases like asthma and COPD. Current treatment with non-steroidal anti-inflammatory drugs (NSAIDs) and Cyclooxygenase (COX)-2 inhibitors are efficacious, but show a prevalence for gastrointestinal and cardiovascular side effects. There is a high need for new treatment options showing equivalent efficacy with an improved side effect profile.

NSAIDs and COX-2 inhibitors reduce inflammation and pain through inhibition of one or both isoformes of COX enzymes. The cyclooxygenase (COX) enzyme exists in two forms, one that is constitutively expressed in many cells and tissues (COX-1), and one that in most cells and tissues is induced by pro-inflammatory stimuli, such as cytokines, during an inflammatory response (COX-2). COXs metabolise arachidonic acid to the unstable intermediate prostaglandin $H_2$ ($PGH_2$). $PGH_2$ is further metabolized to other prostaglandins including $PGE_2$, $PGF_{2\alpha}$, $PGD_2$, prostacyclin and thromboxane $A_2$. These arachidonic acid metabolites are known to have pronounced physiological and pathophysiological activity including pro-inflammatory effects. $PGE_2$ in particular is known to be a strong pro-inflammatory mediator, and is also known to induce fever, inflammation and pain. Consequently, numerous drugs were developed with a view to inhibiting the formation of $PGE_2$, including "NSAIDs" (non-steroidal antiinflammatory drugs) and "coxibs" (selective COX-2 inhibitors). These drugs act predominantly by inhibition of COX-1 and/or COX-2, thereby reducing the formation of $PGE_2$.

However, the inhibition of COXs has the disadvantage that it results in the reduction of the formation of all metabolites downstream of $PGH_2$, some of which are known to have beneficial properties. In view of this, drugs which act by inhibition of COXs are therefore known/suspected to cause adverse biological effects.

For example, the non-selective inhibition of COXs by NSAIDs may give rise to gastrointestinal side-effects and affect platelet and renal function. Even the selective inhibition of COX-2 by coxibs, whilst reducing such gastrointestinal side-effects, is believed to give rise to cardiovascular problems.

An alternative treatment of inflammatory diseases that does not give rise to the above-mentioned side effects would thus be of real benefit in the clinic. In particular, a drug that preferably selectively inhibits the transformation of $PGH_2$ to the pro-inflammatory mediator $PGE_2$ might be expected to reduce the inflammatory response in the absence of a corresponding reduction of the formation of other, beneficial arachidonic acid metabolites. Such inhibition would accordingly be expected to alleviate the undesirable side-effects mentioned above.

$PGH_2$ may be transformed to $PGE_2$ by prostaglandin E synthases (PGES). Two microsomal prostaglandin E synthases (mPGES-1 and mPGES-2), and one cytosolic prostaglandin E synthase (cPGES) have been described.

The leukotrienes (LTs) are formed from arachidonic acid by a set of enzymes distinct from those in the COX/PGES pathway. Leukotriene $B_4$ is known to be a strong proinflammatory mediator, while the cysteinyl-containing leukotrienes $C_4$, $D_4$ and $E_4$ (CysLTs) are mainly very potent bronchoconstrictors and have thus been implicated in the pathobiology of asthma. The biological activities of the CysLTs are mediated through two receptors designated $CysLT_1$ and $CysLT_2$. As an alternative to steroids, leukotriene receptor antagonists (LTRas) have been developed in the treatment of asthma. These drugs may be given orally, but do not control inflammation satisfactorily. The presently used LTRas are highly selective for $CysLT_1$. It may be hypothesised that better control of asthma, and possibly also COPD, may be attained if the activity of both of the CysLT receptors could be reduced. This may be achieved by developing unselective LTRas, but also by inhibiting the activity of proteins, e.g. enzymes, involved in the synthesis of the CysLTs. Among these proteins, 5-lipoxygenase, 5-lipoxygenase-activating protein (FLAP), and leukotriene $C_4$ synthase may be mentioned. A FLAP inhibitor would also decrease the formation of the proinflammatory $LTB_4$.

mPGES-1, FLAP and leukotriene $C_4$ synthase belong to the membrane-associated proteins in the eicosanoid and glutathione metabolism (MAPEG) family. Other members of this family include the microsomal glutathione S-transferases (MGST1, MGST2 and MGST3). For a review, c.f. P.-J. Jacobsson et al in *Am. J. Respir. Crit. Care Med.* 161, S20 (2000). It is well known that compounds prepared as antagonists to one of the MAPEGs may also exhibit inhibitory activity towards other family members, c.f. J. H Hutchinson et al in *J. Med. Chem.* 38, 4538 (1995) and D. Claveau et al in *J. Immunol.* 170, 4738 (2003). The former paper also describes that such compounds may also display notable cross-reactivity with proteins in the arachidonic acid cascade that do not belong to the MAPEG family, e.g. 5-lipoxygenase.

Thus, agents that are capable of inhibiting the action of mPGES-1, and thus reducing the formation of the specific arachidonic acid metabolite $PGE_2$, are likely to be of benefit in the treatment of inflammation. Further, agents that are capable of inhibiting the action of the proteins involved in the synthesis of the leukotrienes are also likely to be of benefit in the treatment of asthma and COPD.

In addition to their anti-inflammatory effect, mPGES-1 inhibitors are also known to be of potential use in treating or preventing a neoplasia, for example as described in international patent application WO 2007/124589. The rationale behind this may stem from the fact that the production of PGE2 is believed to promote the formation, growth and/or metastasis of neoplasias. As mPGES-1 is often expressed with COX-2 in benign and cancerous neoplasias, the inhibition of mPGES-1 (rather than COX-2) may cause the reduction of PGE2 and therefore mPGES-1 inhibitors may be useful for the treatment of benign or malignant neoplasias.

The listing or discussion of an apparently prior-published document in this specification should not necessarily be taken as an acknowledgement that the document is part of the state of the art or is common general knowledge.

DETAILED DESCRIPTION OF THE INVENTION

In a first embodiment, in the general formula I,

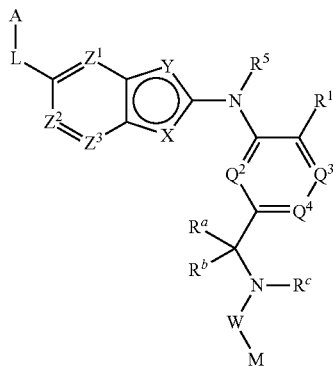

one of X and Y represents —N($R^6$)—; and
the other represents —N=;
one of $Z^1$, $Z^2$ and $Z^3$ independently represents —C($R^7$)= or —N=; and the other two of $Z^1$, $Z^2$ and $Z^3$ represent —C($R^7$)=;
$Q^2$, $Q^3$ and $Q^4$ respectively represent —C($R^2$)=, —C($R^3$)= and —C($R^4$)=; or any one or two of $Q^2$, $Q^3$ or $Q^4$ may alternatively and independently represent —N=;
$R^1$ represents halo, OH, —CN;
 $C_{1-3}$ alkyl, $C_{2-6}$ alkynyl, $OC_{1-3}$ alkyl, which latter three groups are optionally substituted by one or more substituents selected from fluoro, —CN, =O, OH, —OCH$_3$, —OCF$_3$;
$R^2$, $R^3$ and $R^4$ independently represent hydrogen, halo, —CN;
 $C_{1-3}$ alkyl, $OC_{1-3}$ alkyl, which latter two groups are optionally substituted by one or more substituents selected from fluoro, —CN, =O, OH, —OCH$_3$, —OCF$_3$;
$R^a$, $R^b$ independently represent hydrogen, $C_{1-3}$ alkyl,
 or both together with the carbon atom which they are bound to, form a $C_{3-7}$cycloalkylene ring, or a 4-6 membered heterocycloalkylene ring;
$R^c$ represents hydrogen or $C_{1-3}$ alkyl;
W represents —C(O)—, —S(O)—, —S(O)$_2$—, —C(O)O—, or
 —C(O)NR$^d$—, which groups are bound to the nitrogen of the —NR$^c$-moiety via carbon or sulfur atom;
$R^d$ represents hydrogen or $C_{1-3}$ alkyl;
M represents $C_{1-7}$ alkyl, $C_{3-7}$cycloalkyl, both of which groups are optionally substituted by one or more groups selected from:
 fluoro, —OH, —CN, —NH$_2$, —NH(C$_{1-3}$ alkyl), N(C$_{1-3}$ alkyl)$_2$, —OC$_{1-3}$ alkyl,
 —SC$_{1-3}$ alkyl, aryl, heteroaryl [which latter two groups can be substituted by one or more substituents selected from halo, OH, —CN, C$_{1-3}$ alkyl, OC$_{1-3}$ alkyl (which latter two alkyl groups are optionally substituted by one or more fluoro atoms)],
 $C_{1-7}$alkyl, $C_{2-7}$alkynyl, $C_{3-7}$cycloalkyl-C$_{0-2}$ alkyl, 4-7 membered heterocycloalkyl-C$_{0-2}$ alkyl (which latter alkyl, alkynyl, heterocycloalkyl or cycloalkyl groups are optionally substituted by one or more substituents selected from fluoro, —CN, =O, —NH$_2$, —NH(C$_{1-3}$ alkyl), —N(C$_{1-3}$ alkyl)$_2$, —OH, —OC$_{1-3}$ alkyl);
 or
 aryl, heteroaryl, 4-7 membered heterocycloalkyl, all of which groups are optionally substituted by one or more substituents selected from: halo, —OH, —CN, —NH$_2$, —NH(C$_{1-3}$alkyl), —N(C$_{1-3}$ alkyl)$_2$, —OC$_{1-3}$ alkyl, —SC$_{1-3}$ alkyl, aryl, heteroaryl [which latter two groups can be substituted by one or more substituents selected from halo, OH, —CN, C$_{1-3}$ alkyl, —OC$_{1-3}$ alkyl (which latter two alkyl groups are optionally substituted by one or more fluoro atoms)], C$_{1-7}$alkyl, C$_{2-7}$alkynyl, C$_{3-7}$cycloalkyl, 4-7 membered heterocycloalkyl (which latter alkyl, alkynyl, heterocycloalkyl or cycloalkyl groups are optionally substituted by one or more substituents selected from fluoro, —CN, =O, —NH$_2$, —NH (C$_{1-3}$alkyl), N(C$_{1-3}$ alkyl)$_2$, —OH, —OC$_{1-3}$alkyl)];
$R^5$ represents hydrogen; or $C_{1-3}$ alkyl;
$R^6$ represents hydrogen; $C_{1-5}$ alkyl, $C_{3-6}$alkynyl, 4-7 membered heterocycloalkyl-C$_{0-2}$ alkyl or C$_{3-7}$cycloalkyl-C$_{0-2}$ alkyl (which latter four groups are optionally substituted by one or more substituents selected from fluoro, —CN, =O, C$_{1-3}$ alkyl, —OH, —OC$_{1-3}$ alkyl, —NH$_2$, —NH (C$_{1-3}$alkyl), N(C$_{1-3}$ alkyl)$_2$);
each $R^7$ independently represents hydrogen, halo, —CN,
 C$_{1-7}$alkyl, C$_{2-7}$alkynyl, C$_{3-7}$cycloalkyl, C$_{1-5}$ alkyl-O—, C$_{3-7}$cycloalkyl-C$_{0-2}$ alkyl-O—, 4-7 membered heterocycloalkyl-C$_{0-2}$ alkyl-O—, (in which latter six groups the alkyl, alkynyl, cycloalkyl or heterocycloalkyl fragments are optionally substituted by one or more substituents selected from fluoro, —CN, =O, OH, —OC$_{1-3}$ alkyl, —NH$_2$, —NH—C$_{1-3}$ alkyl, N(C$_{1-3}$ alkyl)$_2$ or by one or more C$_{1-3}$ alkyl groups, which can be optionally substituted by one or more fluoro atoms);
 or
 aryl or heteroaryl, which latter two groups can be substituted by one or more substituents selected from halo, OH, —CN, C$_{1-3}$ alkyl, —OC$_{1-3}$ alkyl (in which latter two groups the alkyl fragments are optionally substituted by one or more fluoro atoms);
L represents —C(O)N(R$^8$)—, —N(R$^8$)C(O)—, —S(O)$_2$N(R$^8$)—, —N(R$^8$)S(O)$_2$—, —N(R$^8$)C(O)N(R$^8$)—, —OC(O)N(R$^8$)— or —N(R$^8$)C(O)O—;
A represents hydrogen, C$_{1-8}$ alkyl, C$_{3-8}$ alkynyl, aryl, heteroaryl, aryl-C$_{1-3}$alkyl-, C$_{3-8}$cycloalkyl-C$_{0-3}$alkyl-, 4-7 membered heterocycloalkyl-C$_{0-3}$alkyl-, heteroaryl-C$_{1-3}$alkyl-, in which groups the alkyl-, alkynyl-, cycloalkyl- and heterocycloalkyl-fragments are optionally substituted by one or more substituents selected from R$^{9a}$ and the aryl and heteroaryl fragments are optionally substituted by one or more substituents selected from R$^{9b}$;
or
A-L- together represent one of the following groups

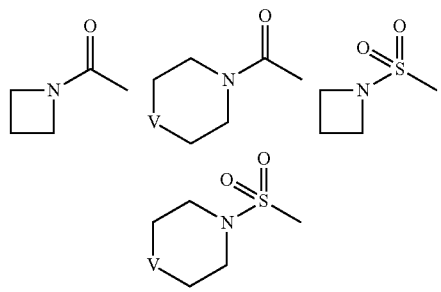

in which
V represents a bond, —CH$_2$CH$_2$—, —CH$_2$CH$_2$CH$_2$—, wherein in each of the latter alkylene groups one methylene [—(CH$_2$)—] unit can optionally be replaced by an oxygen atom, a —NH— or —N($C_{1-3}$ alkyl)-group and each methylene unit can optionally and independently be substituted by one or two of the following groups: fluoro, —CN, =O, —$NH_2$, —NH($C_{1-3}$ alkyl), N($C_{1-3}$ alkyl)$_2$, —OH, —O$C_{1-3}$alkyl);

each $R^8$ independently represents hydrogen, or $C_{1-3}$ alkyl;

each $R^{9a}$ independently represents fluoro, —OH, —CN, =O, —$NH_2$, —NH($C_{1-3}$ alkyl), —N($C_{1-3}$ alkyl)$_2$, —O$C_{1-6}$ alkyl, $C_{1-6}$alkyl, (in which latter four groups the alkyl, fragments are optionally substituted by one or more substituents selected from fluoro, —CN, =O, —$NH_2$, —NH($C_{1-3}$ alkyl), N($C_{1-3}$ alkyl)$_2$, —OH, —O$C_{1-3}$ alkyl) or aryl, heteroaryl [which latter two groups can be substituted by one or more substituents selected from halo, OH, —CN, $C_{1-3}$ alkyl, O$C_{1-3}$ alkyl (which latter two alkyl groups are optionally substituted by one or more fluoro atoms)];

each $R^{9b}$ represents independently halo, —OH, —CN, —$NH_2$, —NH($C_{1-3}$ alkyl), —N($C_{1-3}$ alkyl)$_2$, —O$C_{1-3}$ alkyl, —S$C_{1-3}$ alkyl, aryl, heteroaryl [which latter two groups can be substituted by one or more substituents selected from halo, OH, —CN, $C_{1-3}$ alkyl, O$C_{1-3}$ alkyl (which latter two alkyl groups are optionally substituted by one or more fluoro atoms)], $C_{1-7}$alkyl, $C_{2-7}$alkynyl, $C_{3-7}$cycloalkyl, 4-7 membered heterocycloalkyl (which latter alkyl, alkynyl, heterocycloalkyl or cycloalkyl groups are optionally substituted by one or more substituents selected from fluoro, —CN, =O, —$NH_2$, —NH($C_{1-3}$ alkyl), N($C_{1-3}$ alkyl)$_2$, —OH, O$C_{1-3}$alkyl);

the salts thereof, particularly the physiologically acceptable salts thereof with organic or inorganic acids or bases.

In a second embodiment, in the general formula I,

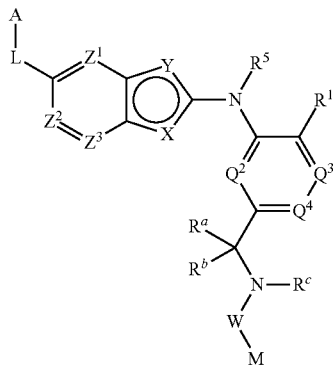

in which one of X and Y represents —N($R^6$)—; and the other represents —N=;

one of $Z^1$, $Z^2$ and $Z^3$ independently represents —C($R^7$)= or —N=; and the other two of $Z^1$, $Z^2$ and $Z^3$ represent —C($R^7$)=;

$Q^2$, $Q^3$ and $Q^4$ respectively represent —C($R^2$)=, —C($R^3$)= and —C($R^4$)=;

or any one or two of $Q^2$, $Q^3$ or $Q^4$ may alternatively and independently represent —N=;

$R^1$ represents halo, OH, —CN;

$C_{1-3}$alkyl, $C_{2-6}$alkynyl, O$C_{1-3}$ alkyl, which latter three groups are optionally substituted by one or more substituents selected from fluoro, —CN, =O, OH, —$OCH_3$, —$OCF_3$;

$R^2$, $R^3$ and $R^4$ independently represent hydrogen, halo, —CN; $C_{1-3}$ alkyl, O$C_{1-3}$ alkyl, which latter two groups are optionally substituted by one or more substituents selected from fluoro, —CN, =O, OH, —$OCH_3$, —$OCF_3$;

$R^a$, $R^b$ independently represent hydrogen, $C_{1-3}$ alkyl, or both together with the carbon atom which they are bound to, form a $C_{3-7}$cycloalkylene ring, or a 4-6 membered heterocycloalkylene ring;

$R^c$ independently represents hydrogen or $C_{1-3}$ alkyl;

W represents —C(O)—, —S(O)—, —S(O)$_2$—, —C(O)O—, or

—C(O)N$R^c$—, which groups are bound to the nitrogen of the —N$R^c$— moiety via carbon or sulfur atom;

M represents $C_{1-7}$alkyl, $C_{3-7}$cycloalkyl, both of which groups are either unsubstituted or substituted by one or more fluoro atoms;

or $C_{1-7}$alkyl, $C_{3-7}$cycloalkyl both of which groups are substituted by one or more groups selected from —OH, —CN, —$NH_2$, —NH($C_{1-3}$ alkyl), N($C_{1-3}$ alkyl)$_2$, —O$C_{1-3}$ alkyl, —S$C_{1-3}$ alkyl, aryl, heteroaryl [which latter two groups can be substituted by one or more substituents selected from halo, OH, —CN, $C_{1-3}$ alkyl, O$C_{1-3}$ alkyl (which latter two alkyl groups are optionally substituted by one or more fluoro atoms)], $C_{1-7}$ alkyl, $C_{2-7}$alkynyl, $C_{3-7}$cycloalkyl, heterocycloalkyl (which latter alkyl, alkynyl, heterocycloalkyl or cycloalkyl groups are optionally substituted by one or more substituents selected from fluoro, —CN, =O, —$NH_2$, —NH($C_{1-3}$ alkyl), —N($C_{1-3}$ alkyl)$_2$, —OH, —O$C_{1-3}$ alkyl);

or aryl, heteroaryl, heterocycloalkyl, all of which groups are optionally substituted by one or more substituents selected from halo, —OH, —CN, —$NH_2$, —NH($C_{1-3}$ alkyl), —N($C_{1-3}$ alkyl)$_2$, —O$C_{1-3}$ alkyl, —S$C_{1-3}$ alkyl, aryl, heteroaryl (which latter two groups can be substituted by one or more substituents selected from halo, OH, —CN, $C_{1-3}$ alkyl, O$C_{1-3}$ alkyl (which latter two alkyl groups are optionally substituted by one or more fluoro atoms)], $C_{1-7}$ alkyl, $C_{2-7}$alkynyl, $C_{3-7}$cycloalkyl, heterocycloalkyl (which latter alkyl, alkynyl, heterocycloalkyl or cycloalkyl groups are optionally substituted by one or more substituents selected from fluoro, —CN, =O, —$NH_2$, —NH($C_{1-3}$ alkyl), N($C_{1-3}$ alkyl)$_2$, —OH, —O$C_{1-3}$alkyl);

$R^5$ represents hydrogen; or $C_{1-3}$ alkyl;

$R^6$ represents hydrogen; $C_{1-3}$ alkyl, $C_{3-6}$alkynyl, heterocycloalkyl, or cycloalkyl (which latter four groups are optionally substituted by one or more substituents selected from fluoro, —CN, =O, $C_{1-3}$ alkyl, —O$C_{1-3}$ alkyl);

each $R^7$ independently represents hydrogen, halo, —CN, $C_{1-7}$ alkyl, $C_{2-7}$ alkynyl, $C_{3-7}$cycloalkyl, —O$C_{1-3}$ alkyl, —O $C_{3-7}$cycloalkyl, —O$C_{3-7}$heterocycloalkyl, in which groups the alkyl fragments are optionally substituted by one or more substituents selected from fluoro, —CN, =O, OH, —O$C_{1-3}$ alkyl, —$NH_2$, —NH—$C_{1-3}$ alkyl, —N($C_{1-3}$ alkyl)$_2$); or aryl or heteroaryl, which latter two groups can be substituted by one or more substituents selected from halo, OH, —CN, $C_{1-3}$ alkyl, —O$C_{1-3}$ alkyl (in which latter two groups the alkyl fragments are optionally substituted by one or more fluoro atoms);

L represents —C(O)N($R^8$)—, —N($R^8$)C(O)—, —S(O)$_2$N($R^8$)—, —N($R^8$)S(O)$_2$—, —N($R^8$)C(O)N($R^8$)—, —OC(O)N($R^8$)— or —N($R^8$)C(O)O—;

A represents $C_{1-8}$ alkyl, $C_{3-8}$alkynyl, aryl, heteroaryl, aryl-$C_{1-3}$alkylene, $C_{3-8}$cycloalkyl-$C_{0-3}$alkylene, heterocycloalkyl-$C_{0-3}$alkyl, heteroaryl-$C_{1-3}$alkylene, in which groups the alkyl-, alkynyl-, cycloalkyl- and heterocycloalkyl-fragments are optionally substituted by one or more substituents selected from $R^{9a}$ and the aryl and heteroaryl fragments are optionally substituted by $R^{9b}$;

or

A-L- together represent one of the following groups

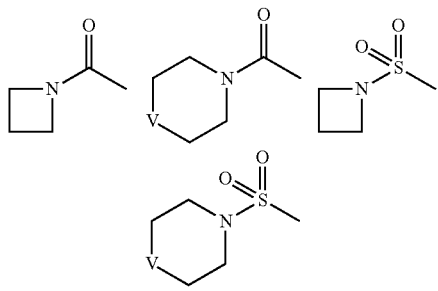

in which

V represents a bond, —CH$_2$—, —CH$_2$CH$_2$—, —CH$_2$CH$_2$CH$_2$—, wherein in each of the latter alkylene groups one methylene [—(CH$_2$)—] unit can optionally be replaced by an oxygen atom, a —NH— or
—NH($C_{1-3}$ alkyl) group and each methylene unit can optionally and independently be substituted by one or two of the following groups: fluoro, —CN, =O, —NH$_2$, —NH($C_{1-3}$ alkyl), N($C_{1-3}$ alkyl)$_2$, —OH, —O$C_{1-3}$ alkyl);

each $R^8$ independently represents hydrogen, or $C_{1-3}$ alkyl;

each $R^{9a}$ independently represents fluoro, —CN, =O, —NH$_2$, —OH, $C_{1-3}$alkyl, —O$C_{1-3}$alkyl, —NH($C_{1-3}$ alkyl), —N($C_{1-3}$ alkyl)$_2$ in which latter three groups the alkyl fragments are optionally substituted by one or more substituents selected from fluoro, —CN, =O, —NH$_2$, —NH($C_{1-3}$ alkyl), N($C_{1-3}$ alkyl)$_2$, —OH, —O$C_{1-3}$ alkyl;

each $R^{9b}$ represents independently halo, —OH, —CN, —NH$_2$, —NH($C_{1-3}$ alkyl), —N($C_{1-3}$alkyl)$_2$, —O$C_{1-3}$ alkyl, —S$C_{1-3}$ alkyl, aryl, heteroaryl [which latter two groups can be substituted by one or more substituents selected from halo, OH, —CN, $C_{1-3}$ alkyl, O$C_{1-3}$ alkyl (which latter two alkyl groups are optionally substituted by one or more fluoro atoms)], $C_{1-7}$ alkyl, $C_{2-7}$alkynyl, $C_{3-7}$cycloalkyl, heterocycloalkyl (which latter alkyl, alkynyl, heterocycloalkyl or cycloalkyl groups are optionally substituted by one or more substituents selected from fluoro, —CN, =O, —NH$_2$, —NH($C_{1-3}$ alkyl), N($C_{1-3}$ alkyl)$_2$, —OH, O $C_{1-3}$alkyl);

the salts thereof, particularly the physiologically acceptable salts thereof with organic or inorganic acids or bases.

A further embodiment of the present invention comprises compounds of the general formula I, namely compounds of formula Ia

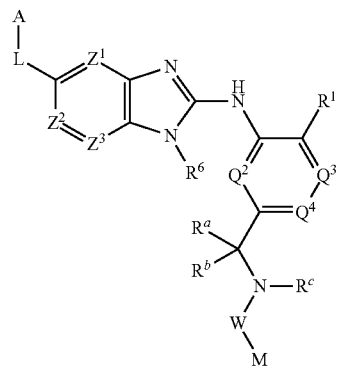

in which A, L, M, $Q^2$, $Q^3$, $Q^4$, $R^1$, $R^6$, $R^a$, $R^b$, $R^c$, W, $Z^1$, $Z^2$, $Z^3$ have the same meaning as defined in any of the preceding embodiments, the salts thereof, particularly the physiologically acceptable salts thereof with organic or inorganic acids or bases.

A further embodiment of the present invention comprises compounds of the formula I, namely compounds of formula Ib

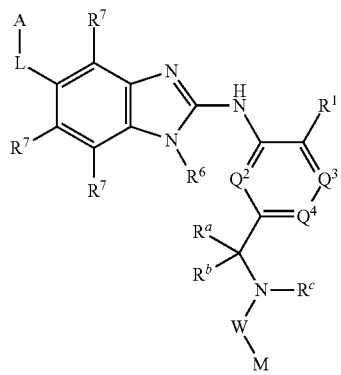

in which A, L, M, $Q^2$, $Q^3$, $Q^4$, $R^1$, $R^6$, $R^7$, $R^a$, $R^b$, $R^c$, W have the same meaning as defined in any of the preceding embodiments, the salts thereof, particularly the physiologically acceptable salts thereof with organic or inorganic acids or bases.

A further embodiment of the present invention comprises compounds of the formula I, namely compounds of formula Ic

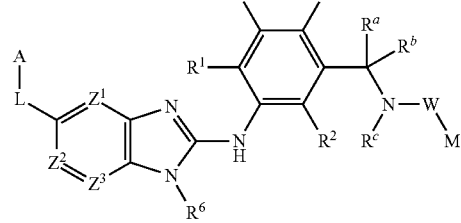

in which A, L, M, $R^1$, $R^2$, $R^3$, $R^4$, $R^6$, $R^a$, $R^b$, $R^c$, W, $Z^1$, $Z^2$, $Z^3$ have the same meaning as defined in any of the preceding embodiments, the salts thereof, particularly the physiologically acceptable salts thereof with organic or inorganic acids or bases.

A further embodiment of the present invention comprises compounds of the formula I, namely compounds of formula Id

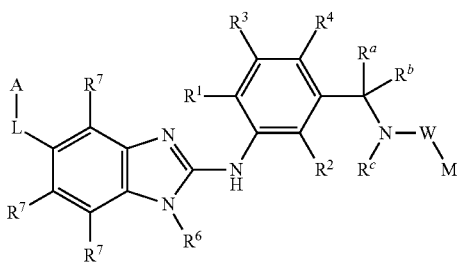

in which A, L, M, $R^1$, $R^2$, $R^3$, $R^4$, $R^6$, $R^7$, $R^a$, $R^b$, $R^c$, W have the same meaning as defined in any of the preceding embodiments, the salts thereof, particularly the physiologically acceptable salts thereof with organic or inorganic acids or bases.

In a further embodiment, in the general formula I, A, L, M, $Q^2$, $Q^3$, $Q^4$, $R^1$, $R^2$, $R^3$, $R^4$, $R^5$, $R^6$, $R^7$, $R^a$, $R^b$, $R^c$, X, Y, $Z^1$, $Z^2$, $Z^3$ have the same meaning as defined in any of the preceding embodiments and W represents —C(O)—, —S(O)$_2$—, which groups are bound to the nitrogen of the —NRc$^c$— moiety via the carbon or sulfur atom;
the salts thereof, particularly the physiologically acceptable salts thereof with organic or inorganic acids or bases.

In a further embodiment, in the general formula I, A, L, $Q^2$, $Q^3$, $Q^4$, $R^1$, $R^2$, $R^3$, $R^4$, $R^5$, $R^6$, $R^7$, $R^a$, $R^b$, $R^c$, W, X, Y, $Z^1$, $Z^2$, $Z^3$ have the same meaning as defined in any of the preceding embodiments and M represents $C_{1-7}$ alkyl, $C_{3-7}$ cycloalkyl, both of which groups are optionally substituted by one or more groups selected from fluoro, —OH, —CN, —NH2, —OC$_{1-3}$ alkyl, —SC$_{1-3}$ alkyl, aryl [which latter aryl group can be substituted by one or more substituents selected from halo, OH, —CN, $C_{1-3}$ alkyl, OC$_{1-3}$ alkyl (which latter two alkyl groups are optionally substituted by one or more fluoro atoms)], $C_{1-7}$ alkyl, $C_{3-7}$ cycloalkyl-$C_{0-2}$-alkyl (which latter alkyl and cycloalkyl groups are optionally substituted by one or more substituents selected from fluoro, —CN, =O, —NH$_2$, —NH($C_{1-3}$ alkyl), —N($C_{1-3}$ alkyl)$_2$, —OH, —OC$_{1-3}$ alkyl);
or
aryl, heteroaryl, 4-7 membered heterocycloalkyl, all of which groups are optionally substituted by one or more substituents selected from halo, —CN,
—OC$_{1-3}$ alkyl, $C_{1-7}$ alkyl, $C_{3-7}$cycloalkyl, (which latter alkyl and cycloalkyl groups are optionally substituted by one or more substituents selected from fluoro, —CN, —OC$_{1-3}$ alkyl);
the salts thereof, particularly the physiologically acceptable salts thereof with organic or inorganic acids or bases.

In a further embodiment, in the general formula I, A, L, M, $Q^2$, $Q^3$, $Q^4$, $R^1$, $R^2$, $R^3$, $R^4$, $R^5$, $R^7$, $R^a$, $R^b$, $R^c$, W, X, Y, $Z^1$, $Z^2$, $Z^3$ have the same meaning as defined in any of the preceding embodiments and $R^6$ represents hydrogen, $C_{1-5}$ alkyl, $C_{3-4}$cycloalkyl-$C_{0-1}$ alkyl, which latter two groups are optionally substituted by one or more substituents selected from fluoro, —OCH$_3$, —NH ($C_{1-3}$ alkyl), N($C_{1-3}$ alkyl)$_2$;

the salts thereof, particularly the physiologically acceptable salts thereof with organic or inorganic acids or bases.

In a further embodiment, in the general formula I, A, L, M, $Q^2$, $Q^3$, $Q^4$, $R^1$, $R^5$, $R^6$, $R^7$, $R^{9a}$, $R^{9b}$, $R^a$, $R^b$, $R^c$, W, X, Y, $Z^1$, $Z^2$, $Z^3$ have the same meaning as defined in any of the preceding embodiments and $R^2$, $R^3$ and $R^4$ independently represent hydrogen, fluoro, chloro- or —CH$_3$ optionally substituted by one or more fluorine atoms;
the salts thereof, particularly the physiologically acceptable salts thereof with organic or inorganic acids or bases.

In a further embodiment, in the general formula I, A, L, M, $Q^2$, $Q^3$, $Q^4$, $R^1$, $R^2$, $R^3$, $R^4$, $R^5$, $R^6$, $R^7$, $R^a$, $R^b$, $R^c$, W, X, Y, $Z^1$, $Z^2$, $Z^3$ have the same meaning as defined in any of the preceding embodiments and each $R^{9a}$ independently represents fluoro, —CN, $C_{1-6}$alkyl, —OC$_{1-6}$alkyl in which latter two groups the alkyl fragments are optionally substituted by one or more fluoro atoms;
each $R^{9b}$ represents independently halo, —CN, —OC$_{1-3}$ alkyl, $C_{1-7}$ alkyl (which latter two groups are optionally substituted by one or more fluoro atoms;
the salts thereof, particularly the physiologically acceptable salts thereof with organic or inorganic acids or bases.

In a further embodiment, in the general formula I, A, L, M, $Q^2$, $Q^3$, $Q^4$, $R^1$, $R^2$, $R^3$, $R^4$, $R^5$, $R^6$, $R^7$, $R^a$, $R^b$, $R^c$, W, X, Y, $Z^1$, $Z^2$, $Z^3$ have the same meaning as defined in any of the preceding embodiments and each $R^{9a}$ independently represents fluoro, —CN, $C_{1-3}$alkyl, —OC$_{1-3}$alkyl in which latter two groups the alkyl fragments are optionally substituted by one or more fluoro atoms;
each $R^{9b}$ represents independently halo, —CN, —OC$_{1-3}$ alkyl, $C_{1-7}$ alkyl (which latter two groups are optionally substituted by one or more fluoro atoms;
the salts thereof, particularly the physiologically acceptable salts thereof with organic or inorganic acids or bases.

In a further embodiment, in the general formula I, A, M, $Q^2$, $Q^3$, $Q^4$, $R^1$, $R^2$, $R^3$, $R^4$, $R^5$, $R^6$, $R^7$, $R^a$, $R^b$, $R^c$, W, X, Y, $Z^1$, $Z^2$, $Z^3$ have the same meaning as defined in any of the preceding embodiments and L represents —C(O)N($R^8$)— or —S(O)$_2$N($R^8$)—, which groups are bound to the 9-membered fused heteroaromatic scaffold via the carbon or sulfur atom, respectively;
or
A-L- together represent one of the following groups

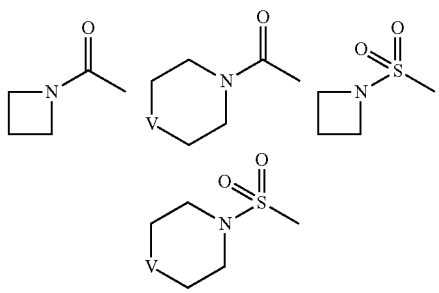

in which
V represents a bond, —CH$_2$—, —CH$_2$CH$_2$—, —CH$_2$CH$_2$CH$_2$—, which latter alkylene groups can optionally be substituted by one or two of the following groups: fluoro, —CN, —OC$_{1-3}$alkyl);

the salts thereof, particularly the physiologically acceptable salts thereof with organic or inorganic acids or bases.

In a further embodiment, in the general formula I, A, M, $Q^2$, $Q^3$, $Q^4$, $R^1$, $R^2$, $R^3$, $R^4$, $R^5$, $R^6$, $R^7$, $R^a$, $R^b$, $R^c$, W, X, Y, $Z^1$, $Z^2$, $Z^3$ have the same meaning as defined in any of the preceding embodiments and L represents —C(O)NH— or —S(O)$_2$NH—, which groups are bound to the 9-membered fused heteroaromatic scaffold via the carbon or sulfur atom, respectively;
the salts thereof, particularly the physiologically acceptable salts thereof with organic or inorganic acids or bases.

In a further embodiment, in the general formula I, L, A, M, $Q^2$, $Q^3$, $Q^4$, $R^1$, $R^2$, $R^3$, $R^4$, $R^5$, $R^6$, $R^a$, $R^b$, $R^c$, W, X, Y, $Z^1$, $Z^2$, $Z^3$ have the same meaning as defined in any of the preceding embodiments and each $R^7$ represents hydrogen, halo, $C_{1-5}$ alkyl-O—, $C_{3-5}$cycloalkyl-$C_{0-2}$ alkyl-O—, 4-5-membered heterocycloalkyl-$C_{0-2}$ alkyl-O— (in which latter three groups the alkyl, cycloalkyl or heterocycloalkyl fragments are optionally substituted by one or more substituents selected from fluoro, —O$C_{1-3}$ alkyl or by one or more $C_{1-3}$ alkyl groups, which can be optionally substituted by one or more fluoro atoms);
the salts thereof, particularly the physiologically acceptable salts thereof with organic or inorganic acids or bases.

In a further embodiment, in the general formula I, L, M, $Q^2$, $Q^3$, $Q^4$, $R^1$, $R^2$, $R^3$, $R^4$, $R^5$, $R^6$, $R^7$, $R^a$, $R^b$, $R^c$, W, X, Y, $Z^1$, $Z^2$, $Z^3$ have the same meaning as defined in any of the preceding embodiments and A represents hydrogen, $C_{1-6}$ alkyl, $C_{3-6}$alkynyl, phenyl, 5-6-membered heteroaryl,
$C_{3-6}$cycloalkyl-$C_{0-2}$alkyl-, 4-6-membered heterocycloalkyl-$C_{0-2}$alkyl, phenyl-$C_{1-3}$alkyl-, 5-6-membered heteroaryl-$C_{1-3}$alkyl in which groups the alkyl-, alkynyl-, cycloalkyl- and heterocycloalkyl-fragments are optionally substituted by one or two substituents selected from $R^{9a}$ and the phenyl, thienyl and pyridyl fragments are optionally substituted by one or two substituents selected from $R^{9b}$;
each $R^{9a}$ independently represents fluoro, phenyl, $C_{1-2}$alkyl, —O$C_{1-4}$alkyl which latter two groups are optionally substituted by one to three fluoro atoms;
each $R^{9b}$ represents independently fluoro, chloro, bromo, $C_{1-2}$ alkyl, —O$C_{1-2}$ alkyl which latter two groups are optionally substituted by one or more fluoro;
the salts thereof, particularly the physiologically acceptable salts thereof with organic or inorganic acids or bases.

In a further embodiment, in the general formula I, A, L, $Q^2$, $Q^3$, $Q^4$, $R^1$, $R^2$, $R^3$, $R^4$, $R^5$, $R^6$, $R^7$, $R^a$, $R^b$, $R^c$, W, X, Y, $Z^1$, $Z^2$, $Z^3$ have the same meaning as defined in any of the preceding embodiments and M represents $C_{1-6}$ alkyl, $C_{3-6}$cycloalkyl, 4-6-membered heterocycloalkyl, all of which groups are optionally substituted by one or more groups selected from fluoro, —OH, —CN, —NH$_2$, phenyl, —CF$_3$, $C_{1-2}$ alkyl, $C_{3-5}$cycloalkyl-$C_{0-1}$ alkyl;
or phenyl, 5-6-membered heteroaryl both of which are optionally substituted by one or more substituents independently selected from fluoro, chloro, methyl, —CF$_3$, methoxy;
the salts thereof, particularly the physiologically acceptable salts thereof with organic or inorganic acids or bases.

In a further embodiment, in the general formula I, A, L, M, $Q^2$, $Q^3$, $Q^4$, $R^2$, $R^3$, $R^4$, $R^5$, $R^6$, $R^7$, $R^a$, $R^b$, $R^c$, W, X, Y, $Z^1$, $Z^2$, $Z^3$ have the same meaning as defined in the any of the preceding embodiments and $R^1$ represents fluoro, chloro, bromo, $C_{1-2}$ alkyl, $C_{1-2}$ alkoxy, the latter two groups of which are optionally substituted by one or more fluoro;
the salts thereof, particularly the physiologically acceptable salts thereof with organic or inorganic acids or bases.

In a further embodiment, in the general formula I, A, L, M, $Q^2$, $Q^3$, $Q^4$, $R^1$, $R^2$, $R^3$, $R^4$, $R^5$, $R^6$, $R^7$, W, X, Y, $Z^1$, $Z^2$, $Z^3$ have the same meaning as defined in any of the preceding embodiments and $R^a$, $R^b$ and $R^c$ represent hydrogen,
the salts thereof, particularly the physiologically acceptable salts thereof with organic or inorganic acids or bases.

A further embodiment of the present invention comprises compounds of the formula I, namely compounds of formula Ie

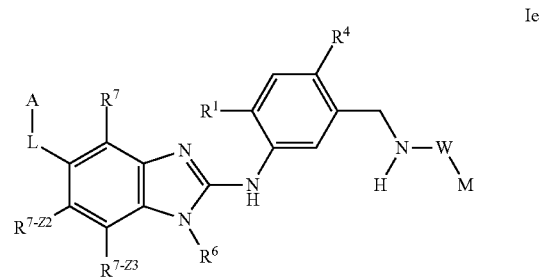

in which
A represents hydrogen, $C_{1-6}$ alkyl, phenylpropargyl, phenyl, $C_{3-6}$cycloalkyl-$C_{0-2}$alkyl-, tetrahydrofuranyl-$C_{0-2}$alkyl, pyrrolidinyl-$C_{0-2}$alkyl, piperidin-$C_{0-2}$alkyl, pyridyl-$C_{1-2}$alkyl-, in which groups the alkyl-, alkynyl-, cycloalkyl- and heterocycloalkyl-fragments are optionally substituted by one or more substituents selected from $R^{9a}$ and the phenyl and pyridyl fragments are optionally substituted by one or more substituents selected from $R^{9b}$;
each $R^{9a}$ independently represents fluoro, $C_{1-2}$alkyl, —O$C_{1-4}$alkyl in which latter two groups the alkyl fragments are optionally substituted by one or more fluoro atoms;
each $R^{9b}$ represents independently fluoro, chloro, bromo,
L represents —C(O)NH— or —S(O)$_2$NH—, which groups are bound to the 9-membered fused heteroaromatic scaffold via the carbon or sulfur atom, respectively;
W represents —C(O)—, —S(O)$_2$—;
M represents $C_{1-4}$ alkyl, $C_{3-6}$cycloalkyl which latter two groups are optionally substituted by one or more groups selected from fluoro, —OH, —CN, —NH$_2$, phenyl, CF$_3$, $C_{1-2}$ alkyl, cyclopropyl-methyl;
or
represents oxetanyl or tetrahydrofuranyl, both of which groups are optionally substituted by a CH$_3$-group;
or phenyl, thienyl both of which are optionally substituted by one or two substituents independently selected from fluoro or chloro,
$R^1$ represents fluoro, chloro, bromo, CH$_3$, CH$_2$F, CHF$_2$, CF$_3$, —OCH$_3$;
$R^4$ represents hydrogen or fluoro;
$R^6$ represents hydrogen; $C_{1-3}$ alkyl, $C_{3-5}$ cycloalkyl-$C_{0-1}$ alkyl, which latter two groups are optionally substituted by one or more substituents selected from fluoro, —OCH$_3$, —NH($C_{1-3}$ alkyl), N($C_{1-3}$ alkyl)$_2$;
$R^{7-Z2}$ represents hydrogen, halo, —O$C_{1-5}$alkyl, in which latter group the alkyl is optionally substituted by one or more fluoro atoms;
$R^{7-Z1}$ and $R^{7-Z3}$ independently represent hydrogen or fluoro;

the salts thereof, particularly the physiologically acceptable salts thereof with organic or inorganic acids or bases.

TERMS AND DEFINITIONS USED

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids.

The pharmaceutically acceptable salts of the present invention can be synthesized from the parent compound which contains a basic or acidic moiety by conventional chemical methods. Generally, such salts can be prepared by reacting the free acid or base forms of theses compounds with a stoichiometric amount of the appropriate base or acid in water or in an organic solvent, or in a mixture of the two; generally, non-aqueous media like ether, ethyl acetate, ethanol isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

Examples of pharmaceutically active salts for each of the compounds which are the subject of this description include, without being restricted thereto, salts which are prepared from pharmaceutically acceptable acids or bases, including organic and inorganic acids and bases. If the preferred compound is basic, salts may be prepared from pharmaceutically acceptable acids. When selecting the most preferred salt, or to clarify whether a salt or the neutral compound is used, properties such as bioavailability, ease of manufacture, workability and shelf life are taken into consideration, inter alia.

Suitable pharmaceutically acceptable acids include acetic acid, benzenesulphonic acid (besylate), benzoic acid, p-bromophenylsulphonic acid, camphorsulphonic acid, carbonic acid, citric acid, ethanesulphonic acid, fumaric acid, gluconic acid, glutamic acid, hydrobromic acid, hydrochloric acid, hydriodic acid, isethionic acid, lactic acid, maleic acid, malic acid, mandelic acid, methanesulphonic acid (mesylate), mucinic acid, nitric acid, oxalic acid, pamoic acid, pantothenic acid, phosphoric acid, succinic acid, sulphuric acid, tartaric acid, p-toluenesulphonic acid and the like. Examples of pharmaceutically acceptable salts include, without being restricted thereto, acetate, benzoate, hydroxybutyrate, bisulphate, bisulphite, bromide, butyne-1,4-dioate, caproate, chloride, chlorobenzoate, citrate, dihydrogen phosphate, dinitrobenzoate, fumarate, glutaminate, glycollate, heptanoate, hexyne-1,6-dioate, hydroxybenzoate, iodide, lactate, maleate, malonate, mandelate, metaphosphate, methanesulphonate, methoxybenzoate, methylbenzoate, monohydrogen phosphate, naphthalene-1-sulphonate, naphthalene-2-sulphonate, oxalate, phenylbutyrate, phenylproprionate, phosphate, phthalate, phenylacetate, propanesulphonate, propiolate, propionate, pyroglutaminate, pyrophosphate, pyrosulphate, sebacate, suberate, succinate, sulphate, sulphite, sulphonate, tartrate, trifluoroacetate, xylenesulphonate and the like.

"Isomers": It will be appreciated that the compounds of the present invention may contain one or more asymmetrically substituted carbon atoms and therefore they may be isolated in racemic or in optically active forms (i.e. in form of their corresponding enantiomers or diasteromers).

In certain instances, an enantiomer or a diastereomer of a compound of Formula I may display superior activity compared with the other. When required, diastereomers may be separated from diastereomeric mixture of the compounds using conventional, e.g. fractional crystallisation or HPLC techniques. The desired enantiomers may be obtained by methods well known to the skilled man in the art i.e. by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography (see for example Thomas J. Tucker, et al, J. Med. Chem. 1994, 37, 2437-2444), or by reaction with an appropriate chiral reagent or chiral catalyst all under conditions known to the skilled person (e.g. Mark A. Huffman, et al, J. org. Chem. 1995, 60 1590-1594).

Compounds of the invention may contain double bonds and may thus exist as E (entgegen) and Z (zusammen) geometric isomers about each individual double bond. All such isomers and mixtures thereof are included within the scope of the invention.

Compounds of the invention may also exhibit tautomerism. All tautomeric forms and mixtures thereof are included within the scope of the invention. For instance, a compound containing the moiety "1H-benzimidazole" may be considered to be identical to a corresponding compound containing a "3H-benzimidazole" moiety.

All chiral, enantiomeric, diastereomeric, racemic forms, tautomeric and all geometric isomeric forms of a structure are included within the scope of invention, unless the specific stereochemistry or isomer form is specifically indicated. Obviously, the isomer which is pharmacologically most effective and most free from side effects is preferred.

The subject-matter of this invention also includes deuterated compounds of general formula I, i.e. in which one or more hydrogen atoms, for example one, two, three, four or five hydrogen atoms, are replaced by the hydrogen isotope deuterium.

The term "$C_{1-3}$-alkyl" (including those which are part of other groups) means alkyl groups with 1 to 3 carbon atoms, the term "$C_{1-4}$-alkyl" means branched and unbranched alkyl groups with 1 to 4 carbon atoms, the term "$C_{1-6}$-alkyl" means branched and unbranched alkyl groups with 1 to 6 carbon atoms and the term "$C_{1-8}$-alkyl" means branched and unbranched alkyl groups with 1 to 8 carbon atoms. Examples include: methyl, ethyl, n-propyl, iso-propyl, n-butyl, iso-butyl, sec-butyl, tert-butyl, n-pentyl, neopentyl, n-hexyl, n-heptyl and n-octyl. The abbreviations Me, Et, n-Pr, i-Pr, n-Bu, i-Bu, t-Bu, etc. may optionally also be used for the groups mentioned above. Unless stated otherwise, the definitions propyl and butyl include all the possible isomeric forms of the groups in question. Thus, for example, propyl includes n-propyl and iso-propyl, butyl includes iso-butyl, sec-butyl and tert-butyl. The term "alkyl" also includes alkyl groups wherein 1-3 hydrogen atoms are replaced by fluorine atoms.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —($CH_2$)—, —($CH_2$—$CH_2$)—, —(CH($CH_3$))—, —($CH_2$—$CH_2$—$CH_2$)—, —(C($CH_3$)$_2$)—, —(CH($CH_2CH_3$))—, —(CH($CH_3$)—$CH_2$)—, —($CH_2$—CH($CH_3$))—, —($CH_2$—$CH_2$—$CH_2$—$CH_2$)—, —($CH_2$—$CH_2$—CH($CH_3$))—, —(CH($CH_3$)—$CH_2$—$CH_2$)—, —($CH_2$—CH($CH_3$)—$CH_2$)—, —($CH_2$—C($CH_3$)$_2$)—, —(C($CH_3$)$_2$—$CH_2$)—, —(CH($CH_3$)—CH($CH_3$))—, —($CH_2$—CH($CH_2CH_3$))—, —(CH($CH_2CH_3$)—$CH_2$)—, —(CH($CH_2CH_2CH_3$))—, —(CHCH($CH_3$)$_2$)— and —C($CH_3$)($CH_2CH_3$)—.

The term "$C_{3-8}$-cycloalkyl" (including those which are part of other groups) means cyclic alkyl groups with 3 to 8 carbon atoms and the term "$C_{3-6}$-cycloalkyl" means cyclic alkyl groups with 3 to 6 carbon atoms. Examples include: cyclopropyl, cyclobutyl, cyclopentyl, cyclohexyl, cycloheptyl or cyclooctyl and also include the following structures

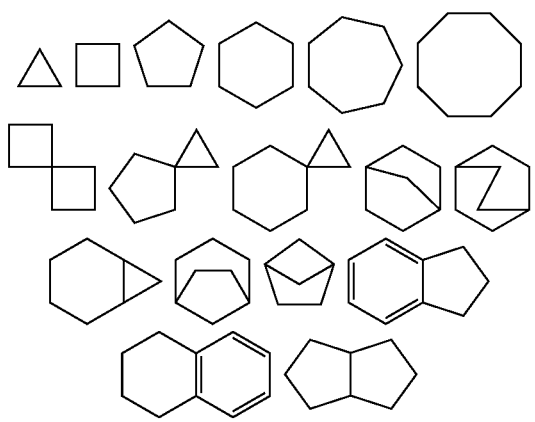

Unless otherwise stated, the cyclic alkyl groups may be substituted by one or more groups selected from among methyl, ethyl, iso-propyl, tert-butyl, hydroxy, fluorine, chlorine, bromine and iodine. These cycloalkyls may additionally be annelated (i.e. fused) to a benzene ring, so that nine- to twelve-membered bicyclic heterocycles are formed.

The term "$C_{2-6}$-alkenyl" (including those which are part of other groups) means branched and unbranched alkenyl groups with 2 to 6 carbon atoms, provided that they have at least one double bond. Alkenyl groups with 2 to 4 carbon atoms are preferred. Examples include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-butenyl, 2-butenyl and 3-butenyl, 1-methyl-1-propenyl, 1-methyl-2-propenyl etc.

The term "$C_{2-7}$-alkynyl" (including those which are part of other groups) means branched and unbranched alkynyl groups with 2 to 7 carbon atoms, provided that they have at least one triple bond. Alkynyl groups with 2 to 4 carbon atoms are preferred. Examples of these include: ethynyl, propynyl, butynyl, pentynyl or hexynyl. Unless stated otherwise, the definitions propynyl, butynyl, pentynyl and hexynyl include all the possible isomeric forms of the groups in question. Thus, for example, propynyl includes 1-propynyl and 2-propynyl, butynyl includes 1-butynyl, 2-butynyl and 3-butynyl, 1-methyl-1-propynyl, 1-methyl-2-propynyl etc.

The term "halo" or "halogen", when used herein, includes fluoro, chloro, bromo and iodo. Unless stated otherwise, fluorine, chlorine and bromine are regarded as preferred halogens.

The term "4-7 membered heterocycloalkyl" means stable 4-, 5-, 6- or 7-membered monocyclic heterocyclic ring systems which may be both saturated and monounsaturated. One or two of the ring carbon atoms may independently be replaced by heteroatoms which are selected from among oxygen, nitrogen and sulphur, the latter two of which heteroatoms may optionally be oxidised (so forming N-oxide, sulfoxide or sulfon). The previously mentioned heterocycles may be linked to the rest of the molecule via a carbon atom or a nitrogen atom. Examples for the 4-, 5-, 6- or 7-membered heterocyclic ring systems include:

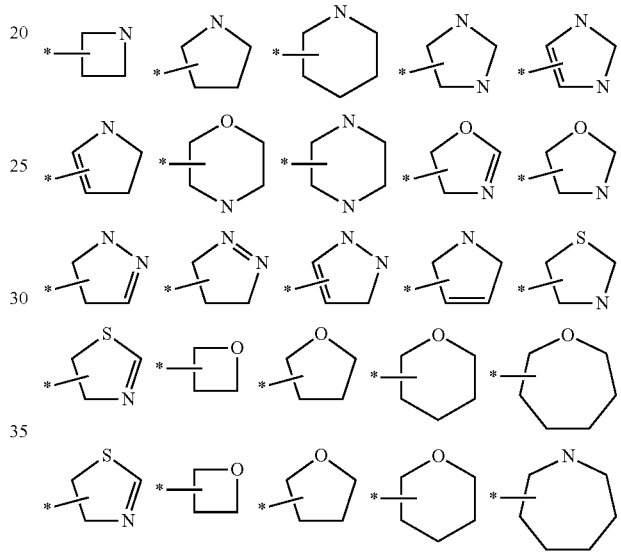

These heterocycloalkyls may additionally be annelated (i.e. fused) to a benzene ring, so that eight- or eleven-membered bicyclic heterocycles are formed.

The term "aryl" (including those which are part of other groups) means aromatic ring systems with 6 or 14 carbon atoms (e.g. $C_{6-10}$ aryl). Such groups may be monocyclic, bicyclic or tricyclic and have between 6 and 14 ring carbon atoms. Examples include phenyl, 1-naphthyl or 2-naphthyl. The preferred aryl group is phenyl. Unless otherwise mentioned, the aromatic groups may be substituted by one or more groups selected from among methyl, ethyl, n-propyl, iso-propyl, tert-butyl, hydroxy, methoxy, trifluoromethoxy, fluorine, chlorine, bromine and iodine, while the groups may be identical or different.

The term "heteroaryl" means five- or six-membered heterocyclic aromatic groups which may contain one, two, three or four heteroatoms, selected from among oxygen, sulphur and nitrogen, and which additionally contain a sufficient number of conjugated double bonds to form an aromatic system. These heteroaryls may additionally be annelated (i.e. fused) to a benzene ring, so that nine- or ten-membered bicyclic heteroaryls are formed.

Examples for the five- or six-membered heterocyclic aromatic groups include:

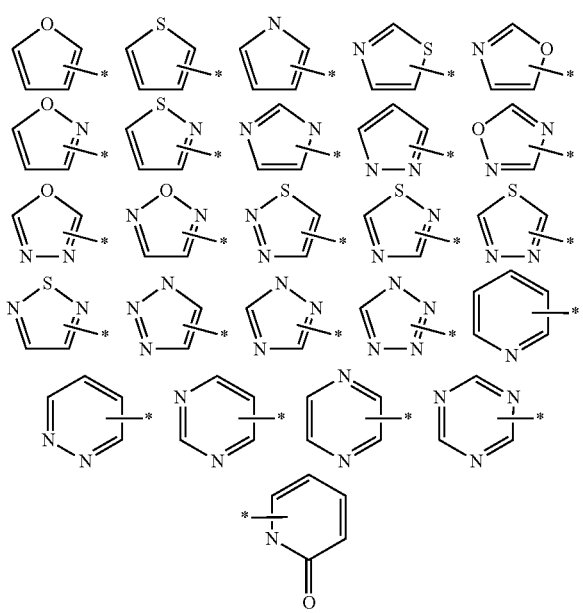

Examples for the nine- or ten-membered heterocyclic aromatic groups include:

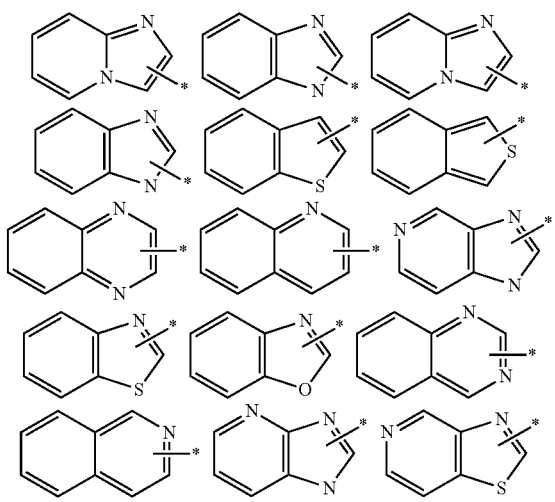

Unless otherwise stated, the heteroaryls mentioned previously may be substituted by one or more groups selected from among methyl, ethyl, n-propyl, iso-propyl, tert-butyl, hydroxy, methoxy, trifluoromethoxy, fluorine, chlorine, bromine and iodine, while the groups may be identical or different. In addition, a nitrogen atom present in the heteroaryl group may be oxidised, thus forming an N-oxide.

For the avoidance of doubt, in cases in which the identity of two or more substituents in a compound of formula I may be the same, the actual identities of the respective substituents are not in any way interdependent. For example, in the situation in which $Z^1$ and $Z^2$ both represent =C($R^7$)—, then the respective =C($R^7$)— groups in question may be the same or different. Similarly, when groups are substituted by more than one substituent as defined herein, the identities of those individual substituents are not to be regarded as being interdependent. For example, when the A group represents $C_{1-8}$ alkyl substituted by two $R^{9a}$ groups, in which, in both cases, $R^{9a}$ represents —N($C_{1-3}$ alkyl)$_2$, then the identities of the two —N($C_{1-3}$ alkyl)$_2$ groups are not to be regarded as being interdependent, i.e. the two —N($C_{1-3}$ alkyl)$_2$ moieties may be the same or different. Similarly, also the $C_{1-3}$ alkyl groups within one particular —N($C_{1-3}$ alkyl)$_2$ group are independent of one another, i.e. they may be the same or different from each other.

For the avoidance of doubt, when preferred features are mentioned herein, then such features may be taken independently of other preferred features or conjunctively with other preferred features.

The skilled person will appreciate that compounds of formula I that are the subject of this invention include those that are stable. That is, compounds of the invention include those that are sufficiently robust to survive isolation from e.g. a reaction mixture to a useful degree of purity.

Methods of Preparation

Compounds of the present invention can be prepared in accordance with techniques that are well known to those skilled in the art, for example as described hereinafter and in the experimental section. According to a further aspect of the invention there is provided a process for the preparation of a compound of formula I, which process can be performed for example according to the following schemes A-E.

Scheme A ($R^5$ = H, all other variable groups are as defined in claim 1):

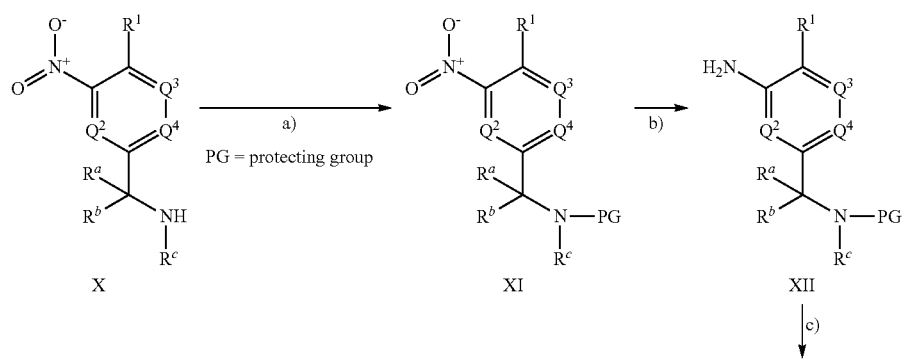

-continued

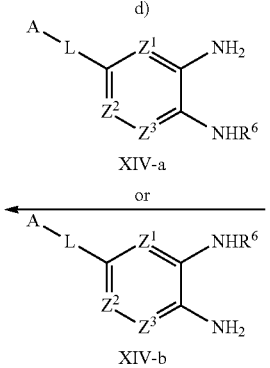

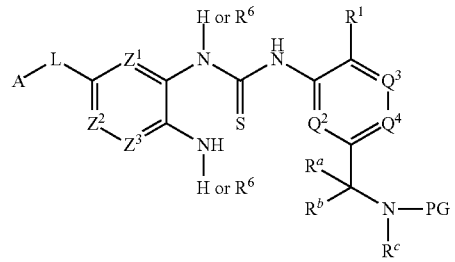

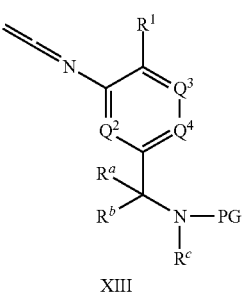

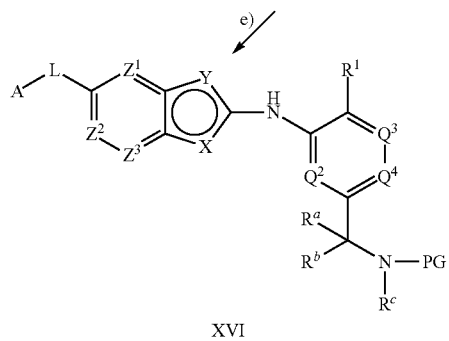

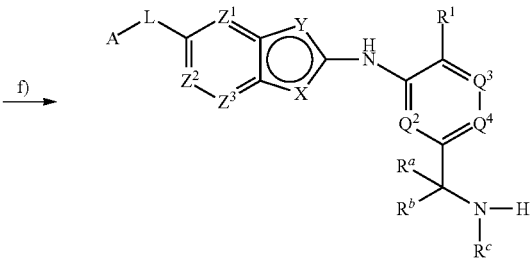

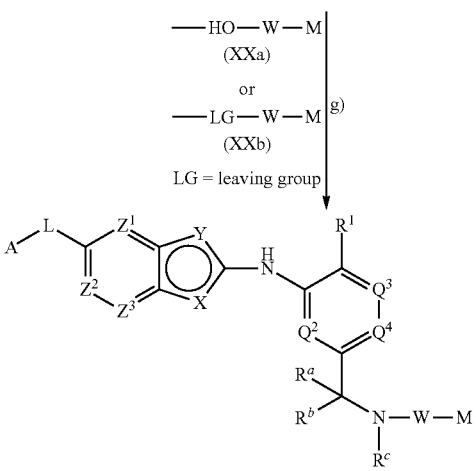

The protecting group PG which is introduced in a step a) is a standard nitrogen protecting group, well known to those skilled in the art, for example a nitrogen protecting group as described in "*Protective Groups in Organic Synthesis*", 3$^{rd}$ edition, T. W. Greene & P. G. M. Wutz, Wiley-Interscience (1999), for example a tert-butoxycarbonyl-, benzyloxycarbonyl-, ethoxycarbonyl-, methoxycarbonyl-, allyloxycarbonyl- or trifluormethylcarbonyl group.

Step a) can be performed according to literature procedures as described in "*Protective Groups in Organic Synthesis*", 3$^{rd}$ edition, T. W. Greene & P. G. M. Wutz, Wiley-Interscience (1999) for example with reagents like 2-(tert-Butoxycarbonyloxyimino)-2-phenylacetonitrile (BOC—ON), Di-tert-butyl dicarbonate (BOC$_2$O), Di-methyl dicarbonate, Di-ethyl dicarbonate, Ethyl chloroformate, Methyl chloroformate, Allyl chloroformate, Benzyl chloroformate or Trifluoroacetic acid chloride under conditions which are known from the literature preferably in presence of a base for example sodium hydroxide, triethylamine, diisopropyl ethyl amine, 4-dimethylamino-pyridine. Appropriate solvent for this step is for example dichloromethane, tetrahydrofuran (THF), acetonitrile, dimethylformamide (DMF), dimethylacetamide, N methylpyrrolidone or mixtures of the above mentioned solvents.

Step b) can be performed with H$_2$/Raney-Nickel, H$_2$/Palladium on carbon, Fe-powder/aqueous NH$_4$Cl, Fe/HCl, Zn/HCl, Na$_2$S$_2$O$_4$, SnCl$_2$/HCl, Zn/HCl or NaBH$_4$/CuCl or according to procedures described in the literature for example R. Larock, *Comprehensive Organic Transformations*, VCH Verlagsgemeinschaft, Weinheim (1989). Appropriate solvent for this step is for example dichloromethane, tetrahydrofuran (THF), acetonitrile, dimethylformamide (DMF), dimethylacetamide, N methylpyrrolidone, ethanol, methanol, isopropanol or mixtures of the above mentioned solvents.

Step c) can be performed according to standard literature procedures for example with reagents such as 1,1'-thiocarbonyldi-2-pyridone or 1,1'-thiocarbonyldiimidazole or with thiophosgene in a solvent as for example dichloromethane or dimethylformamide and optionally under addition of a base like 4-dimethylamino-pyridine or triethylamine.

Step d) can be performed under standard conditions known to those skilled in the art in presence of a suitable solvent such as diethyl ether, dimethylformamide, dichloromethane, acetononitrile and/or tetrahydrofuran. The coupling reaction is preferably performed in the presence of a base such as NaOH, KOH, NaHCO$_3$, triethylamine, N-ethyldiisopropylamine, 4-dimethylamino-pyridine or other appropriate bases.

Step e) is preferably performed in the presence of a suitable 'coupling' reagent. As 'coupling' reagent for instance a carbodiimide based compound such as dicyclohexylcarbodiimide (DCC), 1-ethyl-3-(3-dimethylaminopropyl) carbodiimide (or salt, e.g. hydrochloride, thereof) or N,N-diisopropylcarbodiimide (DIC) can be used. The reaction may proceed at any suitable temperature (e.g. one between about 0° C. to about 200° C.), and may also be performed in the presence of an additive (such as 2,2,2-trifluoro-N,O-bis-(trimethylsilyl)-acetamide). Appropriate co-solvent for this step is for example dichloromethane, tetrahydrofuran (THF), acetonitrile, dimethylformamide (DMF), dimethylacetamide, N methylpyrrolidone or mixtures of the above mentioned solvents.

Step d and e can be performed in a step-wise reaction under isolation of the intermediate XV or without isolation of XV.

Step f) Protecting groups may be removed in accordance with techniques that are well known to those skilled in the art and as described hereinafter. For example, protected compounds/intermediates described herein may be converted chemically to unprotected compounds using HCl or H$_2$SO$_4$ solutions, trifluoro acetic acid, KOH; Ba(OH)$_2$, Pd on carbon, trimethylsilyl iodide or other conditions as described in "*Protective Groups in Organic Synthesis*", 3$^{rd}$ edition, T. W. Greene & P. G. M. Wutz, Wiley-Interscience (1999). Appropriate co-solvent for this step is for example dichloromethane, tetrahydrofuran (THF), acetonitrile, dimethylformamide (DMF), dimethylacetamide, N methylpyrrolidone or mixtures of the above mentioned solvents.

Step g): The coupling of the amine XVII with the acid XXa can be performed with an additional in-situ activating agent like 1-propylphosphonic acid cyclic anhydride, O-(benzotriazol-1-yl)-N,N,N',N'-tetramethyluronium tetrafluoroborate or hexafluorophosphate, N,N'-dicyclohexylcarbodiimide, 1-(3-dimethylaminopropyl)-3-ethylcarbodiimide, carbonyldiimidazole, oxalyl chloride or other activating agents of the state of the art.

The coupling reaction is preferably performed in the presence of a base such as NaOH, KOH, NaHCO$_3$, triethylamine, N-ethyldiisopropylamine, N,N,-dimethylaminopyridine or other appropriate bases of the state of the art and for example described in described in Houben-Weyl, "Methods in Organic Synthesis", Vol. E22a, p 425ff.

Alternatively, the coupling of the amine XVII can be performed with an activated acid derivative XXb, where the leaving group LG can be for example, a fluorine, chlorine, bromine, azide or an isopropyloxy-C(O)—O anion. The coupling reaction is preferably performed in the presence of a base such as NaOH, KOH, NaHCO$_3$, triethylamine, N-ethyldiisopropylamine, 4-dimethylamino-pyridine or other appropriate bases under conditions which are for example described in Houben-Weyl, "Methods in Organic Synthesis", Vol. E22a, p 425ff.

If step g) is carried out in presence of trimethylaluminium or triethylaluminium the leaving group in XXb can also be a methoxy or ethoxy group.

The above mentioned coupling reactions are performed in an appropriate solvent for example like dichloromethane, tetrahydrofuran (THF), acetonitrile, dimethylformamide (DMF), dimethylacetamide, N methylpyrrolidone or in mixtures of the above mentioned solvents.

Scheme B (R$^5$ = alkyl chains according to the definitions above, other variable groups are as defined in claim 1)

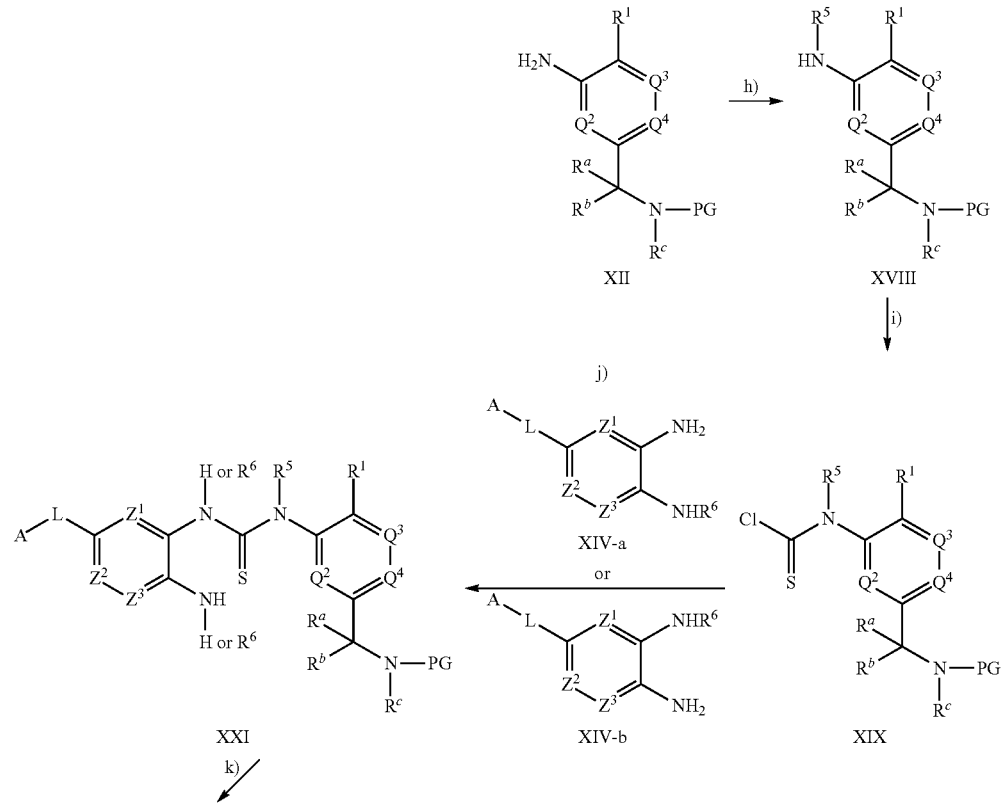

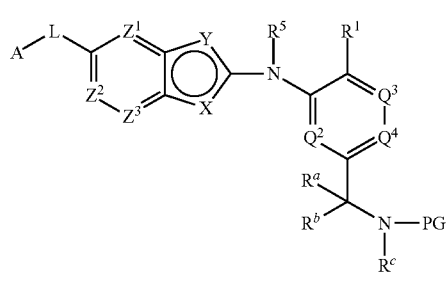

-continued

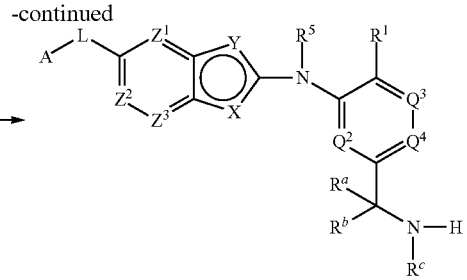

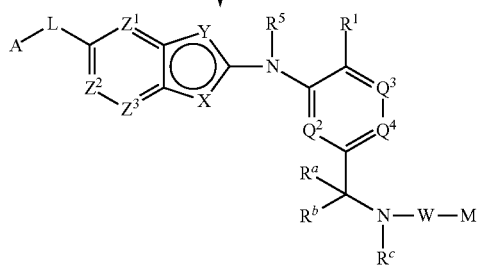

I-2

Step h) The reductive amination is performed according to known procedures for example with sodium triacetoxyborohydride, sodium borohydride or sodium cyanoborhydride in an appropriate solvent like tetrahydrofuran or dichlormethane under addition of acetic acid or trifluoro acetic acid if appropriate, or with Palladium on charcoal under a hydrogen atmosphere in tetrahydrofuran or ethanol or methanol or isopropanol or dimethylformamide, preferably in the presence of acetic acid or trifluoro acetic acid.

Step i) can be performed according to standard literature procedures for example with reagents such as thiophosgene in an appropriate solvent as for example dichloromethane or dimethylformamide optionally under addition of a base like 4-dimethylamino-pyridine or triethylamine.

Step j) can be performed under standard conditions known to those skilled in the art in presence of a suitable solvent such as diethyl ether, dimethylformamide, dichloromethane, acetononitrile and/or tetrahydrofuran). The coupling reaction is preferably performed in the presence of a base such as NaOH, KOH, NaHCO$_3$, triethylamine, N-ethyldiisopropylamine, 4-dimethylamino-pyridine or other appropriate bases.

Step k) is preferably performed in the presence of a suitable coupling reagent as for example a carbodiimide based compound such as dicyclohexylcarbodiimide (DCC), 1-ethyl-3-(3-dimethylaminopropyl) carbodiimide (or salt, e.g. hydrochloride, thereof) or N,N-diisopropylcarbodiimide (DIC). The reaction may proceed at any suitable temperature (e.g. one between about 0° C. to about 200° C.), and may also be performed in the presence of an additive (such as 2,2,2-trifluoro-N,O-bis-(trimethylsilyl)-acetamide). Appropriate co-solvent for this step is for example dichloromethane, tetrahydrofuran, acetonitrile, dimethylformamide, dimethylacetamide, N methylpyrrolidone or mixtures of the above mentioned solvents.

Step j and k can be performed in a step-wise reaction under isolation of the intermediate XXI or without isolation of XXI.

Step l) Protecting groups may be removed in accordance with techniques that are well known to those skilled in the art and as described hereinafter. For example, protected compounds/intermediates described herein may be converted chemically to unprotected compounds using HCl or H$_2$SO$_4$ solutions, trifluoro acetic acid, KOH; Ba(OH)$_2$, Pd on carbon, trimethylsilyl iodide or other conditions as described in "*Protective Groups in Organic Synthesis*", 3$^{rd}$ edition, T. W. Greene & P. G. M. Wutz, Wiley-Interscience (1999). T Appropriate co-solvent for this step is for example dichloromethane, tetrahydrofuran, acetonitrile, dimethylformamide, dimethylacetamide, N methylpyrrolidone, methanol, ethanol or mixtures of the above mentioned solvents.

Step m): The coupling of the amine XXIII with the acid XXa can be performed with an additional in-situ activating agent like 1-propylphosphonic acid cyclic anhydride, O-(benzotriazol-1-yl)-N,N,N',N'-tetramethyluronium tetrafluoroborate or hexafluorophosphate, N,N'-dicyclohexylcarbodiimide, 1-(3-dimethylaminopropyl)-3-ethylcarbodiimide, carbonyldiimidazole, oxalyl chloride or other activating agents of the state of the art.

The coupling reaction is preferably performed in the presence of a base such as NaOH, KOH, NaHCO$_3$, triethylamine, N-ethyldiisopropylamine, N,N,-dimethylaminopyridine or other appropriate bases of the state of the art and for example described in described in Houben-Weyl, "Methods in Organic Synthesis", Vol. E22a, p 425ff.

Alternatively, the coupling of the amine XXIII can be performed with an activated acid derivative XXb, where the leaving group LG can be for example, a fluorine, chlorine, bromine, azide or an isopropyloxy-C(O)—O anion. The coupling reaction is preferably performed in the presence of a base such as NaOH, KOH, NaHCO$_3$, triethylamine, N-ethyldiisopropylamine, 4-dimethylamino-pyridine or other appropriate bases under conditions which are for example described in Houben-Weyl, "Methods in Organic Synthesis", Vol. E22a, p 425ff.

If step g) is carried out in presence of trimethylaluminium or triethylaluminium the leaving group in XXb can also be a methoxy or ethoxy group.

The above mentioned coupling reactions are performed in an appropriate solvent for example like dichloromethane, tetrahydrofuran, acetonitrile, dimethylformamide (DMF), dimethylacetamide, N methylpyrrolidone or in mixtures of the above mentioned solvents.

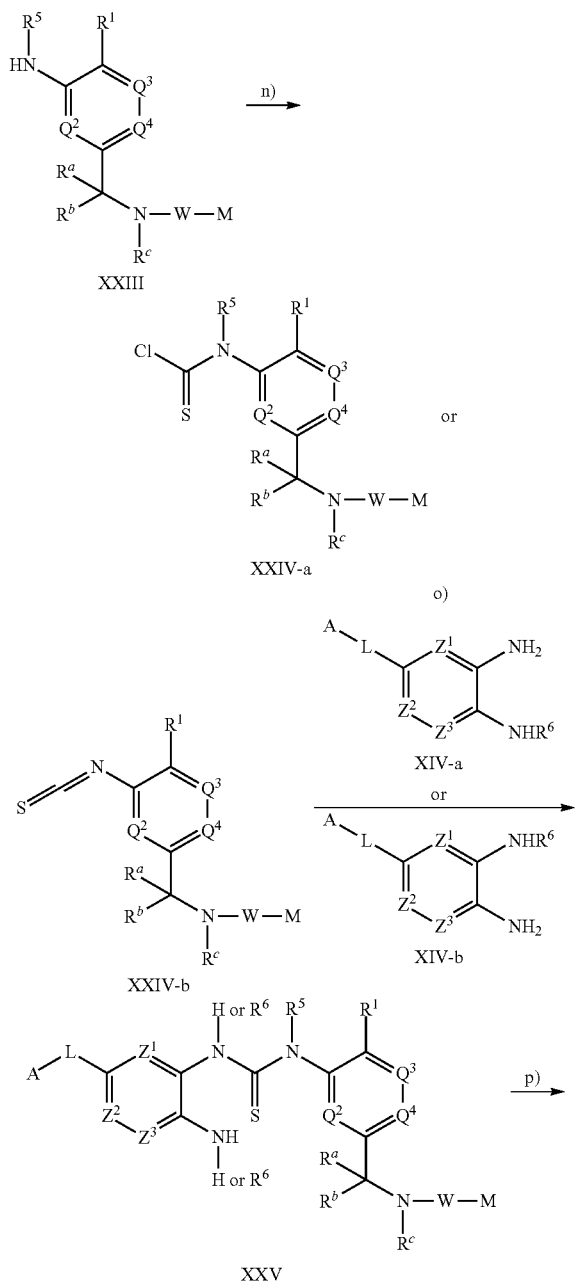

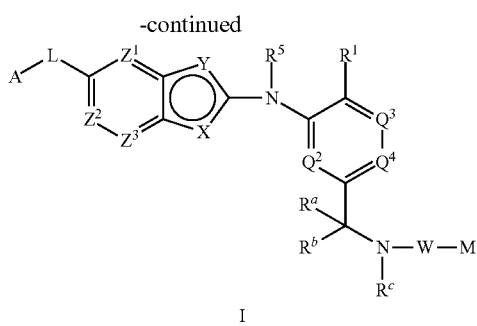

Step n) can be performed according to standard literature procedures for example with reagents such as 1,1'-thiocarbonyldi-2-pyridone or 1,1'-thiocarbonyldiimidazole or with thiophosgene in a solvent as for example dichloromethane or dimethylformamide and optionally under addition of a base like 4-dimethylamino-pyridine or triethylamine.

Step o) can be performed under standard conditions known to those skilled in the art in presence of a suitable solvent such as diethyl ether, dimethylformamide, dichloromethane, acetononitrile and/or tetrahydrofuran. The coupling reaction is preferably performed in the presence of a base such as NaOH, KOH, NaHCO$_3$, triethylamine, N-ethyldiisopropylamine, 4-dimethylamino-pyridine or other appropriate bases.

Step p) is preferably performed in the presence of a suitable 'coupling' reagent. 'Coupling' reagent for instance a carbodiimide based compound such as dicyclo-hexylcarbodiimide (DCC), 1-ethyl-3-(3-dimethylaminopropyl) carbodiimide (or salt, e.g. hydrochloride, thereof) or N,N-diisopropylcarbodiimide (DIC) can be used. The reaction may proceed at any suitable temperature (e.g. one between about 0° C. to about 200° C.), and may also be performed in the presence of an additive (such as 2,2,2-trifluoro-N,O-bis-(trimethylsilyl)-acetamide). Appropriate co-solvent for this step is for example dichloromethane, tetrahydrofuran (THF), acetonitrile, dimethylformamide (DMF), dimethylacetamide, N methylpyrrolidone or mixtures of the above mentioned solvents.

Step o and p can be performed in a step-wise reaction under isolation of the intermediate XXV or without isolation of XXV.

Building blocks XXIX-a or XXIX-b can also be used as precursors according to Scheme D. (PG1=protecting group).

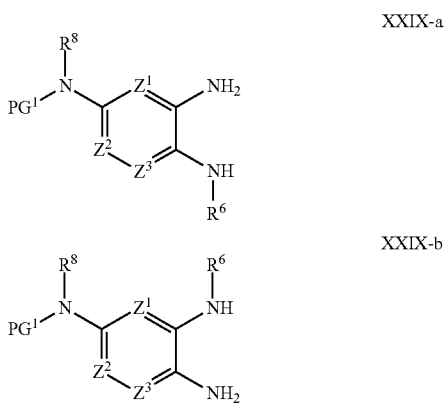

Scheme D (all variable groups except L are as defined in claim 1):

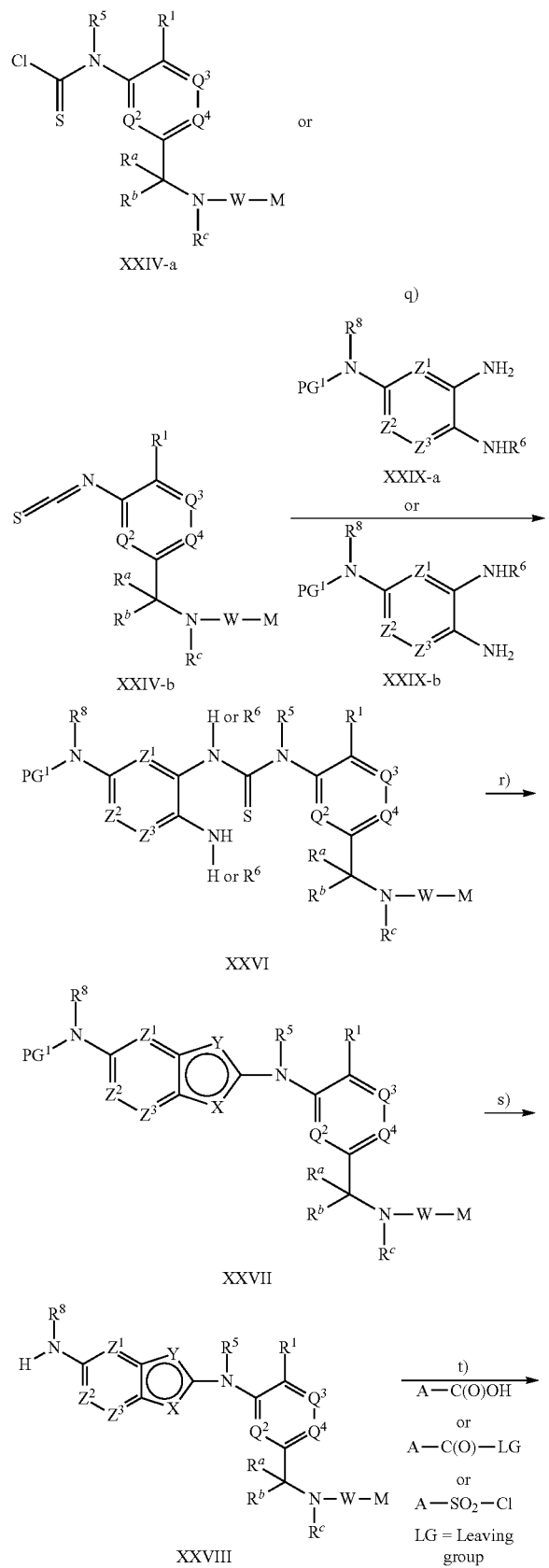

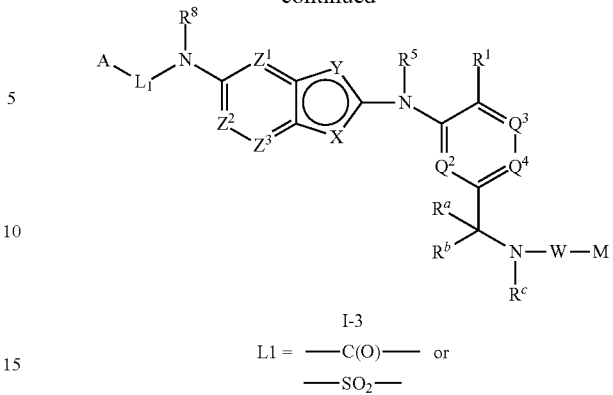

The protecting group $PG^1$ is a standard nitrogen protecting group, well known to those skilled in the art, for example a nitrogen protecting group as described in "*Protective Groups in Organic Synthesis*", $3^{rd}$ edition, T. W. Greene & P. G. M. Wutz, Wiley-Interscience (1999), for example a tert-butoxycarbonyl-, benzyloxycarbonyl-, ethoxycarbonyl-, methoxycarbonyl-, allyloxycarbonyl- or trifluormethylcarbonyl group.

Step q) can be performed under standard conditions known to those skilled in the art in presence of a suitable solvent such as diethyl ether, dimethylformamide, dichloromethane, acetononitrile and/or tetrahydrofuran. The coupling reaction is preferably performed in the presence of a base such as NaOH, KOH, NaHCO₃, triethylamine, N-ethyldiisopropylamine, 4-dimethylamino-pyridine or other appropriate bases.

Step r) is preferably performed in the presence of a suitable 'coupling' reagent. As 'coupling' reagent for instance a carbodiimide based compound such as dicyclohexyl-carbodiimide (DCC), 1-ethyl-3-(3-dimethylaminopropyl) carbodiimide (or salt, e.g. hydrochloride, thereof) or N,N-diisopropylcarbodiimide (DIC) can be used. The reaction may proceed at any suitable temperature (e.g. one between about 0° C. to about 200° C.), and may also be performed in the presence of an additive (such as 2,2,2-trifluoro-N,O-bis-(trimethylsilyl)-acetamide). Appropriate co-solvent for this step is for example dichloromethane, tetrahydrofuran (THF), acetonitrile, dimethylformamide (DMF), dimethylacetamide, N methylpyrrolidone or mixtures of the above mentioned solvents.

Step q and r can be performed in a step-wise reaction under isolation of the intermediate XXVII or without isolation of XXVII.

Step s): The protecting group PG1 may be removed in accordance with techniques that are well known to those skilled in the art and as described hereinafter. For example, protected compounds/intermediates described herein may be converted chemically to unprotected compounds using HCl or H₂SO₄ solutions, trifluoro acetic acid, KOH; Ba(OH)₂, Pd on carbon, trimethylsilyl iodide or other conditions as described in "*Protective Groups in Organic Synthesis*", $3^{rd}$ edition, T. W. Greene & P. G. M. Wutz, Wiley-Interscience (1999). Appropriate co-solvent for this step is for example dichloromethane, tetrahydrofuran (THF), acetonitrile, dimethylformamide (DMF), dimethylacetamide, N methylpyrrolidone, methanol, ethanol or mixtures of the above mentioned solvents.

Step t): The coupling of the amine XXVIII with the acid A-COOH can be performed with an additional in-situ activating agent like 1-propylphosphonic acid cyclic anhydride, O-(benzotriazol-1-yl)-N,N,N',N'-tetramethyluronium tetrafluoroborate or hexafluorophosphate, N,N'-dicyclohexylcarbodiimide, 1-(3-dimethylaminopropyl)-3-ethylcarbodiimide, carbonyldiimidazole, oxalyl chloride or other activating agents of the state of the art. The coupling reaction is preferably performed in the presence of a base such as NaOH, KOH, NaHCO$_3$, triethylamine, N-ethyldiisopropylamine, N,N,-dimethylaminopyridine or other appropriate bases of the state of the art and for example described in described in Houben-Weyl, "Methods in Organic Synthesis", Vol. E22a, p 425ff.

Alternatively, the coupling of the amine XXVIII can be performed with an activated acid derivative A-C(O)-LG, where the leaving group LG can be for example, a fluorine, chlorine, bromine, azide or an isopropyloxy-C(O)—O anion or with A-SO$_2$—Cl. The coupling reaction is preferably performed in the presence of a base such as NaOH, KOH, NaHCO$_3$, triethylamine, N-ethyldiisopropylamine, N,N,-dimethylaminopyridine or other appropriate bases under conditions which are for example described in Houben-Weyl, "Methods in Organic Synthesis", Vol. E22a, p 425ff.

The above mentioned coupling reactions are performed in an appropriate solvent for example like dichloromethan, tetrahydrofurane (THF), acetonitrile, dimethylformamide (DMF), dimethylacetamide, N methylpyrrolidone or in mixtures of the above mentioned solvents.

Building blocks XXX-a or XXX-b can also be used as precursors according to Scheme E.

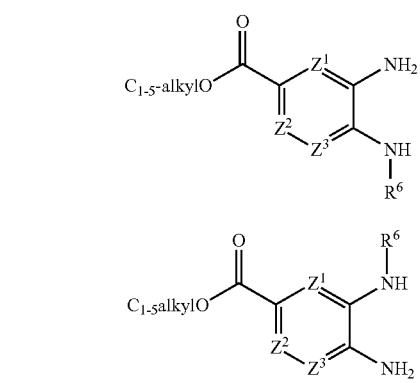

Scheme E (all variable groups except L are as defined in claim 1):

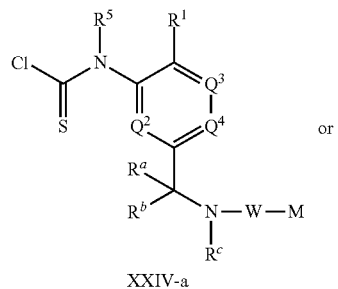

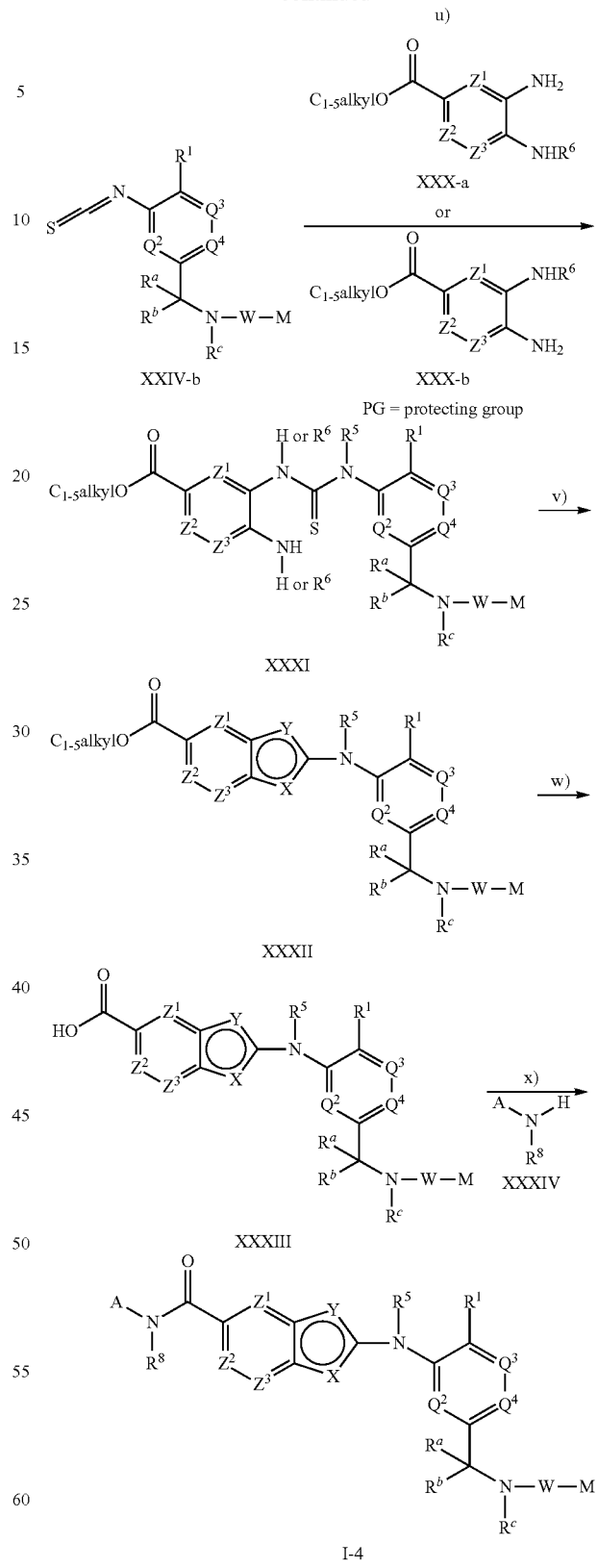

Step u) can be performed under standard conditions known to those skilled in the art in presence of a suitable solvent such as diethyl ether, dimethylformamide, dichloromethane, acetonitrile and/or tetrahydrofuran. The coupling reaction is preferably performed in the presence of a base such as NaOH, KOH, NaHCO$_3$, triethylamine, N-ethyldiisopropylamine, 4-dimethylamino-pyridine or other appropriate bases.

Step v) is preferably performed in the presence of a suitable 'coupling' reagent. As 'coupling' reagent for instance a carbodiimide based compound such as dicyclohexyl-carbodiimide (DCC), 1-ethyl-3-(3-dimethylaminopropyl) carbodiimide (or salt, e.g. hydrochloride, thereof) or N,N-diisopropylcarbodiimide (DIC) can be used. The reaction may proceed at any suitable temperature (e.g. one between about 0° C. to about 200° C.), and may also be performed in the presence of an additive (such as 2,2,2-trifluoro-N,O-bis-(trimethylsilyl)-acetamide). Appropriate co-solvent for this step is for example dichloromethane, tetrahydrofuran (THF), acetonitrile, dimethylformamide (DMF), dimethylacetamide, N methylpyrrolidone or mixtures of the above mentioned solvents.

Step u and v can be performed in a step-wise reaction under isolation of the intermediate XXXI or without isolation of XXXI.

Step w) can be performed under known saponification methods for example with aquous NaOH or KOH in ethanol, methanol or dioxane.

Step x) The coupling of the amine XXXIV with the acid XXXIII can be performed with an additional in-situ activating agent like 1-propylphosphonic acid cyclic anhydride, O-(benzotriazol-1-yl)-N,N,N',N'-tetramethyluronium tetrafluoroborate or hexafluorophosphate, N,N'-dicyclohexyl-carbodiimide, 1-(3-dimethylaminopropyl)-3-ethylcarbodiimide, carbonyldiimidazole, oxalyl chloride or other activating agents of the state of the art.

The coupling reaction is preferably performed in the presence of a base such as NaOH, KOH, NaHCO$_3$, triethylamine, N-ethyldiisopropylamine, N,N,-dimethylaminopyridine or other appropriate bases of the state of the art and for example described in described in Houben-Weyl, "Methods in Organic Synthesis", Vol. E22a, p 425ff.

The above mentioned coupling reaction is performed in an appropriate solvent for example dichloromethane, tetrahydrofuran (THF), acetonitrile, dimethylformamide (DMF), dimethylacetamide, N methylpyrrolidone or in mixtures of the above mentioned solvents.

It will be appreciated by those skilled in the art that, in the processes described above and hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Chemistry*", edited by J W F McOmie, Plenum Press (1973), and "*Protective Groups in Organic Synthesis*", 3$^{rd}$ edition, T. W. Greene & P. G. M. Wutz, Wiley-Interscience (1999).

The conditions for all individual steps in the above mentioned schemes e.g. protection/deprotection steps, reductive aminations, amide formations and others are well known to the expert and are described in the standard literature such as the Houben-Weyl: Methoden der organischen Chemie, Georg-Thieme-Verlag, Stuttgart and are exemplified in more detail in the experimental section.

Compounds of formula I (including I-1 through I-4) may be isolated from their reaction mixtures using conventional techniques.

Biological Assay

The basis of the assay used is to measure the inhibition of microsomal prostaglandin E$_2$ synthase-1 (mPGES-1) dependent prostaglandin (PG) E$_2$ formation from PGH$_2$ by different compounds. Thus, the formation of PGE$_2$ is used as signal and a lowering of this signal can be interpreted as inhibition of mPGES-1. Similar assays to measure inhibition of mPGES-1 have previously been described in the literature [1, 2].

List of Reagents Used:
  Glutathione (Sigma, G-4251)
  Freeze culture in Rosetta *E. coli* expression strain.
  LB growth media with Ampillicillin (Amp) final concentration in culture 50 µg/ml
  Chloroamphenicol stock 34 mg/ml (chloro) final concentration in culture 34 µg/ml
  Sterile growth flasks for 500 ml-1 liter cultures
  0.1 M KP$_i$ buffer pH 7.4
  9.25% HCl
  PGH$_2$ (0.25 mM)
  Fe(II) Cl$_2$ tetrahydrate, 99% (Sigma, 220229)
  384-well plate with compounds
  96-well plate, polypropylene (Thermo fast 96 skirted VWR)
  384-well plate polypropylene PCR plate (Greiner 785201)
  Greiner 384-well plate pp (In vitro cat. no. 781280)
  Adhesive sealing film for 96-well plates (Sigma-Aldrich)
  Aluminium foil (PCR foil, 310-0030-127-471 from Labora)
  PBS (GIBCO 14040)
  Prostaglandin E$_2$ Assay (Cisbio, cat. no. 62P2APEC)
  Biomek FX robot (Beckman Coulter)
  Biomek NX robot (Beckman Coulter)
  Multidrop; micro or combi (ThermoLabsystems)
  Plate reader: Safire2 (Tecan)

Microsomes from Rosetta *E. coli* bacteria expressing recombinant human mPGES-1 can be derived as described below:

Inoculate 5 ml LB with Amp and Chloro with bacteria from freeze culture. Incubate over night at 37° C. with 200 rpm. Thereafter, inoculate 500-800 ml LB containing Amp and Chloro with the 5 ml on culture and grow to OD640 of 0.6-0.8. Chill the culture to +4° C. before induction. Induce the culture with IPTG at a final concentration of 400 µM. Express the protein at room temp 18-23° C. with 200 rpm shaking over night.

The following steps can be performed on the following day:
1. Spin down the cells in 250 ml centrifuge flasks for 15 min at 7000 rpm
2. Dissolve the pellet from 250 ml culture in 12.5 ml homogenization buffer
3. Disintegrate the cells by sonication, 4×10 seconds at 35% amplitude
4. Add 2.5 ml MgCl2 (100 mM) and DNase 12.5 µl (0.8 mg/ml) and incubate on ice for 30 min
5. Spin down the bacteria debris and save the supernatant, 7000 rpm for 15 min 6. Isolate the protein containing membranes in the supernatant by ultracentrifugation 45000×g for 1 hour.
7. Discard the supernatant and dissolve the pellet in 20 mM KPi buffer and aliquot the enzyme and store aliquots at −80° C.

Before each experiment is performed an aliquot of the enzyme is thawed and it can then be dissolved in 0.1 M $KP_i$ pH 7.4 buffer containing 2.5 mM GSH. 50 µl of this enzyme solution is subsequently dispensed in a 384-well plate at room temperature. 0.5 µl of the inhibitor dissolved in DMSO is thereafter added to each well and incubated for 25 minutes at room temperature. Subsequently, 2 µl of $PGH_2$ dissolved in an appropriate solvent is added to each well and after one minute at room temperature, the acidified stop solution containing $FeCl_2$ is added. 4 µl of the total volume is transferred to a separate plate and diluted 750-fold in two separate steps before quantification of $PGE_2$.

In order to quantitate the amount of $PGE_2$ that has been formed, a homogenous time resolved fluorescent (HTRF) detection of $PGE_2$ can be performed by the use of a commercially available kit from CisBio essentially according to the manufacturer's protocol. Briefly, 10 µl of the diluted sample is transferred to a white 384-well plate and the following steps can be performed in a sequential manner at room temperature or as indicated.

- 5 µL reconstitution buffer as supplied by the manufacturer is added to the negative control (NC) wells.
- The plate is covered with adhesive sealing film.
- The plate can now be centrifuged at 1200 rpm for 1 minute.
- The NC samples are covered with sealing film.
- 250 µl d2 labeled $PGE_2$ ($d2$-$PGE_2$) can be diluted in 4750 µL reconstitution buffer as supplied by the manufacturer
- 250 µl Eu3+-cryptate can be diluted in 4750 µl reconstitution buffer as supplied by the manufacturer
- 5 µl $d2$-$PGE_2$ can now be added to rows 1 to 24, by using a multidrop. The sealing film is thereafter removed from the NC wells.
- 5 µl Eu3+-cryptate labeled anti-$PGE_2$ can now be added to rows 1 to 24 by using a Multidrop.
- The plate can now be covered with sealing film.
- The plate can now be centrifuge at 1200 rpm for 1 minute and place at 4° C. overnight.

After the over night incubation the fluorescence is measured by the use of an appropriate microplate reader. The fluorescence of Eu3+-cryptate and $d2$-$PGE_2$ are measured using the following excitation and emission wavelength, europium cryptate: $\lambda_{max}^{ex}=307$ nm, $\lambda_{max}^{em}=620$ nm and d2: $\lambda_{max}^{ex}=620$ nm, $\lambda_{max}^{em}=665$ nm), respectively. The extent of the specific HTRF is measured as a ratio of the emission intensity at 665 nm vs. that at 620 nm. A standard curve using synthetic $PGE_2$ is used to quantify the amount of $PGE_2$ in unknown samples. The degree of inhibition can be calculated as percent inhibition by dividing the amount of $PGE_2$ formed in unknown samples by the amount of $PGE_2$ formed in control samples.

LITERATURE REFERENCES

1. Riendeau, D., R. Aspiotis, D. Ethier, Y. Gareau, E. Grimm, J. Guay, S. Guiral, H. Juteau, J. Mancini, N. Methot, J. Rubin, and R. Friesen, *Inhibitors of the inducible microsomal prostaglandin E2 synthase (mPGES-1) derived from MK-886*. Bioorg Med Chem Lett, 2005. 15(14): p. 3352-3355.
2. Cote, B., L. Boulet, C. Brideau, D. Claveau, D. Ethier, R. Frenette, M. Gagnon, A. Giroux, J. Guay, S. Guiral, J. Mancini, E. Martins, F. Masse, N. Methot, D. Riendeau, J. Rubin, D. Xu, H. Yu, Y. Ducharme, and R. Friesen, *Substituted phenanthrene imidazoles as potent, selective, and orally active mPGES-1 inhibitors*. Bioorg Med Chem Lett, 2007. 17(24): p. 6816-6820.

Test Results:

Table 1 demonstrates the mPGES-1 inhibitory effect (in %-inhibition) measured for selected compounds at a concentration of 10 µM (unless otherwise specified) in the HTRF assay as described above. The examples show that 10 M of the compound inhibit $PGE_2$ production to the indicated degree. These data reflect a successful mPGES-1 inhibition for the given compound examples.

TABLE 1

| mPGES-1 inhibitory effect (in % -inhibition) of compounds of the invention at a concentration of 10 µM in the HTRF assay ||
|---|---|
| Example # | % inhibition |
| 1 | 100 |
| 3 | 100 |
| 4 | 83 |
| 5 | 100 |
| 6 | 100 |
| 7 | 98 |
| 8 | 98 |
| 9 | 98 |
| 10 | 100 |
| 11 | 100 |
| 12 | 100 |
| 13 | 100 |
| 14 | 100 |
| 15 | 99 |
| 16 | 80 |
| 17 | 95 |
| 18 | 98 |
| 19 | 98 |
| 20 | 100 |
| 21 | 100 |
| 22 | 98 |
| 23 | 100 |
| 24 | 97 |
| 25 | 99 |
| 26 | 100 |
| 27 | 100 |
| 28 | 100 |
| 29 | 99 |
| 30 | 98 |
| 31 | 99 |
| 32 | 98 |
| 33 | 93 |
| 34 | 100 |
| 35 | 100 |
| 36 | 100 |
| 37 | 100 |
| 38 | 100 |
| 39 | 100 |
| 40 | 98 |
| 41 | 100 |
| 42 | 100 |
| 43 | 100 |
| 44 | 100 |
| 45 | 100 |
| 46 | 100 |
| 47 | 100 |
| 48 | 100 |
| 49 | 100 |
| 50 | 100 |
| 51 | 94 |
| 52 | 96 |
| 53 | 100 |
| 54 | 98 |
| 55 | 68 |

Table 2 demonstrates the mPGES-1 inhibitory effect ($IC_{50}$) measured for selected examples in the HTRF assay as described above. These data reflect a successful mPGES-1 inhibition for the given compound examples.

TABLE 2 mPGES-1 inhibitory effect (IC$_{50}$ values in nM)
of compounds of the invention in
the HTRF assay

| example | IC50 [nM] | example | IC50 [nM] | example | IC50 [nM] | example | IC50 [nM] |
|---|---|---|---|---|---|---|---|
| 59 | 2 | 69 | 1 | 79 | 4 | 87 | 2 |
| 60 | 1 | 70 | 3 | 80 | 9 | 88 | 2 |
| 61 | 1 | 71 | 2 | 81 | 2 | 89 | 2 |
| 62 | 1 | 72 | 3 | 82 | 3 | 90 | 1 |
| 63 | 2 | 73 | 3 | 83 | 3 | 91 | 4 |
| 64 | 2 | 74 | 4 | 84 | 4 | 92 | 7 |
| 65 | 300 | 75 | 3 | 85 | 2 | 93 | 2 |
| 66 | 3 | 76 | 3 | 86 | 1 | 94 | 3 |
| 67 | 2 | 77 | 4 | 57 | 1 | 95 | 1 |
| 68 | 3 | 78 | 3 | 58 | 3 | 96 | 1 |
| 97 | 5 | 98 | 6 | 99 | >100 | 100 | 5 |

Method of Treatment

The present invention relates to compounds of formula I which are useful in the prevention and/or treatment of a disease and/or condition in which the inhibition of prostaglandin E synthases, in particular that of the microsomal prostaglandin E$_2$ synthase-1 (mPGES-1) is of therapeutic benefit, including but not limited to the treatment and/or prevention of inflammatory diseases and/or associated conditions.

The term "inflammation" will be understood to include any inflammatory disease, disorder or condition per se, any condition that has an inflammatory component associated with it, and/or any condition characterised by inflammation as a symptom, including inter alia acute, chronic, ulcerative, specific, allergic and necrotic inflammation, and other forms of inflammation known to those skilled in the art. The term thus also includes, for the purposes of this invention, inflammatory pain, pain generally and/or fever.

Where a condition has an inflammatory component associated with it, or a condition characterised by inflammation as a symptom, the skilled person will appreciate that compounds of the invention may be useful in the treatment of the inflammatory symptoms and/or the inflammation associated with the condition.

Compounds of the invention may also have effects that are not linked to inflammatory mechanisms, such as in the reduction of bone loss in a subject. Such conditions include osteoporosis, osteoarthritis, Paget's disease and/or periodontal diseases.

A further aspect of the present invention relates to a compound of formula I as a medicament.

Another aspect of the present invention is the use of compounds of formula I for the treatment and/or prevention of a disease and/or condition in which the inhibition of the mPGES-1 is of therapeutic benefit.

A further aspect of the present invention is the use of a compound of formula I for the treatment and/or prevention of inflammatory diseases and/or associated conditions.

The present invention also relates to the use of compounds of formula I for the treatment and/or prevention of the following diseases and conditions:
1. Rheumatic diseases or autoimmune diseases or muscoskeletal diseases: all forms of rheumatic diseases including e.g. soft tissue rheumatism, rheumatoid arthritis, polymyalgia rheumatica, reactive arthritis, tenosynovitis, gout or metabolic arthritis, bursitis, tendonitis, juvenile arthritis, spondyloarthropathies like e.g. spondylitis, ankylosing spondylitis, psoriatric arthropathy; sarcoidosis, fibromyalgia, myositis, polymyositis, osteoarthritis, traumatic arthritis, collagenoses of any origin e.g. systemic lupus erythematosus, scleroderma, dermatomyositis, Still's Disease, Sjögren syndrome, Felty syndrome; rheumatic fever and rheumatic heart disease, diseases of blood vessels like vasculitis, polyarthritis nodosa, Behcet's syndrome, giant cell arthritis, Wegener's granulomatosis, Henoch-Schönlein purpura; psoriatic arthritis, fungal arthritis, in particular including pain associated with any of the aforementioned conditions;
2. Headaches such as migraines with and without aura, tension-type headaches, cluster headaches and headaches with different origins;
3. Sympathetically maintained pain like complex regional pain syndrome Type I and II;
4. Neuropathic pain such as low back pain, hip pain, leg pain, non-herpetic neuralgia, post herpetic neuralgia, diabetic neuropathy, nerve injury-induced pain, acquired immune deficiency syndrome (AIDS) related neuropathic pain, head trauma, toxin and chemotherapy caused nerve injuries, phantom limb pain, multiple sclerosis, root avulsions, painful traumatic mononeuropathy, painful polyneuropathy, thalamic pain syndrome, post-stroke pain, central nervous system injury, post surgical pain, carpal tunnel syndrome, trigeminal neuralgia, post mastectomy syndrome, postthoracotomy syndrome, stump pain, repetitive motion pain, neuropathic pain associated hyperalgesia and allodynia, alcoholism and other drug-induced pain;
5. Cancer pain induced by or associated with tumors such as bone tumors, lymphatic leukemia; Hodgkin's disease, malignant lymphoma; lymphogranulomatoses; lymphosarcoma; solid malignant tumors; extensive metastases
6. Visceral disorders such as chronic pelvic pain, pancreatitis, peptic ulcer, interstitial cystitis, cystitis, renal colic, angina, dysmenorrhoea, menstruation, gynaecological pain, irritable bowel disease (IBS), inflammatory bowel disease, Crohn's disease and ulcerative colitis, nephritis, prostatitis, vulvodynia, non-ulcer dyspepsia, non-cardiac chest pain, myocardial ischemia;
7. Inflammation associated diseases of ear, nose, mouth and throat like influenza and viral/bacterial infections such as the common cold, allergic rhinitis (seasonal and perennial), pharyngitis, tonsillitis, gingivitis, larhyngitis, sinusitis, and vasomotor rhinitis, fever, hay fever, thyroiditis, otitis, dental conditions like toothache, perioperative and post-operative conditions, trigeminal neuralgia, uveitis; iritis, allergic keratitis, conjunctivitis, blepharitis, neuritis nervi optici, choroiditis, glaucoma and sympathetic opthalmia, as well as pain thereof.
8. Neurological diseases such as cerebral oedema and angioedema, cerebral dementia like e.g. Parkinson's and Alzheimers disease, senile dementia; multiple sclerosis, stroke, myasthenia gravis, brain and meningeal infections like encephalomyelitis, meningitis, including HIV as well as schizophrenia, delusional disorders, autism, affective disorders and tic disorders;
9. Work-related diseases like pneumoconiosis, including aluminosis, anthracosis, asbestosis, chalicosis, ptilosis, siderosis, silicosis, tabacosis and byssinosis;
10. Lung diseases such as asthma including allergic asthma (atopic or non-atopic) as well as exercise-induced bronchoconstriction, occupational asthma, viral- or bacterial exacerbation of asthma, other non-allergic asthmas and "wheezy-infant syndrome", Chronic obstructive pulmonary disease (COPD) including emphysema, adult respiratory distress syndrome, bronchitis, pneumonia, adult respiratory distress syndrome (ARDS), pigeon fancier's disease, farmers lung;

11. Skin diseases such as psoriasis and eczema, dermatitis, sunburn, burns as well as sprains and strains and tissue trauma;

12. Vascular and heart diseases which are inflammation-related like artheriosclerosis including cardiac transplant atherosclerosis, panarteritis nodosa, periarteritis nodosa, arteritis temporalis, Wegner granulomatosis, giant cell arthritis, reperfusion injury and erythema nodosum, thrombosis (e.g. deep vein thrombosis, renal, hepathic, portal vein thrombosis); coronary artery disease, aneurysm, vascular rejection, myocardial infarction, embolism, stroke, thrombosis including venous thrombosis, angina including unstable angina, coronary plaque inflammation, bacterial-induced inflammation including *Chlamydia*-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries, artery restenosis;

13. Diabetes-associated symptoms such as diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion);

14. Benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers effecting epithelial cells throughout the body; neoplasias like gastrointestinal cancer, Barrett's esophagus, liver cancer, bladder cancer, pancreatic cancer, ovarian cancer, prostate cancer, cervical cancer, lung cancer, breast cancer and skin cancer; adenomatous polyps, including familial adenomatous polyposis (FAP) as well preventing polyps from forming in patients at risk of FAP.

15. Various other disease states and conditions like epilepsy, septic shock e.g. as antihypovolemic and/or antihypotensive agents, sepsis, osteoporosis, benign prostatic hyperplasia and hyperactive bladder, nephritis, pruritis, vitiligo, disturbances of visceral motility at respiratory, genitourinary, gastrointestinal or vascular regions, wounds, allergic skin reactions, mixed-vascular and non-vascular syndromes, septic shock associated with bacterial infections or with trauma, central nervous system injury, tissue damage and postoperative fever, syndromes associated with itching.

Preferred according to the present invention is the use of a compound of formula I for the treatment and/or prevention of pain; in particular pain that is associated with any one of the diseases or conditions listed above.

Another aspect of the present invention is a method for the treatment and/or prevention of above mentioned diseases and conditions, which method comprises the administration of an effective amount of a compound of formula I to a human being.

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise.

Dosage

The term "effective amount" refers to an amount of a compound, which confers a therapeutic effect on the treated patient. The effect may be objective (i.e. measurable by some test or marker) or subjective (i.e. the subject gives an indication of or feels an effect). Compounds of the invention may be administered at varying doses. Oral, pulmonary and topical dosages may range from between about 0.01 mg/kg of body weight per day (mg/kg/day) to about 100 mg/kg/day, preferably about 0.01 to about 100 mg/kg/day, and more preferably about 0.1 to about 25 mg/kg/day. For e.g. oral administration, the compositions typically contain between about 0.01 mg to about 5000 mg, and preferably between about 1 mg to about 2000 mg, of the active ingredient. Intravenously, the most preferred doses will range from about 0.001 to about 10 mg/kg/hour during constant rate infusion. Advantageously, compounds may be administered in a single daily dose, or the total daily dosage may be administered in divided doses of two, three or four times daily. In any event, the physician, or the skilled person, will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention.

Pharmaceutical Formulations

Suitable preparations for administering the compounds of formula I will be apparent to those with ordinary skill in the art and include for example tablets, pills, capsules, suppositories, lozenges, troches, solutions, syrups, elixirs, sachets, injectables, inhalatives and powders etc. Such formulations may be prepared in accordance with standard and/or accepted pharmaceutical practice.

Depending on e.g. potency and physical characteristics of the compound of the invention (i.e. active ingredient), the content of the pharmaceutically active compound(s) should be in the range from 1 to 99 wt.-%, preferably 10 to 90 wt.-%, more preferably 20 to 70 wt.-%, of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

A further aspect of the invention is a pharmaceutical formulation including a compound of formula I in admixture with a pharmaceutically acceptable adjuvant, diluent or carrier.

Combination Therapy

The compounds according to the present invention can be combined with other treatment options known to be used in the art in connection with a treatment of any of the indications the treatment of which is in the focus of the present invention.

Among such treatment options that are considered suitable for combination with the treatment according to the present inventions are:

non-steroidal antiinflammatory drugs (NSAIDs) including COX-2 inhibitors;
opiate receptor agonists;
Cannabionoid agonists;
Sodium channel blockers;

N-type calcium channel blockers;
serotonergic and noradrenergic modulators;
corticosteroids;
histamine H1 receptor antagonists;
histamine H2 receptor antagonists;
proton pump inhibitors;
leukotriene antagonists and 5-lipoxygenase inhibitors;
local anesthetics;
VR1 agonists and antagonists;
Nicotinic acetylcholine receptor agonists;
P2X3 receptor antagonists;
NGF agonists and antagonists;
NK1 and NK2 antagonists;
NMDA antagonist;
potassium channel modulators;
GABA modulators;
serotonergic and noradrenergic modulators
anti-migraine drugs.

Said list is not considered to have a limiting character. In the Following Representative Examples of Such Treatment Options Shall be Given.

Non-steroidal antiinflammatory drugs (NSAIDs) including COX-2 inhibitors:propionic acid derivatives (alminoprofen, benoxaprofen, bucloxic acid, carprofen, fenhufen, fenoprofen, flubiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (meclofenamic acid, mefenamic acid, and tolfenamic acid), biphenylcarboxylic acid derivatives, oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib) and the like;

Antiviral drugs like acyclovir, tenovir, pleconaril, peramivir, pocosanol and the like.

Antibiotic drugs like gentamicin, streptomycin, geldanamycin, doripenem, cephalexin, cefaclor, ceftazichine, cefepime, erythromycin, vancomycin, aztreonam, amoxicillin, bacitracin, enoxacin, mafenide, doxycycline, chloramphenicol and the like;

Opiate receptor agonists: morphine, propoxyphene (Darvon), tramadol, buprenorphin and the like.

Glucocorticosteroids such as bethamethasone, budesonide, dexamethasone, hydrocortisone, methylprednisolone, prednisolone, prednisone, triamcinolone and deflazacort;

immunosuppressive, immunomodulatory, or cytsostatic drugs including but not limited to hydroxychlorquine, D-penicillamine, sulfasalizine, auranofin, gold mercaptopurine, tacrolimus, sirolimus, mycophenolate mofetil, cyclosporine, leflunomide, methotrexate, azathioprine, cyclophosphamide and glatiramer acetate and novantrone, fingolimod (FTY720), minocycline and thalidomide and the like;

anti-TNF antibodies or TNF-receptor antagonists such as but not limited to Etanercept, Infliximab, Adalimumab (D2E7), CDP 571, and Ro 45-2081 (Lenercept), or biologic agents directed against targets such as but not limited to CD-4, CTLA-4, LFA-1, IL-6, ICAM-1, C5 and Natalizumab and the like;

IL-1 receptor antagonists such as but not limited to Kineret;

Sodium channel blockers: carbamazepine, mexiletine, lamotrigine, tectin, lacosamide and the like.

N-type calcium channel blockers: Ziconotide and the like.

Serotonergic and noradrenergic modulators: paroxetine, duloxetine, clonidine, amitriptyline, citalopram;

Histamine H1 receptor antagonists: bromophtniramint, chlorpheniramine, dexchlorpheniramine, triprolidine, clemastine, diphenhydramine, diphenylpyraline, tripelennamine, hydroxyzine, methdiJazine, promethazine, trimeprazine, azatadine, cyproheptadine, antazoline, pheniramine pyrilamine, astemizole, terfenadine, loratadine, cetirizine, deslo-ratadine, fexofenadine and levocetirizine and the like;

Histamine H2 receptor antagonists: cimetidine, famotidine and ranitidine and the like;

Proton pump inhibitors: omeprazole, pantoprazole and esomeprazole and the like;

Leukotriene antagonists and 5-lipoxygenase inhibitors: zafirlukast, mon-telukast, pranlukast and zileuton and the like;

Local anesthetics such as ambroxol, lidocaine and the like;

Potassium channel modulators: like retigabine;

GABA modulators: lacosamide, pregabalin, gabapentin and the like;

Anti-migraine drugs: sumatriptan, zolmitriptan, naratriptan, eletriptan, telcegepant and the like;

NGF antibodies such as RI-724 and the like.

Combination therapy is also possible with new principles for the treatment of pain e.g. P2X3 antagonists, VR1 antagonists, NK1 and NK2 antagonists, NMDA antagonists, mGluR antagonists and the like.

The combination of compounds is preferably a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased pharmacological effect, or some other beneficial effect of the combination compared with the individual components.

EXPERIMENTAL SECTION

Preparation of Examples for Compounds of the General Formula I

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:

ABBREVIATIONS

AcOH acetic acid
aq aqueous
BSTFA (N,O-bis(trimethylsilyl)trifluoroacetamide
Boc tert.-butoxycarbonyl
conc concentrated
DCM dichloromethane
DIC diisopropylcarbodiimide DIPEA N-ethyldiisopropylamine
DMAP N,N-dimethylaminopyridine
DMSO dimethylsulphoxide
DMF N,N-dimethylformamide
dppf (1,1'-Bis(diphenylphosphino)ferrocene
EDC 1-(3-dimethylaminopropyl)-3-ethylcarbodiimide hydrochloride
EtOAc ethyl acetate
Et2O diethyl ether
EtOH ethanol
HATU O-(7-azabenzotriazol-1-yl)-N,N,N',N'-tetramethyluronium-hexafluoro-phosphate
HBTU O-(benzotriazol-1-yl)-N,N,N',N'-tetramethyluronium hexafluorophosphate
HPLC high performance liquid chromatography
i-PrOH isopropanol
KOtBu potassium tert.-butylate
MeCN acetonitrile
MeOH methanol
MS mass spectrometry
MTBE methyl-tert-butyl ether
NMR nuclear magnetic resonance
PE petrol ether
PPA 1-propylphosphonic-acid cyclic anhydride
RP reversed phase
rt room temperature
$R_f$ retention factor
$R_t$ retention time
sat saturated
TBTU O-(benzotriazol-1-yl)-N,N,N',N'-tetramethyluronium tetrafluoroborate
TCDI thiocarbonyl diimidazole
TEA triethylamine
THF tetrahydrofuran
TFA trifluoroacetic acid
TLC thin layer chromatography Analytical Methods The TLC data was obtained by using the following tlc plates
a) Silica gel plates 60 F254 Merck No 1.05714.0001 abbreviated in the experimental part as "silica gel"
b) Reversed phase plates: RP-8 F 254s Merck No: 1.15684.0001 abbreviated in the experimental part as "RP-8".
c) Aluminiumoxide plates 60 F254 Merck 1.05713.0001 abbreviated in the experimental part as "Alox"

The $R_f$ values given were determined without chamber saturation.

The HPLC/MS data, where specified, were obtained under the following conditions:

Agilent 1100 with quarternary pump, Gilson G215 Autosampler, HP diode array detector.

The diode array detection took place in a wavelength range from 210-550 nm
Range of mass-spectrometric detection: m/z 120 to m/z 1000
The following methods were used:
Method A:
Mobile Phase:
E1: water with 0.15% formic acid
E2: acetonitrile
Eluent Gradient C (Unpolar):

| time in min | % E1 | % E2 | flow rate in mL/min |
| --- | --- | --- | --- |
| 0.0 | 95 | 5 | 1.6 |
| 2.00 | 10 | 90 | 1.6 |
| 5.00 | 10 | 90 | 1.6 |
| 5.50 | 90 | 10 | 1.6 |

The following column was used as the stationary phase: (column temperature: constant at 25° C.): Zorbax Stable Bond C18, 1.8 µm, 3.0×30 mm
Method B:
Mobile Phase:
E1: water with 0.15% formic acid
E2: acetonitrile

| time in min | % E1 | % E2 | flow rate in mL/min |
| --- | --- | --- | --- |
| 0.0 | 95 | 5 | 1.6 |
| 2.00 | 10 | 90 | 1.6 |
| 5.00 | 10 | 90 | 1.6 |
| 5.50 | 90 | 10 | 1.6 |

The following column was used as the stationary phase: (column temperature: constant at 25° C.): Zorbax StableBond C18, 3.5 µm, 4.6×75 mm The following compounds are accompanied by structural drawings. The skilled person will appreciate that the rules of valency must be adhered to and hence there must be a certain number of bonds attached to each atom, which may not necessarily be depicted on the drawings. For example, in the case where a nitrogen heteroatom is depicted with only one or two bonds attached to it, the skilled person will realise that it should be attached to an additional one or two bonds (a total of three), in which such bonds are normally attached to one or two hydrogen atoms (so forming a —NH$_2$ or —N(H)— moiety).

Example 1

2-[5-(1-Acetamidoethyl)-2-chlorophenylamino]-N-(4-bromophenyl)-1-methylbenzimidazole-5-carboxamide

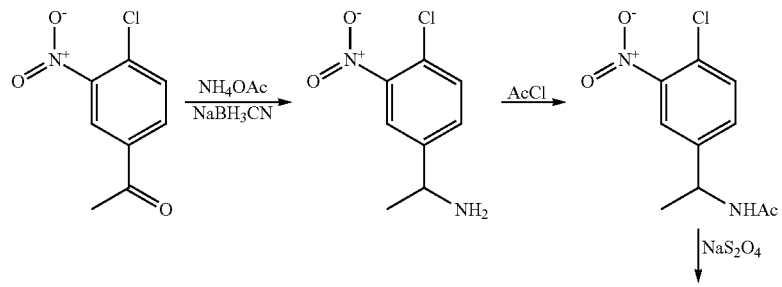

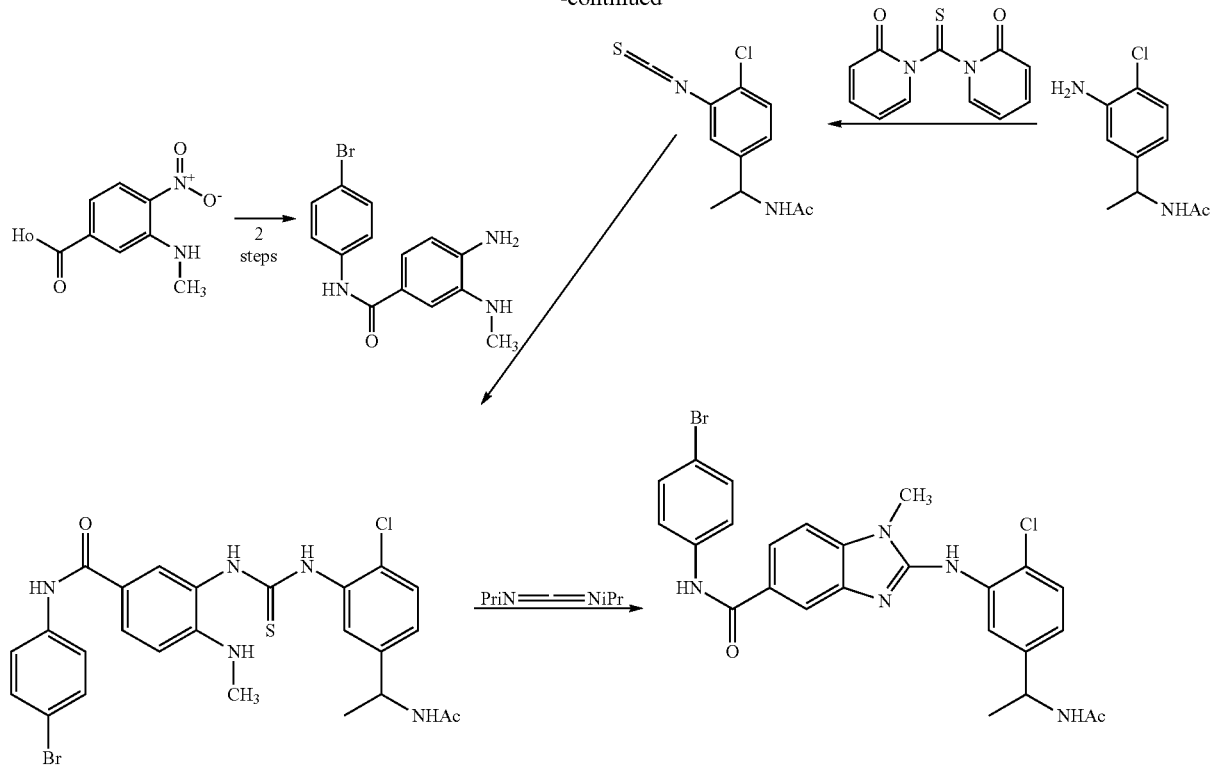

(a) 4-Chloro-1-methyl-3-nitrobenzylamine

Ammonium acetate (3.86 g, 50 mmol), NaBH₃CN (0.22 g, 3.5 mmol), and 3 Å molecular sieves (25 g) were added to a mixture of 4-chloro-3-nitroacetophenone (1.00 g, 5 mmol) in MeOH (15 mL) at rt. The mixture was stirred at rt for 20 h and NaHCO₃ (aq, sat) and EtOAc were added. The mixture was filtered and the aq layer washed with EtOAc. The combined organic phases were dried over Na₂SO₄ and concentrated to give the sub-title compound. Yield: 0.27 g (27%).

(b) N-[1-(4-Chloro-3-nitrophenyl)ethyl]acetamide

TEA (0.28 mL, 2.0 mmol) followed by acetylchloride (96 L, 1.3 mmol) were added to 4-chloro-methyl-3-nitrobenzylamine (0.27 g, 1.3 mmol) in THF (5 mL) at rt. The mixture was stirred at rt for 3.5 h and additional acetylchloride (20 L, 0.27 mmol) was added. After 1 h at rt, NaHCO₃ (aq, 5%) was added and the mixture extracted with EtOAc.

The combined extracts were dried over Na₂SO₄ and conc to give the sub-title compound.
Yield: 0.30 g (92%).

(c) N-[1-(3-Amino-4-chlorophenyl)ethyl]acetamide

A solution of sodium dithionite (1.08 g, 6.1 mmol) in H₂O (4 mL) was added to a vigorously stirred mixture of N-[1-(4-chloro-3-nitrophenyl)ethyl]acetamide (0.30 g, 1.2 mmol) in EtOH (20 mL) at 55° C. After 4 h at 55° C. additional sodium dithionite (0.20 g, 1.1 mmol) was added and stirring was continued at 55° C. for 1.5 h. The mixture was allowed to cool and NaHCO₃ (aq, sat) was added. The mixture was extracted with EtOAc and the combined extracts were dried over Na₂SO₄ and concentrated to give the sub-title compound.
Yield: 90 mg (34%).

(d) N-[1-(4-Chloro-3-isothiocyanatophenyl)ethyl]acetamide

N-[1-(3-Amino-4-chlorophenyl)ethyl]acetamide (90 mg, 0.2 mmol) was added to a mixture of 1,1'-thiocarbonyldi-2-pyridone (69 mg, 0.2 mmol), DMAP (7 mg, 0.05 mmol) and DCM (2 mL) at rt. The mixture was concentrated and used in the next step without further purification.

(e) 3-Nitro-N-(4-bromophenyl)-4-methylaminobenzamide

A mixture of 3-Nitro-4-methylaminobenzoic acid (196 mg, 1.00 mmol), 20 ml DCM, 0.15 ml pyridine and 160 mg 1-Chloro-N,N,2-trimethylprop-1-enylamine was stirred until a clear solution was obtained. 4-Bromoaniline (172 mg, 1.0 mmol) was added and the mixture was stirred for 16 h. The mixture was filtered through a pad of ALOX B and concentrated. 5 ml DMF and 20 ml H₂O were added and the precipitate was collected and dried. Yield: 240 mg (68%).

(f) 3-Amino-N-(4-bromophenyl)-4-methylaminobenzamide

A mixture of 3-Nitro-N-(4-bromophenyl)-4-methylaminobenzamide (120 mg, 0.34 mmol), 10 ml THF, 10 ml MeOH and 30 mg 5%-Pt-on-carbon was stirred for 4 h under a hydrogen atmosphere (3.5 bar). The catalyst was removed by filtration and the mixture was concentrated and used in the next step without further purification.

45

(g) 3-{3-[5-(1-Acetamidoethyl)-2-chlorophenyl]thioureido}-N-(4-bromophenyl)-4-(methylamino)benzamide N-[1-(4-Chloro-3-isothiocyanatophenyl)ethyl]acetamide in DMF (2 mL) was added to a mixture of 3-amino-N-(4-bromophenyl)-4-methylaminobenzamide (87 mg, 0.2 mmol, crude material from the step above) in DMF (2 mL) at rt. The mixture was stirred at rt overnight and concentrated. The residue was purified by chromatography to give the sub-title compound. Yield: 130 mg.

(h) 2-[5-(1-Acetamidoethyl)-2-chlorophenylamino]-N-(4-bromophenyl)-1-methylbenzimidazole-5-carboxamide N,N-Diisopropylcarbodiimide (46 L, 0.2 mmol) was added to 3-{3-[5-(1-acet-amidoethyl)-2-chlorophenyl]thio-

46 ureido}-N-(4-bromophenyl)-4-(methylamino)benzamide (130 mg, 0.2 mmol) in DMF (2 mL) at rt. The mixture was stirred at 80° C. for 2 h, cooled and concentrated. The residue was purified by chromatography to give the title compound.

Yield: 30 mg (24%). MS m/z: 540 [M+H]$^+$.

HPLC-method A: $R_t$=1.60 min

Example 2

2-[5-(tert.Butylcarbonylaminomethyl)-2-chlorophenylamino]-6-chloro-N-(2,2,2-trifluorethyl)-benzimidazole-5-carboxamide

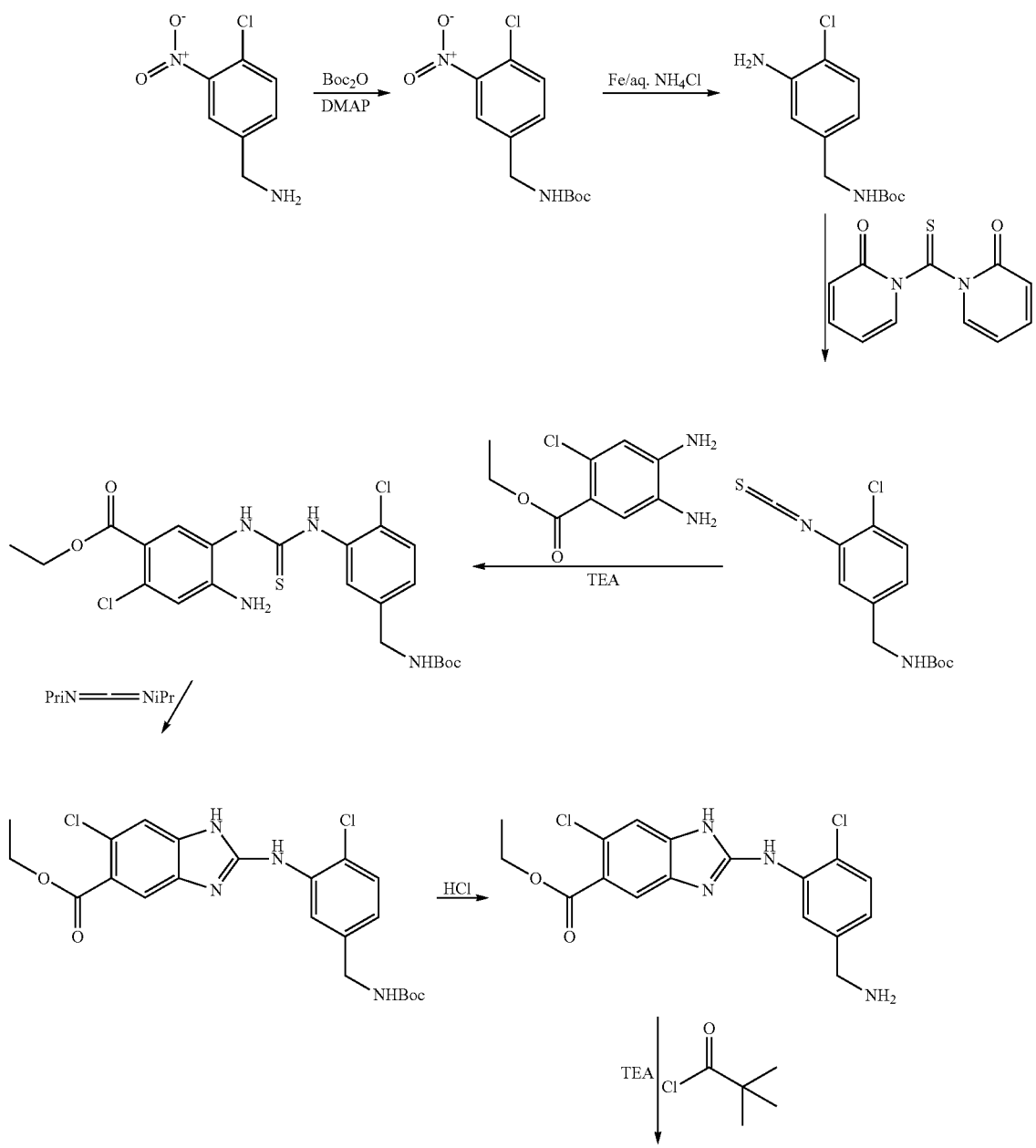

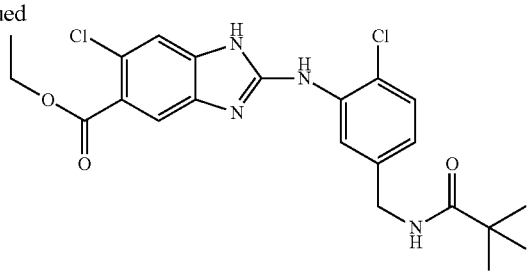

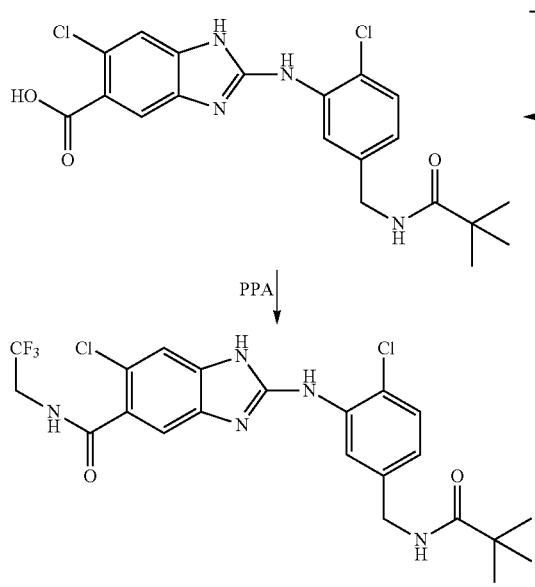

(a) tert-Butyl 4-chloro-3-nitrobenzylcarbamate

Di-tert-butyl dicarbonate (21.05 g, 96.5 mmol) in DCM (30 mL) was added to an ice-cooled mixture of 4-chloro-3-nitrobenzylamine (15 g, 80.4 mmol), DMAP (0.49 g, 4 mmol) and DCM (100 mL). The mixture was stirred at rt for 12 h, poured into ammonia and extracted with DCM. The combined extracts were washed with brine and concentrated.

The residue was washed with $Et_2O$ to give the sub-title compound which was used directly in the next step without any further purification.

(b) tert-Butyl 3-amino-4-chlorobenzylcarbamate

A mixture of tert-butyl 4-chloro-3-nitrobenzylcarbamate (crude material from step (b)), Fe powder (17.65 g, 316 mmol), $NH_4Cl$ (aq, sat, 100 mL) and EtOH (100 mL) was heated at 90° C. for 4 h and allowed to cool. The pH was adjusted to ~10 and the mixture was filtered through Celite. The solids were washed with EtOAc and EtOH and the combined filtrates concentrated to remove the organic solvents. The residue was added to ammonia and the mixture was extracted with DCM. The combined extracts were washed with brine, dried over $Na_2SO_4$ and concentrated. Crystallization from EtOAc/petroleum ether gave the sub-title compound. Yield: 15.5 g (75% from 4-chloro-3-nitrobenzylamine).

(c) tert-Butyl 4-chloro-3-isothiocyanatobenzylcarbamate

The sub-title compound was prepared from tert-butyl 3-amino-4-chlorobenzylcarbamate, in accordance with Example 1, step (d).

(d) Ethyl-2-[5-(tert.butoxycarbonylaminomethyl)-2-chlorophenylamino]-6-chloro-benzimidazole-5-carboxylate The sub-title compound was prepared in two steps from tert-Butyl-4-chloro-3-isothiocyanatobenzylcarbamate and Ethyl-2-chloro-4,5-diamino-benzoic acid in accordance with Example 1, step (g) with additional TEA and Example 1, step (h).

(e) Ethyl-2-[5-(aminomethyl)-2-chlorophenylamino]-6-chloro-benzimidazole-5-carboxylate A mixture of 1.15 g (2.4 mmol) Ethyl-2-[5-(tert.butylcarbonylaminomethyl)-2-chlorophenylamino]-benzimidazole-5-carboxylate and 10 ml 4M HCl in Dioxane was stirred overnight. The reaction mixture was concentrated under reduced pressure to give the sub-title compound. Yield: 1.0 g (100%).

(f) Ethyl-2-[5-(tert.butylcarbonylaminomethyl)-2-chlorophenylamino]-6-chloro-benzimidazole-5-carboxylate A mixture of Ethyl-2-[5-(aminomethyl)-2-chlorophenylamino]-6-chloro-benzimidazole-5-carboxylate (1.00 g, 2.4 mmol), pivaloyl chloride (0.296 ml, 2.4 mmol), 1.5 ml TEA and 50 ml THF were stirred for 18 h at rt. The mixture was concentrated, diluted with EtOAc, washed 2× with $H_2O$, dried over $Na_2SO_4$ and concentrated. The residue was purified by chromatography to give the sub-title compound. Yield 0.92 g (83%).

(g) 2-[5-(tert.butylcarbonylaminomethyl)-2-chlorophenylamino]-6-chloro-benzimidazole-5-carboxylic acid A mixture of Ethyl-2-[5-(tert.butylcarbonylaminomethyl)-2-chlorophenylamino]-6-chloro-benzimidazole-5-carboxylate (0.91 g, 1.9 mmol) in 20 ml EtOH was treated with 1 N NaOH (3.9 ml+0.98 ml+0.98 ml) for 4 h at rt, for 5 h at 50° C. and for 3 d at rt. The mixture was concentrated, diluted with $H_2O$, acidified with 1 N HCl and cooled in an ice bath. The precipitate was filtered, washed with ice water and dried to give the sub-title compound. Yield 0.81 g (95%).

(h) 2-[5-(tert.Butylcarbonylaminomethyl)-2-chlorophenylamino]-6-chloro-N-(2,2,2-trifluorethyl)-benzimidazole-5-carboxamide A mixture of 2-[5-(tert.butylcarbonylaminomethyl)-2-chlorophenylamino]-6-chloro-benzimidazole-5-carboxylic acid (0.15 g, 0.345 mmol), 2,2,2-Trifluoroethylamine (2×0.027 ml, 0.345 mmol), 1-propylphosphonic-acid cyclic anhydride (PPA, 0.244 ml, 50% in EtOAc), 0.12 ml TEA and 10 ml MeCN was stirred for 48 h at 60° C. an concentrated. The residue was purified by chromatography to give the title compound. Yield 17 mg (10%) m/z: 516 [M+H]$^+$.

HPLC-method B: $R_t$=2.35 min.

Example 3

6-Chloro-2-{2-chloro-5-[(1-methylcyclohexylamido)methyl]phenylamino}-N-cyclopentyl-1-methylbenzimidazole-5-carboxamide

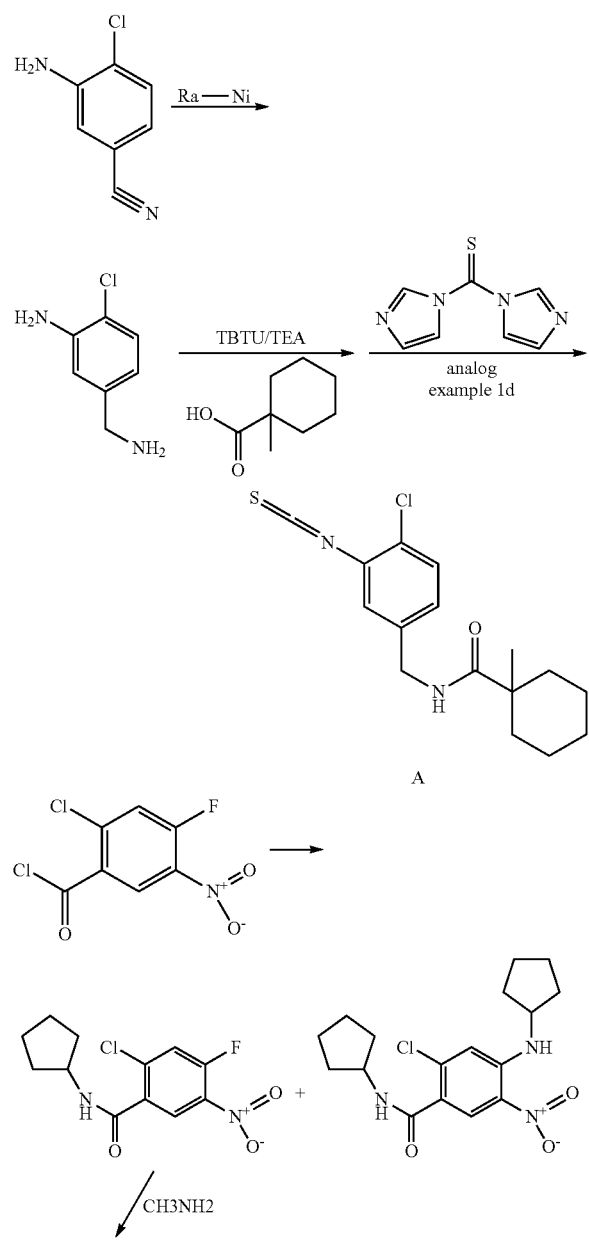

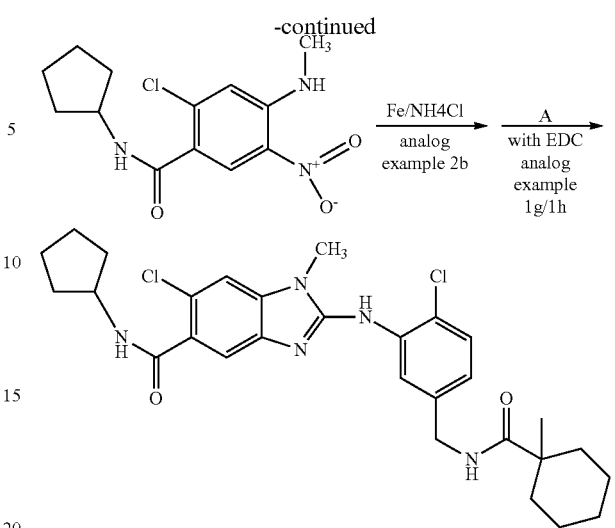

(a) 2-Chloro-N-cyclopentyl-4-fluoro-5-nitrobenzamide and 2-Chloro-N-cyclopentyl-4-cyclopentylamino-5-nitrobenzamide 2-Chloro-4-fluoro-5-nitrobenzoyl chloride (1.5 g, 6.30 mmol) was added to a mixture of cyclopentylamine (430 L, 12.6 mmol), TEA (1.76 mL, 12.6 mmol) and DCM (30 mL) at −20° C. After 12 h at rt, the mixture was diluted with DCM and washed with NH$_4$OH (aq sat). The organic layer was washed with H$_2$O and brine, dried over Na$_2$SO$_4$, concentrated and purified by HPLC to afford 510 mg (28%) of 2-chloro-N-cyclopentyl-4-fluoro-5-nitrobenzamide and 300 mg (14%) of 2-chloro-N-cyclopentyl-4-cyclopentylamino-5-nitrobenzamide.

(b) 2-Chloro-N-cyclopentyl-4-methylamino-5-nitrobenzamide

N-Methylamine in MeOH (2 M, 2.0 mL, 4.0 mmol) was added to 2-chloro-N-cyclopentyl-4-fluoro-5-nitrobenzamide (230 mg, 0.79 mmol) in EtOH. The mixture was heated at 50° C. for 12 h in a sealed vessel, cooled and concentrated. The residue was purified by chromatography to give the sub-title compound. Yield: 150 mg (64%).

(c) 5-Amino-2-chloro-N-cyclopentyl-4-methylaminobenzamide

The sub-title compound was prepared from 2-chloro-N-cyclopentyl-4-methylamino-5-nitrobenzamide in accordance with Example 2, step (b).

(d) 3-Amino-4-chloro-benzylamine

A mixture of 3-Amino-4-chloro-benzonitrile (1.32 g, 8.33 mmol), Ra-Nickel (0.25 g) and 80 ml NH$_3$ in MeOH was stirred for 4 h at rt under H$_2$-atmosphere (3 bar). The mixture was filtered and concentrated and the sub-title compound was used without further purification.

(e) N-(4-Chloro-3-aminobenzyl)-1-methylcyclohexylamide

A mixture of 3-Amino-4-chloro-benzylamine (0.69 g, 4.17 mmol), 1-Methyl-cyclohexane-1-carboxylic acid (0.59 g, 4.17 mmol), 1.47 g TBTU, 1.45 ml TEA and 30 ml THF was stirred for 6 h at rt. The mixture was concentrated, diluted with EtOAc, washed 2× with 2M NaOH and 1× with brine, dried with $Na_2SO_4$ filtered and concentrated to give the sub-title compound. Yield: 1.17 g (100%).

(f) N-(4-Chloro-3-isothiocyanatobenzyl)-1-methyl-cyclohexylamide

The sub-title compound was prepared from N-(4-Chloro-3-aminobenzyl)-1-methylcyclohexylamide analogous to Example 1, step (d) but with 1,1'-thiocarbonyldiimidazole instead of 1,1'-thiocarbonyldi-2-pyridone.

(g) 6-Chloro-2-{2-chloro-5-[(1-methylcyclohexyla-mido)methyl]phenylamino}-N-cyclopentyl-1-meth-ylbenzimidazole-5-carboxamide The title compound was prepared from N-(4-chloro-3-isothiocyanatobenzyl)-1-methylcyclohexylamide and 5-amino-2-chloro-N-cyclopentyl-4-methylaminobenzamide analogous to Example 1, steps (g and h), but without isolation of the thioureido derivative and with EDC as coupling reagent instead of N,N-diisopropylcarbodiimide. 200 MHz 1H-NMR (DMSO-$d_6$, ppm) 8.43 (1H, s) 8.20 (1H, d, J=7.4 Hz) 8.10 (1H, t, J=5.6 Hz) 7.84-7.78 (1H, m) 7.52-7.48 (1H, m) 7.42 (1H, d, J=8.2 Hz) 7.26-7.22 (1H, m) 7.00-6.91 (1H, m) 4.31-4.08 (3H, m) 3.69 (3H, s) 1.98-1.76 (4H, m) 1.68-1.16 (14H, m) 1.06 (3H, s).

MS m/z: 556 $[M+H]^+$.

Example 4

N-{4-Chloro-3-[5-(1-pyrrolidinylcarbonyl)-2-benz-imidazolylamino]benzyl}-1-methylcyclohexylamide

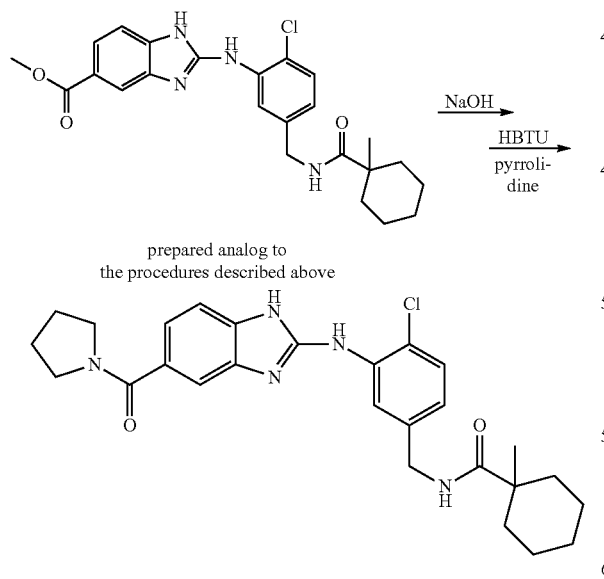

(a) 2-{2-Chloro-5-[(1-methylcyclohexylamido)me-thyl]phenylamino}benzimidazole-5-carboxylic acid A mixture of methyl 2-{2-chloro-5-[(1-methylcyclohexy-lamido)methyl]phenylamino}benzimidazole-5-carboxylate (910 mg, 2.0 mmol), NaOH (aq, 2 M, 3.0 mL, 6.0 mmol) and dioxane (15 mL) was heated at 90° C. for 12 h and concentrated. The residue was partitioned between NaOH (aq, 2 M) and MTBE. The aq phase was acidified to pH ~4-5 with HCl (aq, 4 M). The precipitate was collected, washed with $H_2O$ and dried to give the sub-title compound. Yield: 873 mg (99%).

(b) N-{4-Chloro-3-[5-(1-pyrrolidinylcarbonyl)-2-benzimidazolylamino]benzyl}-1-methylcyclohexyla-mide TEA (130 L; 0.91 mmol) followed by HBTU (171 mg, 0.45 mmol) was added to 2-{2-chloro-5-[(1-methylcyclohexyla-mido)methyl]phenylamino}benzimidazole-5-carboxylic acid (200 mg, 0.45 mmol) in DMF (3 mL). After 10 min at rt, pyrrolidine (37 L, 0.45 mmol) in DMF (1 mL) was added. After 12 h at rt, the mixture was concentrated and the residue partitioned between water and DCM. The aq layer was extracted with DCM and the combined extracts were washed with brine, dried over $Na_2SO_4$ and concentrated. The residue was purified by chromatography to give the title compound. Yield 127 mg (57%).

400 MHz $^1$H-NMR (DMSO-$d_6$, ppm) 11.22-11.08 (1H, m) 8.83-8.69 (1H, m) 8.55 (1H, s) 8.12 (1H, t, J=5.8 Hz) 7.58-7.44 (1H, m) 7.41-7.28 (2H, m) 7.26-7.18 (1H, m) 6.89-6.82 (1H, m) 4.28 (2H, d, J=5.8 Hz) 3.50-3.41 (4H, m) 2.01-1.91 (2H, m) 1.89-1.75 (4H, m) 1.47-1.16 (8H, m) 1.12 (3H, s).

MS m/z: 494 $[M+H]^+$.

Example 5 tert-Butyl 5-chloro-2-{2-chloro-5-[(1-methylcyclo-hexylamido)methyl]phenylamino}-1-methyl-6-benz-imidazolylcarbamate

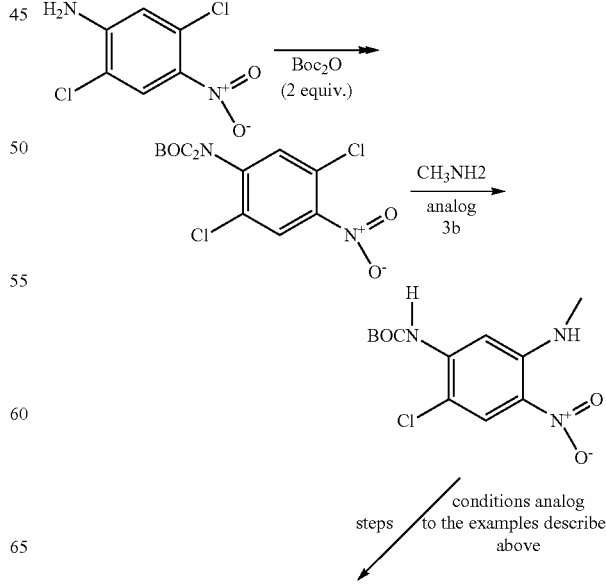

-continued

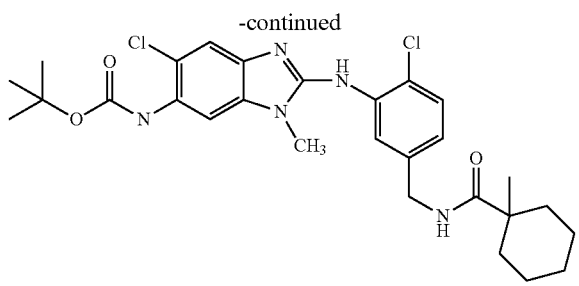

(a) Di-tert-butyl-2,5-dichloro-4-nitrophenylimidodicarbonate

Di-tert-butyldicarbonate (4.58 g, 21.0 mmol) was added in portions to a mixture of 2,5-dichloro-4-nitroaniline (2.07 g, 10.0 mmol), DMAP (61.1 mg, 0.5 mmol) and THF (15 mL). After 12 h at rt the mixture was concentrated and the residue partitioned between EtOAc and citric acid (aq, 1 M). The organic layer was washed with brine, dried over $Na_2SO_4$ and concentrated. The residue was washed with petroleum ether to give the sub-title compound. Yield 3.67 g (91%).

(b) tert-Butyl 2-chloro-5-(methylamino)-4-nitrophenylcarbamate

The sub-title compound was prepared from di-tert-butyl-2,5-dichloro-4-nitrophenylimidodicarbonate in accordance with Example 3, step (b).

(c) tert-Butyl 4-amino-2-chloro-5-(methylamino) phenylcarbamate)

The sub-title compound was prepared from tert-butyl 2-chloro-5-(methylamino)-4-nitrophenylcarbamate in accordance with Example 2, step (b).

(d) tert-Butyl 5-chloro-2-{2-chloro-5-[(1-methylcyclohexylamido)methyl]-phenylamino}-1-methyl-6-benzimidazolylcarbamate The title compound was prepared from N-(4-chloro-3-isothiocyanatobenzyl)-1-methylcyclohexylamide and tert-butyl 4-amino-2-chloro-5-(methylamino)phenylcarbamate) in accordance to the procedures described above.
200 MHz $^1$H-NMR (DMSO-$d_6$, ppm) 8.55 (1H, s) 8.40 (1H, s) 8.12 (1H, t, J=5.2) 7.80-7.74 (1H, m) 7.48-7.29 (3H, m) 7.01-6.89 (1H, m) 4.26 (2H, d, J=6.0) 3.66 (3H, s) 2.00-1.85 (2H, m) 1.46 (9H, s) 1.42-1.10 (8H, m) 1.06 (3H, s).
MS m/z: 560 [M+H]$^+$.

Example 6

N-{4-chloro-3-[5-chloro-6-(cyclopentylamido)-1-methyl-2-benzimidazolylamino]benzyl}-1-methylcyclohexylamide

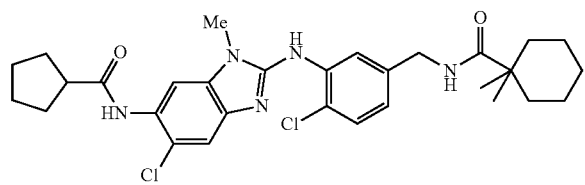

(a) N-[4-Chloro-3-(6-amino-5-chloro-1-methyl-2-benzimidazolylamino)benzyl]-1-methylcyclohexylamide A mixture of tert-butyl 5-chloro-2-{2-chloro-5-[(1-methylcyclohexylamido)methyl]-phenylamino}-1-methyl-6-benzimidazolylcarbamate (400 mg, 0.71 mmol), TFA (0.5 mL; 6.7 mmol) and DCM (10 mL) was heated at 80° C. for 3 h in a sealed tube. The mixture was cooled, diluted with DCM and washed with NaHCO$_3$ (aq, sat; Caution: gas evolution!) and dried over Na$_2$SO$_4$. Concentration gave the sub-title compound. Yield: 320 mg (98%).

(b) N-{4-chloro-3-[5-chloro-6-(cyclopentylamido)-1-methyl-2-benzimidazolylamino]benzyl}-1-methyl-cyclohexylamide The title compound was prepared from N-[4-chloro-3-(6-amino-5-chloro-1-methyl-2-benzimidazolylamino)benzyl]-1-methylcyclohexylamide and cyclopentylcarboxylic acid and HBTU in accordance with Example 4, step (b).
200 MHz $^1$H-NMR (DMSO-$d_6$, ppm) 9.37 (1H, s) 8.42 (1H, s) 8.12 (1H, t, J=5.8 Hz) 7.84-7.72 (1H, m) 7.51 (1H, s) 7.43 (1H, d, J=8.2 Hz) 7.36 (1H, s) 6.96 (1H, dd, J=8.2, 1.2 Hz) 4.27 (2H, d, J=5.8 Hz) 3.67 (3H, s) 2.98-2.79 (1H, m) 2.04-1.0 (21H, m). MS
m/z: 556 [M+H]$^+$.

Example 7

N-{4-Chloro-3-[5-(N-cyclopentylsulfamoyl)-1-methyl-2-benzimidazolylamino]benzyl}-1-methylcyclohexylamide

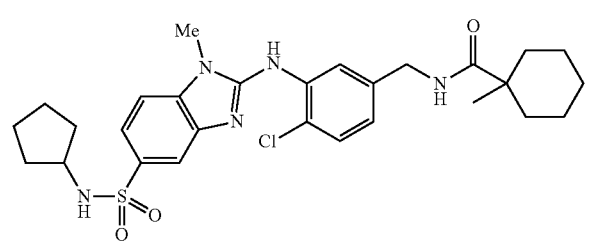 [SMILES: Cn1c(Nc2cc(CNC(=O)C3(C)CCCCC3)ccc2Cl)nc2cc(S(=O)(=O)NC3CCCC3)ccc21]

(a) 4-Chloro-N-cyclopentyl-3-nitrobenzenesulfonamide

Cyclopentylamine (1.5 mL, 15.6 mmol) in MeCN (10 mL) was added over 10 min to an ice-cooled solution of 4-chloro-3-nitrobenzenesulfonyl chloride (2.0 g, 7.8 mmol) in MeCN (20 mL). After 1 h at rt the mixture was poured into ice-water and extracted with EtOAc. The combined extracts were washed with brine, dried over Na$_2$SO$_4$ and concentrated to give the sub-title compound. Yield 2.2 g (92%).

(b) N-Cyclopentyl-4-methylamino-3-nitrobenzenesulfonamide

The sub-title compound was prepared from 4-chloro-N-cyclopentyl-3-nitrobenzenesulfonamide and methylamine in accordance with Example 3, step (b).

(c) 3-Amino-N-cyclopentyl-4-methylaminobenzene-sulfonamide

The sub-title compound was prepared from N-cyclopentyl-4-methylamino-3-nitrobenzenesulfonamide in accordance with Example 2, step (b).

(d) N-{4-Chloro-3-[5-(N-cyclopentylsulfamoyl)-1-methyl-2-benzimidazolylamino]benzyl}-1-methylcyclohexylamide The title compound was prepared from N-(4-chloro-3-isothiocyanatobenzyl)-1-methylcyclohexylamide and 3-amino-N-cyclopentyl-4-methylaminobenzenesulfonamide) in accordance with Example 3, step (g).

200 MHz $^1$H-NMR (DMSO-d$_6$, ppm) 8.51 (1H, s) 8.13 (1H, t, J=6.0) 7.87-7.81 (1H, m) 7.58-7.39 (4H, m) 7.04-6.94 (1H, m) 4.28 (2H, d, J=6.0) 3.47 (3H, s) 3.38-3.28 (1H, m, overlapped with H$_2$O) 2.01-1.86 (2H, m) 1.60-1.11 (16H, m) 1.06 (3H, s). MS m/z: 558 [M+H]$^+$.

Example 8

2-{2-Chloro-5-[(1-methylcyclopropylamido)methyl]phenylamino}-N-cyclohexylmethyl-1-methylbenzimidazole-5-carboxamide

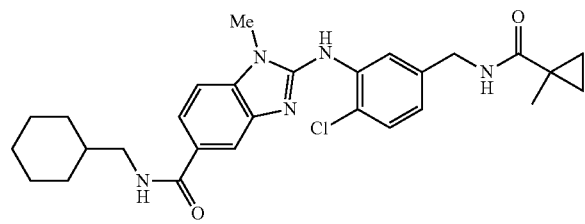 [SMILES: Cn1c(Nc2cc(CNC(=O)C3(C)CC3)ccc2Cl)nc2cc(C(=O)NCC3CCCCC3)ccc21]

(a) 2-(5-Aminomethyl-2-chlorophenylamino)-N-cyclohexylmethyl-1-methylbenzimidazole-5-carboxamide A mixture of 2-(2-chloro-5-cyanophenylamino)-N-cyclohexylmethyl-1-methylbenzimidazole-5-carboxamide (500 mg, 1.19 mmol, prepared in analogy to the experimental procedures described above) and EtOH (20 mL) was saturated with ammonia. Freshly prepared Raney-Nickel (7 mg, 0.12 mmol) was added and the mixture was hydrogenated (rt, 70 atm) for 48 h. The mixture was filtered through Celite and the filter cake washed with EtOAc. The combined filtrates were concentrated and the residue treated with a mixture of petroleum ether and diethyl ether to give the sub-title compound. Yield: 500 mg (98%).

(h) 2-{2-Chloro-5-[(1-methylcyclopropylamido)methyl]phenylamino}-N-cyclo-hexylmethyl-1-methylbenzimidazole-5-carboxamide The title compound was prepared from 2-(5-aminomethyl-2-chlorophenylamino)-N-cyclohexylmethyl-1-methylbenzimidazole-5-carboxamide and 1-methylcyclopropylcarboxylic acid and HBTU in accordance with Example 4, step (b).
200 MHz $^1$H-NMR (DMSO-d$_6$, ppm) 8.38 (1H, s) 8.33-8.22 (1H, m) 8.19-8.08 (1H, m) 7.91-7.80 (2H, m) 7.66-7.57 (1H, m) 7.42 (1H, d, J=8.2 Hz) 7.37 (1H, d, J=8.2 Hz) 7.00-6.89 (1H, m) 4.24 (2H, d, J=5.6 Hz) 3.71 (3H, s) 3.15-2.99 (2H, m) 1.79-1.45 (7H, m) 1.27 (3H, s) 1.21-1.06 (3H, m) 1.00-0.80 (5H, m). MS m/z: 508 [M+H]$^+$.

Example 9

2-{2-Chloro-5-[(2-thienylsulfonamido)methyl]phenylamino}-N-cyclohexylmethyl-1-methylbenzimidazole-5-carboxamide

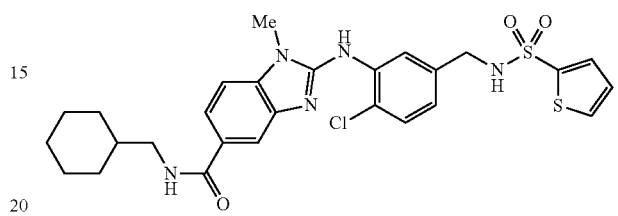

Thiophene-2-sulfonyl chloride (64 mg, 0.35 mmol) in MeCN (1 mL) was added to a mixture of 2-(5-aminomethyl-2-chlorophenylamino)-N-cyclohexylmethyl-1-methylbenzimidazole-5-carboxamide (150 mg, 0.35 mmol), TEA (150 L, 1.1 mmol) and MeCN (2 mL). After 12 h at rt the mixture was diluted with DCM and washed with NH$_3$ (aq, sat) and brine, dried over Na$_2$SO$_4$ and concentrated. The residue was purified by chromatography to give the title compound. Yield: 36 mg (18%). 200 MHz $^1$H-NMR (DMSO-d$_6$, ppm) 8.50-8.36 (2H, m) 8.35-8.22 (1H, m) 7.94-7.82 (3H, m) 7.69-7.57 (2H, m) 7.42 (1H, d, J=8.2 Hz) 7.37 (1H, d, J=8.2 Hz) 7.18-7.11 (1H, m) 7.04-6.95 (1H, m) 4.09-3.96 (2H, m) 3.71 (3H, s) 3.14-3.00 (2H, m) 1.77-1.47 (7H, m) 1.29-1.07 (4H, m). MS m/z: 572 [M+H]$^+$.

Example 10

4-Bromo-N-(2-{2-chloro-5-[(1-methylcyclopropylamido)methyl]phenylamino}-1-methyl-5-benzimidazolyl)benzamide

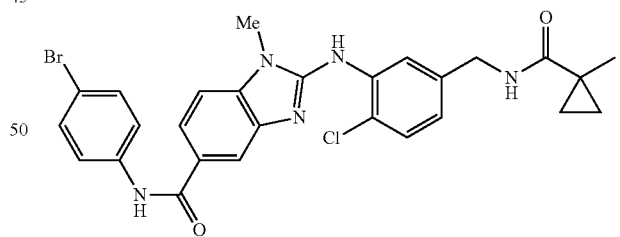

(a) 2-[5-(Aminomethyl)-2-chlorophenylamino]-N-(4-bromophenyl)-1-methylbenzimidazole-5-carboxamide TFA (1.5 mL) was added to tert-butyl 3-[5-(4-bromophenylcarbamoyl)-1-methyl-2-benzimidazolylamino]-4-chlorobenzylcarbamate (960 mg. 1.7 mmol prepared in analogy to the experimental procedures described above) in DCM (20 mL) at rt. After 16 h at rt TFA (2 mL) was added and the mixture was stirred at rt for 16 h, diluted with DCM and washed with NaHCO$_3$ (aq, sat) and brine, dried and concentrated to give the sub-title compound which was used in the next step without further purification. Yield: 706 mg (90%)

(b) 4-Bromo-N-(2-{2-chloro-5-[(1-methylcyclopropylamido)methyl]phenylamino}-1-methyl-5-benzimidazolyl)benzamide The title compound was synthesized from 2-[5-(aminomethyl)-2-chlorophenylamino]-N-(4-bromophenyl)-1-methylbenzimidazole-5-carboxamide and 1-methylcyclopropyl carboxylic acid and HBTU in accordance with Example 4, step (b).

200 MHz $^1$H-NMR (DMSO-$d_6$, ppm) 10.24 (1H, s) 8.53-8.47 (1H, m) 8.17 (1H, t, J=6.0 Hz) 8.03 (1H, d, J=1.2 Hz) 7.89-7.71 (4H, m) 7.60-7.40 (4H, m) 7.00 (1H, dd, J=8.2, 1.8 Hz) 4.27 (2H, d, J=6.0 Hz) 3.76 (3H, s) 1.29 (3H, s) 1.00-0.93 (2H, m) 0.55-0.48 (2H, m). MS m/z: 566 [M+H]$^+$.

Example 11

2-{2-chloro-5-[(1-trifluoromethylcyclopropylamido)methyl]phenylamino}-N-cyclopropylmethyl-1-methylbenzimidazole-5-carboxamide

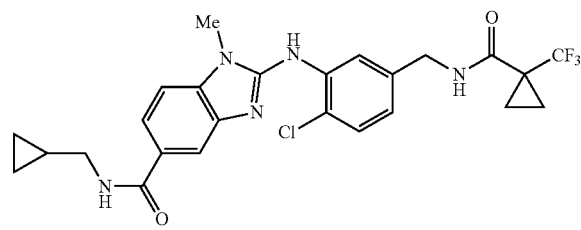 [SMILES: Cn1c(Nc2cc(CNC(=O)C3(C(F)(F)F)CC3)ccc2Cl)nc2cc(C(=O)NCC3CC3)ccc21]

(a) 4-Methylamino-3-nitrobenzoic acid

TEA (13 mL) and methylamine (2 M in MeOH, 35 mL, 70 mmol) was added to 3,4-dinitrobenzoic acid (10 g, 47.2 mmol) in EtOH (50 mL) at rt. After 24 h at rt the mixture was concentrated and H$_2$O was added to the residue. The mixture was filtered and acidified with AcOH. The solids were collected and dried to give the sub-title compound. Yield: 7.5 g (81%).

(b) Methyl 4-methylamino-3-nitrobenzoate

HCl was bubbled through a mixture of 4-methylamino-3-nitrobenzoic acid (7.41 g, 37.8 mmol), DMF (60 mL) and MeOH (250 mL) at reflux for 10 h. The mixture was allowed to cool, filtered and concentrated. NaHCO$_3$ (aq, sat) was added to the residue which was extracted with EtOAc. The combined extracts were washed with brine, dried and concentrated to give the sub-title compound.
Yield: 2.5 g (32%).

(c) Methyl 3-amino-4-methylaminobenzoate

Fe powder (3.4 g, 60 mmol) was added to a mixture of methyl 4-methylamino-3-nitrobenzoate (2.5 g, 12.0 mmol), AcOH (10 mL) and MeOH (100 mL) at reflux. The mixture was heated at reflux for 30 min and allowed to cool to rt. The pH was adjusted to ~8 by addition of NaHCO$_3$ (aq, sat) and the mixture was filtered through Celite. The filter cake was washed with EtOH and the combined filtrates were concentrated and the residue extracted with EtOAc. The combined extracts were washed with brine, dried and concentrated to give the sub-title compound. Yield: 1.91 g (88%)

(d) Methyl 2-{5-[(tert-Butoxycarbonylamino)methyl]-2-chlorophenylamino}-1-methylbenzimidazole-5-carboxylate The sub-title compound was prepared from tert-butyl 4-chloro-3-isothiocyanatobenzylcarbamate (see Example 2d) and methyl 3-amino-4-methylaminobenzoate according to Example 3, step (g).

(e) Methyl 2-[5-(aminomethyl)-2-chlorophenylamino]-1-methylbenzo[d]imidazole-5-carboxylate The sub-title compound was prepared from methyl 2-{5-[(tert-butoxycarbonyl-amino)methyl]-2-chlorophenylamino}-1-methylbenzimidazole-5-carboxylate in accordance with the procedure in Example 10, step (a).

(f) Methyl 2-{2-chloro-5-[(1-trifluoromethylcyclopropylamido)methyl]phenylamino}-1-methylbenzimidazole-5-carboxylate The sub-title compound was prepared from methyl 2-[5-(aminomethyl)-2-chlorophenylamino]-1-methylbenzo[d]imidazole-5-carboxylate, and 1-trifluoromethylcyclopropylcarboxylic acid and TBTU in accordance with the procedure in Example 3, step (e).

(g) 2-{2-Chloro-5-[(1-trifluoromethylcyclopropylamido)methyl]phenylamino}-1-methylbenzimidazole-5-carboxylic acid A mixture of methyl 2-{2-chloro-5-[(1-trifluoromethylcyclopropylamido)methyl]-phenylamino}-1-methylbenzimidazole-5-carboxylate (1.36 g, 2.8 mmol), NaOH (aq, 2 M, 15 mL) and dioxane (15 mL) was heated at reflux for 45 min. The mixture was allowed to cool and concentrated, and HCl (aq, 1 M) was added. The solids were collected, washed with H$_2$O, and dried to give the sub-title compound. Yield: 1.01 g (77%).

(h) 2-{2-chloro-5-[(1-trifluoromethylcyclopropylamido)methyl]phenylamino}-N-cyclopropylmethyl-1-methylbenzimidazole-5-carboxamide The title compound was prepared from 2-{2-chloro-5-[(1-trifluoromethylcyclo-propylamido)methyl]phenylamino}-1-methylbenzimidazole-5-carboxylic acid and cyclopropylmethylamine and TBTU in accordance with the procedure in Example 3, step (e).

400 MHz $^1$H-NMR (DMSO-$d_6$, ppm) (signals of minor tautomer are not assigned) 8.50-8.34 (3H, m) 7.95-7.89 (1H, m) 7.88-7.82 (1H, m) 7.70-7.63 (1H, m) 7.45 (1H, d, J=8.2 Hz) 7.40 (1H, d, J=8.4 Hz) 6.99-6.92 (1H, m) 4.28 (2H, d, J=5.8 Hz) 3.73 (3H, s) 3.18-3.11 (2H, m) 1.40-0.98 (5H, m) 0.45-0.38 (2H, m) 0.26-0.20 (2H, m). MS m/z: 520 [M+H]$^+$.

The following compounds were synthesized in analogy to the methods of preparation described above in detail.

| Ex. | Chemical structure<br>Name<br>¹H-NMR | MS m/z [M + H]⁺ |
|---|---|---|
| 12 | N-{4-Chloro-3-[1-methyl-5-(1-pyrrolidinylcarbonyl)-2-benzimidazolylamino]benzyl}-1-methylcyclohexylamide<br>400 MHz ¹H-NMR (DMSO-d₆, ppm) 8.43-8.27 (1H, br s) 8.12-8.03 (1H, m) 7.82-7.68 (1H, br s) 7.46-7.21 (4H, m) 6.97-6.88 (1H, m) 4.25 (2H, d, J = 6.0 Hz) 3.76-3.59 (3H, br s) 3.49-3.39 (4H, m) 1.94-1.75 (6H, m) 1.40-1.14 (8H, m) 1.04 (3H, s) | 508 |
| 13 | 2-{2-Chloro-5-[(1-methylcyclohexylamido)methyl]phenylamino}-N-cyclopentylbenzimidazole-5-carboxamide<br>400 MHz ¹H-NMR (DMSO-d₆, ppm) 11.22-11.11 (1H, m) 8.83-8.72 (1H, m) 8.58 (1H, s) 8.14-8.05 (2H, m) 7.94-7.83 (1H, m) 7.61-7.54 (1H, m) 7.42-7.27 (2H, m) 6.89-6.83 (1H, m) 4.31-4.17 (3H, m) 1.99-1.82 (4H, m) 1.73-1.65 (2H, m) 1.57-1.19 (12H, m) 1.11 (3H, s) | 508 |
| 14 | 2-{2-Chloro-5-[(1-methylcyclohexylamido)methyl]phenylamino}-N-cyclopentyl-1-methylbenzimidazole-5-carboxamide<br>400 MHz ¹H-NMR (DMSO-d₆, ppm) 8.31 (1H, s) 8.12-8.04 (2H, m) 7.89 (1H, d, J = 1.4 Hz) 7.83 (1H, d, J = 1.8 Hz) 7.63 (1H, dd, J = 8.4, 1.4 Hz) 7.41 (1H, d, J = 8.2 Hz) 7.36 (1H, d, J = 8.4 Hz) 6.93 (1H, dd, J = 8.2, 1.8 Hz) 4.25 (2H, d, J = 6.0 Hz) 3.70 (3H, s) 1.93-1.83 (4H, m) 1.71-1.66 (2H, m) 1.56-1.49 (4H, m) 1.41-1.16 (8H, m) 1.04 (3H, s) | 522 |
| 15 | N-(2-tert-Butoxyethyl)-2-{2-chloro-5-[(1-methylcyclohexylamido)methyl]phenylamino}-1-methylbenzimidazole-5-carboxamide<br>200 MHz ¹H-NMR (DMSO-d₆, ppm) 8.38-8.25 (2H, m) 8.09 (1H, t, J = 6.0 Hz) 7.87-7.82 (1H, m) 7.78 (1H, d, J = 1.6 Hz) 7.67-7.58 (1H, m) 7.42 (1H, d, J = 8.2 Hz) 7.37 (1H, d, J = 8.4 Hz) 6.94 (1H, dd, J = 8.2, 1.6 Hz) 4.25 (2H, d, J = 6.0 Hz) 3.69 (3H, s) 3.46-3.33 (4H, m, overlapped with H₂O) 1.98-1.82 (2H, m) 1.40-1.09 (19H, m) 1.03 (3H, s) | 554 |

-continued

| Chemical structure |
| Name |
| Ex. ¹H-NMR | MS m/z [M + H]⁺ |

16

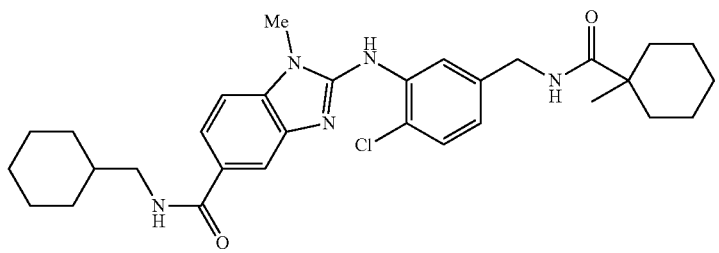 [SMILES: Cn1c(Nc2cc(CNC(=O)C3(C)CCCCC3)ccc2Cl)nc2cc(C(=O)NCC3CCCCC3)ccc21]

550

2-{2-Chloro-5-[(1-methylcyclohexylamido)methyl]phenylamino}-N-cyclohexylmethyl-1-methylbenzimidazole-5-carboxamide
200 MHz ¹H-NMR (DMSO-d₆, ppm) 8.37-8.22 (2H, m) 8.08 (1H, t, J = 5.8 Hz) 7.89-7.79 (2H, m) 7.66-7.58 (1H, m) 7.42 (1H, d, J = 8.2 Hz) 7.37 (1H, d, J = 8.4 Hz) 6.93 (1H, dd, J = 8.2, 1.6 Hz) 4.25 (2H, d, J = 5.8 Hz) 3.70 (3H, s) 3.08 (2H, t, J = 6.0 Hz) 1.98-1.83 (2H, m) 1.80-0.77 (24H, m)

17

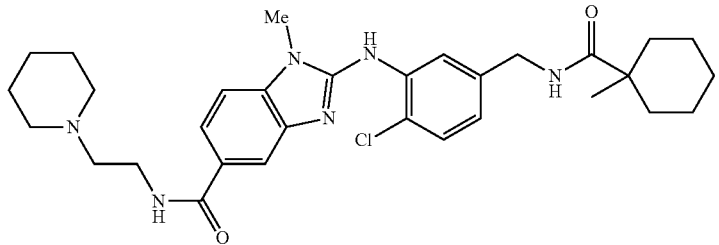 [SMILES: Cn1c(Nc2cc(CNC(=O)C3(C)CCCCC3)ccc2Cl)nc2cc(C(=O)NCCN3CCCCC3)ccc21]

565

2-{2-Chloro-5-[(1-methylcyclohexylamido)methyl]phenylamino]-1-methyl-N-[2-(1-piperidinyl)ethyl]benzimidazole-5-carboxamide
200 MHz ¹H-NMR (DMSO-d₆, ppm) 8.35 (1H, s) 8.26-8.17 (1H, m) 8.14-8.04 (1H, m) 7.87-7.76 (2H, m) 7.65-7.56 (1H, m) 7.45-7.33 (2H, m) 6.98-6.89 (1H, m) 4.25 (2H, d, J = 5.8 Hz) 3.70 (3H, s) 3.41-3.24 (2H, m, overlapped with water) 2.44-2.30 (6H, m) 1.96-1.83 (2H, m) 1.53-1.15 (14H, m) 1.04 (3H, s)

18

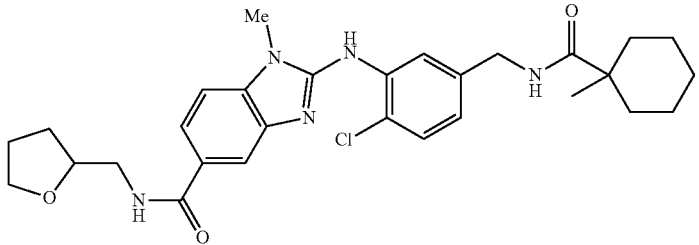 [SMILES: Cn1c(Nc2cc(CNC(=O)C3(C)CCCCC3)ccc2Cl)nc2cc(C(=O)NCC3CCCO3)ccc21]

538

2-{2-Chloro-5-[(1-methylcyclohexylamido)methyl]phenylamino]-1-methyl-N-[(2-tetrahydrofuryl)methyl]benzimidazole-5-carboxamide
200 MHz ¹H-NMR (DMSO-d₆, ppm) 8.41-8.29 (2H, m) 8.15-8.03 (1H, m) 7.90-7.74 (2H, m) 7.69-7.58 (1H, m) 7.45-7.31 (2H, m) 6.99-6.85 (1H, m) 4.25 (2H, d, J = 5.8 Hz) 4.06-3.88 (1H, m) 3.83-3.53 (5H, m) 1.99-1.72 (6H, m) 1.68-1.50 (1H, m) 1.45-1.10 (9H, m) 1.04 (3H, s)

| Ex. | Chemical structure<br>Name<br>¹H-NMR | MS m/z [M + H]⁺ |
|---|---|---|
| 19 | 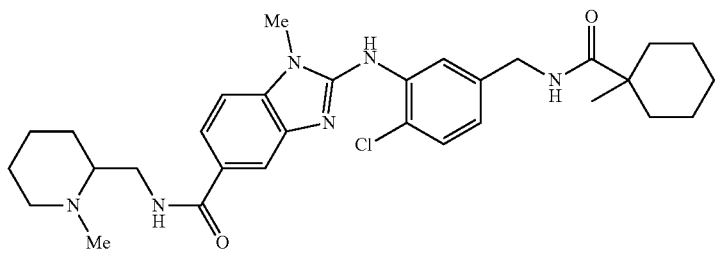 [SMILES: CN1CCCCC1CNC(=O)c1ccc2c(c1)nc(Nc1cc(CNC(=O)C3(C)CCCCC3)ccc1Cl)n2C]<br>2-{2-Chloro-5-[(1-methylcyclohexylamido)methyl]phenylamino]-1-methyl-N-[(1-methyl-2-piperidinyl)methyl]benzimidazole-5-carboxamide<br>200 MHz ¹H-NMR (DMSO-d₆, ppm) 8.41-8.34 (1H, m) 8.31-8.20 (1H, m) 8.15-8.03 (1H, m) 7.90-7.77 (2H, m) 7.67-7.57 (1H, m) 7.46-7.33 (2H, m) 6.99-6.88 (1H, m) 4.25 (2H, d, J = 6.0 Hz) 3.70 (3H, s) 3.64-3.46 (2H, m) 3.38-3.22 (2H, overlapped with H₂O) 3.03-2.89 (1H, m) 2.50 (3H, s, overlapped with DMSO) 1.98-1.83 (2H, m) 1.78-1.18 (14H, m) 1.04 (3H, s) | 565 |
| 20 | 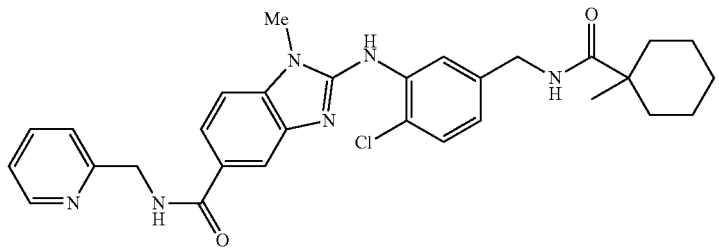 [SMILES: Cn1c(Nc2cc(CNC(=O)C3(C)CCCCC3)ccc2Cl)nc2cc(C(=O)NCc3ccccn3)ccc21]<br>2-{2-Chloro-5-[(1-methylcyclohexylamido)methyl]phenylamino}-1-methyl-N-(2-pyridinylmethyl)benzimidazole-5-carboxamide<br>200 MHz ¹H-NMR (DMSO-d₆, ppm) 8.96 (1H, t, J = 5.8 Hz) 8.53-8.46 (1H, m) 8.42-8.32 (1H, m) 8.15-8.02 (1H, m) 7.99-7.88 (1H, m) 7.85-7.64 (3H, m) 7.47-7.19 (4H, m) 6.99-6.86 (1H, m) 4.56 (2H, d, J = 5.4 Hz) 4.25 (2H, d, J = 5.8 Hz) 3.71 (3H, s) 1.98-1.83 (2H, m) 1.43-1.12 (8H, m) 1.04 (3H, s) | 545 |
| 21 | 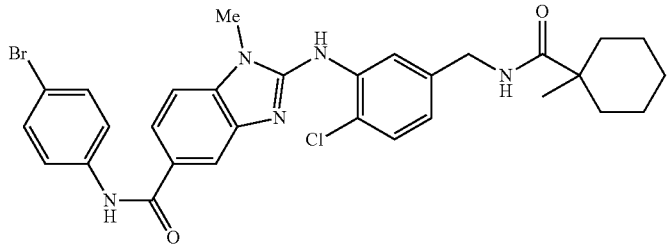 [SMILES: Cn1c(Nc2cc(CNC(=O)C3(C)CCCCC3)ccc2Cl)nc2cc(C(=O)Nc3ccc(Br)cc3)ccc21]<br>N-(4-Bromophenyl)-2-{2-chloro-5-[(1-methylcyclohexylamido)methyl]-phenylamino}-1-methylbenzimidazole-5-carboxamide<br>200 MHz ¹H-NMR (DMSO-d₆, ppm) 10.23 (1H, s) 8.43 (1H, s) 8.10 (1H, t, J = 6.0 Hz) 8.04-7.98 (1H, m) 7.86-7.70 (4H, m) 7.56-7.39 (4H, m) 6.96 (1H, dd, J = 8.2, 1.8 Hz) 4.26 (2H, d, J = 6.0 Hz) 3.73 (3H, s) 1.98-1.85 (2H, m) 1.43-1.13 (8H, m) 1.04 (3H, s) | 608 |

| | |
|---|---|
| Chemical structure<br>Name<br>Ex. ¹H-NMR | MS m/z [M + H]⁺ |
| 22 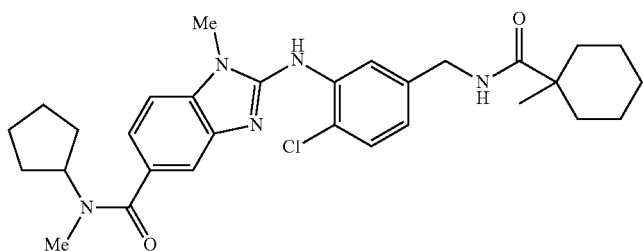 [SMILES: CN(C(=O)c1ccc2c(c1)nc(Nc1cc(CNC(=O)C3(C)CCCCC3)ccc1Cl)n2C)C1CCCC1]<br><br>2-{2-Chloro-5-[(1-methylcyclohexylamido)methyl]phenylamino}-N-cyclopentyl-N,1-dimethylbenzimidazole-5-carboxamide<br>200 MHz ¹H-NMR (DMSO-d₆, ppm) 8.35 (1H, s) 8.10 (1H, t, J = 5.8 Hz) 7.78-7.72 (1H, m) 7.46-7.32 (2H, m) 7.28-7.22 (1H, m) 7.11-7.02 (1H, m) 6.98-6.89 (1H, m) 4.42-4.16 (3H, m) 3.69 (3H, s) 2.81 (3H, s) 1.97-1.84 (2H, m) 1.74-1.55 (7H, m) 1.46-1.12 (11H, m) 1.03 (3H, s) | 536 |
| 23 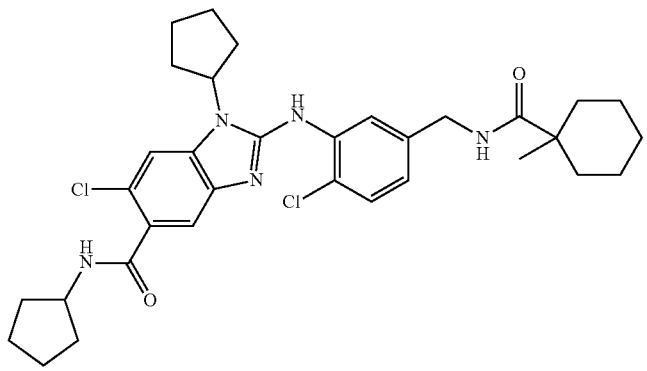 [SMILES: CC1(C(=O)NCc2ccc(Cl)c(Nc3nc4cc(C(=O)NC5CCCC5)c(Cl)cc4n3C3CCCC3)c2)CCCCC1]<br><br>6-Chloro-2-{2-chloro-5-[(1-methylcyclohexylamido)methyl]phenylamino}-N,1-dicyclopentylbenzimidazole-5-carboxamide<br>200 MHz ¹H-NMR (DMSO-d₆, ppm) 8.47 (1H, s) 8.24-8.03 (2H, m) 7.56-7.20 (4H, m) 7.02-6.89 (1H, m) 5.05-4.82 (1H, m) 4.32-4.05 (3H, m) 2.09-1.20 (26H, m) 1.03 (3H, s) | 610 |
| 24 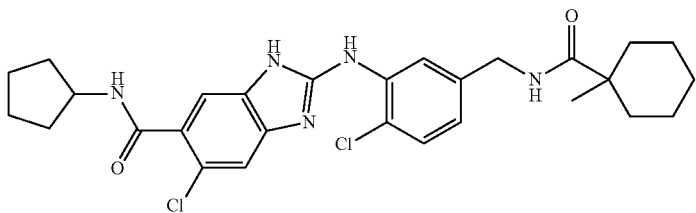<br><br>6-Chloro-2-{2-chloro-5-[(1-methylcyclohexylamido)methyl]phenylamino}-N-cyclopentylbenzimidazole-5-carboxamide<br>200 MHz ¹H-NMR (DMSO-d₆, ppm) 11.16 (1H, s) 8.98-8.84 (1H, m) 8.59-8.51 (1H, m) 8.27-8.06 (2H, m) 7.50-7.23 (3H, m) 6.91-6.82 (1H, m) 4.36-4.07 (3H, m) 2.02-1.76 (4H, m) 1.71-1.19 (14H, m) 1.12 (3H, s) | 542 |

| Chemical structure<br>Name<br>Ex. ¹H-NMR | MS m/z [M + H]⁺ |
|---|---|
| 25 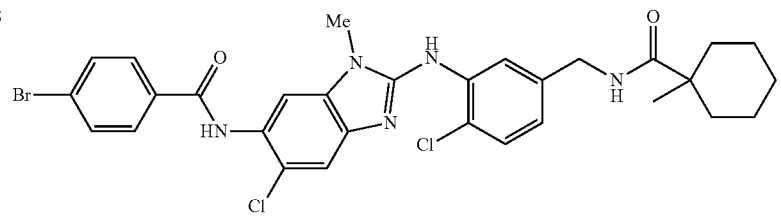

4-Bromo-N-(5-chloro-2-{2-chloro-5-[(1-methylcyclohexylamido)methyl]phenylamino}-1-methyl-6-benzimidazolyl)benzamide 200 MHz ¹H-NMR (DMSO-d₆, ppm) 10.15 (1H, s) 8.48 (1H, s) 8.14 (1H, t, J = 5.8 Hz) 8.03-7.91 (2H, m) 7.85-7.72 (3H, m) 7.55 (1H, s) 7.49-7.40 (2H, m) 6.98 (1H, dd, J = 8.2, 1.8 Hz) 4.28 (2H, d, J = 5.8 Hz) 3.70 (3H, s) 2.02-1.84 (2H, m) 1.52-1.10 (8H, m) 1.08 (3H, s) | 642 |
| 26 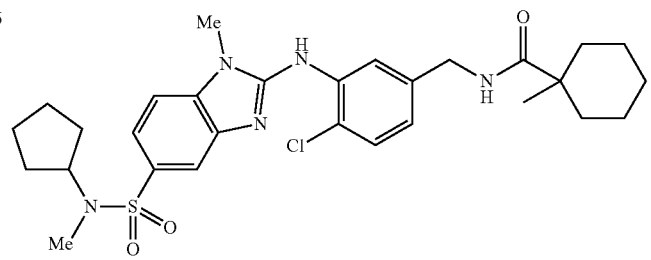

N-{4-Chloro-3-[5-(N-cyclopentyl-N-methylsulfamoyl)-1-methyl-2-benzimidazolylamino]benzyl}-1-methylcyclohexylamide 200 MHz ¹H-NMR (DMSO-d₆, ppm) 8.54 (1H, s) 8.14 (1H, t, J = 5.2) 7.91-7.85 (1H, m) 7.66-7.61 (1H, m) 7.55-7.40 (3H, m) 7.05-6.95 (1H, m) 4.34-4.12 (3H, m) 3.75 (3H, s) 2.61 (3H, s) 2.02-1.87 (2H, m) 1.54-1.11 (16H, m) 1.08 (3H, s) | 572 |
| 27 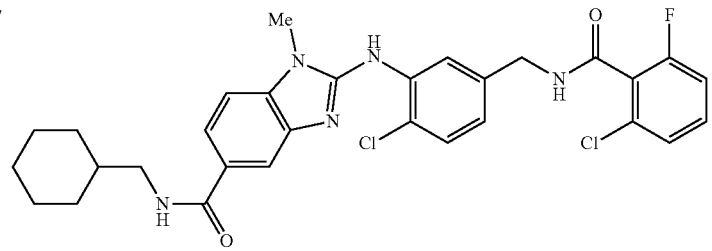

2-{2-Chloro-5-[(2-chloro-6-fluorobenzamido)methyl]phenylamino}-N-cyclohexylmethyl-1-methylbenzimidazole-5-carboxamide 200 MHz ¹H-NMR (DMSO-d₆, ppm) 9.27 (1H, t, J = 5.6 Hz) 8.37-8.24 (1H, m) 7.94-7.59 (3H, m) 7.55-7.20 (6H, m) 7.18-7.05 (1H, m) 4.46 (2H, d, J = 5.6 Hz) 3.69 (3H, s) 3.08 (2H, t, J = 6.0 Hz) 1.79-1.42 (7H, m) 1.33-1.04 (4H, m) | 582 |

| Chemical structure Name | |
|---|---|
| Ex. ¹H-NMR | MS m/z [M + H]⁺ |

28 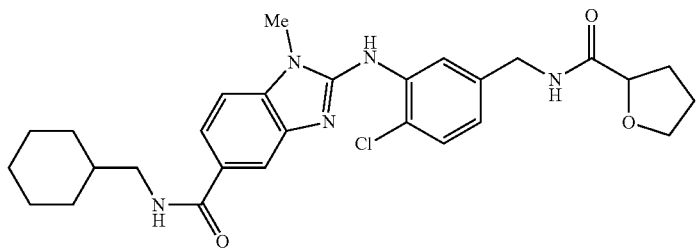 [SMILES: Cn1c(Nc2cc(CNC(=O)C3CCCO3)ccc2Cl)nc2cc(C(=O)NCC3CCCCC3)ccc21] 524

2-{2-Chloro-5-[(2-tetrahydrofurylamido)methyl]phenylamino}-N-cyclohexylmethyl-1-methylbenzimidazole-5-carboxamide 200 MHz ¹H-NMR (DMSO-d₆, ppm) 8.42-8.26 (3H, m) 7.93-7.80 (2H, m) 7.65-7.61 (1H, m) 7.44-7.35 (2H, m) 6.97-6.93 (1H, m) 4.35-4.13 (3H, m) 3.92-3.68 (2H, m, overlapped with H₂O) 3.32 (3H, s) 3.12-3.05 (2H, m) 2.17-1.97 (1H, m) 1.89-1.50 (8H, m) 1.27-1.07 (4H, m) 0.98-0.82 (2H, m)

29 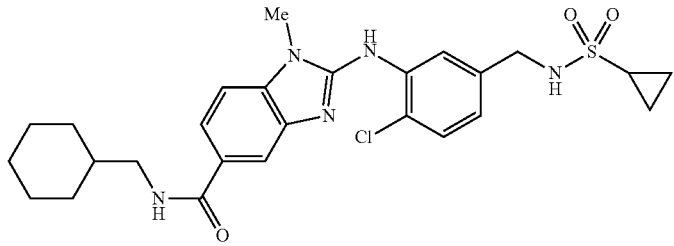 [SMILES: Cn1c(Nc2cc(CNS(=O)(=O)C3CC3)ccc2Cl)nc2cc(C(=O)NCC3CCCCC3)ccc21] 530

N-(2-{2-Chloro-5-[(cyclopropylsulfonamido)methyl]phenylamino}-1-methyl-5-benzimidazolyl)cyclohexylacetamide 200 MHz ¹H-NMR (DMSO-d₆, ppm) 8.39 (1H, s) 8.31-8.23 (1H, m) 7.90-7.85 (1H, m) 7.83-7.76 (1H, m) 7.66-7.57 (1H, m) 7.47-7.31 (3H, m) 6.99-6.90 (1H, m) 4.10 (2H, d, J = 5.8 Hz) 3.70 (3H, s) 3.13-3.02 (2H, m) 1.76-1.54 (6H, m) 1.28-1.13 (4H, m) 0.99-0.86 (6H, m)

30 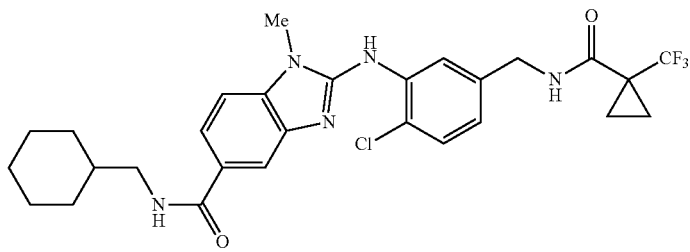 [SMILES: Cn1c(Nc2cc(CNC(=O)C3(C(F)(F)F)CC3)ccc2Cl)nc2cc(C(=O)NCC3CCCCC3)ccc21] 562

2-{2-chloro-5-[(1-trifluoromethylcyclopropylamido)methyl]phenyl-amino}-N-cyclohexylmethyl-1-methylbenzimidazole-5-carboxamide 200 MHz ¹H-NMR (DMSO-d₆, ppm) 8.47-8.34 (2H, m) 8.33-8.24 (1H, m) 7.91-7.82 (2H, m) 7.67-7.58 (1H, m) 7.43 (1H, d, J = 8.2 Hz) 7.38 (1H, d, J = 8.2 Hz) 6.98-6.87 (1H, m) 4.26 (2H, d, J = 6.0 Hz) 3.71 (3H, s) 3.14-3.02 (2H, m) 1.77-1.53 (6H, m) 1.38-1.10 (7H, m) 1.00-0.82 (2H, m)

-continued

| Chemical structure Name | |
|---|---|
| Ex. ¹H-NMR | MS m/z [M + H]⁺ |

31 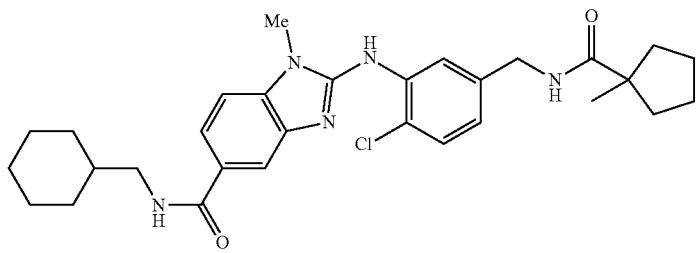 [SMILES: Cn1c(Nc2cc(CNC(=O)C3(C)CCCC3)ccc2Cl)nc2cc(C(=O)NCC3CCCCC3)ccc21] 536

2-{2-Chloro-5-[(1-methylcyclopentylamido)methyl]phenylamino}-N-cyclohexylmethyl-1-methylbenzimidazole-5-carboxamide
200 MHz ¹H-NMR (DMSO-$d_6$, ppm) 8.37-8.22 (2H, m) 8.16-8.04 (1H, m) 7.90-7.78 (2H, m) 7.67-7.56 (1H, m) 7.45-7.31 (2H, m) 6.97-6.84 (1H, m) 4.24 (2H, d, J = 5.8 Hz) 3.70 (3H, s) 3.13-3.02 (2H, m) 2.04-1.89 (2H, m) 1.72-1.47 (10H, m) 1.42-1.29 (2H, m) 1.22-1.08 (6H, m) 1.00-0.81 (2H, m)

32 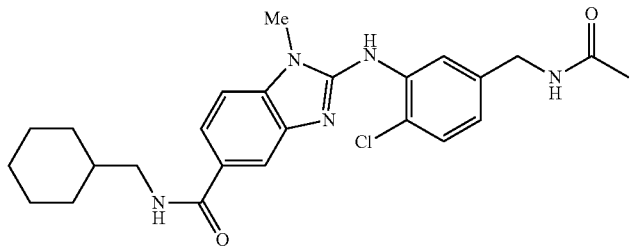 [SMILES: CC(=O)NCc1ccc(Cl)c(Nc2nc3cc(C(=O)NCC4CCCCC4)ccc3n2C)c1] 468

2-[5-(Acetamidomethyl)-2-chlorophenylamino]-N-cyclohexylmethyl-1-methylbenzimidazole-5-carboxamide
200 MHz ¹H-NMR (DMSO-$d_6$, ppm) 8.46-8.36 (2H, m) 8.34-8.22 (1H, m) 7.91-7.80 (2H, m) 7.67-7.57 (1H, m) 7.47-7.30 (2H, m) 7.03-6.92 (1H, m) 4.22 (2H, d, J = 5.2 Hz) 3.71 (3H, s) 3.14-3.00 (2H, m) 1.86 (3H, s) 1.77-1.51 (6H, m) 1.25-1.07 (3H, m) 1.00-0.80 (2H, m)

33 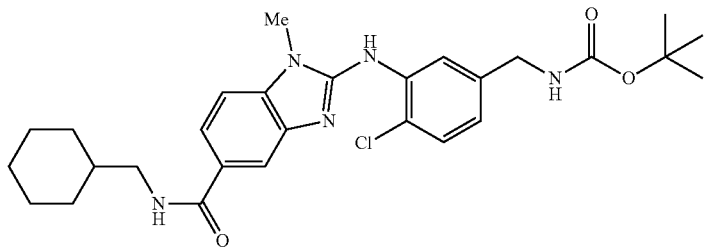 [SMILES: Cn1c(Nc2cc(CNC(=O)OC(C)(C)C)ccc2Cl)nc2cc(C(=O)NCC3CCCCC3)ccc21] 526 tert-Butyl-4-chloro-3-[5-(cyclohexylmethylcarbamoyl)-1-methyl-2-benzimidazolylamino+benzylcarbamate
200 MHz ¹H-NMR (DMSO-$d_6$, ppm) 8.39 (1H, s) 8.31-8.23 (1H, m) 7.90-7.85 (1H, m) 7.83-7.76 (1H, m) 7.66-7.57 (1H, m) 7.47-7.31 (3H, m) 6.99-6.90 (1H, m) 4.10 (2H, d, J = 5.8 Hz) 3.70 (3H, s) 3.13-3.02 (2H, m) 1.76-1.54 (6H, m) 1.35 (9H, s) 1.24-1.08 (3H, m) 1.02-0.79 (2H, m)

| Chemical structure Name | | |
|---|---|---|
| Ex. ¹H-NMR | | MS m/z [M + H]⁺ |
| 34 | tert-Butyl 3-[5-(4-bromophenylcarbamoyl)-1-methyl-2-benzimidazolylamino]-4-chlorobenzylcarbamate<br>200 MHz ¹H-NMR (DMSO-$d_6$, ppm) 10.22 (1H, s) 8.48 (1H, s) 8.08-8.00 (1H, m) 7.86-7.70 (4H, m) 7.54-7.39 (5H, m) 7.03-6.93 (1H, m) 4.11 (2H, d, J = 5.8 Hz) 3.74 (3H, s) 1.36 (9H, s). | 584 |
| 35 | N-(4-Bromophenyl)-2-{2-chloro-5-[(4,4-difluorocyclohexylamido)-methyl]phenylamino}-1-methylbenzimidazole-5-carboxamide<br>200 MHz ¹H-NMR (DMSO-$d_6$, ppm) 10.25 (1H, s) 8.56-8.40 (2H, m) 8.02 (1H, d, J = 1.0 Hz) 7.90-7.70 (4H, m) 7.59-7.42 (4H, m) 6.97 (1H, dd, J = 8.2, 1.8 Hz) 4.27 (2H, d, J = 6.0 Hz) 3.76 (3H, s) 2.69-1.50 (9H, m, overlapped with DMSO) | 630 |
| 36 | N-(4-Bromophenyl)-2-{2-chloro-5-[(2-chloro-6-fluorobenzamido)methyl]phenylamino}-1-methylbenzimidazole-5-carboxamide<br>200 MHz ¹H-NMR (DMSO-$d_6$, ppm) 10.25 (1H, s) 9.30 (1H, t, J = 5.8 Hz) 8.55 (1H, s) 8.08-8.02 (1H, m) 7.96-7.90 (1H, m) 7.85-7.72 (3H, m) 7.56-7.22 (7H, m) 7.18-7.10 (1H, m) 4.48 (2H, d, J = 5.8 Hz) 3.77 (3H, s) | 640 |

| Ex. | Chemical structure<br>Name<br>¹H-NMR | MS m/z [M + H]⁺ |
|---|---|---|
| 37 | 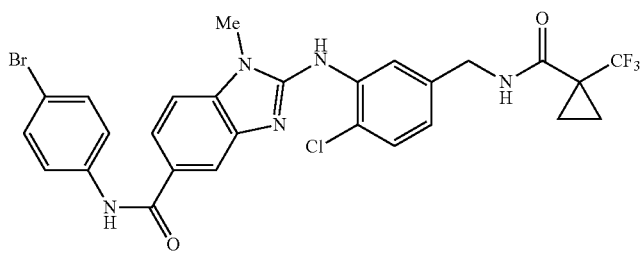 [SMILES: Cn1c(Nc2cc(CNC(=O)C3(C(F)(F)F)CC3)ccc2Cl)nc2cc(C(=O)Nc3ccc(Br)cc3)ccc21]<br>N-(4-Bromophenyl)-2-{2-chloro-5-[(1-trifluoromethylcyclopropylamido)methyl]phenylamino}-1-methylbenzimidazole-5-carboxamide<br>200 MHz ¹H-NMR (DMSO-d₆, ppm) 10.23 (1H, s) 8.50-8.36 (2H, m) 8.01 (1H, s) 7.86-7.68 (4H, m) 7.54-7.38 (4H, m) 6.99-6.90 (1H, m) 4.26 (2H, d, J = 5.8 Hz) 3.73 (3H, s) 1.39-1.16 (4H, m) | 620 |
| 38 | 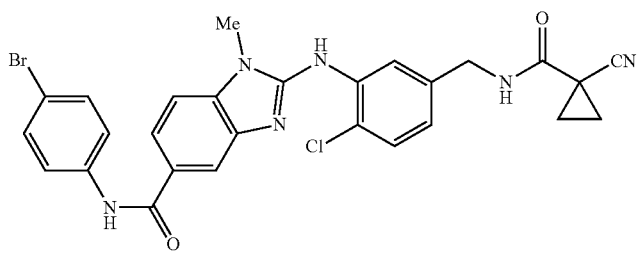<br>N-(4-Bromophenyl)-2-{2-chloro-5-[(1-cyanocyclopropylamido)methyl]-phenylamino}-1-methylbenzimidazole-5-carboxamide<br>200 MHz ¹H-NMR (DMSO-d₆, ppm) 10.23 (1H, s) 8.23 (1H, t, J = 5.6 Hz) 8.50 (1H, s) 8.05-7.98 (1H, m) 7.85-7.69 (4H, m) 7.54-7.40 (4H, m) 7.00 (1H, dd, J = 8.2, 1.8 Hz) 4.28 (2H, d, J = 5.6 Hz) 3.74 (3H, s) 1.60-1.46 (4H, m) | 577 |
| 39 | 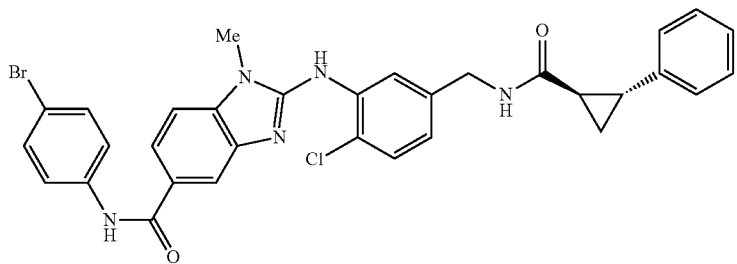 [SMILES: Cn1c(Nc2cc(CNC(=O)[C@@H]3C[C@H]3c3ccccc3)ccc2Cl)nc2cc(C(=O)Nc3ccc(Br)cc3)ccc21]<br>N-(4-Bromophenyl)-2-{2-chloro-5-[(trans-2-phenylcyclopropylamido)-methyl]phenylamino}-1-methylbenzimidazole-5-carboxamide<br>200 MHz ¹H-NMR (DMSO-d₆, ppm) 10.22 (1H, s) 8.73-8.63 (1H, m) 8.50 (1H, s) 8.05-8.00 (1H, m) 7.87-7.68 (4H, m) 7.53-7.41 (4H, m) 7.23-7.00 (6H, m) 4.34-4.22 (2H, m) 3.73 (3H, s) 2.32-2.18 (1H, m) 1.96-1.83 (1H, m) 1.42-1.29 (1H, m) 1.26-1.14 (1H, m) | 628 |

| Ex. | Chemical structure / Name / ¹H-NMR | MS m/z [M + H]⁺ |
|---|---|---|
| 40 | 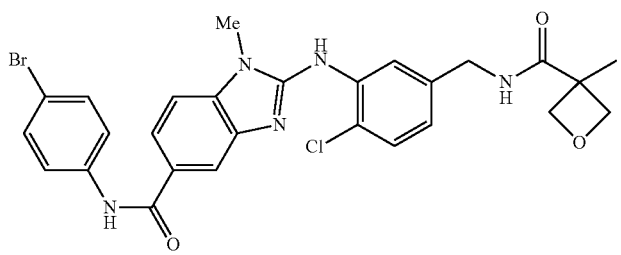 [SMILES: Cn1c(Nc2cc(CNC(=O)C3(C)COC3)ccc2Cl)nc2cc(C(=O)Nc3ccc(Br)cc3)ccc21]  N-(4-Bromophenyl)-2-{2-chloro-5-[(3-methyl-3-oxetanylamido)methyl]-phenylamino}-1-methylbenzimidazole-5-carboxamide<br>200 MHz ¹H-NMR (DMSO-d₆, ppm) 10.24 (1H, s) 8.58-8.44 (2H, m) 8.03-7.98 (1H, m) 7.91-7.86 (1H, m) 7.84-7.70 (3H, m) 7.54-7.40 (4H, m) 7.03-6.93 (1H, m) 4.76 (2H, d, J = 6.0 Hz) 4.32-4.19 (4H, m) 3.74 (3H, s) 1.51 (3H, s) | 582 |
| 41 | 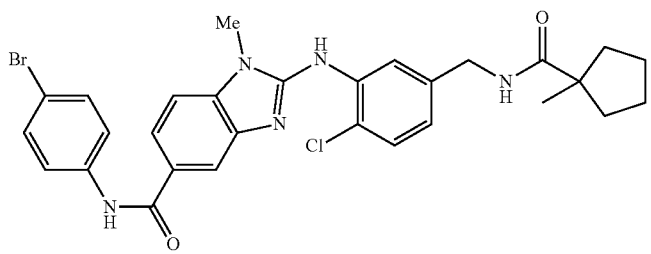 [SMILES: Cn1c(Nc2cc(CNC(=O)C3(C)CCCC3)ccc2Cl)nc2cc(C(=O)Nc3ccc(Br)cc3)ccc21]  N-(4-Bromophenyl)-2-{2-chloro-5-[(1-methylcyclopentylamido)methyl]-phenylamino}-1-methylbenzimidazole-5-carboxamide<br>200 MHz ¹H-NMR (DMSO-d₆, ppm) 10.23 (1H, s) 8.42 (1H, s) 8.17-8.07 (1H, m) 8.02-7.98 (1H, m) 7.86-7.69 (4H, m) 7.54-7.39 (4H, m) 6.98-6.89 (1H, m) 4.24 (2H, d, J = 6.0 Hz) 3.73 (3H, s) 2.06-1.87 (2H, m) 1.6-1.27 (6H, m) 1.15 (3H, s) | 594 |
| 42 | 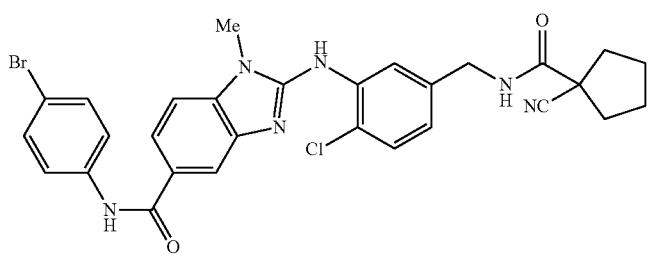 [SMILES: Cn1c(Nc2cc(CNC(=O)C3(C#N)CCCC3)ccc2Cl)nc2cc(C(=O)Nc3ccc(Br)cc3)ccc21]  N-(4-Bromophenyl)-2-{2-chloro-5-[(1-cyanocyclopentylamido)methyl]-phenylamino}-1-methylbenzimidazole-5-carboxamide<br>200 MHz ¹H-NMR (DMSO-d₆, ppm) 10.23 (1H, s) 8.93 (1H, t, J = 6.0 Hz) 8.45 (1H, s) 8.03-7.97 (1H, m) 7.88-7.70 (4H, m) 7.55-7.40 (4H, m) 7.01-6.93 (1H, m) 4.30 (2H, d, J = 6.0 Hz) 3.74 (3H, s) 2.20-2.10 (4H, m) 1.74-1.63 (4H, m) | 605 |

| Chemical structure Name | |
|---|---|
| Ex. ¹H-NMR | MS m/z [M + H]⁺ |

43

2-[5-(Acetamidomethyl)-2-chlorophenylamino]-N-(4-bromophenyl)-1-methylbenzimidazole-5-carboxamide 200 MHz ¹H-NMR (DMSO-d₆, ppm) 10.22 (1H, s) 8.50 (1H ,s) 8.41 (1H, t, J = 6.0 Hz) 8.04-7.99 (1H, m) 7.85-7.69 (4H, m) 7.53-7.40 (4H, m) 7.03-6.95 (1H, m) 4.23 (2H, d, J = 6.0 Hz) 3.74 (3H, s) 1.85 (3H, s)

526

44

N-(4-Bromophenyl)-2-{2-chloro-5-[(2-thienylsulfonamido)methyl]phenylamino}-1-methylbenzimidazole-5-carboxamide 200 MHz ¹H-NMR (DMSO-d₆, ppm) 10.25 (1H, s) 8.54 (1H, s) 8.45 (1H, t, J = 6.4 Hz) 8.08-8.03 (1H, m) 7.96-7.70 (5H, m) 7.63 (1H, dd, J = 3.7, 1.1 Hz) 7.59-7.41 (4H, m) 7.17 (1H, dd, J = 5.1, 3.7 Hz) 7.04 (1H, dd, J = 8.2, 1.8 Hz) 4.06 (2H, d, J = 6.4 Hz) 3.76 (3H, s)

630

45

N-(4-Bromophenyl)-2-{2-chloro-5-[(cyclopropylsulfonamido)methyl]-phenylamino}-1-methylbenzimidazole-5-carboxamide 200 MHz ¹H-NMR (DMSO-d₆, ppm) 10.25 (1H, s) 8.55 (1H, s) 8.05-7.98 (1H, m) 7.97-7.93 (1H, m) 7.85-7.71 (4H, m) 7.57-7.45 (4H, m) 7.20-7.08 (1H, m) 4.20 (2H, d, J = 5.8 Hz) 3.77 (3H, s) 0.94-0.86 (4H, m)

588

| | |
|---|---|
| Chemical structure<br>Name<br>Ex. ¹H-NMR | MS m/z [M + H]⁺ |

46

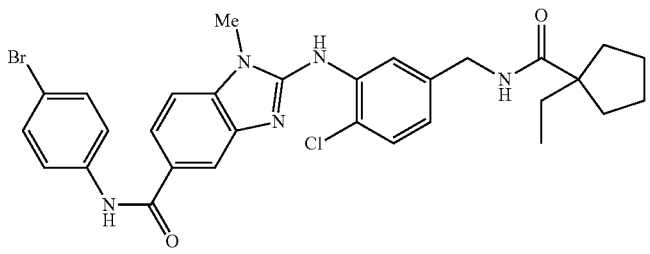 [SMILES: CCC1(C(=O)NCc2ccc(Cl)c(Nc3nc4cc(C(=O)Nc5ccc(Br)cc5)ccc4n3C)c2)CCCC1]

N-(4-Bromophenyl)-2-{2-chloro-5-[(1-ethylcyclopentylamido)methyl]-
phenylamino}-1-methylbenzimidazole-5-carboxamide
200 MHz ¹H-NMR (DMSO-d₆, ppm) 10.23 (1H, s) 8.43 (1H, s) 8.17-
8.07 (1H, m) 8.04-7.98 (1H, m) 7.86-7.70 (4H, m) 7.55-7.38 (4H, m)
7.00-6.91 (1H, m) 4.25 (2H, d, J = 5.6 Hz) 3.73 (3H, s) 2.08-1.92 (2H, m)
1.61-1.30 (8H, m) 0.74-0.60 (3H, m)

608

47

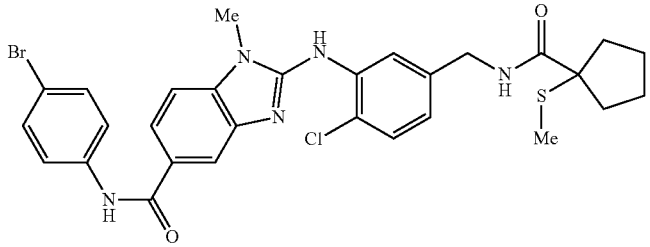 [SMILES: CSC1(C(=O)NCc2ccc(Cl)c(Nc3nc4cc(C(=O)Nc5ccc(Br)cc5)ccc4n3C)c2)CCCC1]

N-(4-Bromophenyl)-2-{2-chloro-5-[(1-methylthiocyclopentylamido)-
methyl]phenylamino}-1-methylbenzimidazole-5-carboxamide
200 MHz ¹H-NMR (DMSO-d₆, ppm) 10.22 (1H, s) 8.48-8.32 (2H, m)
8.04-7.97 (1H, m) 7.86-7.70 (4H, m) 7.54-7.38 (4H, m) 7.04-6.94 (1H,
m) 4.27 (2H, d, J = 5.6 Hz) 3.73 (3H, s) 2.17-2.05 (2H, m) 1.88 (3H, s)
1.77-1.54 (6H, m)

626

48

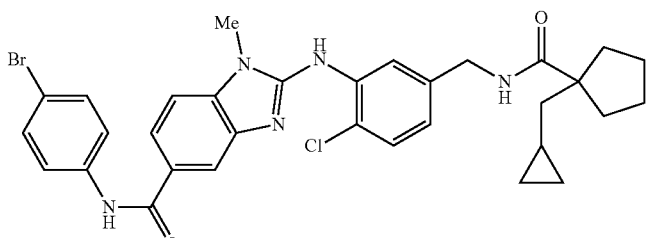

N-(4-Bromophenyl)-2-{2-chloro-5-[(1-cyclopropylmethylcyclopentyl-
amido)methyl]phenylamino}-1-methylbenzimidazole-5-carboxamide
200 MHz ¹H-NMR (DMSO-d₆, ppm) 10.22 (1H, s) 8.43 (1H, s) 8.15-
8.05 (1H, m) 8.03-7.97 (1H, m) 7.87-7.70 (4H, m) 7.54-7.39 (4H, m)
7.02-6.92 (1H, m) 4.25 (2H, d, J = 5.6 Hz) 3.73 (3H, s) 2.09-1.94 (2H, m)
1.55-1.38 (8H, m) 0.58-0.39 (1H, m) 0.30-0.18 (2H, m) −0.044-[−0.16]
(2H, m)

634

| Ex. | Chemical structure<br>Name<br>¹H-NMR | MS m/z [M + H]⁺ |
|---|---|---|
| 49 | 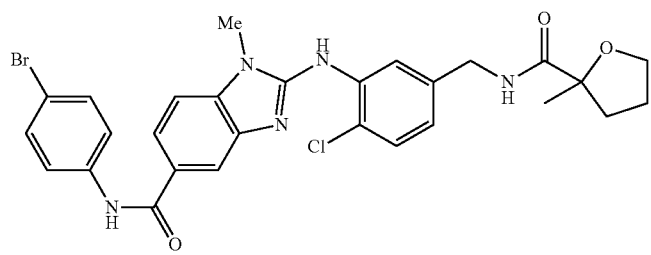<br>N-(4-Bromophenyl)-2-{2-chloro-5-[(2-methyl-2-tetrahydrofurylamido)-methyl]phenylamino}-1-methylbenzimidazole-5-carboxamide<br>200 MHz ¹H-NMR (DMSO-d₆, ppm) 10.18 (1H, s) 8.38 (1H, s) 8.37-8.33 (1H, m) 7.98-7.95 (1H, m) 7.78-7.68 (4H, m) 7.48-7.44 (2H, m) 7.42 (1H, d, J = 8.2 Hz) 7.39 (1H, d, J = 8.2 Hz) 6.91 (1H, dd, J = 8.2 Hz, 1.8 Hz) 4.26-4.14 (2H, m) 3.81-3.75 (2H, m) 3.69 (3H, s) 2.13-2.04 (1H, m) 1.78-1.59 (3H, m) 1.25 (3H, s) | 596 |
| 50 | 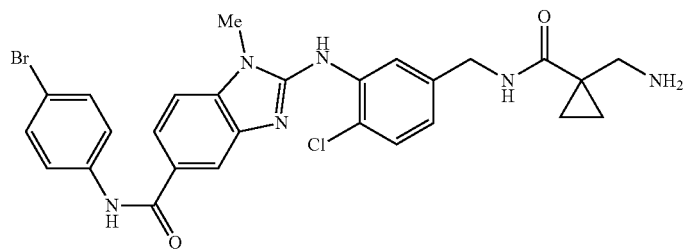 [SMILES: Cn1c(Nc2cc(CNC(=O)C3(CN)CC3)ccc2Cl)nc2cc(C(=O)Nc3ccc(Br)cc3)ccc21]<br>2-(5-{[1-(Aminomethyl)cyclopropylamido]methyl}-2-chlorophenylamino)-N-(4-bromophenyl)-1-methylbenzimidazole-5-carboxamide<br>200 MHz ¹H-NMR (DMSO-d₆, ppm) 10.19 (1H, s) 8.40 (1H, s) 8.19-8.13 (1H, m) 7.99-7.95 (1H, m) 7.86-7.82 (1H, m) 7.78-7.69 (3H, m) 7.49-7.36 (5H, m) 6.96-6.90 (1H, m) 4.22 (2H, d, J = 5.8 Hz) 3.71 (3H, s) 2.89 (2H, s) 1.25-1.17 (2H, m) 0.94-0.88 (2H, m) | 581 |
| 51 | 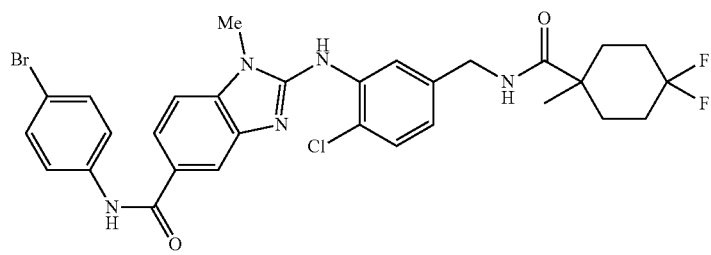 [SMILES: Cn1c(Nc2cc(CNC(=O)C3(C)CCC(F)(F)CC3)ccc2Cl)nc2cc(C(=O)Nc3ccc(Br)cc3)ccc21]<br>N-(4-Bromophenyl)-2-{2-chloro-5-[(4,4-difluoro-1-methylcyclohexyl-amido)methyl]phenylamino}-1-methylbenzimidazole-5-carboxamide | 644 |

| Ex. | Chemical structure<br>Name<br>¹H-NMR | MS m/z [M + H]⁺ |
|---|---|---|
| 52 | 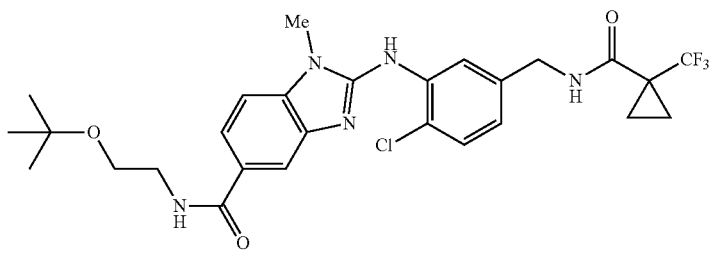 [SMILES: Cn1c(Nc2cc(CNC(=O)C3(C(F)(F)F)CC3)ccc2Cl)nc2cc(C(=O)NCCOC(C)(C)C)ccc21]<br>N-(2-tert-Butoxyethyl)-2-{2-chloro-5-[(1-trifluoromethylcyclopropyl-amido)methyl]phenylamino}-1-methylbenzimidazole-5-carboxamide<br>400 MHz ¹H-NMR (DMSO-d₆, ppm) (signals of minor tautomer are not assigned) 8.48-8.26 (3H, m) 7.92-7.85 (1H, m) 7.85-7.78 (1H, m) 7.68-7.61 (1H, m) 7.44 (1H, d, J = 8.2 Hz) 7.40 (1H, d, J = 8.4 Hz) 7.00-6.91 (1H, m) 4.28 (2H, d, J = 5.8 Hz) 3.72 (3H, s) 3.46-3.39 (2H, m) 3.37-3.30 (2H, m, overlapped with water) 1.40-1.20 (4H, m) 1.13 (9H, s) | 566 |
| 53 | 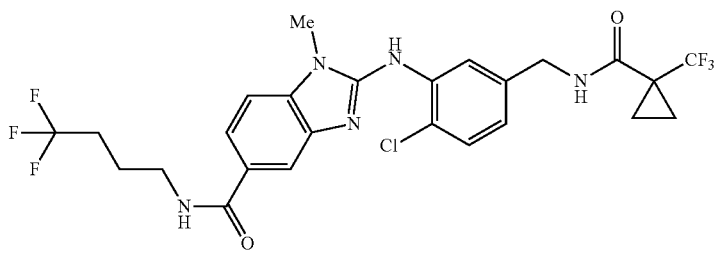 [SMILES: Cn1c(Nc2cc(CNC(=O)C3(C(F)(F)F)CC3)ccc2Cl)nc2cc(C(=O)NCCCC(F)(F)F)ccc21]<br>2-{2-Chloro-5-[(1-trifluoromethylcyclopropylamido)methyl]phenylamino}-1-methyl-N-(4,4,4-trifluorobutyl)benzimidazole-5-carboxamide<br>400 MHz ¹H-NMR (DMSO-d₆, ppm) (signals of minor tautomer are not assigned) 8.46-8.36 (3H, m) 7.90 (1H, d, J = 1.7 Hz) 7.84 (1H, d, J = 2.1 Hz) 7.65 (1H, dd, J = 8.3, 1.7 Hz) 7.45 (1H, d, J = 8.3 Hz) 7.41 (1H, d, J = 8.3 Hz) 6.95 (1H, dd, J = 8.3, 2.1 Hz) 4.28 (2H, d, J = 5.8 Hz) 3.73 (3H, s) 3.38-3.29 (2H, m, overlapped with water) 2.40-2.24 (2H, m) 1.81-1.70 (2H, m) 1.40-1.13 (4H, m) | 578 |
| 54 | 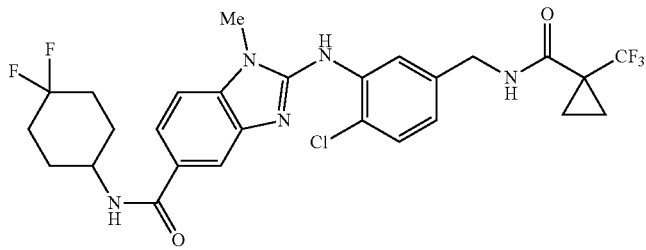 [SMILES: Cn1c(Nc2cc(CNC(=O)C3(C(F)(F)F)CC3)ccc2Cl)nc2cc(C(=O)NC3CCC(F)(F)CC3)ccc21]<br>2-{2-chloro-5-[(1-trifluoromethylcyclopropylamido)methyl]phenylamino}-N-(4,4-difluorocyclohexyl)-1-methylbenzimidazole-5-carboxamide<br>400 MHz ¹H-NMR (DMSO-d₆, ppm) (signals of minor tautomer are not assigned) 8.42 (1H, t, J = 5.9 Hz) 8.38 (1H, s) 8.16 (1H, d, J = 7.8 Hz) 7.93 (1H, d, J = 1.3 Hz) 7.87 (1H, d, J = 2.1 Hz) 7.66 (1H, dd, J = 8.3, 1.3 Hz) 7.45 (1H, d, J = 8.4 Hz) 7.40 (1H, d, J = 8.3 Hz) 6.95 (1H, dd, J = 8.3, 2.1 Hz) 4.28 (2H, d, J = 5.9 Hz) 4.05-3.91 (1H, m) 3.73 (3H, s) 2.15-1.80 (6H, m) 1.73-1.59 (2H, m) 1.39-1.12 (4H, m) | 586 |

| Chemical structure Name | | |
|---|---|---|
| Ex. ¹H-NMR | | MS m/z [M + H]⁺ |

| 55 | | 579 |

2-{2-chloro-5-[(1-trifluoromethylcyclopropylamido)methyl]phenylamino}-1-methyl-N-[2-(1-methyl-2-pyrrolidinyl)ethyl]benzimidazole-5-carboxamide
400 MHz ¹H-NMR (DMSO-d₆, ppm) (signals of minor tautomer are not assigned) 8.46-8.30 (3H, m) 7.90-7.85 (1H, m) 7.85-7.80 (1H, m) 7.66-7.58 (1H, m) 7.44 (1H, d, J = 8.0 Hz) 7.41 (1H, d, J = 8.2 Hz) 6.99-6.91 (1H, m) 4.28 (2H, d, J = 5.8 Hz) 3.73 (3H, s) 2.98-2.87 (1H, m) 2.55-2.35 (2H, m, overlapped with DMSO) 2.21 (3H, s) 2.10-1.81 (4H, m) 1.68-1.55 (2H, m) 1.50-1.11 (6H, m)

| 56 | | 524 |

N-{4-Chloro-3-[6-chloro-5-(3,3-difluoro-pyrrolidin-1-ylcarbonyl)-2-benzimidazolylamino]benzyl}-pivaloylamide
HPLC-Method B: R$_t$ = 2.56 min

| 57 | | 568 |

N-(4-Bromophenyl)-2-{2-chloro-5-[(tert.butylcarbonylamino)methyl]-phenylamino}-1-methylbenzimidazole-5-carboxamide

| 58 | | 606 |

N-(4-Bromophenyl)-2-{2-chloro-5-[((1-trifluoromethyl-cyclopropanecarbonyl)amino)-methyl]phenylamino}-benzimidazole-5-carboxamide

Example 59
N-(4-Bromo-phenyl)-2-(2-chloro-5-{[(1-trifluorom-ethyl-cyclopropanecarbonyl)-amino]-methyl}-phe-nylamino)-6-(2,2-difluoro-ethoxy)-1-methyl-1H-benzimidazole-5-carboxylic acid amide
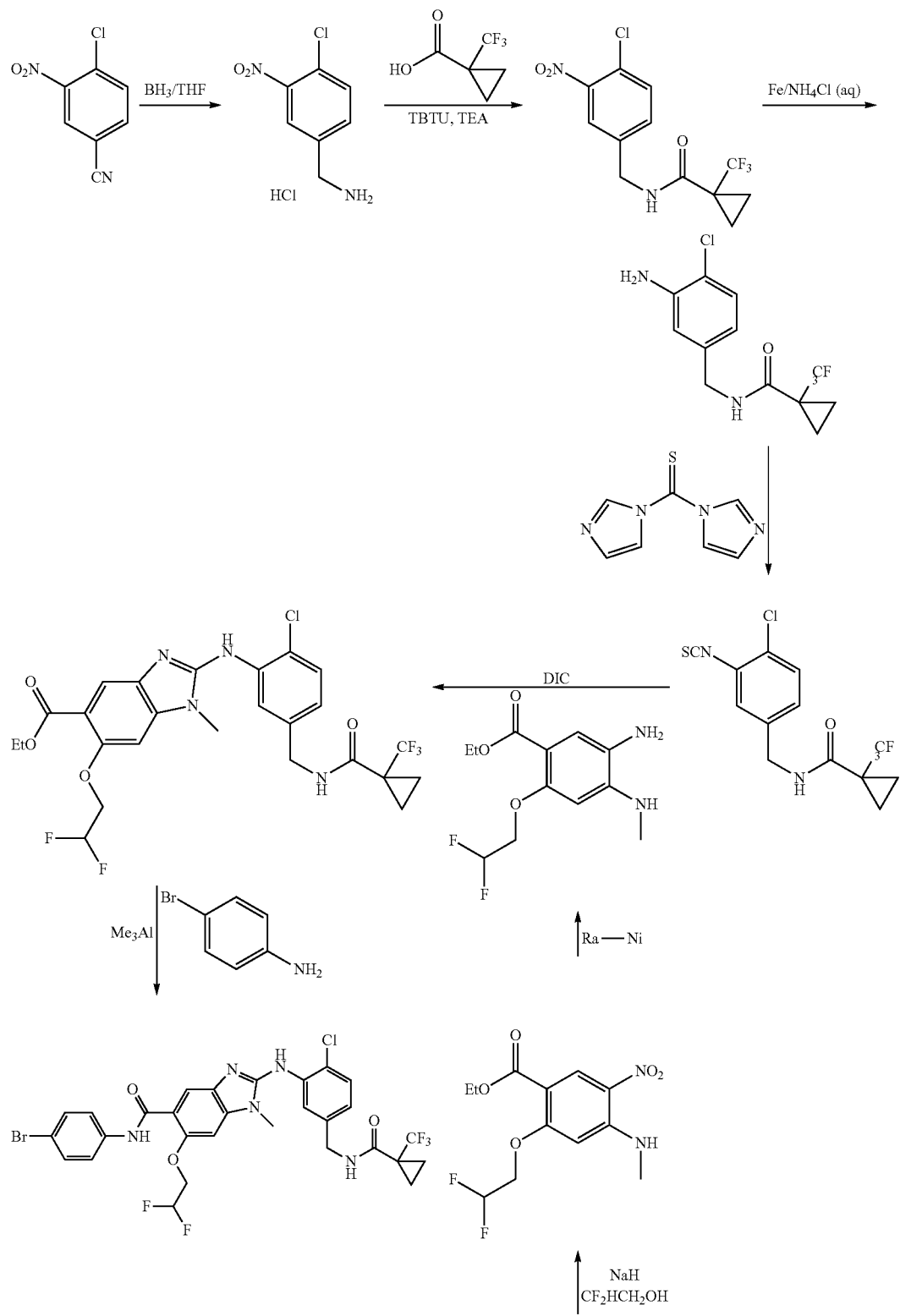

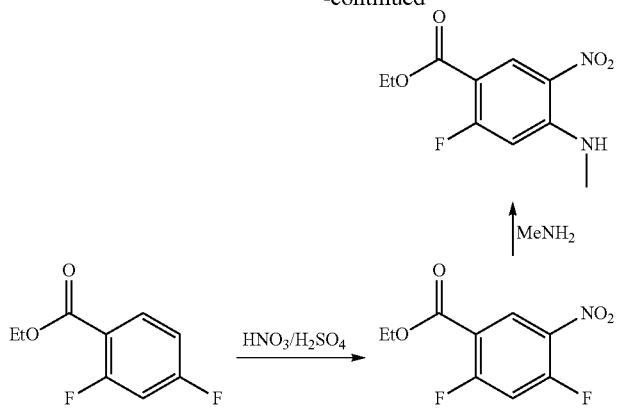

(aa) (4-Chloro-3-nitrophenyl)methylamine hydrochloride

BH$_3$/THF (279 mL; 279 mmol) was added to a solution of 4-chloro-3-nitrobenzonitrile (30 g; 164 mmol) in THF (100 mL) over 30 min at 0° C. and the resulting mixture was stirred over night and allowed to reach rt. MeOH (150 mL) and conc. HCl (60 mL) was added and the resulting mixture was refluxed for 4 h and thereafter concentrated. The residue was treated with water (500 mL) and the resulting precipitate was filtered off. The filtrate was treated with NaCl (120 g) and heated and the resulting precipitate was filtered off to give the sub-title compound. Yield: 24.059 g (65%).

(a) N-(4-Chloro-3-nitrobenzyl)-1-(trifluoromethyl)cyclopropanecarboxamide

TEA (21.7 mL; 156 mmol) was added to a mixture of 1-(trifluoromethyl)-cyclopropanecarboxylic acid (8.00 g; 51.9 mmol) and TBTU (16.7 g; 52 mmol) in DMF (40 mL). After 1 h at rt, a solution of (4-chloro-3-nitrophenyl)methylamine hydrochloride (11.6 g; 52 mmol) in DMF (70 mL) was added dropwise over 30 min. After 17 h at rt, the mixture was concentrated and the residue partitioned between water and MTBE. The organic layer was washed with water, dried over Na$_2$SO$_4$ and concentrated. The residue was purified by column chromatography to give the sub-title compound. Yield: 13.191 g (78%).

(b) N-(3-Amino-4-chlorobenzyl)-1-(trifluoromethyl)cyclopropanecarboxamide

The sub-title compound was prepared from N-(4-chloro-3-nitrobenzyl)-1-(trifluoromethyl)cyclopropanecarboxamide in accordance with Example 2, step (b). Yield: 11.586 g (98%).

(c) N-(4-Chloro-3-isothiocyanatobenzyl)-1-(trifluoromethyl)cyclopropane carboxamide A solution of N-(3-amino-4-chlorobenzyl)-1-(trifluoromethyl)cyclopropane carboxamide (5.21 g; 17.79 mmol) in DCM (40 mL) was added to a solution of TCDI (3.80 g; 21.34 mmol) in DCM (30 mL) at 0° C. After 12 h at rt, the mixture was concentrated and the residue was purified by column chromatography to give the sub-title compound. Yield: 5.00 g (84%).

(d) Ethyl 2,4-difluoro-5-nitrobenzoate

Conc. HNO$_3$ (8 mL) was added dropwise to a mixture of ethyl 2,4-difluorobenzoate (10.0 g; 53.7 mmol) in conc. H$_2$SO$_4$ (8 mL) at 0° C. After 2 h at 0° C., the mixture was poured onto ice and extracted with EtOAc. The organic extracts were washed with saturated NaHCO$_3$ solution (aq) and concentrated to give the sub-title compound. Yield: 11.8 g (95%).

(e) Ethyl 2-fluoro-4-(methylamino)-5-nitrobenzoate

A solution of MeNH$_2$ in THF (21.6 mL; 2 M; 43.3 mmol) was added dropwise to a solution of ethyl 2,4-difluoro-5-nitrobenzoate (5.0 g; 21.6 mmol) in THF (70 mL) at −5° C. The mixture was left over night at rt whereafter an additional portion of MeNH$_2$ in THF (10.0 mL; 2 M; 21.6 mmol) was added at 0° C. After 3 h at rt, water was added and the mixture was concentrated. The resulting precipitate was filtered off and dried to give the sub-title compound. Yield: 5.0 g (96%).

(f) Ethyl 2-(2,2-difluoroethoxy)-4-(methylamino)-5-nitrobenzoate

A solution of 2,2-difluoroethanol (1.7 g; 20.6 mmol) in THF (50 mL) was added to a solution of ethyl 2-fluoro-4-(methylamino)-5-nitrobenzoate (5.0 g; 20.6 mmol) in DMF (100 mL). Sodium hydride (0.824 g; 60%; 20.6 mmol) was added in portions and the mixture was stirred over night at rt. A solution of TFA (30 mL; 0.45 M aq) was added and the mixture was concentrated. The resulting precipitation was filtered off, washed with water, dried and recrystallized from EtOH/water to give the sub-title compound. Yield: 4.8 g (76%).

(g) Ethyl 5-amino-2-(2,2-difluoroethoxy)-4-(methylamino)benzoate

A mixture of ethyl 2-(2,2-difluoroethoxy)-4-(methylamino)-5-nitrobenzoate (2.0 g; 6.57 mmol), Ra—Ni (1.0 g) and THF (100 mL) was stirred under H$_2$-atmosphere (8 atm) over night at rt. Na$_2$SO$_4$ was added and the mixture was stirred another 30 min under H$_2$-atmosphere. The mixture was filtered through celite and the sub-title compound was used in the next step without further purification.

(h) Ethyl 2-(2-chloro-5-{[(1-trifluoromethyl-cyclopropanecarbonyl)-amino]-methyl}-phenylamino)-6-(2,2-difluoro-ethoxy)-1-methyl-1H-benzimidazole-5-carboxylate A mixture of ethyl 5-amino-2-(2,2-difluoroethoxy)-4-(methylamino)benzoate (0.737 g; 2.68 mmol; crude material from step (g)) and N-(4-chloro-3-isothiocyanatobenzyl)-1-(trifluoromethyl)cyclopropane carboxamide (0.900 g; 2.68 mmol) in THF (100 mL) was stirred over night at rt. DIC (0.338 g; 2.68 mmol) was added and the mixture was stirred for 6 h at rt. Another portion of DIC (0.169 g; 1.34 mmol) was added and the mixture stirred for another 6 h at rt. The mixture was concentrated and purified by column chromatography to give the sub-title compound. Yield: 0.790 g (51%).

(i) N-(4-Bromo-phenyl)-2-(2-chloro-5-{[(1-trifluoromethyl-cyclopropanecarbonyl)-amino]-methyl}-phenylamino)-6-(2,2-difluoro-ethoxy)-1-methyl-1H-benzimidazole-5-carboxylic acid amide Me$_3$Al in toluene (0.870 mL; 2 M; 1.74 mmol) was added to a solution of 4-bromoaniline (0.180 g; 1.05 mmol) in 1,4-dioxane (5 mL) and the mixture was stirred for 20 min at rt. The mixture was then added via cannula to a warm (60° C.) solution of ethyl 2-(2-chloro-5-{[(1-trifluoromethyl-cyclopropanecarbonyl)-amino]-methyl}-phenylamino)-6-(2,2-difluoro-ethoxy)-1-methyl-1H-benzimidazole-5-carboxylate_ (0.200 g; 0.35 mmol) in 1,4-dioxane (5 mL). The resulting mixture was stirred at 100° C. over night, cooled to rt and then poured into brine (20 mL) and extracted with EtOAc. The combined extracts were washed with brine, dried over Na$_2$SO$_4$ and concentrated. The residue was purified by column chromatography to give the title compound. Yield: 0.134 g (55%). 400 MHz $^1$H-NMR (DMSO-d$_6$, ppm) 12.3-11.1 (1H, br s) 10.16 (1H, s) 8.45 (1H, t, J=5.9 Hz) 7.69-7.57 (5H, m) 7.53-7.47 (2H, m) 7.45 (1H, d, J=2.0 Hz) 7.34 (1H, dd, J=8.2, 2.0 Hz) 6.48 (1H, tt, J=54.4, 3.3 Hz) 4.53 (2H, td, J=14.5, 3.3 Hz) 4.30 (2H, d, J=5.6 Hz) 3.81 (3H, s) 1.33-1.26 (2H, m) 1.25-1.19 (2H, m). MS m/z: 700, 702, 704 [M+H]$^+$.

The following compounds were synthesized in analogy to the methods of preparation described above in detail.

| Ex. | Chemical structure<br>Name<br>$^1$H-NMR | MS m/z [M + H]$^+$ |
| --- | --- | --- |
| 60 | 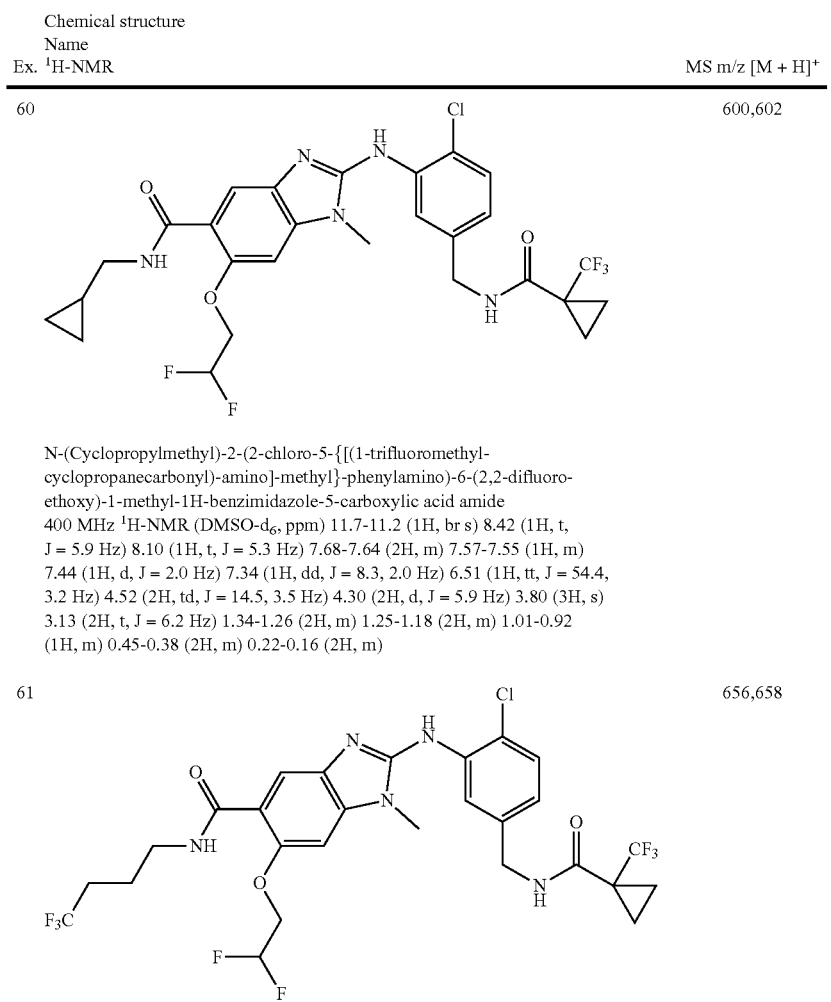<br>N-(Cyclopropylmethyl)-2-(2-chloro-5-{[(1-trifluoromethyl-cyclopropanecarbonyl)-amino]-methyl}-phenylamino)-6-(2,2-difluoro-ethoxy)-1-methyl-1H-benzimidazole-5-carboxylic acid amide<br>400 MHz $^1$H-NMR (DMSO-d$_6$, ppm) 11.7-11.2 (1H, br s) 8.42 (1H, t, J = 5.9 Hz) 8.10 (1H, t, J = 5.3 Hz) 7.68-7.64 (2H, m) 7.57-7.55 (1H, m) 7.44 (1H, d, J = 2.0 Hz) 7.34 (1H, dd, J = 8.3, 2.0 Hz) 6.51 (1H, tt, J = 54.4, 3.2 Hz) 4.52 (2H, td, J = 14.5, 3.5 Hz) 4.30 (2H, d, J = 5.9 Hz) 3.80 (3H, s) 3.13 (2H, t, J = 6.2 Hz) 1.34-1.26 (2H, m) 1.25-1.18 (2H, m) 1.01-0.92 (1H, m) 0.45-0.38 (2H, m) 0.22-0.16 (2H, m) | 600, 602 |
| 61 | N-(4,4,4-Trifluorobutyl)-2-(2-chloro-5-{[(1-trifluoromethyl-cyclopropanecarbonyl)-amino]-methyl}-phenylamino)-6-(2,2-difluoro-ethoxy)-1-methyl-1H-benzimidazole-5-carboxylic acid amide<br>400 MHz $^1$H-NMR (DMSO-d$_6$, ppm)11.2-10.9 (1H, br s) 8.51 (1H, t, J = 5.8 Hz) 8.22 (1H, t, J = 5.8 Hz) 7.74 (1H, d, J = 8.2 Hz) 7.67-7.63 (2H, m) 7.52 (1H, d, J = 1.8 Hz) 7.43 (1H, dd, J = 8.2, 2.0 Hz) 6.55 (1H, tt, J = 54.7, 3.4 Hz) 4.58 (2H, td, J = 14.6, 3.1 Hz) 4.39 (2H, d, J = 5.8 Hz) 3.89 (3H, s) 3.45-3.37 (2H, m) 2.40-2.27 (2H, m) 1.84-1.75 (2H, m) 1.42-1.36 (2H, m) 1.32-1.26 (2H, m) | 656, 658 |

| Chemical structure Name | | |
|---|---|---|
| Ex. ¹H-NMR | | MS m/z [M + H]⁺ |
| 62 | | 664, 666 |

N-(4,4-Difluorocyclohexyl)-2-(2-chloro-5-{[(1-trifluoromethyl-cyclopropanecarbonyl)-amino]-methyl}-phenylamino)-6-(2,2-difluoro-ethoxy)-1-methyl-1H-benzimidazole-5-carboxylic acid amide
400 MHz ¹H-NMR (DMSO-$d_6$, ppm) 9.34-8.29 (2H, m) 7.99-7.95 (1H, m) 7.67-7.62 (3H, m) 7.45-7.42 (1H, m) 7.34 (1H, dd, J = 8.3, 1.7 Hz) 6.62-6.30 (1H, m) 4.54-4.43 (2H, m) 4.30 (2H, d, J = 5.9 Hz) 4.04-3.90 (1H, m) 3.79 (3H, s) 2.06-1.68 (5H, m) 1.60-1.46 (1H, m) 1.34-1.15 (6H, m)

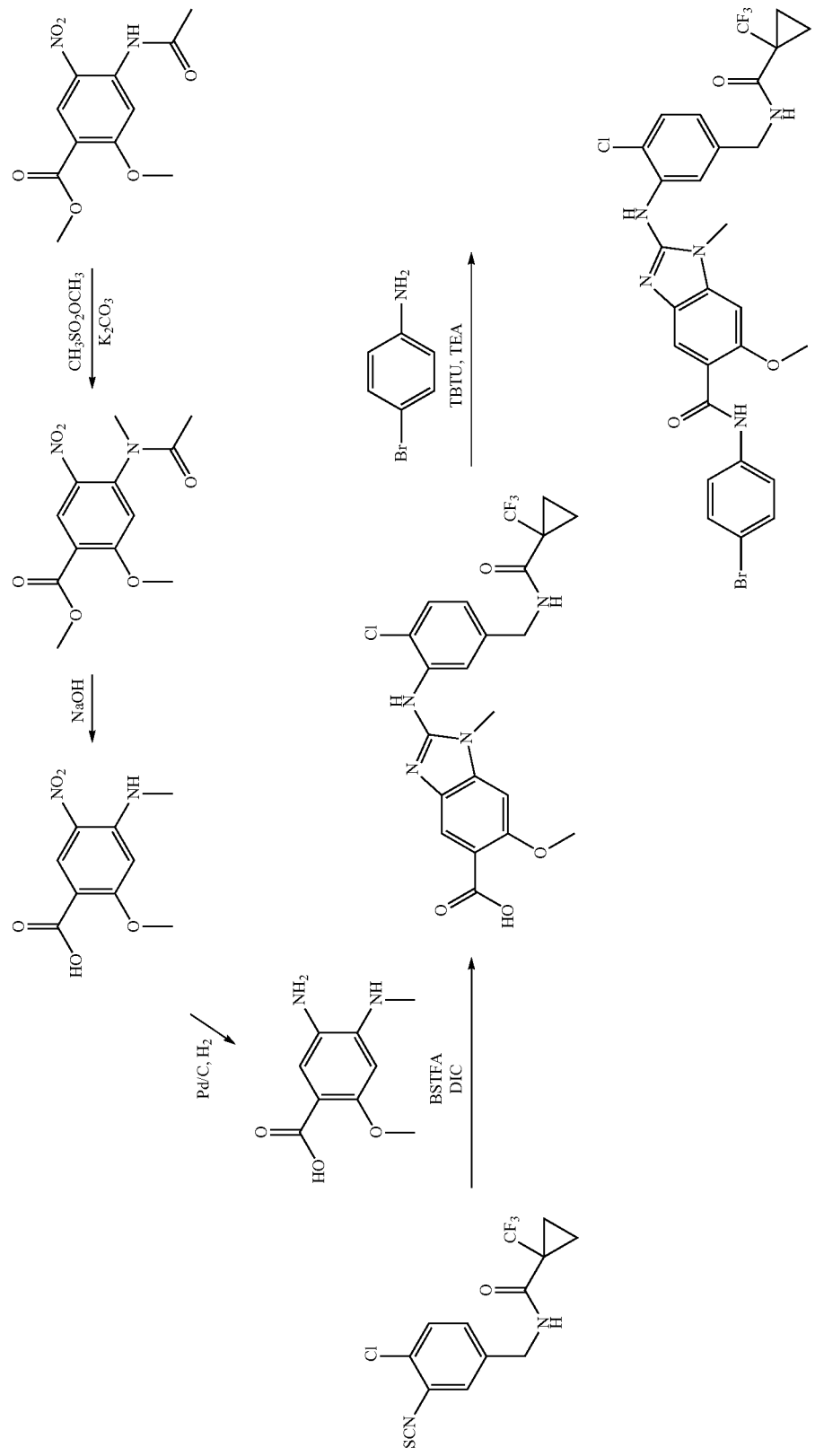

(aa) Methyl 2-methoxy-4-(N-methylacetamido)-5-nitrobenzoate

A mixture of methyl 4-acetamido-2-methoxy-5-nitrobenzoate (2.0 g; 7.5 mmol), methyl methanesulfonate (0.85 g; 7.7 mmol) and K₂CO₃ (2.0 g; 14.5 mmol) in DMF (20 mL) was stirred for 36 h at rt. The mixture was thereafter poured into brine and extracted with EtOAc. The combined extracts were washed with brine, dried over Na₂SO₄, filtered and concentrated to give the crude sub-title compound.

(ab) 2-Methoxy-4-(methylamino)-5-nitrobenzoic acid

A mixture of methyl 2-methoxy-4-(N-methylacetamido)-5-nitrobenzoate (2.1 g; 0.74 mmol), aqueous NaOH (29 mL; 1 M; 29 mmol) and EtOH (30 mL) was refluxed for 2 h. The mixture was thereafter concentrated and the remaining aqueous phase was acidified to strongly acidic pH with acetic acid, sonicated and filtered to give the sub-title compound.

Yield: 1.28 g (76%).

(ac) 5-Amino-2-methoxy-4-(methylamino)benzoic acid

A mixture of 2-methoxy-4-(methylamino)-5-nitrobenzoic acid (7.0 g; 31 mmol), Pd/C (1.0 g), MeOH (25 mL) and THF (75 mL) was stirred under H₂ atmosphere (8 atm) for 24 h at 50° C. A second portion of Pd/C (1.0 g) was added and the mixture hydrogenated for additional 24 h. A third portion of Pd/C (0.5 g) was added and the mixture hydrogenated over night. The suspension was concentrated and the residue stored under argon and was used in the next step without further purification.

(a) 2-(2-chloro-5-{[(1-trifluoromethyl-cyclopropanecarbonyl)-amino]-methyl}-phenylamino)-6-methoxy-1-methyl-1H-benzimidazole-5-carboxylic acid A mixture of N-(4-chloro-3-isothiocyanatobenzyl)-1-(trifluoromethyl)cyclopropane carboxamide (1.71 g; 5.10 mmol) and 5-amino-2-methoxy-4-(methylamino)benzoic acid (1.00 g; 1.00 mmol) in DMF (20 mL) was stirred over night at rt. The mixture was thereafter heated to 60° C. and BSTFA (1.44 g; 5.61 mmol) was added and stirred for 1 h before the addition of DIC (0.772 g; 6.12 mmol). The resulting mixture was stirred at 80° C. for 3 h. Acetic acid (2 mL) was added and the mixture was concentrated and the residue poured in aqueous NaOH (2 M) and pH adjusted to ~3-4. The mixture was extracted with EtOAc and the organic extracts were washed with brine, dried over Na₂SO₄, filtered and concentrated. The residue was recrystallized from EtOAc/petroleum ether to give the sub-title compound. Yield: 0.570 g (22%).

(b) N-(4-Bromo-phenyl)-2-(2-chloro-5-{[(1-trifluoromethyl-cyclopropanecarbonyl)-amino]-methyl}-phenylamino)-6-methoxy-1-methyl-1H-benzimidazole-5-carboxylic acid amide The title compound was prepared from 2-(2-chloro-5-{[(1-trifluoromethyl-cyclopropanecarbonyl)-amino]-methyl}-phenylamino)-6-methoxy-1-methyl-1H-benzimidazole-5-carboxylic acid (92 mg; 0.19 mmol) and 4-bromoaniline (33 mg; 0.19 mmol) in accordance with Example 59, step (a). Yield: 73 mg (59%). 400 MHz ¹H-NMR (DMSO-d₆, ppm) 10.16 (1H, s) 8.40 (1H, t, J=6.0 Hz) 8.25 (1H, s) 7.85-7.81 (1H, m) 7.76-7.68 (3H, m) 7.51-7.46 (2H, m) 7.40 (1H, d, J=8.2 Hz) 7.22-7.17 (1H, m) 6.92-6.86 (1H, m) 4.25 (2H, d, J=6.0 Hz) 3.97 (3H, s) 3.71 (3H, s) 1.37-1.32 (2H, m) 1.23-1.18 (2H, m). MS m/z: 650, 652, 654 [M+H]⁺.

The following compounds were synthesized in analogy to the methods of preparation described above in detail.

| Ex. | Chemical structure<br>Name<br>¹H-NMR | MS m/z [M + H]⁺ |
| --- | --- | --- |
| 64 | 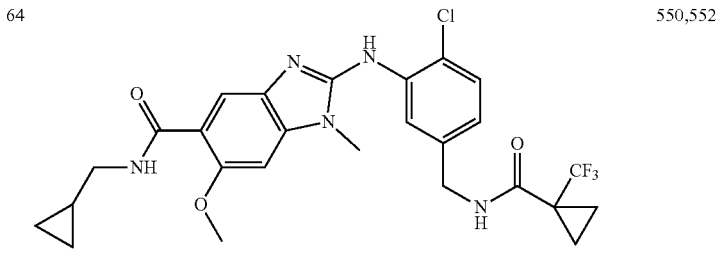<br>N-(Cyclopropylmethyl)-2-(2-chloro-5-{[(1-trifluoromethyl-cyclopropanecarbonyl)-amino]-methyl}-phenylamino)-6-methoxy-1-methyl-1H-benzimidazole-5-carboxylic acid amide<br>400 MHz ¹H-NMR (DMSO-d₆, ppm) 8.41 (1H, t, J = 5.8 Hz) 8.25-8.17 (2H, m) 7.89-7.82 (2H, m) 7.40 (1H, d, J = 8.2 Hz) 7.17-7.14 (1H, m) 6.92-6.86 (1H, m) 4.26 (2H, d, J = 5.8 Hz) 3.95 (3H, s) 3.70 (3H, s) 3.21-3.14 (2H, m) 1.39-1.33 (2H, m) 1.24-1.18 (2H, m) 1.06-0.99 (1H, m) 0.46-0.38 (2H, m) 0.26-0.19 (2H, m) | 550,552 |

| Ex. | Chemical structure Name ¹H-NMR | MS m/z [M + H]⁺ |
|---|---|---|
| 65 | 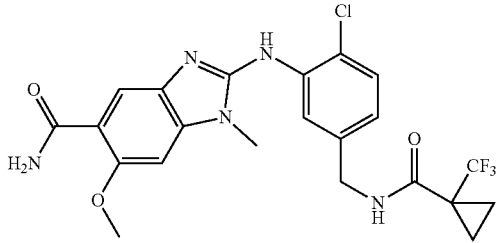 [SMILES: COc1cc2c(cc1C(N)=O)nc(Nc1cc(CNC(=O)C3(C(F)(F)F)CC3)ccc1Cl)n2C]<br>2-(2-chloro-5-{[(1-trifluoromethyl-cyclopropanecarbonyl)-amino]-methyl}-phenylamino)-6-methoxy-1-methyl-1H-benzimidazole-5-carboxylic acid amide<br>400 MHz ¹H-NMR (DMSO-d₆, ppm) 8.39 (1H, t, J = 5.8 Hz) 8.28-8.18 (1H, m) 7.88 (1H, s) 7.82-7.77 (1H, m) 7.66-7.56 (1H, m) 7.39 (1H, d, J = 8.2 Hz) 7.35-7.29 (1H, m) 7.13 (1H, s) 6.88 (1H, dd, J = 8.2, 1.8 Hz) 4.24 (2H, d, J = 5.8 Hz) 3.93 (3H, s) 3.68 (3H, s) 1.37-1.31 (2H, m) 1.22-1.18 (2H, m) | 496, 498 |

Example 66

N-(4-Bromo-phenyl)-2-(2-fluoro-5-{[(1-trifluoromethyl-cyclopropanecarbonyl)-amino]-methyl}-phenylamino)-6-(2,2-difluoro-ethoxy)-1-methyl-1H-benzimidazole-5-carboxylic acid amide

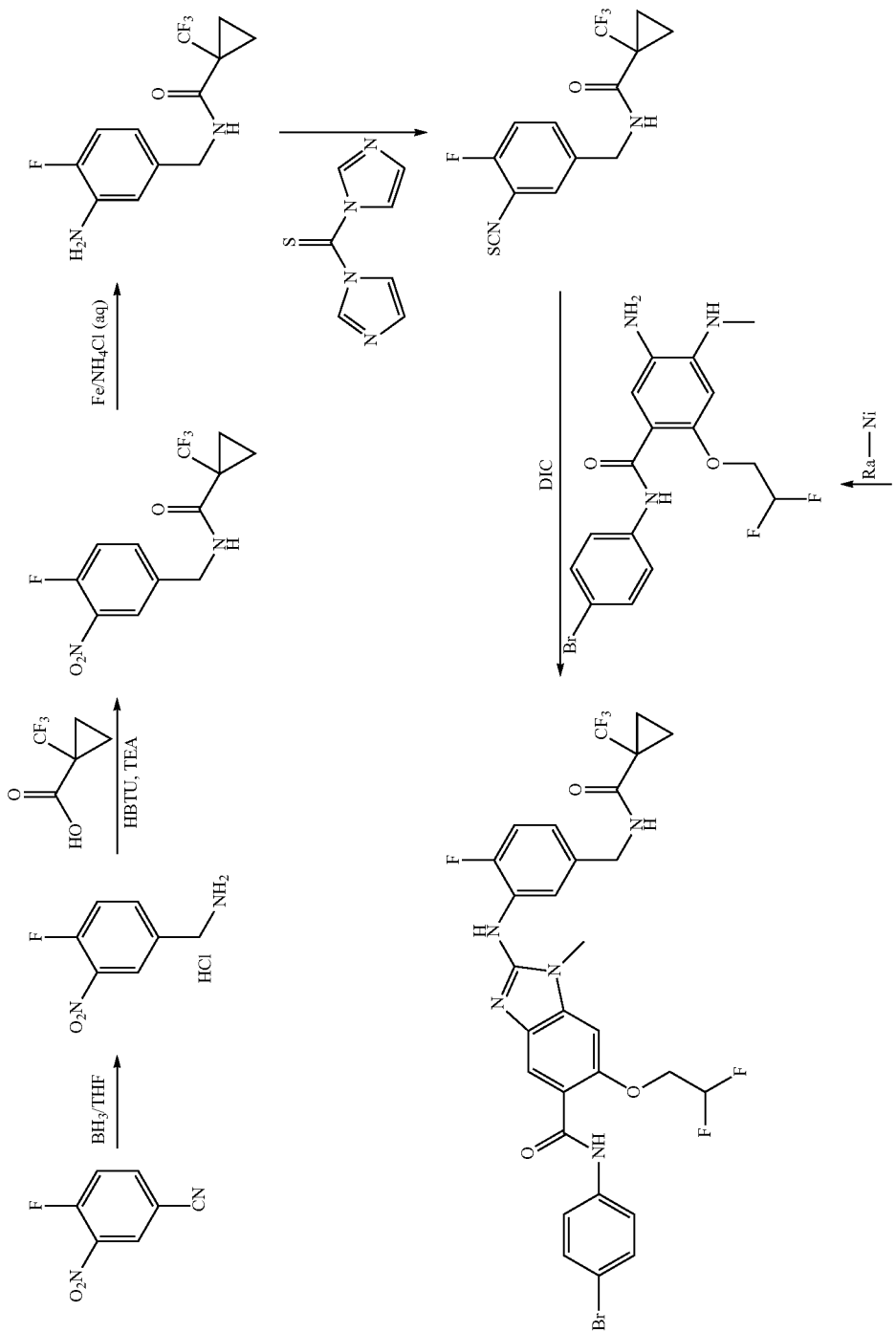

-continued
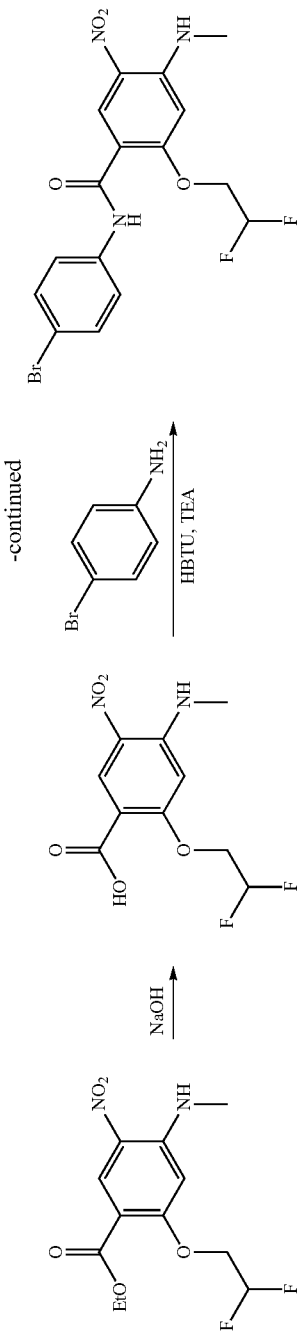

(a) (4-Fluoro-3-nitrophenyl)methylamine hydrochloride

BH$_3$/THF (120 mL; 120 mmol) was added to a solution of 4-fluoro-3-nitrobenzonitrile (10 g; 60 mmol) in THF (50 mL) over 30 min at 0° C. and the resulting mixture was stirred at 0° C. for 1 h and at rt for 3 h. The mixture was acidified to pH ~1, stirred for 1 h at rt, basicified to pH ~7-8 and extracted with EtOAc. The organic extracts were dried over Na$_2$SO$_4$, filtered and concentrated. The residue was dissolved in Et$_2$O and treated with a solution of HCl in 1,4-dioxane to give the sub-title compound. Yield: 8.7 g (70%).

(b) N-(4-Fluoro-3-nitro-benzyl)-1-(trifluoromethyl) cyclopropanecarboxamide

The sub-title compound was prepared in accordance with the procedure in Example 72, step (c) using (4-fluoro-3-nitrophenyl)methylamine hydrochloride (3.0 g; 14.5 mmol), 1-(trifluoromethyl)-cyclopropanecarboxylic acid (2.5 g; 16.0 mmol), HBTU (6.07 g; 16.0 mmol), TEA (5.88 g; 58.1 mmol) and DMF (50 mL). Yield: 3.8 g (85%).

(c) N-(3-Amino-4-fluorobenzyl)-1-(trifluoromethyl) cyclopropanecarboxamide

The sub-title compound was prepared in accordance with the procedure in Example 2, step (b) using N-(4-fluoro-3-nitrobenzyl)-1-(trifluoromethyl)-cyclopropanecarboxamide (3.77 g; 12.3 mmol), Fe (3.45 g; 61.6 mmol), NH$_4$Cl (aq, sat, 30 mL) and EtOH (30 mL). Yield: 3.2 g (76%).

(d) N-(4-Fluoro-3-isothiocyanatobenzyl)-1-(trifluoromethyl)cyclopropane carboxamide A mixture of N-(3-amino-4-fluorobenzyl)-1-(trifluoromethyl)cyclopropanecarboxamide (3.17 g; 11.5 mmol) and TCDI (3.07 g; 17.2 mmol) in DCM (50 mL) was heated over night at 50° C. The mixture was concentrated and the residue purified by column chromatography to give the sub-title compound. Yield: 3 g (82%).

(e) 2-(2,2-Difluoroethoxy)-4-(methylamino)-5-nitrobenzoic acid

The sub-title compound was prepared in accordance with Example 72, step (b) using ethyl 2-(2,2-difluoroethoxy)-4-(methylamino)-5-nitrobenzoate ((950 mg; 3.12 mmol) see Example 59, step (f)), NaOH (3.1 mL; 2 M aq; 6.2 mmol) and 1,4-dioxane (10 mL). Yield: 800 mg (93%).

(f) N-(4-Bromophenyl)-2-(2,2-difluoroethoxy)-4-(methylamino)-5-nitrobenzamide The sub-title compound was prepared in accordance with Example 72, step (c) using 2-(2,2-difluoroethoxy)-4-(methylamino)-5-nitrobenzoic acid (800 mg; 2.90 mmol), 4-bromoaniline (499 mg; 2.90 mmol), HBTU (1.10 g; 2.90 mmol), TEA (587 mg; 5.80 mmol) and DMF (15 mL). Yield: 1.01 g (81%).

(g) 5-Amino-N-(4-bromophenyl)-2-(2,2-difluoroethoxy)-4-(methylamino)benzamide The sub-title compound was prepared by hydrogenation according to procedure 3d using N-(4-bromophenyl)-2-(2,2-difluoroethoxy)-4-(methylamino)-5-nitrobenzamide (1.01 g; 2.34 mmol), Ra—Ni (14 mg), H$_2$ (8 atm) and THF (50 mL). Yield: 905 mg (97%).

(h) N-(4-Bromo-phenyl)-2-(2-fluoro-5-{[(1-trifluoromethyl-cyclopropanecarbonyl)-amino]-methyl}-phenylamino)-6-(2,2-difluoro-ethoxy)-1-methyl-1H-benzimidazole-5-carboxylic acid amide The title compound was prepared in accordance with the procedure in Example 72, step (a) using N-(4-fluoro-3-isothiocyanatobenzyl)-1-(trifluoromethyl)cyclopropane carboxamide (160 mg; 0.50 mmol), 5-amino-N-(4-bromophenyl)-2-(2,2-difluoroethoxy)-4-(methylamino)benzamide (200 mg; 0.50 mmol), DIC (63 mg; 0.50 mmol) and DMF (4 mL). Yield: 25 mg (7%). 400 MHz $^1$H-NMR (DMSO-d$_6$, ppm) 10.06 (1H, s) 8.61 (1H, s) 8.39 (1H, t, J=5.8 Hz) 7.87-7.81 (1H, m) 7.73-7.65 (3H, m) 7.52-7.48 (2H, m) 7.29-7.26 (1H, m) 7.21-7.14 (1H, m) 6.91-6.86 (1H, m) 6.65-6.36 (1H, m) 4.55-4.46 (2H, m) 4.24 (2H, d, J=5.8 Hz) 3.71 (3H, s) 1.39-1.32 (2H, m) 1.23-1.20 (2H, m). MS m/z: 684, 686 [M+H]$^+$.

Example 67

N-(4-Bromo-phenyl)-2-(2-chloro-5-{[(1-trifluoromethyl-cyclopropanecarbonyl)-amino]-methyl}-phenylamino)-6-(2,2-difluoro-ethoxy)-1H-benzimidazole-5-carboxylic acid amide

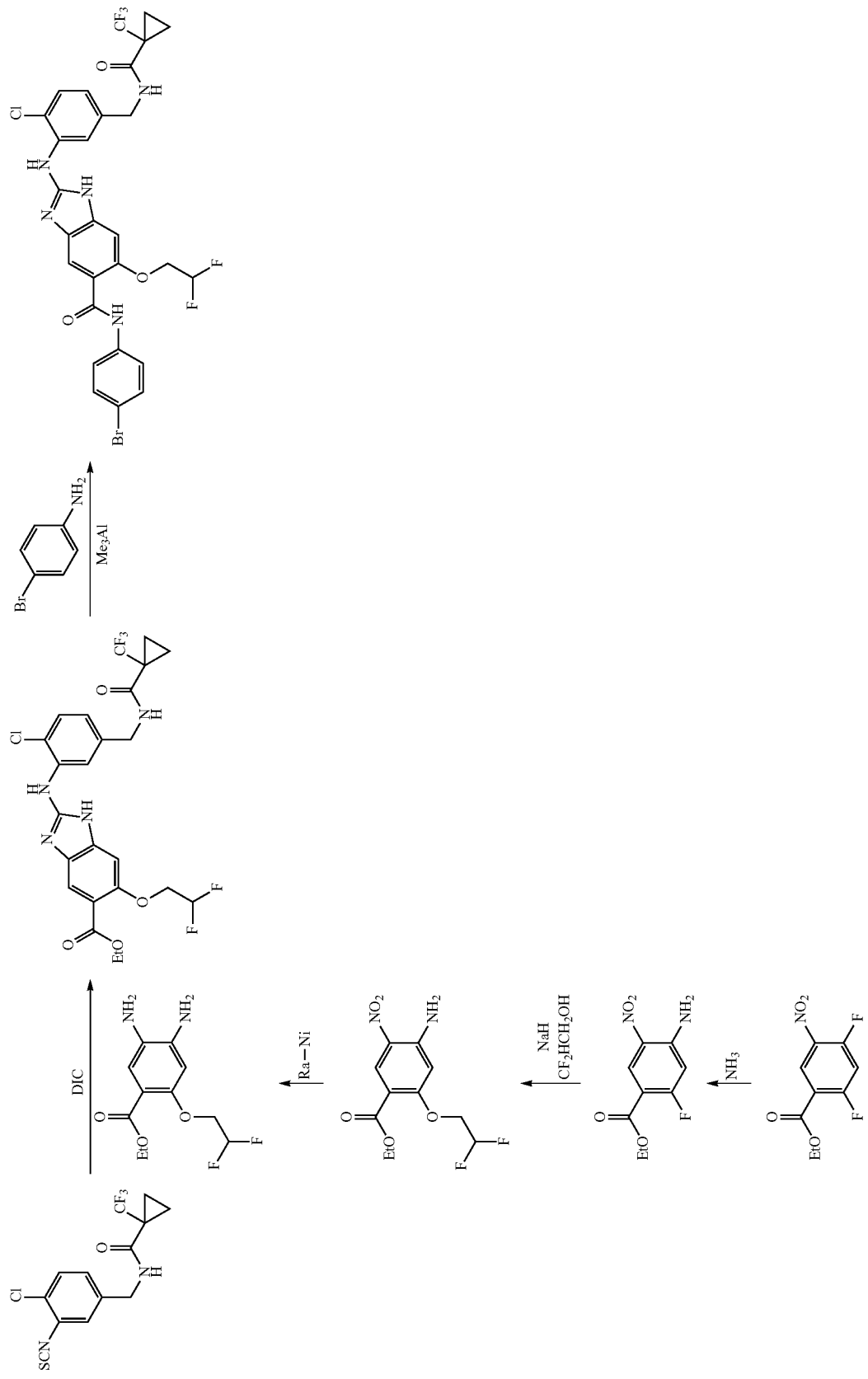

(a) Ethyl 4-amino-2-fluoro-5-nitrobenzoate

A mixture of ethyl 2,4-difluoro-5-nitrobenzoate (5.00 g; 21.6 mmol) (see Example 59 (d)) in THF (100 mL) was treated with $NH_3$ in THF (2.7 mL; 8 M; 21.6 mmol) at 0° C. and the mixture was stirred over night. Another portion of $NH_3$ in THF (1.0 mL; 8M; 8 mmol) was added and the mixture stirred over night. Water (100 mL) was added and the mixture was concentrated. The precipitate was filtered off and dried to give the sub-title compound.
Yield: 4.80 g (98%).

(b) Ethyl 4-amino-2-(2,2-difluoroethoxy)-5-nitrobenzoate

The sub-title compound was prepared in accordance with Example 59 (f) using ethyl 4-amino-2-fluoro-5-nitrobenzoate (4.80 g; 21.0 mmol), 2,2-difluoroethanol (1.73 g; 21.0 mmol), sodium hydride (0.841 g; 60%; 21.0 mmol), THF (100 mL) and DMF (50 mL).
Yield: 2.40 g (39%).

(c) Ethyl 4,5-diamino-2-(2,2-difluoroethoxy)benzoate

The sub-title compound was prepared in accordance with Example 59 (g) using ethyl 4-amino-2-(2,2-difluoroethoxy)-5-nitrobenzoate (1.00 g; 3.44 mmol), Ra—Ni (1.0 g) and THF (50 mL). The sub-title compound was used in the next step without further purification.

(d) Ethyl 2-(2-chloro-5-{[(1-trifluoromethyl-cyclopropanecarbonyl)-amino]-methyl}-phenylamino)-6-(2,2-difluoro-ethoxy)-1H-benzimidazole-5-carboxylate The sub-title compound was prepared in accordance with Example 59 (h) using ethyl 4,5-diamino-2-(2,2-difluoroethoxy)benzoate (0.466 g; 1.79 mmol; crude material from step (c)), N-(4-chloro-3-isothiocyanatobenzyl)-1-(trifluoromethyl)cyclopropane carboxamide (0.600 g; 1.79 mmol), DIC (0.226 g; 1.79 mmol) and THF (40 mL). Yield: 0.620 g (62%).

(e) N-(4-Bromo-phenyl)-2-(2-chloro-5-{[(1-trifluoromethyl-cyclopropanecarbonyl)-amino]-methyl}-phenylamino)-6-(2,2-difluoro-ethoxy)-1H-benzimidazole-5-carboxylic acid amide The title compound was prepared in accordance with Example 59 (i) using ethyl 2-(2-chloro-5-{[(1-trifluoromethyl-cyclopropanecarbonyl)-amino]-methyl}-phenylamino)-6-(2,2-difluoro-ethoxy)-1H-benzimidazole-5-carboxylate (0.200 g; 0.36 mmol), 4-bromoaniline (0.184 g; 1.07 mmol), $Me_3Al$ in toluene (0.900 mL; 2 M; 1.80 mmol) and 1,4-dioxane (10 mL). Yield: 0.115 g (47%). 400 MHz $^1$H-NMR (DMSO-$d_6$, ppm) 11.3-11.1 (1H, br s) 10.17 (1H, s) 9.1-8.8 (1H, br s) 8.65-8.57 (1H, m) 8.53 (1H, t, J=5.8 Hz) 7.95-7.90 (1H, m) 7.80-7.73 (2H, m) 7.63-7.57 (2H, m) 7.49 (1H, d, J=8.4 Hz) 7.31-7.26 (1H, m) 6.94 (1H, dd, J=8.2, 1.6 Hz) 6.59 (1H, tt, J=54.3, 3.1 Hz) 4.57 (2H, td, J=14.9, 3.0 Hz) 4.38 (2H, d, J=5.8 Hz) 1.54-1.47 (2H, m) 1.38-1.31 (2H, m). MS m/z: 686, 688, 690 [M+H]$^+$.

The following compounds were synthesized in analogy to the methods of preparation described above in detail.

| Ex. | Chemical structure<br>Name<br>$^1$H-NMR | MS m/z [M +H]$^+$ |
|---|---|---|
| 68 | 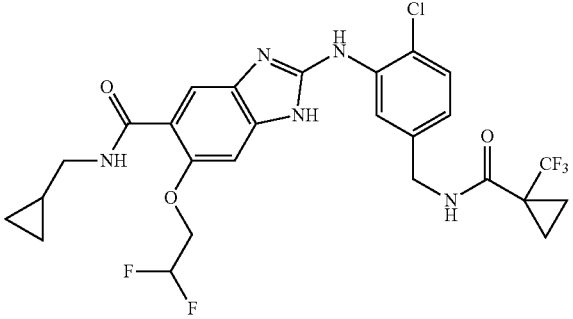 [SMILES: O=C(NCC1CC1)c1cc2nc(Nc3cc(CNC(=O)C4(C(F)(F)F)CC4)ccc3Cl)[nH]c2cc1OCC(F)F]<br>N-(Cyclopropylmethyl)-2-(2-chloro-5-[{(l-trifluoromethyl-cyclopropanecarbonyl)-amino]-methyl}-phenylamino)-6-(2,2-difluoro-ethoxy)-1H-benzimidazole-5-carboxylic acid amide<br>400 MHz $^1$H-NMR (DMSO-$d_6$, ppm) 11.0-10.7 (1H, br s) 8.8-8.5 (1H, br s) 8.36-8.29 (1H, m) 8.25 (1H, t, J = 5.8 Hz) 7.89 (1H, t, J = 5.2 Hz) 7.72-7.68 (1H, m) 7.20 (1H, d, J = 8.1 Hz) 6.97-6.90 (1H, m) 6.64 (1H, dd, J = 8.1, 1.8 Hz) 6.30 (1H, tt, J = 54.3, 3.1 Hz) 4.25 (2H, td, J = 14.8, 3.2 Hz) 4.09 (2H, d, J = 5.8 Hz) 3.00-2.94 (2H, m) 1.27-1.18 (2H, m) 1.09-1.02 (2H, m) 0.85-0.74 (1H, m) 0.28-0.20 (2H, m) 0.05-0.02 (2H, m) | 586,588 |

Example 69

N-(4-Bromo-phenyl)-2-(2-chloro-5-{[(1-trifluoromethyl-cyclopropanecarbonyl)-amino]-methyl}-phenylamino)-6-methoxy-1H-benzimidazole-5-carboxylic acid amide

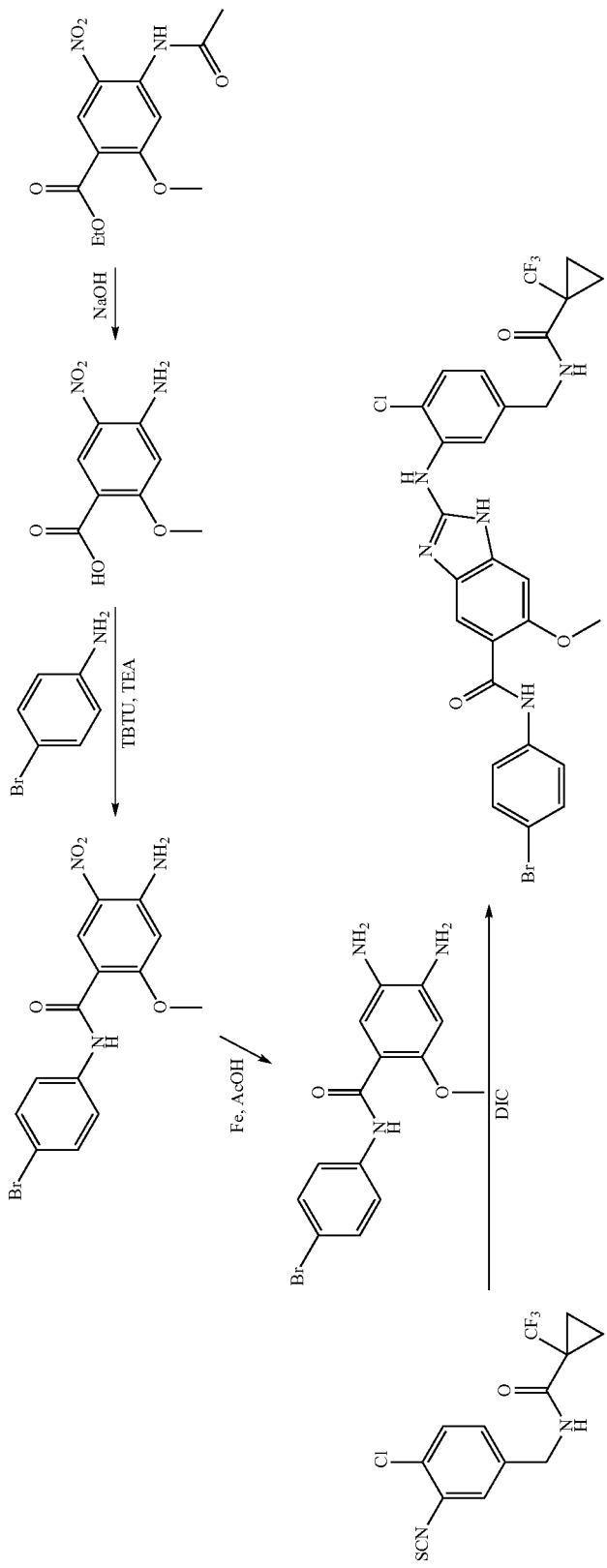

(a) 4-Amino-2-methoxy-5-nitrobenzoic acid

A mixture of ethyl 4-acetamido-2-methoxy-5-nitrobenzoate (4.0 g; 14.9 mmol) and NaOH (40 mL, 1 M aq; 40 mmol) in EtOH (80 mL) was refluxed for 2 h. The mixture was cooled to rt and water (20 mL) was added. The mixture was acidified by HCl (6 M aq) and the sub-title compound was filtered off. Yield: 3.0 g (95%).

(b) 4-Amino-N-(4-bromophenyl)-2-methoxy-5-nitrobenzamide

The sub-title compound was prepared in accordance with the procedure in Example 59, step (a) using 4-amino-2-methoxy-5-nitrobenzoic acid (2.0 g; 9.43 mmol), TBTU (3.33 g; 10.4 mmol), TEA (2.9 mL; 20.8 mmol), 4-bromoaniline (1.62 g; 9.43 mmol) and DMF (70 mL). Yield: 3.41 g (99%).

(c) 4,5-Diamino-N-(4-bromophenyl)-2-methoxybenzamide

A mixture of 4-amino-N-(4-bromophenyl)-2-methoxy-5-nitrobenzamide (1.30 g; 3.55 mmol), THF (80 mL) and EtOH (50 mL) was treated with AcOH (3 mL) and stirred for 15 min at 100° C. To the warm mixture, Fe (1.30 g; 23.3 mmol) was carefully added in portions and the resulting mixture was heated for 2 h at 100° C. The mixture was cooled, filtered through celite and concentrated to give the crude sub-title compound.

(d) N-(4-Bromo-phenyl)-2-(2-chloro-5-{[(1-trifluoromethyl-cyclopropanecarbonyl)-amino]-methyl}-phenylamino)-6-methoxy-1H-benzimidazole-5-carboxylic acid amide The title compound was prepared in accordance with the procedure in Example 72, step (a) using N-(4-chloro-3-isothiocyanatobenzyl)-1-(trifluoromethyl)cyclopropane carboxamide ((200 mg; 0.60 mmol) see Example 59, step (c)), 4,5-diamino-N-(4-bromophenyl)-2-methoxybenzamide (202 mg; 0.60 mmol), DIC (76 mg; 0.60 mmol) and DMF (4 mL). Yield: 63 mg (16%). 400 MHz $^1$H-NMR (DMSO-$d_6$, ppm) 11.12 (0.36H, s, minor tautomer) 11.00 (0.57H, s, major tautomer) 10.22-10.14 (1H, m) 8.94 (0.57H, s, major tautomer) 8.76 (0.36H, s, minor tautomer) 8.61-8.52 (1H, m) 8.48-8.41 (1H, m) 7.86-7.69 (3H, m) 7.53-7.45 (2H, m) 7.42-7.35 (1H, m) 7.21 (0.38H, s, minor tautomer) 7.10 (0.59H, s, major tautomer) 6.87-6.79 (1H, m) 4.29 (2H, d, J=5.8 Hz) 3.93 (3H, s) 1.49-1.39 (2H, m) 1.28-1.23 (2H, m). MS m/z: 636, 638, 640 [M+H]$^+$.

Example 70

N-(4-Bromo-phenyl)-2-(2-chloro-5-{[(1-trifluoromethyl-cyclopropanecarbonyl)-amino]-methyl}-phenylamino)-1-(2-(dimethylamino)ethyl)-1H-benzimidazole-5-carboxylic acid amide

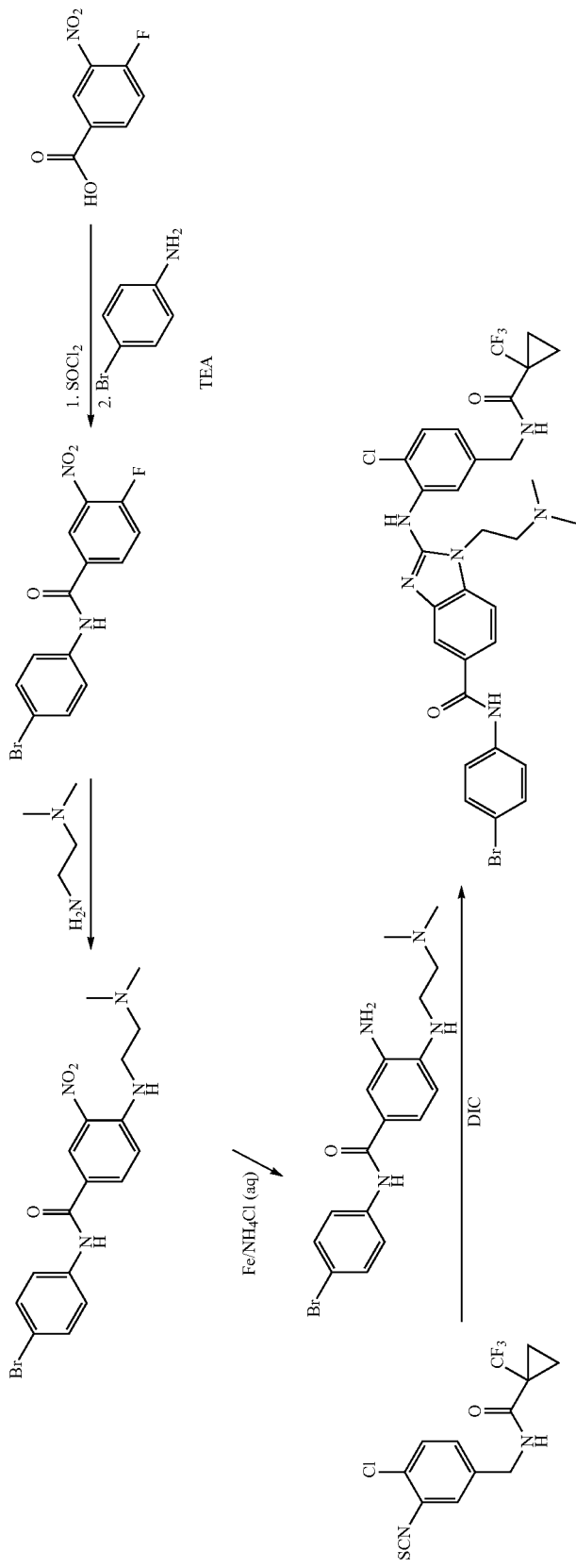

(a) N-(4-Bromophenyl)-4-fluoro-3-nitrobenzamide

A mixture of 4-fluoro-3-nitrobenzoic acid (10.0 g; 54.0 mmol), SOCl$_2$ (20.0 mL; 270 mmol) and DMF (2-3 drops) was refluxed for 4 h, concentrated and the residue was dissolved in DCM (25 mL) and slowly added to a mixture of 4-bromoaniline (9.3 g; 54.1 mmol) and TEA (11.4 mL; 81.0 mmol) in DCM (50 mL) at 0° C. The mixture was stirred for 1 h at rt, concentrated, EtOAc was added and the organic phase was washed with aqueous NaHCO$_3$, aqueous HCl (1 M), dried over Na$_2$SO$_4$, filtered and concentrated to give the sub-title compound. Yield: 18.0 g (98%).

(b) N-(4-Bromophenyl)-4-(2-(dimethylamino)ethylamino)-3-nitrobenzamide

A mixture of N-(4-bromophenyl)-4-fluoro-3-nitrobenzamide (400 mg; 1.18 mmol) and 2-dimethylamino ethylamine (208 mg; 2.36 mmol) in EtOH (5 mL) was stirred over night at 50° C. The mixture was then poured into aqueous NaHCO$_3$ and extracted with EtOAc. The organic layers were dried over Na$_2$SO$_4$, filtered and concentrated. Recrystallization from EtOAc/petroleum ether gave the crude sub-title compound (560 mg).

(c) 3-Amino-N-(4-bromophenyl)-4-(2-(dimethylamino)ethylamino)benzamide

The sub-title compound was prepared in accordance with the procedure in Example 2, step (b) using N-(4-bromophenyl)-4-(2-(dimethylamino)ethylamino)-3-nitrobenzamide (560 mg; 1.38 mmol), Fe (384 mg; 6.88 mmol), NH$_4$Cl (aq, sat, 10 mL) and EtOH (10 mL).

Yield: 475 mg (91%).

(d) N-(4-Bromo-phenyl)-2-(2-chloro-5-{[(1-trifluoromethyl-cyclopropanecarbonyl)-amino]-methyl}-phenylamino)-1-(2-(dimethylamino)ethyl)-1H-benzimidazole-5-carboxylic acid amide The title compound was prepared in accordance with the procedure in Example 72, step (a) using N-(4-chloro-3-isothiocyanatobenzyl)-1-(trifluoromethyl)cyclopropane carboxamide ((222 mg; 0.66 mmol) see Example 59, step (c)), 3-amino-N-(4-bromophenyl)-4-(2-(dimethylamino)ethylamino)benzamide (250 mg; 0.66 mmol), DIC (83 mg; 0.66 mmol) and DMF (4 mL). Yield: 151 mg (34%). 400 MHz $^1$H-NMR (DMSO-d$_6$, ppm) 10.37 (1H, s) 10.22 (1H, s) 8.39 (1H, t, J=5.8 Hz) 8.10 (1H, d, J=1.8 Hz) 8.06 (1H, d, J=1.6 Hz) 7.82-7.71 (3H, m) 7.53-7.46 (3H, m) 7.40 (1H, d, J=8.2 Hz) 6.86 (1H, dd, J=8.2, 1.8 Hz) 4.32-4.21 (4H, m) 2.74-2.68 (2H, m) 2.29 (6H, s) 1.37-1.32 (2H, m) 1.23-1.19 (2H, m).

MS m/z: 677, 679, 681 [M+H]$^+$.

The following compounds were synthesized in analogy to the methods of preparation described above in detail.

| Ex. | Chemical structure<br>Name<br>$^1$H-NMR | MS m/z [M + H]$^+$ |
|---|---|---|
| 71 | N-(4-Bromo-phenyl)-2-(2-chloro-5-{[(1-trifluoromethyl-cyclopropanecarbonyl)-amino]-methyl}-phenylamino)-1-(2-methoxyethyl)-1H-benzimidazole-5-carboxylic acid amide<br>400 MHz $^1$H-NMR (DMSO-d$_6$, ppm) 10.24 (1H, s) 8.64 (1H, s) 8.42 (1H, t, J = 6.0 Hz) 8.21 (1H, d, J = 2.0 Hz) 8.08 (1H, d, J = 1.6 Hz) 7.81-7.74 (3H, m) 7.54 (1H, d, J = 8.4 Hz) 7.52-7.47 (2H, m) 7.43 (1H, d, J = 8.2 Hz) 6.88 (1H, dd, J = 8.2, 2.0 Hz) 4.45-4.38 (2H, m) 4.27 (2H, d, J = 6.0 Hz) 3.77-3.71 (2H, m) 3.34 (3H, s) 1.39-1.34 (2H, m) 1.25-1.19 (2H, m) | 664, 666, 668 |

Example 72

N-(4-Bromo-phenyl)-2-(2-chloro-5-{[(1,1-difluoro-ethylcarbonyl)-amino]-methyl}-phenylamino)-6-(2,2-difluoro-ethoxy)-1-methyl-1H-benzimidazole-5-carboxylic acid amide

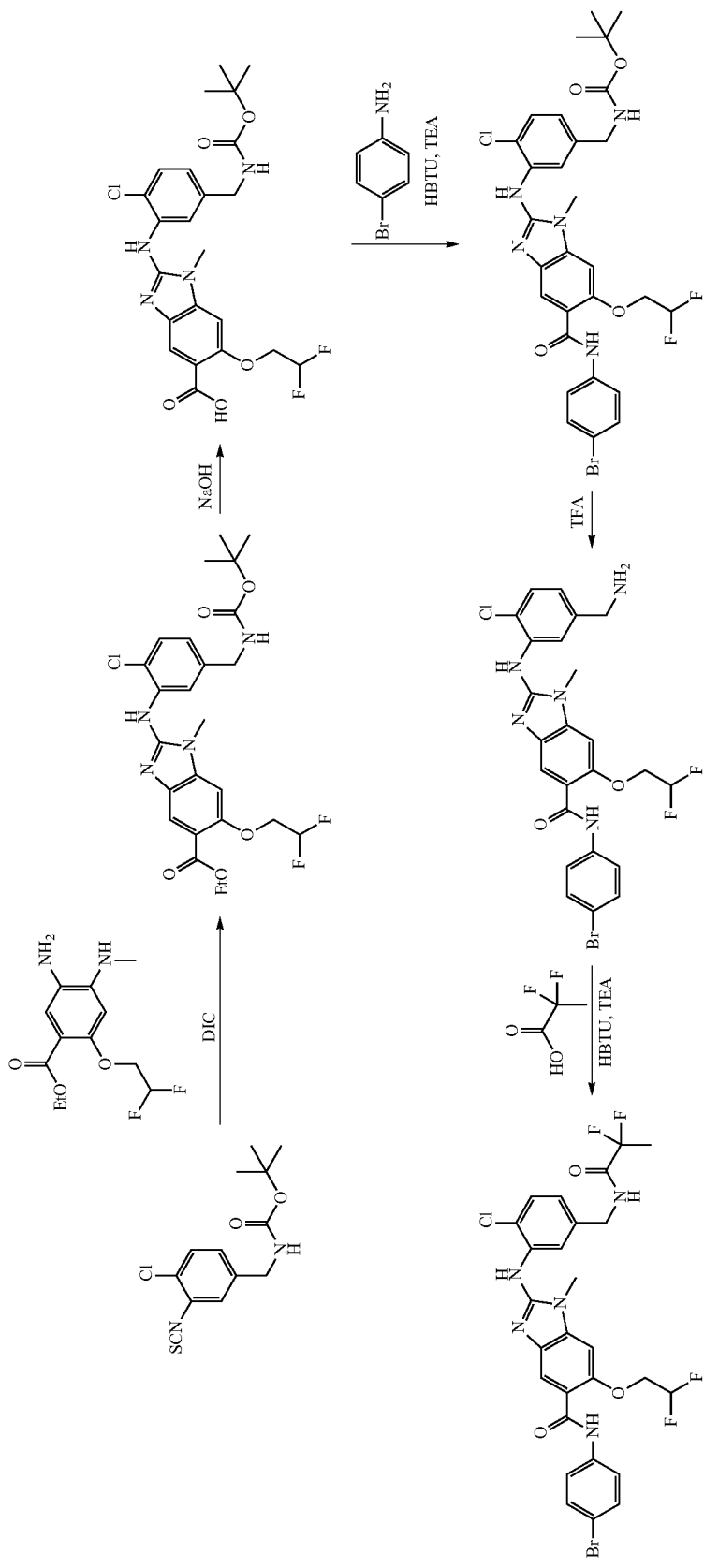

(a) Ethyl-2-(2-chloro-5-{[(tert-butoxycarbonyl)-amino]-methyl}-phenylamino)-6-(2,2-difluoro-ethoxy)-1-methyl-1H-benzimidazole-5-carboxylate A mixture of tert-butyl 4-chloro-3-isothiocyanatobenzyl-carbamate ((see Example 2, step (c)) 974 mg; 3.26 mmol) and ethyl 5-amino-2-(2,2-difluoroethoxy)-4-(methylamino)benzoate ((see Example 59, step (g)) 894 mg; 3.26 mmol) in DMF (10 mL) was stirred over night at rt. DIC (411 mg; 3.26 mmol) was added and the mixture was heated at 90° C. for 1.5 h. The mixture was concentrated and the residue was recrystallized from EtOAc/petroleum ether and washed with $Et_2O$ to give the sub-title compound. Yield: 1.75 g (99%).

(b) 2-(2-Chloro-5-{[(tert-butoxycarbonyl)-amino]-methyl}-phenylamino)-6-(2,2-difluoro-ethoxy)-1-methyl-1H-benzimidazole-5-carboxylic acid A mixture of ethyl-2-(2-chloro-5-{[(tert-butoxycarbonyl)-amino]-methyl}-phenylamino)-6-(2,2-difluoro-ethoxy)-1-methyl-1H-benzimidazole-5-carboxylate (1.35 g; 2.50 mmol), NaOH (4 mL; 2 M aq; 8 mmol) and 1,4-dioxane (15 mL) was refluxed for 3 h. After cooling to rt the mixture was acidified to pH ~5-6 and extracted with EtOAc. The organic extracts were dried over $Na_2SO_4$, filtered and concentrated. The residue was washed with $Et_2O$ to give the sub-title compound. Yield: 1.12 g (88%).

(c) N-(4-Bromo-phenyl)-2-(2-chloro-5-{[(tert-butoxycarbonyl)-amino]-methyl}-phenylamino)-6-(2,2-difluoro-ethoxy)-1-methyl-1H-benzimidazole-5-carboxylic acid amide A mixture of 2-(2-chloro-5-{[(tert-butoxycarbonyl)-amino]-methyl}-phenylamino)-6-(2,2-difluoro-ethoxy)-1-methyl-1H-benzimidazole-5-carboxylic acid (1.12 g; 2.19 mmol), HBTU (831 mg; 2.19 mmol) and TEA (433 mg; 4.38 mmol) in DMF (10 mL) was stirred for 30 min at rt and thereafter added to a solution of 4-bromoaniline (377 mg; 2.19 mmol) in DMF (10 mL). The resulting mixture was stirred over night at rt, poured into brine and extracted with EtOAc. The organic extracts were dried over $Na_2SO_4$, filtered and concentrated. The residue was purified by column chromatography to give the sub-title compound. Yield: 1.35 g (93%).

(d) N-(4-Bromo-phenyl)-2-(2-chloro-5-{[amino]-methyl}-phenylamino)-6-(2,2-difluoro-ethoxy)-1-methyl-1H-benzimidazole-5-carboxylic acid amide A mixture of N-(4-bromo-phenyl)-2-(2-chloro-5-{[(tert-butoxycarbonyl)-amino]-methyl}-phenylamino)-6-(2,2-difluoro-ethoxy)-1-methyl-1H-benzimidazole-5-carboxylic acid amide (1.35 g; 2.03 mmol) and TFA (3.47 g; 30.5 mmol) in DCM (75 mL) was stirred over night at rt. The mixture was cooled to 0° C. and basicified to pH ~10 and extracted with DCM. The organic extracts were dried over $Na_2SO_4$, filtered and concentrated. The residue was washed with a mixture of $Et_2O$ and petroleum ether to give the sub-title compound. Yield: 1.15 g (100%).

(e) N-(4-Bromo-phenyl)-2-(2-chloro-5-{[(1,1-difluoro-ethylcarbonyl)-amino]-methyl}-phenylamino)-6-(2,2-difluoro-ethoxy)-1-methyl-1H-benzimidazole-5-carboxylic acid amide The title compound was prepared in accordance with Example 72, step (c) using N-(4-bromo-phenyl)-2-(2-chloro-5-{[amino]-methyl}-phenylamino)-6-(2,2-difluoro-ethoxy)-1-methyl-1H-benzimidazole-5-carboxylic acid amide (170 mg; 0.30 mmol), 2,2-difluoropropanoic acid (33 mg; 0.30 mmol), HBTU (114 mg; 0.30 mmol), TEA (61 mg; 0.60 mmol) and DMF (3 mL). Yield: 63 mg (32%). 400 MHz $^1$H-NMR (DMSO-$d_6$, ppm) 10.07 (1H, s) 9.30 (1H, t, J=5.8 Hz) 8.35 (1H, s) 7.87-7.82 (1H, m) 7.73-7.60 (3H, m) 7.53-7.39 (3H, m) 7.33-7.27 (1H, m) 6.99-6.90 (1H, m) 6.66-6.34 (1H, m) 4.59-4.44 (2H, m) 4.30 (2H, d, J=5.8 Hz) 3.71 (2.38H, s, major tautomer) 3.43 (0.41H, s, minor tautomer) 1.74 (3H, t, J=19.6 Hz). MS m/z: 656, 658, 660 [M+H]$^+$.

The following compounds were synthesized in analogy to the methods of preparation described above in detail.

| Ex. | Chemical structure<br>Name<br>$^1$H-NMR | MS m/z [M + H]$^+$ |
|---|---|---|
| 73 | N-(4-Bromo-phenyl)-2-(2-chloro-5-{[(1-trifluoromethyl-ethyl-carbonyl)-amino]-methyl}-phenylamino)-6-(2,2-difluoro-ethoxy)-1-methyl-1H-benzimidazole-5-carboxylic acid amide<br>400 MHz $^1$H-NMR (DMSO-$d_6$, ppm) 10.06 (1H, s) 8.86-8.76 (1H, m) 8.34 (1H, s) 7.87-7.81 (1H, m) 7.76-7.59 (3H, m) 7.53-7.38 (3H, m) 7.34-7.27 (1H, m) 6.99-6.88 (1H, m) 6.67-6.33 (1H, m) 4.59-4.43 (2H, m) 4.35-4.21 (2H, m) 3.71 (2.61H, s, major tautomer) 3.42 (0.46H, s, minor tautomer) 3.37-3.30 (1H, m) 1.25 (3H, d, J = 7.0 Hz) | 688, 690, 692 |

| Ex. | Chemical structure<br>Name<br>¹H-NMR | MS m/z [M + H]⁺ |
|---|---|---|
| 74 | 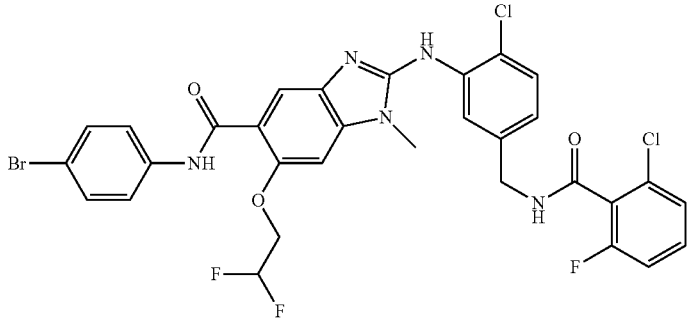 [SMILES: Cn1c(Nc2cc(CNC(=O)c3c(F)cccc3Cl)ccc2Cl)nc2cc(C(=O)Nc3ccc(Br)cc3)c(OCC(F)F)cc21]<br>N-(4-Bromo-phenyl)-2-(2-chloro-5-{[(2-chloro-6-fluorophenylcarbonyl)-amino]-methyl}-phenylamino)-6-(2,2-difluoro-ethoxy)-1-methyl-1H-benzimidazole-5-carboxylic acid amide<br>400 MHz ¹H-NMR (DMSO-$d_6$, ppm) 10.11-9.95 (1H, m) 9.29-9.12 (1H, m) 8.39 (1H, s) 7.94-7.81 (1H, m) 7.76-7.58 (3H, m) 7.54-7.38 (4H, m) 7.36-7.20 (3H, m) 7.12-7.02 (1H, m) 6.68-6.34 (1H, m) 4.57-4.39 (4H, m) 3.71 (2.48H, s, major tautomer) 3.43 (0.46H, s, minor tautomer) | 720, 722, 724 |
| 75 | 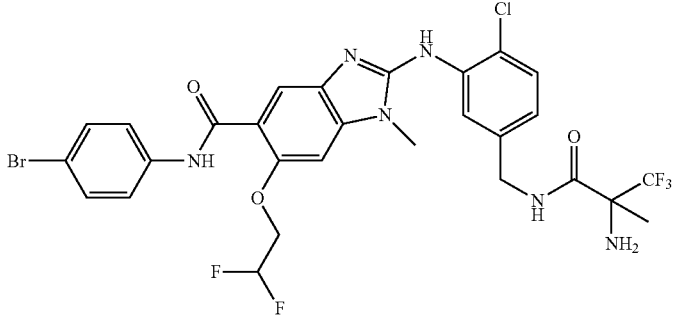 [SMILES: Cn1c(Nc2cc(CNC(=O)C(C)(N)C(F)(F)F)ccc2Cl)nc2cc(C(=O)Nc3ccc(Br)cc3)c(OCC(F)F)cc21]<br>N-(4-Bromo-phenyl)-2-(2-chloro-5-{[(1-amino-1-trifluoromethyl-ethyl-carbonyl)-amino]-methyl}-phenylamino)-6-(2,2-difluoro-ethoxy)-1-methyl-1H-benzimidazole-5-carboxylic acid amide<br>400 MHz ¹H-NMR (DMSO-$d_6$, ppm) 10.09-9.96 (1H, m) 8.68 (1H, t, J = 6.2 Hz) 8.32 (1H, s) 7.85-7.77 (1H, m) 7.73-7.58 (3H, m) 7.53-7.45 (2H, m) 7.42 (1H, d, J = 8.2 Hz) 7.33-7.27 (1H, m) 6.98-6.91 (1H, m) 6.66-6.34 (1H, m) 4.57-4.44 (2H, m) 4.34-4.20 (2H, m) 3.70 (2.38H, s, major tautomer) 3.42 (0.43H, s, minor tautomer) 2.55 (2H, s) 1.37 (3H, s) | 703, 705, 707 |
| 76 | 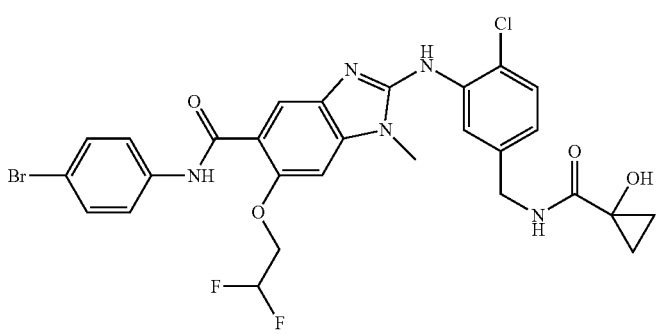 [SMILES: Cn1c(Nc2cc(CNC(=O)C3(O)CC3)ccc2Cl)nc2cc(C(=O)Nc3ccc(Br)cc3)c(OCC(F)F)cc21]<br>N-(4-Bromo-phenyl)-2-(2-chloro-5-{[(1-hydroxycyclopropanecarbonyl)-amino]-methyl}-phenylamino)-6-(2,2-difluoro-ethoxy)-1-methyl-1H-benzimidazole-5-carboxylic acid amide<br>400 MHz ¹H-NMR (DMSO-$d_6$, ppm) 10.11-9.95 (1H, m) 8.47 (1H, t, J = 6.2 Hz) 8.41-8.33 (1H, m) 7.79-7.59 (4H, m) 7.53-7.47 (2H, m) 7.41 (1H, d, J = 8.2 Hz) 7.32-7.27 (1H, m) 7.03-6.96 (1H, m) 6.66-6.35 (1H, m) 6.22 (1H, s) 4.56-4.44 (2H, m) 4.27 (2H, d, J = 6.2 Hz) 3.70 (2.64H, s, major tautomer) 3.43 (0.37H, s, minor tautomer) 1.03-0.95 (2H, m) 0.84-0.77 (2H, m) | 648, 650, 652 |

| Ex. | Chemical structure<br>Name<br>¹H-NMR | MS m/z [M + H]⁺ |
|---|---|---|
| 77 | 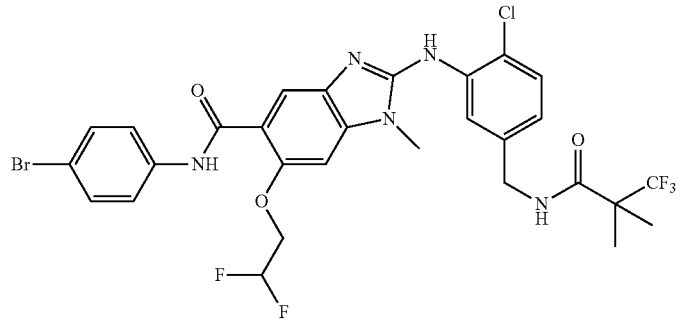 [SMILES: Cn1c(Nc2cc(CNC(=O)C(C)(C)C(F)(F)F)ccc2Cl)nc2cc(C(=O)Nc3ccc(Br)cc3)c(OCC(F)F)cc21]<br><br>N-(4-Bromo-phenyl)-2-(2-chloro-5-{[(1-methyl-1-trifluoromethyl-ethylcarbonyl)-amino]-methyl}-phenylamino)-6-(2,2-difluoro-ethoxy)-1-methyl-1H-benzimidazole-5-carboxylic acid amide<br>400 MHz ¹H-NMR (DMSO-d₆, ppm) 10.06 (1H, s) 8.62-8.50 (1H, m) 8.35-8.23 (1H, m) 7.91-7.82 (1H, m) 7.74-7.63 (3H, m) 7.53-7.47 (2H, m) 7.43-7.38 (1H, m) 7.34-7.28 (1H, m) 6.95-6.85 (1H, m) 6.65-6.37 (1H, m) 4.56-4.47 (2H, m) 4.27 (2H, d, J = 5.6 Hz) 3.71 (3H, s) 1.36 (6H, s) | 702, 704, 706 |

Example 78

N-(4-Bromo-phenyl)-2-(2-chloro-5-{[(tert-butylcarbonyl)-amino]-methyl}-phenylamino)-6-(2,2-difluoro-ethoxy)-1-methyl-1H-benzimidazole-5-carboxylic acid amide

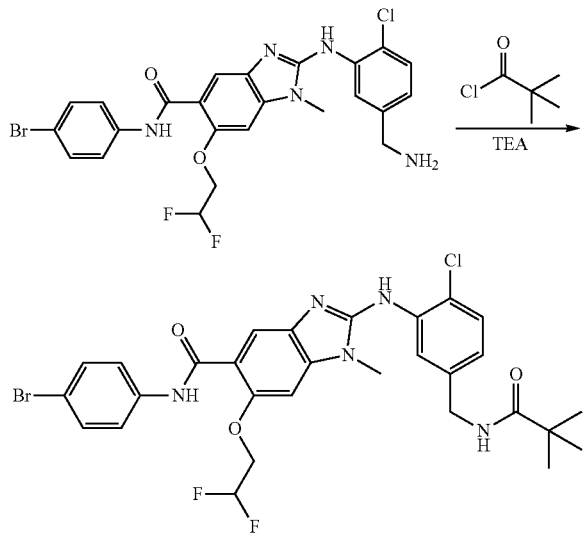

A solution of pivaloyl chloride (34 mg; 0.28 mmol) in DCM (1 mL) was added dropwise to a mixture of N-(4-bromo-phenyl)-2-(2-chloro-5-{[amino]-methyl}-phenylamino)-6-(2,2-difluoro-ethoxy)-1-methyl-1H-benzimidazole-5-carboxylic acid amide ((see Example 72, step (d)) 150 mg; 0.27 mmol), TEA (41 mg; 0.41 mmol) and DCM (2 mL) at 0° C. The resulting mixture was stirred over night at rt, poured into water and extracted with DCM. The organic extracts were washed with brine, dried over Na₂SO₄, filtered and concentrated. The residue was recrystallized from EtOAc/petroleum ether to give the title compound.

Yield: 119 mg (68%). 400 MHz ¹H-NMR (DMSO-d₆, ppm) 10.09-9.96 (1H, m) 8.27 (1H, s) 8.10 (1H, t, J=5.8 Hz) 7.89-7.84 (1H, m) 7.75-7.61 (3H, m) 7.54-7.46 (2H, m) 7.39 (1H, d, J=8.2 Hz) 7.33-7.27 (1H, m) 6.95-6.87 (1H, m) 6.67-6.35 (1H, m) 4.58-4.44 (2H, m) 4.22 (2H, d, J=5.8 Hz) 3.70 (2.63H, s, major tautomer) 3.42 (0.33H, s, minor tautomer) 1.10 (9H, s). MS m/z: 648, 650, 652 [M+H]⁺.

The following compounds were synthesized in analogy to the methods of preparation described above in detail.

| Ex. | Chemical structure<br>Name<br>¹H-NMR | MS m/z [M + H]⁺ |
|---|---|---|
| 79 | 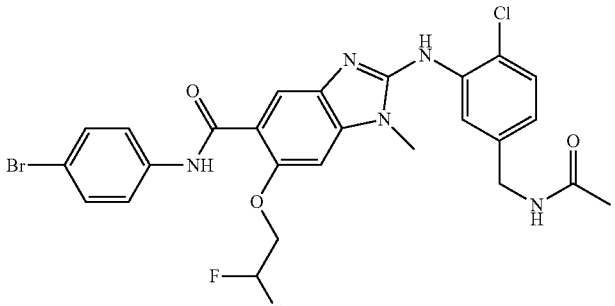<br>N-(4-Bromo-phenyl)-2-(2-chloro-5-{[(methylcarbonyl)-amino]-methyl}-phenylamino)-<br>6-(2,2-difluoro-ethoxy)-1-methyl-1H-benzimidazole-5-carboxylic acid amide<br>400 MHz ¹H-NMR (DMSO-d₆, ppm) 10.09-9.96 (1H, m) 8.45-8.24 (2H, m) 7.82-7.75<br>(1H, m) 7.74-7.59 (3H, m) 7.53-7.38 (3H, m) 7.33-7.26 (1H, m) 7.00-6.91 (1H, m)<br>6.68-6.31 (1H, m) 4.57-4.43 (2H, m) 4.21 (2H, d, J = 6.0 Hz) 3.70 (2.58H, s, major<br>tautomer) 3.42 (0.38H, s, minor tautomer) 1.84 (3H, s) | 606, 608, 610 |
| 80 | 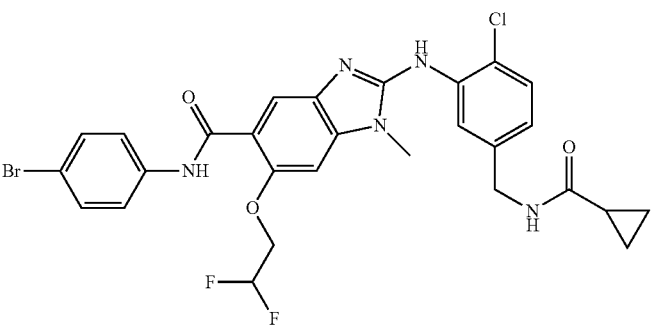 [SMILES: Cn1c(Nc2cc(CNC(=O)C3CC3)ccc2Cl)nc2cc(C(=O)Nc3ccc(Br)cc3)c(OCC(F)F)cc21]<br>N-(4-Bromo-phenyl)-2-(2-chloro-5-{[(cyclopropylcarbonyl)-amino]-methyl}-phenylamino)-<br>6-(2,2-difluoro-ethoxy)-1-methyl-1H-benzimidazole-5-carboxylic acid amide<br>400 MHz ¹H-NMR (DMSO-d₆, ppm) 10.09- 9.96 (1H, m) 8.62-8.56 (1H, m) 8.37 (1H, s) 7.80-<br>7.76 (1H, m) 7.73-7.62 (3H, m) 7.53-7.47 (2H, m) 7.41 (1H, d, J = 8.2 Hz) 7.33-7.27 (1H, m)<br>6.98-6.92 (1H, m) 6.65-6.35 (1H, m) 4.55-4.45 (2H, m) 4.24 (2H, d, J = 5.8 Hz) 3.70 (2.36H, s,<br>major tautomer) 3.42 (0.47H, s, minor tautomer) 1.61-1.53 (1H, m) 0.69-0.59 | 632, 634, 636 |
| 81 | 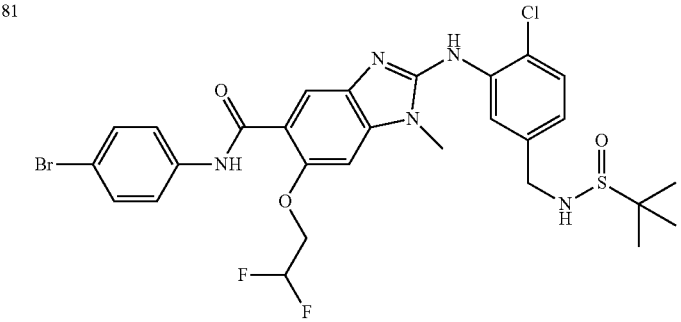<br>N-(4-Bromo-phenyl)-2-(2-chloro-5-{[(tert-butylsulfinyl)-amino]-methyl}-phenylamino)-<br>6-(2,2-difluoro-ethoxy)-1-methyl-1H-benzimidazole-5-carboxylic acid amide<br>400 MHz ¹H-NMR (DMSO-d₆, ppm) 10.10-9.95 (1H, m) 8.32 (1H, s) 8.01 (1H, s) 7.75-7.58<br>(3H, m) 7.56-7.36 (3H, m) 7.35-7.26 (1H, m) 7.14-6.98 (1H, m) 6.68-6.33 (1H, m) 5.84-5.73<br>(1H, m) 4.59-4.42 (2H, m) 4.24-4.03 (2H, m) 3.71 (2.53H, s, major tautomer) 3.43 (0.46H, s,<br>minor tautomer) 1.12 (9H, s) | 668, 670, 672 |

Example 82

N-(4-Bromo-phenyl)-2-(2-chloro-5-{[(tert-butylsulfonyl)-amino]-methyl}-phenylamino)-6-(2,2-difluoro-ethoxy)-1-methyl-1H-benzimidazole-5-carboxylic acid amide

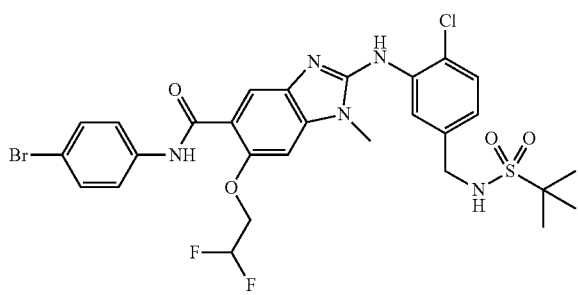 [SMILES: Cn1c(Nc2cc(CNS(=O)(=O)C(C)(C)C)ccc2Cl)nc2cc(C(=O)Nc3ccc(Br)cc3)c(OCC(F)F)cc21]

A mixture of N-(4-bromo-phenyl)-2-(2-chloro-5-{[(tert-butylsulfinyl)-amino]-methyl}-phenylamino)-6-(2,2-difluoro-ethoxy)-1-methyl-1H-benzimidazole-5-carboxylic acid amide (100 mg; 0.15 mmol), m-chloroperoxybenzoic acid (28 mg; 0.16 mmol) and DCM (20 mL) was stirred over night at rt. The mixture was basicified to pH ~8-9 and extracted with EtOAc. The organic extracts were dried over $Na_2SO_4$, filtered and concentrated. The residue was purified by column chromatography to give the title compound. Yield: 24 mg (23%). 200 MHz $^1$H-NMR (DMSO-$d_6$, ppm) 10.06-10.02 (1H, m) 7.75-7.62 (4H, m) 7.54-7.44 (4H, m) 7.27-7.17 (2H, m) 6.95-6.84 (1H, m) 6.57-6.49 (1H, m) 4.58-4.42 (2H, m) 4.16-4.09 (2H, m) 3.57-3.51 (3H, m) 1.29 (9H, s). MS m/z: 684, 686, 690 [M+H]$^+$.

Example 83

N-(4-Bromo-phenyl)-2-(2-trifluoromethyl-5-{[(1-trifluoromethyl-cyclopropanecarbonyl)-amino]-methyl}-phenylamino)-6-(2,2-difluoro-ethoxy)-1-methyl-1H-benzimidazole-5-carboxylic acid amide

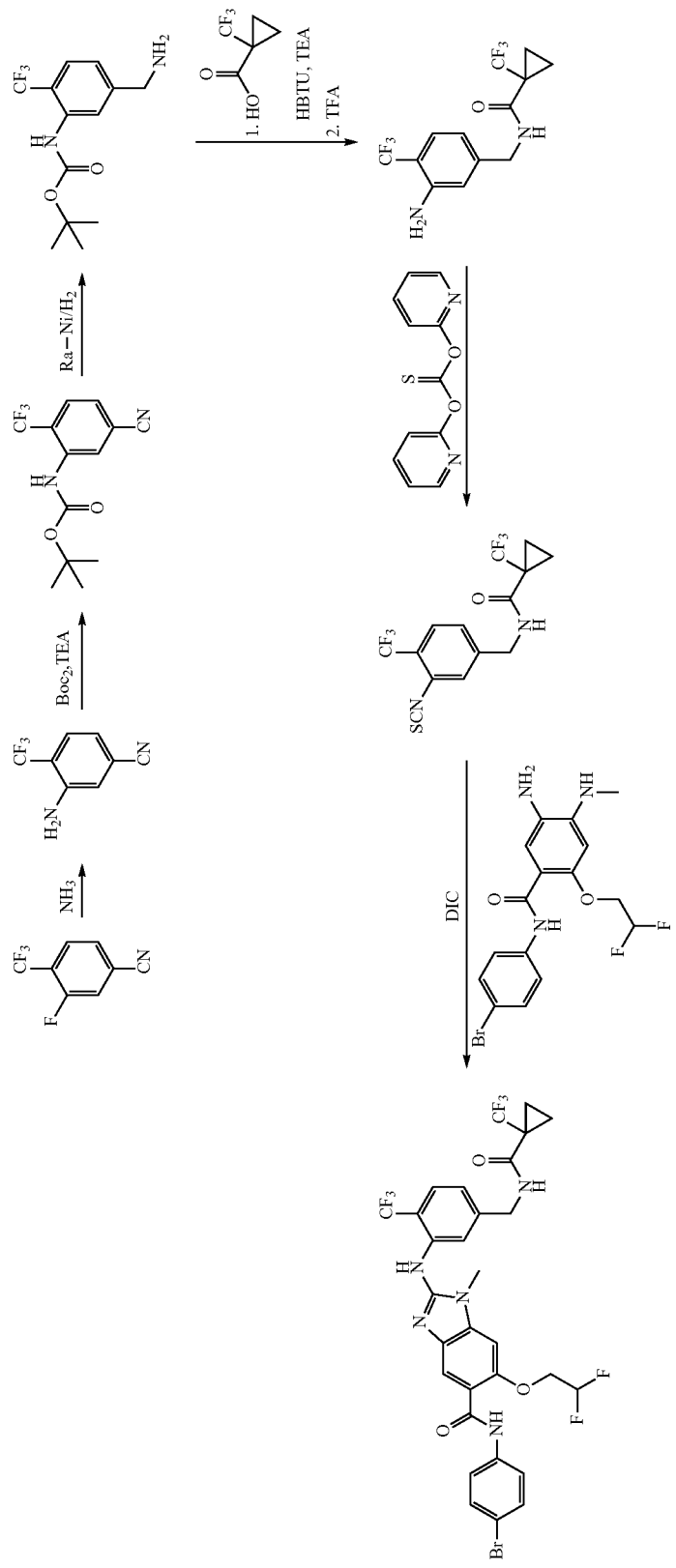

(a) 3-Amino-4-(trifluoromethyl)benzonitrile

A closed pressure tube charged with 3-fluoro-4-(trifluoromethyl)benzonitrile (10.0 g; 52.9 mmol) and liquid NH$_3$ (60 mL) was heated for 6 days at 90° C. The tube was cooled to −60° C. and opened. The mixture was allowed to stir for 1 h at rt. The residue was treated with brine and extracted with EtOAc to give the crude sub-title compound (10.2 g).

(b) tert-Butyl N-[5-cyano-2-(trifluoromethyl)phenyl]-carbamate

A mixture of 3-amino-4-(trifluoromethyl)benzonitrile (10.0 g; 53.7 mmol), DCM (100 mL) and TEA (8.2 mL; 59 mmol) was treated dropwise with a solution of Boc$_2$O (12.9 g; 59.1 mmol) in DCM (50 mL) at 0° C. and thereafter stirred over night. Another portion of Boc$_2$O in DCM and DMAP (656 mg; 5.37 mmol) was added and the mixture was stirred for another 12 h at rt, washed with water and brine, dried over Na$_2$SO$_4$, filtered and concentrated. The residue was purified by column chromatography to give the sub-title compound. Yield: 8.50 g (55%).

(c) tert-Butyl N-[5-(aminomethyl)-2-(trifluoromethyl)phenyl]-carbamate

The sub-title compound was prepared in accordance with the procedure in Example 59, step (g) using tert-butyl N-[5-cyano-2-(trifluoromethyl)phenyl]-carbamate (8.5 g; 29.7 mmol), Ra—Ni (174 mg; 2.97 mmol), H$_2$ (5 atm) and THF (60 mL). Yield: 8 g (93%).

(d) N-(3-Amino-4-(trifluoromethyl)-benzyl)-1-(trifluoromethyl)-cyclopropanecarboxamide The sub-title compound was prepared in accordance with the procedures in Example 72, step (c) and Example 72, step (d) using tert-butyl N-[5-(aminomethyl)-2-(trifluoromethyl)phenyl]-carbamate (2.09 g; 7.20 mmol), 1-(trifluoromethyl)-cyclopropanecarboxylic acid (1.11 g; 7.20 mmol), HBTU (2.73 g; 7.20 mmol), TEA (2.19 g; 21.6 mmol), DMF (25 mL), TFA (10 mL) and DCM (50 mL). Yield: 1.8 g (77%).

(e) N-(4-Trifluoromethyl-3-isothiocyanato-benzyl)-1-(trifluoromethyl)cyclopropane carboxamide A mixture of N-(3-amino-4-(trifluoromethyl)-benzyl)-1-(trifluoromethyl)-cyclopropanecarboxamide (1.60 g; 4.90 mmol), di-(2-pyridyl)thionocarbonate (1.71 g; 7.36 mmol) and THF (40 mL) was stirred in a pressure tube for 2 days at 60° C. The mixture was concentrated and the residue purified by column chromatography to give the sub-title compound. Yield: 1.29 g (72%).

(f) N-(4-Bromo-phenyl)-2-(2-trifluoromethyl-5-{[(1-trifluoromethyl-cyclopropanecarbonyl)-amino]-methyl}-phenylamino)-6-(2,2-difluoro-ethoxy)-1-methyl-1H-benzimidazole-5-carboxylic acid amide The title compound was prepared in accordance with the procedure in Example 72, step (a) using N-(4-trifluoromethyl-3-isothiocyanato-benzyl)-1-(trifluoromethyl)cyclopropane carboxamide (184 mg; 0.50 mmol), 5-amino-N-(4-bromophenyl)-2-(2,2-difluoroethoxy)-4-(methylamino)benzamide (200 mg; 0.50 mmol), DIC (63 mg; 0.50 mmol) and DMF (4 mL). Yield: 59 mg (16%). 400 MHz $^1$H-NMR (DMSO-d$_6$, ppm) 10.62 (0.57H, s, major tautomer) 10.09-9.96 (1H, m) 8.47-8.41 (0.38H, m, minor tautomer) 8.36-8.28 (1H, m) 7.72-7.61 (3H, m) 7.58-7.47 (3H, m) 7.36-7.28 (1H, m) 7.12-6.84 (2H, m) 6.67-6.35 (1H, m) 4.58-4.45 (2H, m) 4.34-4.25 (2H, m) 3.64 (0.96H, s, minor tautomer) 3.41 (1.93H, s, major tautomer) 1.31-1.17 (4H, m). MS m/z: 734, 736 [M+H]$^+$.

Example 84

2-(2-Chloro-4-fluoro-5-{[(1-(trifluoromethyl)cyclopropanecarbonyl)amino]methyl}-phenylamino)-6-(2,2-difluoroethoxy)-1-methyl-N-(trans-4-trifluoromethyl-cyclohex-1-yl)-1H-benzo[d]imidazole-5-carboxamide

(a) 4-Chloro-2-fluoro-5-nitrobenzonitrile

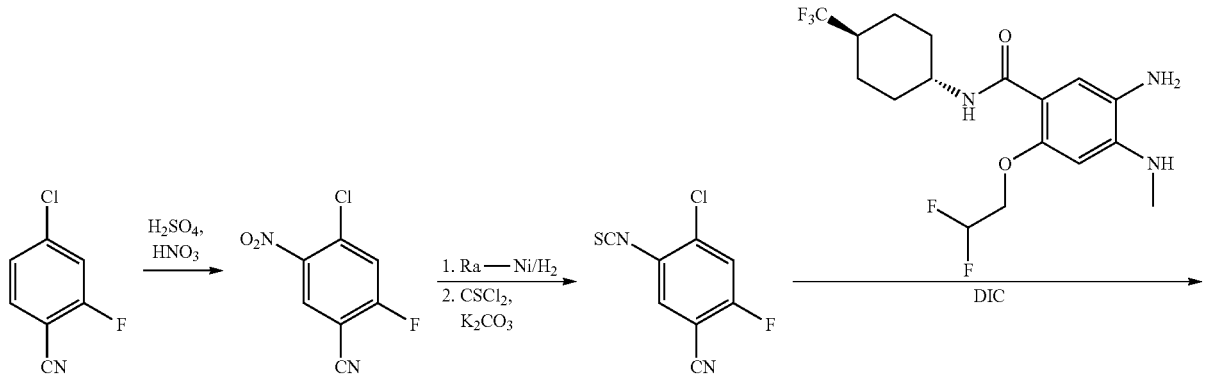

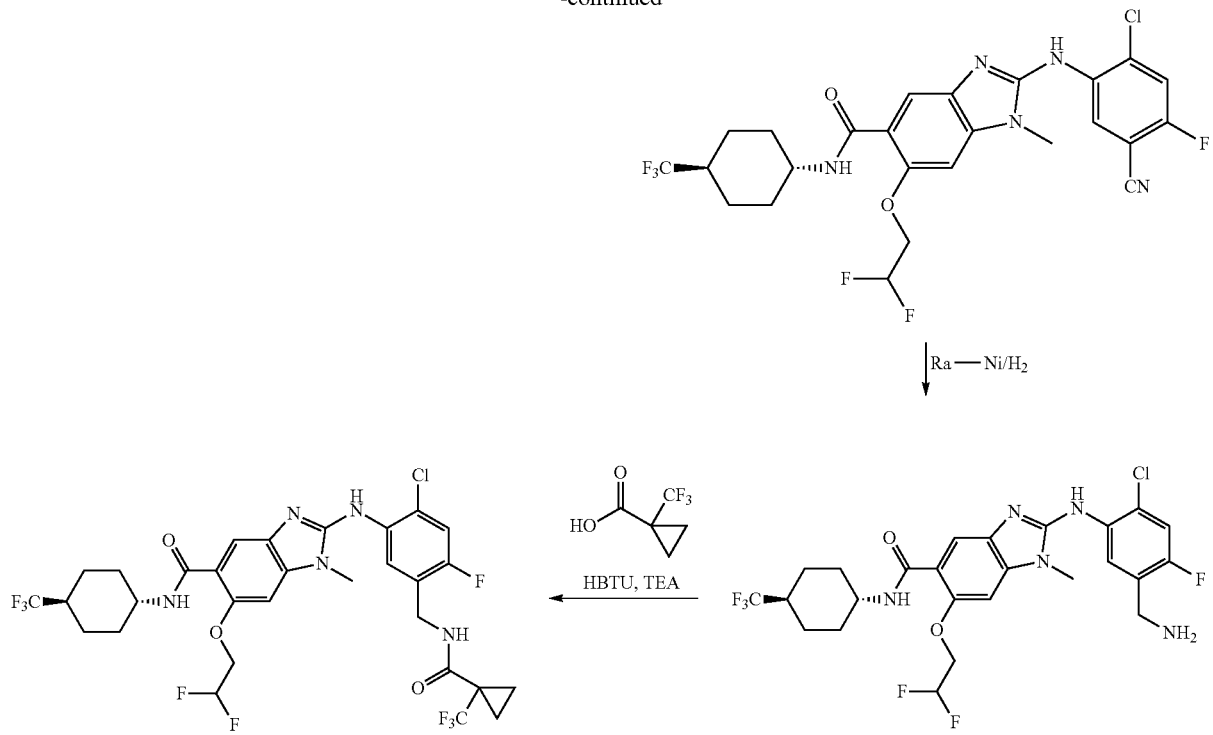

A mixture of 4-chloro-2-fluorobenzonitrile (4.62 g; 29.7 mmol) in conc. H₂SO₄ (42 mL) was treated dropwise with conc. HNO₃ (3.9 mL) at 1-2° C. After stirring at 1-2° C. for 2 h the mixture was poured into ice and filtered to give the sub-title compound. Yield: 5.18 g (87%).

(b) 4-Chloro-2-fluoro-5-isothiocyanatobenzonitrile

H₂ was passed through a mixture of 4-chloro-2-fluoro-5-nitrobenzonitrile (1.0 g; 5.0 mmol) and Ra—Ni (29 mg, 0.50 mmol) in THF (50 mL) for 6 h. The mixture was filtered through celite. CSCl₂ (2.29 g; 19.9 mmol), K₂CO₃ (3.45 g; 25.0 mmol) was added and the resulting mixture was stirred over night at rt and concentrated. The residue was purified by column chromatography to give the sub-title compound. Yield: 840 mg (79%).

(c) 2-[(2-Chloro-5-cyano-4-fluorophenyl)-amino]-6-(2,2-difluoroethoxy)-1-methyl-N-(trans-4-trifluoromethyl-cyclohex-1-yl)-1H-benzo[d]imidazole-5-carboxamide The sub-title compound was prepared in accordance with the procedure in Example 72, step (a) using 4-chloro-2-fluoro-5-isothiocyanatobenzonitrile (270 mg; 1.27 mmol), 5-amino-2-(2,2-difluoroethoxy)-4-(methylamino)-N-((trans)-4-(trifluoromethyl)cyclohexyl)benzamide [502 mg; 1.27 mmol, prepared from 4-trans-trifluoromethyl-cyclohexylamine and 2-(2,2-difluoroethoxy)-4-(methylamino)-5-nitrobenzoic acid in analogy to Example 66, step (f+g)], DIC (160 mg; 1.27 mmol) and DMF (10 mL). Yield: 210 mg (29%).

(d) 2-[5-(Aminomethyl)-2-chloro-4-fluoro-phenyl]amino-6-(2,2-difluoroethoxy)-1-methyl-N-(trans-4-trifluoromethyl-cyclohex-1-yl)-1H-benzo[d]imidazole-5-carboxamide The sub-title compound was prepared in accordance with Example 3d, using 2-[(2-chloro-5-cyano-4-fluoro-phenyl)-amino]-6-(2,2-difluoroethoxy)-1-methyl-N-(trans-4-trifluoromethyl-cyclohex-1-yl)-1H-benzo[d]imidazole-5-carboxamide (210 mg; 0.37 mmol), Ra—Ni (3 mg), H₂ (5 atm) and THF (10 mL). Yield: 150 mg (70%).

(e) 2-(2-Chloro-4-fluoro-5-{[(1-(trifluoromethyl)cyclopropanecarbonyl)amino]methyl}-phenylamino)-6-(2,2-difluoroethoxy)-1-methyl-N-(trans-4-trifluoromethyl-cyclohex-1-yl)-1H-benzo[d]imidazole-5-carboxamide The title compound was prepared in accordance with the procedure in Example 72, step (c) using 2-[5-(aminomethyl)-2-chloro-4-fluoro-phenyl]amino-6-(2,2-difluoroethoxy)-1-methyl-N-(trans-4-trifluoromethyl-cyclohex-1-yl)-1H-benzo[d]imidazole-5-carboxamide (150 mg; 0.26 mmol), 1-(trifluoromethyl)-cyclopropanecarboxylic acid (40 mg; 0.26 mmol), HBTU (99 mg; 0.26 mmol), TEA (53 mg; 0.52 mmol) and DMF (4 mL). Yield: 39 mg (21%). 400 MHz ¹H-NMR (DMSO-d₆, ppm) 8.40 (1H, t, J=5.8 Hz) 8.32 (1H, s) 7.90-7.82 (2H, m) 7.78-7.74 (1H, m) 7.44 (1H, d, J=9.6 Hz) 7.23-7.19 (1H, m) 6.63-6.34 (1H, m) 4.51-4.40 (2H, m) 4.29 (2H, d, J=5.8 Hz) 3.78-3.65 (4H, m) 2.28-2.17 (1H, m) 2.03-1.97 (2H, m) 1.91-1.85 (2H, m) 1.39-1.19 (8H, m). MS m/z: 714, 716 [M+H]⁺.

The following compounds were synthesized in analogy to the methods of preparation described above in detail.

| Ex. | Chemical structure Name ¹H-NMR | MS m/z [M + H]⁺ |
|---|---|---|
| 85 | 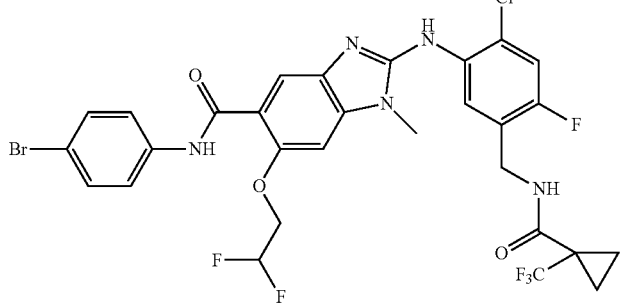<br>N-(4-Bromophenyl)-2-(2-chloro-4-fluoro-5-{[(1-trifluoromethyl-cyclopropanecarbonyl)amino]methyl}phenylamino)-6-(2,2-difluoroethoxy)-1-methyl-1H-benzo[d]imidazole-5-carboxamide<br>400 MHz ¹H-NMR (DMSO-d₆, ppm) 10.09-9.94 (1H, m) 8.46-8.22 (2H, m) 7.84 (1H, d, J = 7.6 Hz) 7.73-7.61 (3H, m) 7.53-7.42 (3H, m) 7.31-7.27 (1H, m) 6.66-6.36 (1H, m) 4.55-4.46 (2H, m) 4.29 (2H, d, J = 5.8 Hz) 3.70 (3H, s) 1.39-1.19 (4H, m) | 718, 720, 722 |

Example 86

N-(3-Chloro-4-fluoro-phenyl)-2-(2-chloro-5-{[(tert-butylcarbonyl)-amino]-methyl}-phenylamino)-6-(2,2-difluoro-ethoxy)-1-methyl-1H-benzimidazole-5-carboxylic acid amide

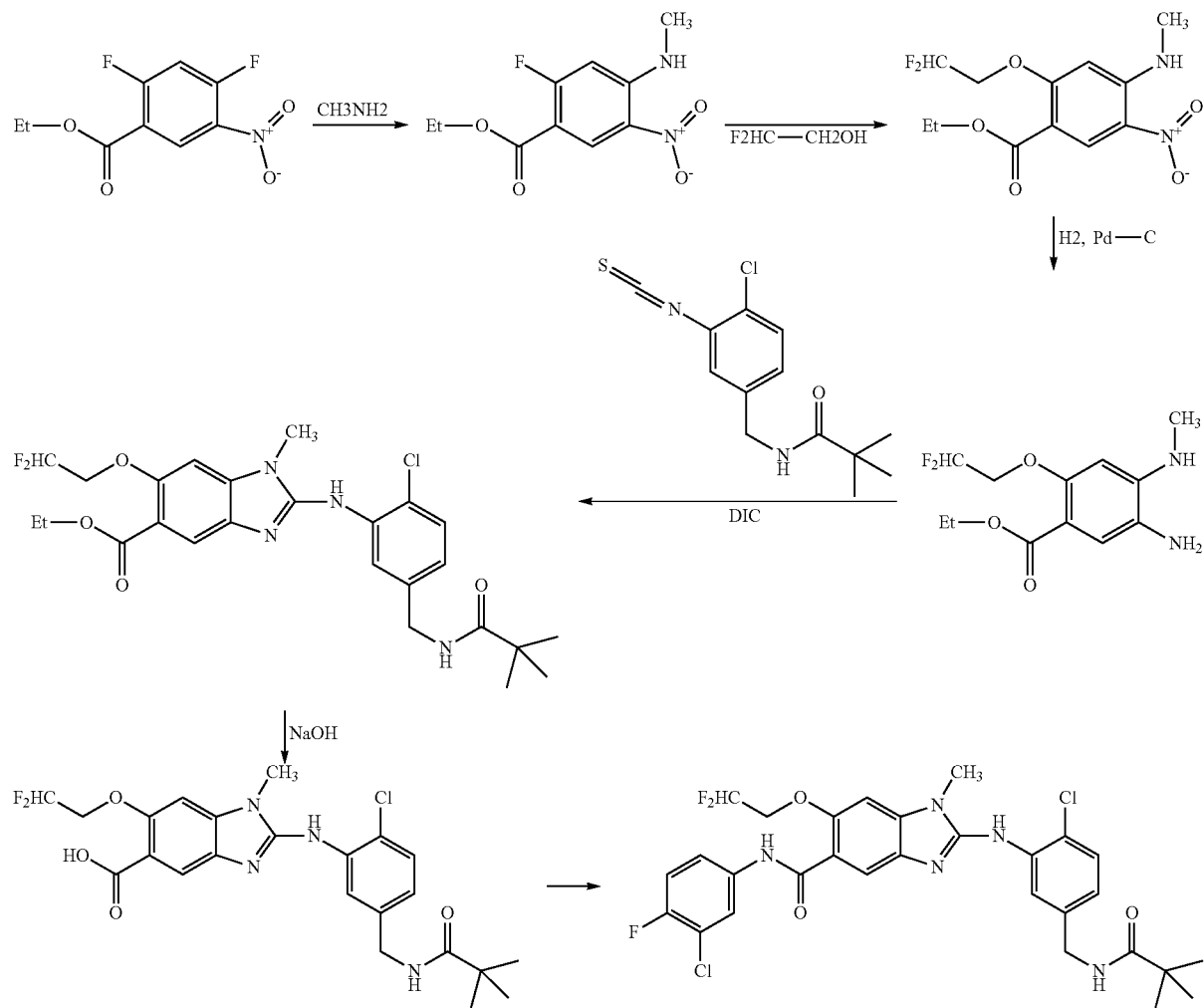

(a) Ethyl 2-fluoro-4-methylamino-5-nitro-benzoate

A 2N solution of methylamine in THF (11.5 ml, 23.0 mmol) was added at −5° C. to ethyl-2,4-difluoro-5-nitro-benzoate (2.50 g, 10.8 mmol) in 20 ml THF and the cooling bath was removed. After 15 min at room temperature, the mixture was concentrated i.vac., 50 ml DCM were added, the organic phase was washed with water and dried with MgSO$_4$. After concentration i.vac. the crude product was triturated with ethanol to give the cristalline product.

Yield: 1.72 g (66%); MS m/z: 243 [M+H]$^+$.

(b) Ethyl 2-(2,2-difluoroethoxy)-4-methylamino-5-nitro-benzoate

KOtBu (0.26 g, 95%, 2.39 mmol) was added to a mixture of 2,2-difluoroethanol (0.16 ml, 2.48 mmol) and 10 ml THF. It was stirred for 15 min, ethyl 2-fluoro-4-methylamino-5-nitro-benzoate (0.40 g, 1.65 mmol) was added and it was stirred for 3 d. The mixture was diluted with water, concentrated i.vac. and the crude product was collected by filtration.

Yield: 0.47 g (94%); TLC: silica gel, PE/EtOAc 60:40, R$_f$=0.35.

(c) Ethyl 2-(2,2-difluoroethoxy)-4-methylamino-5-amino-benzoate

Ethyl 2-(2,2-difluoroethoxy)-4-methylamino-5-nitro-benzoate (0.47 g, 1.54 mmol) was hydrogenated with 10% Pd/C (50 mg) in 15 ml MeOH for 18 h (50 psi H$_2$), filtered and concentrated.

Yield: 0.35 g (83%); TLC: silica gel, DCM/EtOH 95:5, R$_f$=0.4.

(d) Ethyl 2-(2-chloro-5-{[(tert.butylcarbonyl)amino]methyl}phenylamino)-6-(2,2-difluoroethoxy)-1-methyl-1H-benzo[d]imidazole-5-carboxylate The sub-title compound was prepared from ethyl 2-(2,2-difluoroethoxy)-4-methylamino-5-amino-benzoate and N-(4-chloro-3-isothiocyanatobenzyl)-2,2-dimethylpropionamide with DIC in DMF at r.t. in analogy to example 72a. The crude material was directly used in the next step.

(e) 2-(2-Chloro-5-{[(tert.butylcarbonyl)amino]methyl}phenylamino)-6-(2,2-difluoroethoxy)-1-methyl-1H-benzo[d]imidazole-5-carboxylic acid The sub-title compound was prepared from crude ethyl 2-(2-chloro-5-{[(tert.butylcarbonyl)amino]methyl}phenylamino)-6-(2,2-difluoroethoxy)-1-methyl-1H-benzo[d]imidazole-5-carboxylate_with NaOH in analogy to example 2g.

Yield: (85% for two steps); TLC: silica gel, DCM/EtOH 95:5, R$_f$=0.2. MS m/z: 495/497 [M+H]$^+$.

(f) N-(3-Chloro-4-fluoro-phenyl)-2-(2-chloro-5-{[(tert-butylcarbonyl)-amino]-methyl}-phenylamino)-6-(2,2-difluoro-ethoxy)-1-methyl-1H-benzimidazole-5-carboxylic acid amide The title compound was prepared from 2-(2-chloro-5-{[(tert.butylcarbonyl)amino]methyl}-phenylamino)-6-(2,2-difluoroethoxy)-1-methyl-1H-benzo[d]imidazole-5-carboxylic acid and 3-chloro-4-fluoro-aniline with HATU and TEA in THF in analogy to example 3e and purified via flash chromatography.

Yield: (57%);

TLC: silica gel, DCM/EtOH 95:5, R$_f$=0.2. HPLC R$_t$=1.40 min (method A)

MS m/z: 622/624 [M+H]$^+$.

The following compounds were synthesized in analogy to the methods of preparation described above in detail.

| Ex. | Chemical structure<br>Name<br>$^1$H-NMR | MS m/z [M + H]$^+$ |
|---|---|---|
| 87 | N-(Cyclopropylmethyl)-2-(2-chloro-5-{[(tert-butylcarbonyl)-amino]-methyl}-phenylamino)-6-(2,2-difluoro-ethoxy)-1-methyl-1H-benzimidazole-5-carboxylic acid amide<br>TLC: silica gel, DCM/EtOH 95:5, R$_f$= 0.25.<br>HPLC R$_t$ = 1.23 min (method A) | 548 |

| Ex. | Chemical structure<br>Name<br>¹H-NMR | MS m/z [M + H]⁺ |
|---|---|---|
| 88 | N-(2,2-Dimethylcyclopropyl-methyl)-2-(2-chloro-5-{[(tert-butylcarbonyl)-amino]-methyl}-phenylamino)-6-(2,2-difluoro-ethoxy)-1-methyl-1H-benzimidazole-5-carboxylic acid amide<br>TLC: silica gel, DCM/EtOH 95:5, $R_f$ = 0.32. | 576 |
| 89 | N-(Cyclobutylmethyl)-2-(2-chloro-5-{[(tert-butylcarbonyl)-amino]-methyl}-phenylamino)-6-(2,2-difluoro-ethoxy)-1-methyl-1H-benzimidazole-5-carboxylic acid amide<br>TLC: silica gel, DCM/EtOH 9:1, $R_f$ = 0.62. | 562 |
| 90 | N-(3-Phenylpropargyl)-2-(2-chloro-5-{[(tert-butylcarbonyl)-amino]-methyl}-phenylamino)-6-(2,2-difluoro-ethoxy)-1-methyl-1H-benzimidazole-5-carboxylic acid amide<br>TLC: silica gel, DCM/EtOH 95:5, $R_f$ = 0.3.<br>HPLC $R_t$ = 1.34 min (method A) | 608 |

Example 91

2-({5-[(tert.Butoxycarbonyl)amino]methyl}-2-trifluoromethyl-phenylamino)-6-methoxy-N-(trans-4-trifluoromethyl-cyclohex-1-yl)-1H-benzo[d]imidazole-5-carboxamide

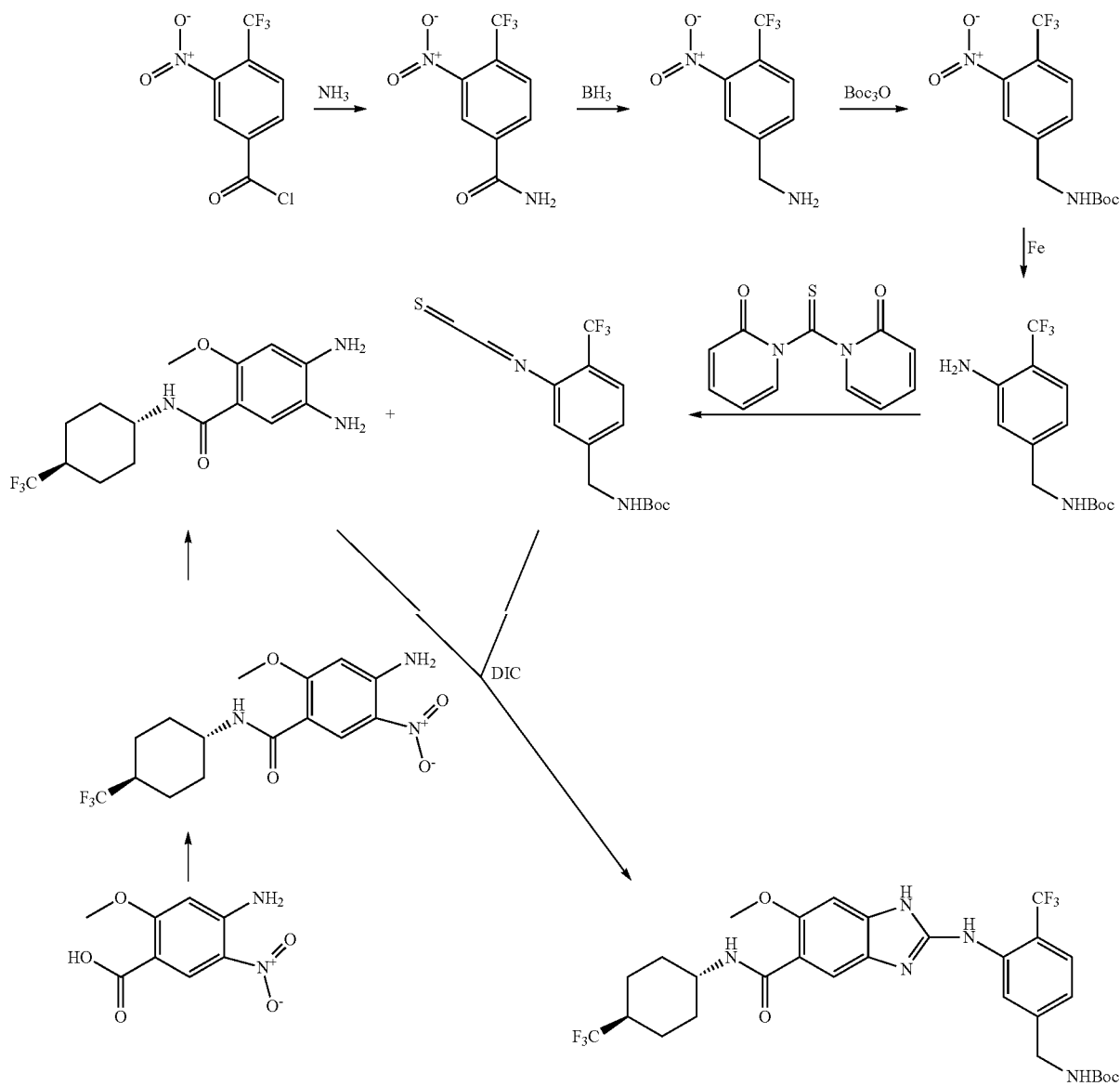

(a) 3-Nitro-4-trifluoromethyl-benzoic acid amide

3-Nitro-4-trifluoromethyl-benzoylchloride (5.32 g, 21 mmol) in 30 ml THF was added dropwise into 30 ml of conc ammonia. The mixture was stirred overnight, filtered and the precipitate was washed with water.

Yield: 3.05 g (62%); MS m/z: 233 [M+H]⁻. TLC: silica gel, DCM/EtOH 95:5, $R_f$=0.3.

(b) 3-Nitro-4-trifluoromethyl-benzylamine

A 1 M solution of Borane in THF (51 ml, 51 mmol) was added at 0° C. to 3-nitro-4-trifluoromethyl-benzoic acid amide (3.00 g, 12.8 mmol) in 50 ml THF and it was stirred for 3 days. Methanol was carefully added and it was stirred for 30 min at r.t and 2 h at reflux. Then it was concentrated i.vac.; NaOH was added (pH 8) and the mixture was extracted with EtOAc. The organic layer was dried with $Na_2SO_4$, filtered and concentrated to furnish the crude subtitle compound.

(c) tert.-Butyl-N-(3-nitro-4-trifluoromethyl-benzyl)carbamate

The sub-title compound was prepared from crude 3-nitro-4-trifluoromethyl-benzylamine with di-tertbutyl-dicarbonate in analogy to example 2a.

TLC: silica gel, DCM/EtOH 95:5, $R_f$=0.73. MS m/z: 321 [M+H]⁺.

147

(d) tert.-Butyl-N-(3-amino-4-trifluoromethyl-benzyl) carbamate

The sub-title compound was prepared from tert.-butyl-N-(3-nitro-4-trifluoromethyl-benzyl)carbamate with powdered iron in analogy to example 2b.

TLC: silica gel, DCM/EtOH 95:5, $R_f$=0.51. MS m/z: 291 [M+H]$^+$.

(e) tert.-Butyl-N-(3-isothiocyanato-4-trifluoromethyl-benzyl)carbamate

The sub-title compound was prepared from tert.-butyl-N-(3-amino-4-trifluoromethyl-benzyl)carbamate with 1,1'-thiocarbonyldi-2-pyridone in analogy to example 1d.

Yield: 86%; TLC: silica gel, DCM/EtOH 95:5, $R_f$=0.8.

(f) N-(trans-4-Trifluoromethyl-cyclohex-1-yl)-2-methoxy-4-amino-5-nitro benzoic acid amide The sub-title compound was prepared from 2-methoxy-4-amino-5-nitro benzoic acid and trans-4-trifluoromethyl-cyclohexylamine with TBTU and TEA in DMF in analogy to example 3e._Yield: quantitative; TLC: silica gel, DCM/EtOH 9:1, $R_f$=0.68.

(g) N-(trans-4-Trifluoromethyl-cyclohex-1-yl)-2-methoxy-4,5-diamino benzoic acid amide The sub-title compound was prepared from N-(trans-4-trifluoromethyl-cyclohex-1-yl)-2-methoxy-4-amino-5-nitro benzoic acid amide with Ra—Ni in analogy to example 59g.

Yield: 99%; TLC: silica gel, DCM/EtOH 9:1, $R_f$=0.40.

(h) 2-({5-[(tert.Butoxycarbonyl)amino]methyl}-2-trifluoromethyl-phenylamino)-6-methoxy-N-(trans-4-trifluoromethyl-cyclohex-1-yl)-1H-benzo[d]imidazole-5-carboxamide The title compound was prepared from N-(trans-4-trifluoromethyl-cyclohex-1-yl)-2-methoxy-4,5-diamino benzoic acid amide_and tert.-Butyl-N-(3-isothiocyanato-4-trifluoromethyl-benzyl)carbamate with DIC in analogy to example 72a.

Yield: 77%; TLC: silica gel, DCM/EtOH 95:5, $R_f$=0.3. MS m/z: 630 [M+H]$^+$.

Example 92

2-({5-[(2-Amino-3,3,3-trifluoro-propionyl)amino]methyl}-2-trifluoromethyl-phenylamino)-6-methoxy-N-(trans-4-trifluoromethyl-cyclohex-1-yl)-1H-benzo[d]imidazole-5-carboxamide

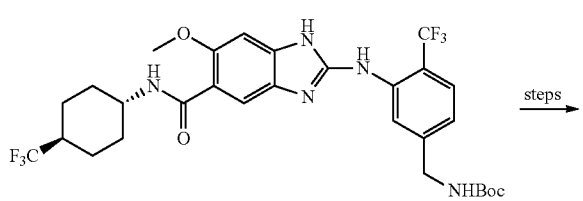

steps →

148

-continued

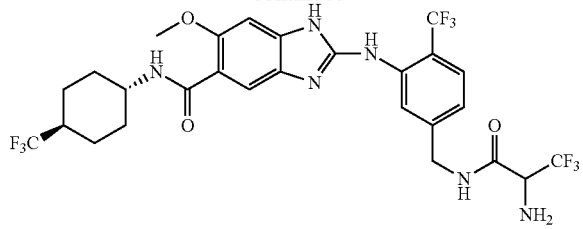

(a) 2-(5-Aminomethyl-2-trifluoromethyl-phenylamino)-6-methoxy-N-(trans-4-trifluoromethyl-cyclohex-1-yl)-1H-benzo[d]imidazole-5-carboxamide The title compound was prepared from 2-({5-[(tert.butoxycarbonyl)amino]methyl}-2-trifluoromethyl-phenylamino)-6-methoxy-N-(trans-4-trifluoromethyl-cyclohex-1-yl)-1H-benzo[d]imidazole-5-carboxamide and 6M HCl in THF in analogy to example 2e.

Yield: 76%; TLC: silica gel, DCM/EtOH/NH3 aq 90:10:1, $R_f$=0.2. MS m/z: 530 [M+H]$^+$.

(b) 2-(5-{[(2-tert.Butoxycarbonylamino-3,3,3-trifluoro-propionyl)amino]methyl}-2-trifluoromethyl-phenylamino)-6-methoxy-N-(trans-4-trifluoromethyl-cyclohex-1-yl)-1H-benzo[d]imidazole-5-carboxamide The title compound was prepared from 2-(5-aminomethyl-2-trifluoromethyl-phenylamino)-6-methoxy-N-(trans-4-trifluoromethyl-cyclohex-1-yl)-1H-benzo[d]imidazole-5-carboxamide and 2-tert.butoxycarbonylamino-3,3,3-trifluoro-propionic acid with TBTU, and TEA in THF_in analogy to example 3e.

Yield: 70%; HPLC $R_t$=1.38 min (method A). TLC: silica gel, DCM/EtOH 95:5:1, $R_f$=0.3. MS m/z: 755 [M+H]$^+$.

(c) 2-({5-[(2-Amino-3,3,3-trifluoropropionyl)amino]methyl}-2-trifluoromethyl-phenylamino)-6-methoxy-N-(trans-4-trifluoromethyl-cyclohex-1-yl)-1H-benzo[d]imidazole-5-carboxamide The title compound was prepared from 2-(5-{[(2-tert.Butoxycarbonylamino-3,3,3-trifluoro-propionyl)amino]methyl}-2-trifluoromethyl-phenylamino)-6-methoxy-N-(trans-4-trifluoromethyl-cyclohex-1-yl)-1H-benzo[d]imidazole-5-carboxamide and_6M HCl in THF in analogy to example 2e.

Yield: 99%; HPLC $R_t$=1.23 min (method A). TLC: silica gel, DCM/EtOH/aq.NH$_3$ 95:5:1, $R_f$=0.55. MS m/z: 655 [M+H]$^+$.

The following compounds were synthesized in analogy to the methods of preparation described above in detail.

| Ex. | Chemical structure<br>Name<br>¹H-NMR | MS m/z [M + H]⁺ |
|---|---|---|
| 93 | ![structure] <br>N-(trans-4-Trifluoromethyl-cyclohex-1-yl)-2-(2-trifluoromethyl-5-{[(1-trifluoromethylcyclopropane-carbonyl)amino]-methyl}-phenylamino)-6-methoxy-1H-benzimidazole-5-carboxylic acid amide<br>TLC: silica gel, DCM/EtOH/aq.NH₃ 90:10:1, $R_f$ = 0.65.<br>HPLC $R_t$ = 1.32 min (method A) | 666 |
| 94 | ![structure]<br>N-(trans-4-Trifluoromethyl-cyclohex-1-yl)-2-(2-trifluoromethyl-5-{[(1-hydroxy-cyclopropane-carbonyl)amino]-methyl}-phenylamino)-6-methoxy-1H-benzimidazole-5-carboxylic acid amide<br>TLC: silica gel, DCM/EtOH/aq.NH₃ 90:10:1, $R_f$ = 0.55.<br>HPLC $R_t$ = 1.22 min (method A) | 614 |

Example 95

N-(trans-4-Trifluoromethyl-cyclohex-1-yl)-1-methyl-2-(2-trifluoromethyl-5-{[(tert-butylcarbonyl)-amino]-methyl}-phenylamino)-6-(2,2-difluoro-ethoxy)-1H-benzimidazole-5-carboxylic acid amide

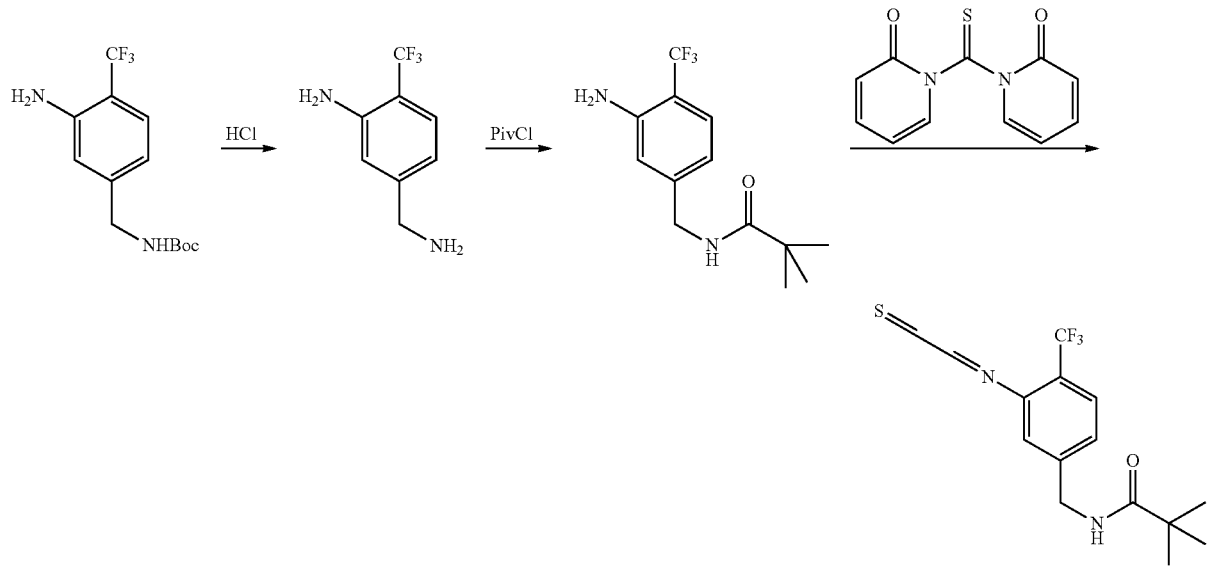

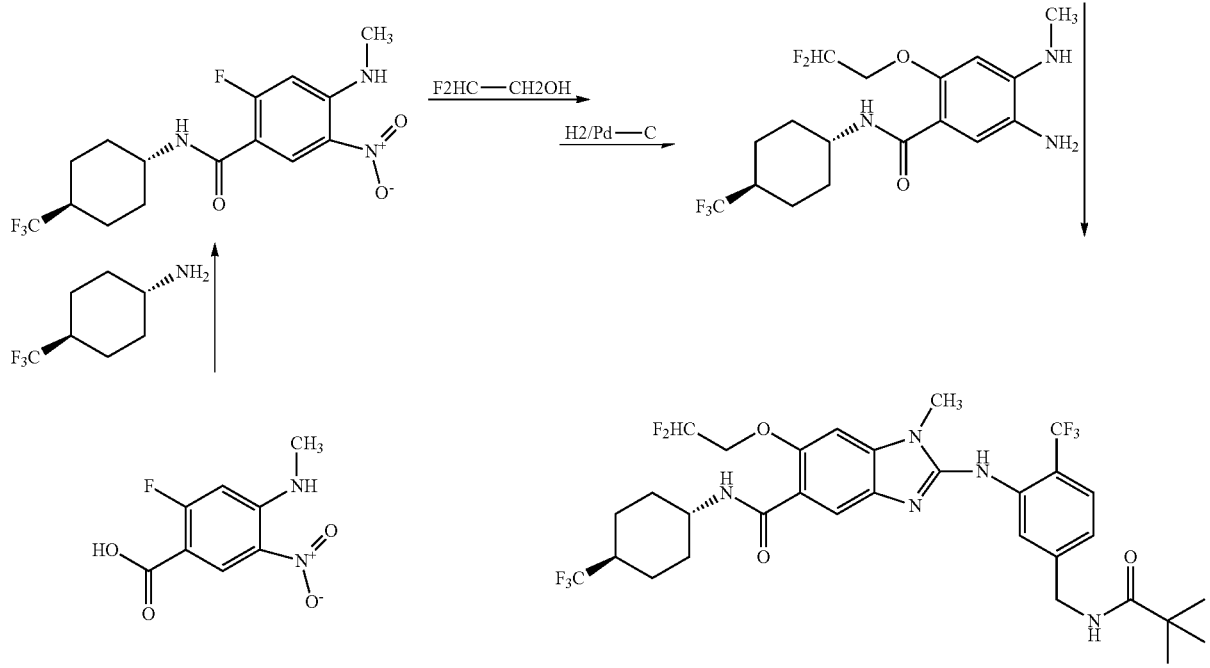

(a) 3-Amino-4-trifluoromethyl-benzylamine

The title compound was prepared from tert.-butyl-N-(3-amino-4-trifluoromethyl-benzyl)carbamate and 6M HCl in THF in analogy to example 2e.

Yield: 99%; HPLC $R_t$=0.68 min (method A). MS m/z: 191 [M+H]$^+$.

(b) N-(3-Amino-4-trifluoromethyl-benzyl)-pivaloyl amide

The sub-title compound was prepared from 3-amino-4-trifluoromethyl-benzylamine and pivaloylchloride with TEA in analogy to example 1b.

Yield: 96%; HPLC $R_t$=1.31 min (method A). MS m/z: 275 [M+H]$^+$.

(c) N-(3-Isothiocyanato-4-trifluoromethyl-benzyl)-pivaloylamide

The sub-title compound was prepared from N-(3-amino-4-trifluoromethyl-benzyl)-pivaloyl amide with 1,1'-thiocarbonyldi-2-pyridone in analogy to example 1d.

Yield: 72%; TLC: silica gel, DCM/EtOH 95:5, $R_f$=0.75.

(d) 5-Nitro-2-fluoro-4-(methylamino)-N-(trans-4-trifluoromethyl.cyclohex-1-yl)-benzamide The sub-title compound was prepared from 4-trans-trifluoromethyl-cyclohexylamine and 2-fluoro-4-(methylamino)-5-nitrobenzoic acid with DIPEA and TBTU in analogy to example 3e.

Yield: 70%; HPLC $R_t$=1.44 min (method A). MS m/z: 364 [M+H]$^+$.

(e) 5-Nitro-2-(2,2-difluoroethoxy)-4-(methylamino)-N-(trans-4-trifluoromethyl-cyclohex-1-yl)-benzamide The sub-title compound was prepared from 5-nitro-2-fluoro-4-(methylamino)-N-(trans-4-trifluoromethyl.cyclohex-1-yl)-benzamide and 2,2-difluoroethanol with KOtBu in analogy to example 86b.

Yield: 89%; HPLC $R_t$=1.47 min (method A). MS m/z: 426 [M+H]$^+$.

(f) 5-Amino-2-(2,2-difluoroethoxy)-4-(methylamino)-N-(trans-4-trifluoromethyl-cyclohex-1-yl)-benzamide The sub-title compound was prepared from 5-nitro-2-(2,2-difluoroethoxy)-4-(methylamino)-N-(trans-4-trifluoromethyl-cyclohex-1-yl)-benzamide, hydrogen and Pd/C in analogy to example 86c.

Yield: 98%; HPLC $R_t$=1.24 min (method A). MS m/z: 396 [M+H]$^+$.

(g) N-(trans-4-Trifluoromethyl-cyclohex-1-yl)-1-methyl-2-(2-trifluoromethyl-5-{[(tert-butylcarbonyl)-amino]-methyl}-phenylamino)-6-(2,2-difluoroethoxy)-1H-benzimidazole-5-carboxylic acid amide The sub-title compound was prepared from 5-amino-2-(2,2-difluoroethoxy)-4-(methylamino)-N-(trans-4-trifluoromethyl-cyclohex-1-yl)-benzamide and N-(3-isothiocyanato-4-trifluoromethyl-benzyl)-pivaloylamide in analogy to example 72a.

Yield: 51%; HPLC $R_t$=1.38 min (method A). MS m/z: 678 [M+H]$^+$. TLC: silica gel, DCM/EtOH 95:5, $R_f$=0.3.

The following compounds were synthesized in analogy to the methods of preparation described above in detail.

| Ex. | Chemical structure<br>Name<br>¹H-NMR | MS m/z [M + H]⁺ |
|---|---|---|
| 96 | N-(trans-4-Trifluoromethyl-cyclohex-1-yl)-2-(2-trifluoromethyl-5-{[(tert-butylcarbonyl)-amino]-methyl}-phenylamino)-6-(2,2-difluoro-ethoxy)-1H-benzimidazole-5-carboxylic acid amide<br>TLC: silica gel, DCM/EtOH 95:5, R$_f$ = 0.25.<br>HPLC R$_t$ = 1.35 min (method A) | 664 |
| 97 | N-(trans-4-Trifluoromethyl-cyclohex-1-yl)-1-methyl-2-(2-chloro-5-{[(tert-butylcarbonyl)-amino]-methyl}-phenylamino)-6-(2-fluoro-ethoxy)-1H-benzimidazole-5-carboxylic acid amide<br>HPLC R$_t$ = 1.32 min (method A) | 626 |
| 98 | N-(trans-4-Trifluoromethyl-cyclohex-1-yl)-1-methyl-2-(2-chloro-5-{[(tert-butylcarbonyl)-amino]-methyl}-phenylamino)-6-(2,2,2-trifluoro-ethoxy)-1H-benzimidazole-5-carboxylic acid amide<br>TLC: silica gel, DCM/EtOH 95:5, R$_f$ = 0.43.<br>HPLC R$_t$ = 1.37 min (method A) | 662 |

Example 99

N-(trans-4-Trifluoromethyl-cyclohex-1-yl)-2-(2-methoxy-5-{[(tert-butylcarbonyl)-amino]-methyl}-phenylamino)-6-chloro-1H-benzimidazole-5-carboxylic acid amide

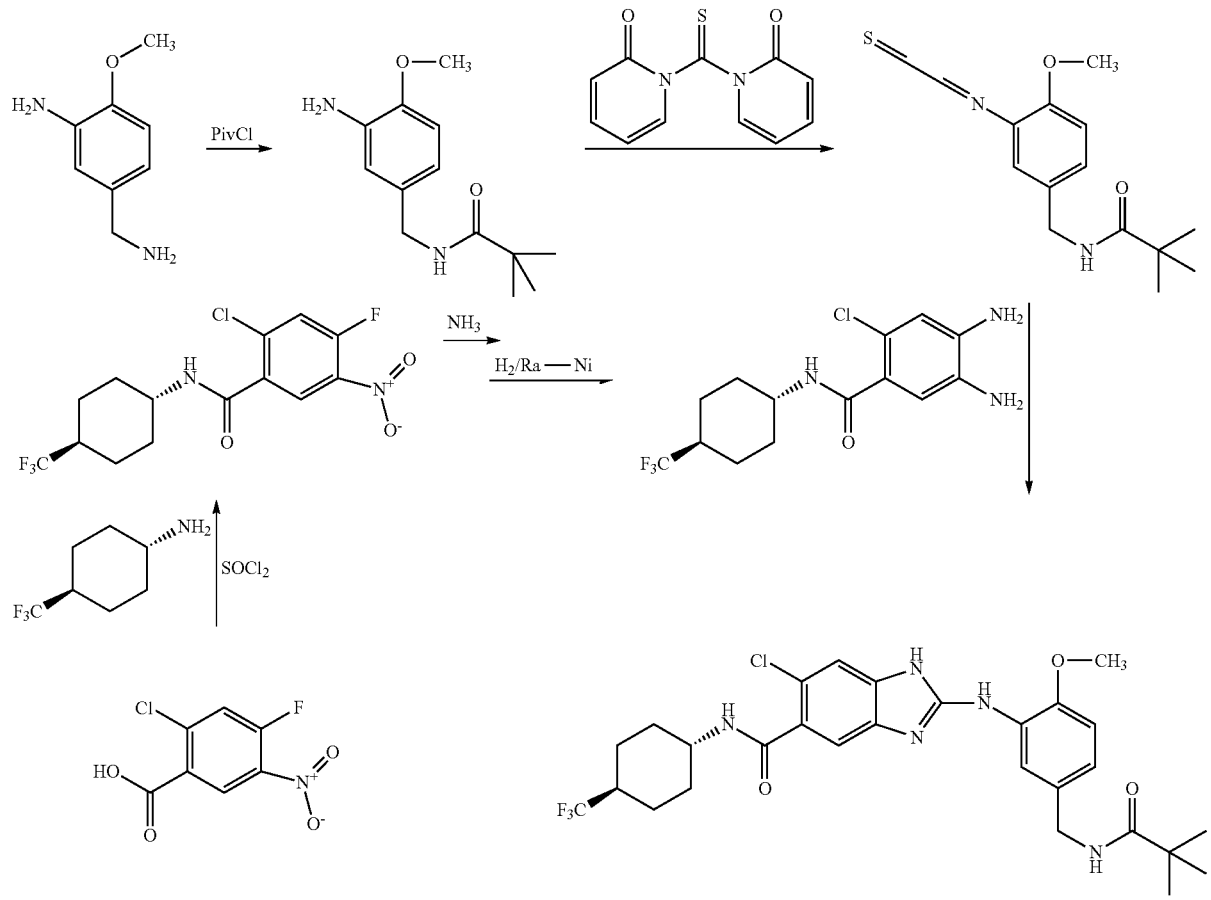

(a) N-(3-Amino-4-methoxy-benzyl)-pivaloyl amide

The sub-title compound was prepared from 3-amino-4-methoxy-benzylamine and pivaloylchloride with TEA in analogy to example 1b. Yield: 30%; MS m/z: 237 [M+H]$^+$.

(b) N-(3-Isothiocyanato-4-methoxy-benzyl)-pivaloylamide

The sub-title compound was prepared from N-(3-amino-4-methoxy-benzyl)-pivaloyl amide with 1,1'-thiocarbonyldi-2-pyridone in analogy to example 1d.
Yield: 99%; MS m/z: 279 [M+H]$^+$.

(c) 5-Nitro-2-chloro-4-fluoro-N-(trans-4-trifluoromethyl-cyclohex-1-yl)-benzamide The sub-title compound was prepared from 2-chloro-4-fluoro-5-nitrobenzoic acid—which was converted into the corresponding acid chloride with thionyl chloride—and 4-trans-trifluoromethyl-cyclohexylamine according to example 70a.
Yield: 100%; MS m/z: 369 [M+H]+.

(d) 5-Nitro-2-chloro-4-amino-N-(trans-4-trifluoromethyl-cyclohex-1-yl)-benzamide Conc. ammonia (0.8 ml) was added portionwise at −10° C. to a mixture of 5-nitro-2-chloro-4-fluoro-N-(trans-4-trifluoromethyl-cyclohex-1-yl)-benzamide (0.20 g, 0.54 mmol) and 10 ml THF and it was stirred overnight at room temperature. Water was added and the mixture was conc. i.vac. The residue was triturated with water and filtered. The filter cake was washed with water and dried to obtain the crude subtitle compound (MS m/z: 366 [M+H]$^+$).

(e) 4,5-Diamino-2-chloro-N-(trans-4-trifluoromethyl-cyclohex-1-yl)-benzamide 5-Nitro-2-chloro-4-amino-N-(trans-4-trifluoromethyl-cyclohex-1-yl)-benzamide was hydrogenated with Ra—Ni in analogy to example 66g. The crude material was directly used without further purification.

(f) N-(trans-4-Trifluoromethyl-cyclohex-1-yl)-2-(2-methoxy-5-{[(tert-butylcarbonyl)-amino]-methyl}-phenylamino)-6-chloro-1H-benzimidazole-5-carboxylic acid amide The compound was prepared from 4,5-diamino-2-chloro-N-(trans-4-trifluoromethyl-cyclohex-1-yl)-benzamide and N-(3-isothiocyanato-4-methoxy-benzyl)-pivaloylamide in analogy to example 72a.
Yield: 32%; MS m/z: 580 [M+H]+.

Example 100

N-(4-Bromo-phenyl)-2-(2-chloro-5-{[(tert-butylcarbonyl)-amino]-methyl}-phenylamino)-6-(2,2-difluoro-ethoxy)-1-(2,2-difluoroethyl)-1H-benzimidazole-5-carboxylic acid amide

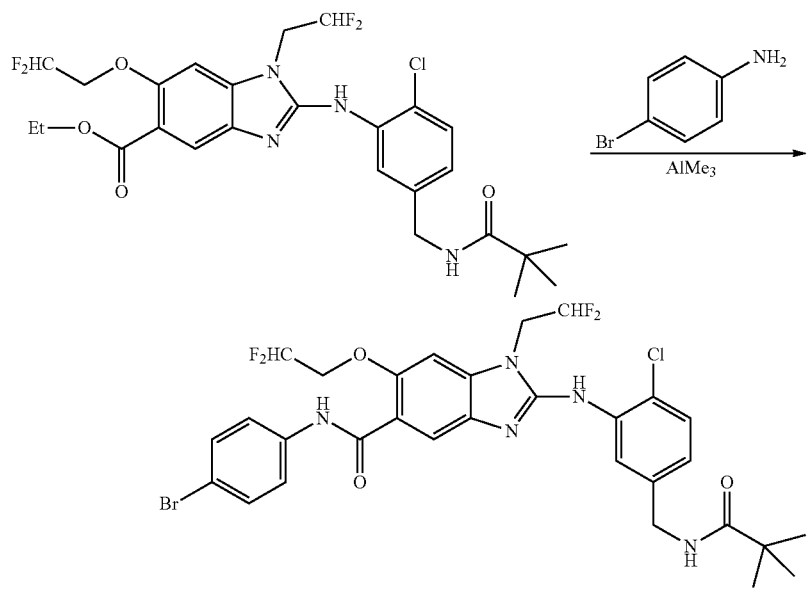

Ethyl 2-(2-chloro-5-{[(tert.butylcarbonyl)amino]methyl}phenylamino)-6-(2,2-difluoroethoxy)-1-(2,2-difluoroethyl)-1H-benzo[d]imidazole-5-carboxylate (prepared in analogy to example 86a-d) and 4-bromoaniline where coupled using trimethylaluminium in analogy to example 59i.
Yield: (57%). TLC: silica gel, DCM/EtOH 9:1, $R_f$=0.6. MS m/z: 698 [M+H]$^+$.

The invention claimed is:
1. A compound of formula I:

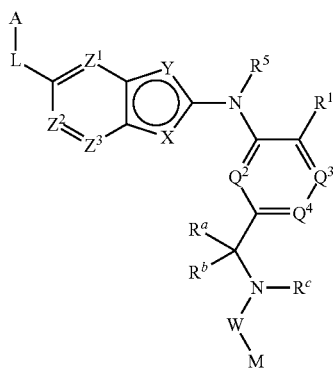

I one of X and Y represents —N(R$^6$)—; and
the other represents —N=;
one of Z$^1$, Z$^2$ and Z$^3$ independently represents —C(R$^7$)= or —N=; and
the other two of Z$^1$, Z$^2$ and Z$^3$ represent —C(R$^7$)=;
Q$^2$, Q$^3$ and Q$^4$ respectively represent —C(R$^2$)=, —C(R$^3$)= or —C(R$^4$)=;
or any one or two of Q$^2$, Q$^3$ or Q$^4$ may alternatively and independently represent —N=;
R$^1$ represents halo, OH, —CN;
C$_{1-3}$ alkyl, C$_{2-6}$alkynyl, OC$_{1-3}$ alkyl, which latter three groups are optionally substituted by one or more substituents selected from fluoro, —CN, =O, OH, —OCH$_3$, or —OCF$_3$;
R$^2$ represents hydrogen, —CN or a OC$_{1-3}$ alkyl optionally substituted by one or more substituents selected from fluoro, —CN, =O, OH, —OCH$_3$, or —OCF$_3$;
R$^3$ and R$^4$ independently represent hydrogen, —CN;
C$_{1-3}$ alkyl, or OC$_{1-3}$ alkyl, which latter two groups are optionally substituted by one or more substituents selected from fluoro, —CN, =O, OH, —OCH$_3$, or —OCF$_3$;
R$^a$, R$^b$ independently represent hydrogen, or C$_{1-3}$ alkyl,
or both together with the carbon atom which they are bound to, form a C$_{3-7}$cycloalkylene ring, or a 4-6 membered heterocycloalkylene ring;
R$^c$ represents hydrogen or C$_{1-3}$ alkyl;
W represents —C(O)—, —S(O)—, —S(O)$_2$—, —C(O)O—, or
—C(O)NR$^d$—, which groups are bound to the nitrogen of the —NR$^c$— moiety via carbon or sulfur atom;
R$^d$ represents hydrogen or C$_{1-3}$ alkyl;
M represents C$_{1-7}$alkyl, C$_{3-7}$cycloalkyl, both of which groups are optionally substituted by one or more groups selected from fluoro, —OH, —CN, —NH$_2$, —NH(C$_{1-3}$ alkyl), N(C$_{1-3}$ alkyl)$_2$, —OC$_{1-3}$ alkyl, —SC$_{1-3}$ alkyl, aryl, heteroaryl [which latter two groups can be substituted by one or more substituents selected from halo, OH,
—CN, C$_{1-3}$ alkyl, OC$_{1-3}$ alkyl (which latter two alkyl groups are optionally substituted by one or more fluoro atoms)],
C$_{1-7}$alkyl, C$_{2-7}$alkynyl, C$_{3-7}$cycloalkyl-C$_{0-2}$ alkyl, 4-7 membered heterocycloalkyl-C$_{0-2}$ alkyl (which latter alkyl, alkynyl, heterocycloalkyl or cycloalkyl groups are optionally substituted by one or more substituents selected from fluoro, —CN, =O, —NH$_2$, —NH(C$_{1-3}$alkyl), —N(C$_{1-3}$ alkyl)$_2$, —OH, —OC$_{1-3}$ alkyl);

or aryl, heteroaryl, 4-7 membered heterocycloalkyl, all of which groups are optionally substituted by one or more substituents selected from halo, —OH, —CN, —NH$_2$, —NH(C$_{1-3}$alkyl), —N(C$_{1-3}$ alkyl)$_2$, —OC$_{1-3}$ alkyl, —SC$_{1-3}$ alkyl, aryl, heteroaryl [which latter two groups can be substituted by one or more substituents selected from halo, OH, —CN, C$_{1-3}$ alkyl, —OC$_{1-3}$ alkyl (which latter two alkyl groups are optionally substituted by one or more fluoro atoms)], C$_{1-7}$alkyl, C$_{2-7}$ alkynyl, C$_{3-7}$cycloalkyl, or 4-7 membered heterocycloalkyl (which latter alkyl, alkynyl, heterocycloalkyl or cycloalkyl groups are optionally substituted by one or more substituents selected from fluoro, —CN, =O, —NH$_2$, —NH(C$_{1-3}$alkyl), N(C$_{1-3}$ alkyl)$_2$, —OH, or —OC$_{1-3}$alkyl)];

R$^5$ represents hydrogen; or C$_{1-3}$ alkyl;

R$^6$ represents hydrogen; C$_{1-5}$ alkyl, C$_{3-6}$alkynyl, 4-7 membered heterocycloalkyl-C$_{0-2}$ alkyl or C$_{3-7}$cycloalkyl-C$_{0-2}$ alkyl (which latter four groups are optionally substituted by one or more substituents selected from fluoro, —CN, =O, C$_{1-3}$ alkyl, —OH, —OC$_{1-3}$ alkyl, —NH$_2$, —NH(C$_{1-3}$alkyl), or N(C$_{1-3}$ alkyl)$_2$);

each R$^7$ independently represents hydrogen, halo, —CN, C$_{1-7}$alkyl, C$_{2-7}$alkynyl, C$_{3-7}$cycloalkyl, C$_{1-5}$ alkyl-O—, C$_{3-7}$cycloalkyl-C$_{0-2}$ alkyl-O—, 4-7 membered heterocycloalkyl-C$_{0-2}$ alkyl-O—, (in which latter six groups the alkyl, alkynyl, cycloalkyl or heterocycloalkyl fragments are optionally substituted by one or more substituents selected from fluoro, —CN, =O, OH, —OC$_{1-3}$ alkyl, —NH$_2$, —NH—C$_{1-3}$ alkyl, N(C$_{1-3}$ alkyl)$_2$ or by one or more C$_{1-3}$ alkyl groups, which can be optionally substituted by one or more fluoro atoms);

or aryl or heteroaryl, which latter two groups can be substituted by one or more substituents selected from halo, OH, —CN, C$_{1-3}$ alkyl, or —OC$_{1-3}$ alkyl (in which latter two groups the alkyl fragments are optionally substituted by one or more fluoro atoms);

L represents —C(O)N(R$^8$)—, —N(R$^8$)C(O)—, —S(O)$_2$N(R$^8$)—, —N(R$^8$)S(O)$_2$—, —N(R$^8$)C(O)N(R$^8$)—, —OC(O)N(R$^8$)— or —N(R$^8$)C(O)O—;

A represents hydrogen, C$_{1-8}$ alkyl, C$_{3-8}$alkynyl, aryl, heteroaryl, aryl-C$_{1-3}$alkyl-, C$_{3-8}$cycloalkyl-C$_{0-3}$alkyl-, 4-7 membered heterocycloalkyl-C$_{0-3}$alkyl-, or heteroaryl-C$_{1-3}$alkyl-, in which groups the alkyl-, alkynyl-, cycloalkyl- and heterocycloalkyl-fragments are optionally substituted by one or more substituents selected from R$^{9a}$ and the aryl and heteroaryl fragments are optionally substituted by one or more substituents selected from R$^{9b}$;

or

A-L- together represent one of the following groups

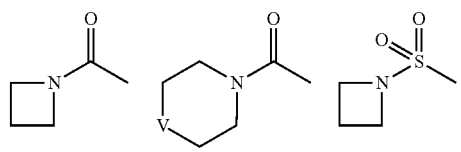

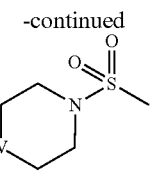

in which

V represents a bond, —CH$_2$CH$_2$—, —CH$_2$CH$_2$CH$_2$—, wherein in each of the latter alkylene groups one methylene [—(CH$_2$)—] unit can optionally be replaced by an oxygen atom, a —NH— or —N(C$_{1-3}$ alkyl)-group and each methylene unit can optionally and independently be substituted by one or two of the following groups: fluoro, —CN, =O, —NH$_2$, —NH(C$_{1-3}$ alkyl), N(C$_{1-3}$ alkyl)$_2$, —OH, or —OC$_{1-3}$alkyl);

each R$^8$ independently represents hydrogen, or C$_{1-3}$ alkyl;

each R$^{9a}$ independently represents fluoro, —OH, —CN, =O, —NH$_2$, —NH(C$_{1-3}$ alkyl), —N(C$_{1-3}$ alkyl)$_2$, —OC$_{1-6}$alkyl, C$_{1-6}$alkyl, (in which latter four groups the alkyl, fragments are optionally substituted by one or more substituents selected from fluoro, —CN, =O, —NH$_2$, —NH(C$_{1-3}$ alkyl), N(C$_{1-3}$ alkyl)$_2$, —OH, —OC$_{1-3}$ alkyl) or aryl, or heteroaryl [which latter two groups can be substituted by one or more substituents selected from halo, OH, —CN, C$_{1-3}$ alkyl, or OC$_{1-3}$ alkyl (which latter two alkyl groups are optionally substituted by one or more fluoro atoms)];

each R$^{9b}$ represents independently halo, —OH, —CN, —NH$_2$, —NH(C$_{1-3}$ alkyl), —N(C$_{1-3}$ alkyl)$_2$, —OC$_{1-3}$ alkyl, —SC$_{1-3}$ alkyl, aryl, heteroaryl [which latter two groups can be substituted by one or more substituents selected from halo, OH, —CN, C$_{1-3}$ alkyl, or OC$_{1-3}$ alkyl (which latter two alkyl groups are optionally substituted by one or more fluoro atoms)], C$_{1-7}$ alkyl, C$_{2-7}$alkynyl, C$_{3-7}$cycloalkyl, 4-7 membered heterocycloalkyl (which latter alkyl, alkynyl, heterocycloalkyl or cycloalkyl groups are optionally substituted by one or more substituents selected from fluoro, —CN, =O, —NH$_2$, —NH(C$_{1-3}$ alkyl), N(C$_{1-3}$ alkyl)$_2$, —OH, or OC$_{1-3}$ alkyl);

or a salt thereof.

2. A compound according to claim 1 having formula Ia:

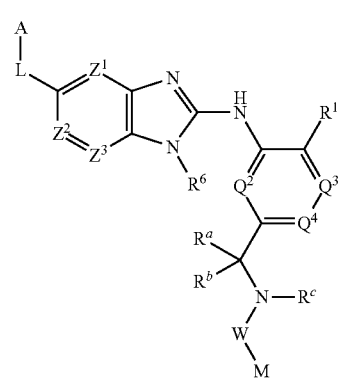

Ia in which A, L, M, Q$^2$, Q$^3$, Q$^4$, R$^1$, R$^6$, R$^a$, R$^b$, R$^c$, W, Z$^1$, Z$^2$, Z$^3$ have the same meaning as defined in claim 1, or a salt thereof.

3. A compound according to claim 1 having formula Ib:

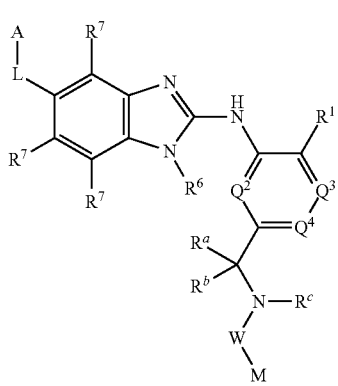

in which A, L, M, $Q^2$, $Q^3$, $Q^4$, $R^1$, $R^6$, $R^7$, $R^a$, $R^b$, $R^c$, W have the same meaning as defined in claim 1,
or a salt thereof.

4. A compound according to claim 1 having formula Ic:

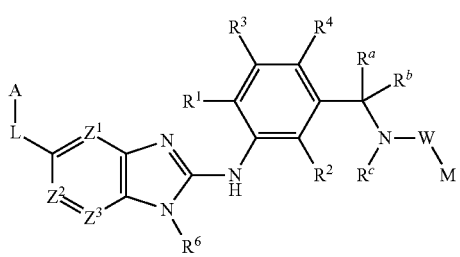

in which A, L, M, $R^1$, $R^2$, $R^3$, $R^4$, $R^6$, $R^a$, $R^b$, $R^c$, W, $Z^1$, $Z^2$, $Z^3$ have the same meaning as defined in claim 1,
or a salt thereof.

5. A compound according to claim 1 having formula Id:

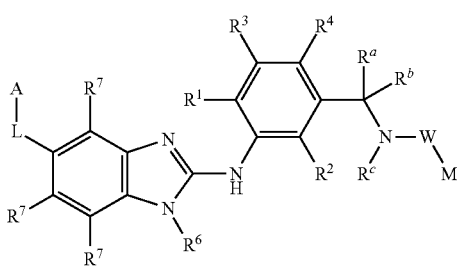

in which A, L, M, $R^1$, $R^2$, $R^3$, $R^4$, $R^6$, $R^7$, $R^a$, $R^b$, $R^c$, W have the same meaning as defined in claim 1,
or a salt thereof.

6. A compound according to claim 1, wherein
W represents —C(O)—, or —S(O)$_2$—, which groups are bound to the nitrogen of the —NR$^c$-moiety via carbon or sulfur atom;
or a salt thereof.

7. A compound according to claim 1, wherein
M represents $C_{1-7}$alkyl, or $C_{3-7}$cycloalkyl, both of which groups are optionally substituted by one or more groups selected from:
fluoro, —OH, —CN, —NH2, —OC$_{1-3}$ alkyl, —SC$_{1-3}$ alkyl, aryl [which latter aryl group can be substituted by one or more substituents selected from halo, OH, —CN, $C_{1-3}$ alkyl, OC$_{1-3}$ alkyl (which latter two alkyl groups are optionally substituted by one or more fluoro atoms)], $C_{1-7}$alkyl, $C_{3-7}$cycloalkyl-$C_{0-2}$-alkyl (which latter alkyl and cycloalkyl groups are optionally substituted by one or more substituents selected from fluoro, —CN, =O, —NH$_2$, —NH($C_{1-3}$ alkyl), —N($C_{1-3}$ alkyl)$_2$, —OH, —OC$_{1-3}$ alkyl);
or
aryl, heteroaryl, 4-7 membered heterocycloalkyl, all of which groups are optionally substituted by one or more substituents selected from halo, —CN, —OC$_{1-3}$ alkyl, $C_{1-7}$alkyl, or $C_{3-7}$cycloalkyl, (which latter alkyl and cycloalkyl groups are optionally substituted by one or more substituents selected from fluoro, —CN, or —OC$_{1-3}$alkyl);
or a salt thereof.

8. A compound according to claim 1, wherein
$R^6$ represents hydrogen; $C_{1-5}$ alkyl, or $C_{3-5}$cycloalkyl-$C_{0-1}$ alkyl, which latter two groups are optionally substituted by one or more substituents selected from fluoro, —OCH$_3$, —NH($C_{1-3}$alkyl), or N($C_{1-3}$ alkyl)$_2$;
or a salt thereof.

9. A compound according to claim 1, wherein
$R^2$ represents hydrogen;
$R^3$ and $R^4$ independently represent hydrogen or —CH$_3$ optionally substituted by one or more fluorine atoms;
or a salt thereof.

10. A compound according to claim 1, wherein
L represents —C(O)NH— or —S(O)$_2$NH—, which groups are bound to the 9-membered fused heteroaromatic scaffold via the carbon or sulfur atom, respectively;
or a salt thereof.

11. A compound according to claim 1, wherein
each $R^7$ represents hydrogen, halo, $C_{1-5}$ alkyl-O—, $C_{3-5}$ cycloalkyl-$C_{0-2}$ alkyl-O—, or 4-5-membered heterocycloalkyl-$C_{0-2}$ alkyl-O— (in which latter three groups the alkyl, cycloalkyl or heterocycloalkyl fragments are optionally substituted by one or more substituents selected from fluoro, —OC$_{1-3}$ alkyl or by one or more $C_{1-3}$ alkyl groups, which can be optionally substituted by one or more fluoro atoms);
or a salt thereof.

12. A compound according to claim 1, wherein
A represents hydrogen, $C_{1-6}$ alkyl, $C_{3-6}$alkynyl, phenyl, 5-6-membered heteroaryl, $C_{3-6}$cycloalkyl-$C_{0-2}$alkyl-, 4-6-membered heterocycloalkyl-$C_{0-2}$alkyl, phenyl-$C_{1-3}$alkyl-, or 5-6-membered heteroaryl-$C_{1-3}$alkyl in which groups the alkyl-, alkynyl-, cycloalkyl- and heterocycloalkyl-fragments are optionally substituted by one or two substituents selected from $R^{9a}$ and the phenyl, thienyl and pyridyl fragments are optionally substituted by one or two substituents selected from $R^{9b}$;
each $R^{9a}$ independently represents fluoro, phenyl, $C_{1-2}$alkyl, or —OC$_{1-4}$alkyl which latter two groups are optionally substituted by one to three fluoro atoms;
each $R^{9b}$ represents independently fluoro, chloro, bromo, $C_{1-2}$ alkyl, or —OC$_{1-2}$ alkyl which latter two groups are optionally substituted by one or more fluoro;
or a salt thereof.

13. A compound according to claim 1, wherein
M represents $C_{1-6}$ alkyl, $C_{3-6}$cycloalkyl, 4-6-membered heterocycloalkyl, all of which groups are optionally substituted by one or more groups selected from fluoro, —OH, —CN, —NH$_2$, phenyl, —CF$_3$, C$_{1-2}$ alkyl, or C$_{3-5}$cycloalkyl-C$_{0-1}$ alkyl;

or phenyl, or 5-6-membered heteroaryl both of which are optionally substituted by one or more substituents independently selected from fluoro, chloro, methyl, —CF$_3$, —OCH$_3$;

or a salt thereof.

14. A compound according to claim 1, having formula Ie:

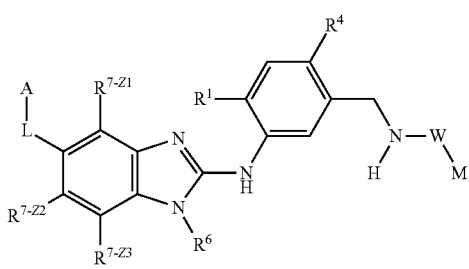

Ie in which

A represents hydrogen, C$_{1-6}$ alkyl, phenylpropargyl, phenyl, C$_{3-6}$cycloalkyl-C$_{0-2}$alkyl-, tetrahydrofuranyl-C$_{0-2}$alkyl, pyrrolidinyl-C$_{0-2}$alkyl, piperidin-C$_{0-2}$alkyl, or pyridyl-C$_{1-2}$alkyl-, in which groups the alkyl-, alkynyl-, cycloalkyl- and heterocycloalkyl fragments are optionally substituted by one or more substituents selected from R$^{9a}$ and the phenyl and pyridyl fragments are optionally substituted by one or more substituents selected from R$^{9b}$;

each R$^{9a}$ independently represents fluoro, C$_{1-2}$alkyl, or —OC$_{1-4}$alkyl in which latter two groups the alkyl fragments are optionally substituted by one or more fluoro atoms;

each R$^{9b}$ represents independently fluoro, chloro, or bromo,

L represents —C(O)NH— or —S(O)$_2$NH—, which groups are bound to the 9-membered fused heteroaromatic scaffold via the carbon or sulfur atom, respectively;

W represents —C(O)—, or —S(O)$_2$—;

M represents C$_{1-4}$ alkyl, or C$_{3-6}$cycloalkyl which latter two groups are optionally substituted by one or more groups selected from fluoro, —OH, —CN, —NH$_2$, phenyl, CF$_3$, C$_{1-2}$ alkyl, or cyclopropyl-methyl;

or represents oxetanyl or tetrahydrofuranyl, both of which groups are optionally substituted by a CH$_3$-group;

or phenyl, or thienyl both of which are optionally substituted by one or two substituents independently selected from fluoro or chloro, R$^1$ represents fluoro, chloro, bromo, CH$_3$, CH$_2$F, CHF$_2$, CF$_3$, or —OCH$_3$;

R$^4$ represents hydrogen;

R$^6$ represents hydrogen, C$_{1-3}$ alkyl, or C$_{3-4}$cycloalkyl-C$_{0-1}$ alkyl, which latter two groups are optionally substituted by one or more substituents selected from fluoro, —OCH$_3$, —NH(C$_{1-3}$ alkyl), or N(C$_{1-3}$ alkyl)$_2$;

R$^{7-Z2}$ represents hydrogen, halo, or —OC$_{1-5}$alkyl, in which latter group the alkyl is optionally substituted by one or more fluoro atoms;

R$^{7-Z1}$ and R$^{7-Z3}$ independently represent hydrogen or fluoro;

or a salt thereof.

15. A compound according to claim 1, selected from the following Examples 1 to 83 and 86-100:

| Example | Structure |
|---|---|
| 1 | 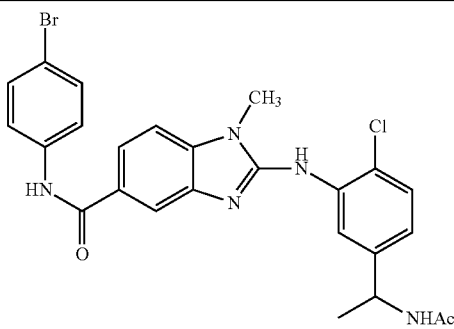 |
| 2 | 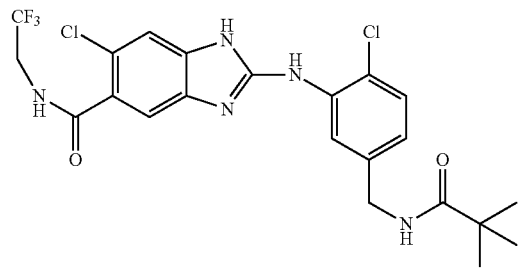 [SMILES: CC(C)(C)C(=O)NCc1ccc(Cl)c(Nc2nc3cc(C(=O)NCC(F)(F)F)c(Cl)cc3[nH]2)c1] |

-continued
| Example | Structure |
|---|---|
| 3 | 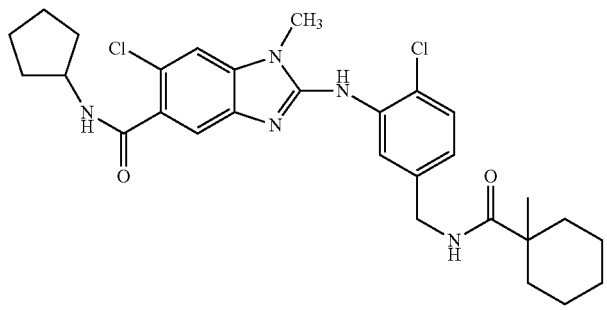 [SMILES: Cn1c(Nc2cc(CNC(=O)C3(C)CCCCC3)ccc2Cl)nc2cc(C(=O)NC3CCCC3)c(Cl)cc21] |
| 4 | 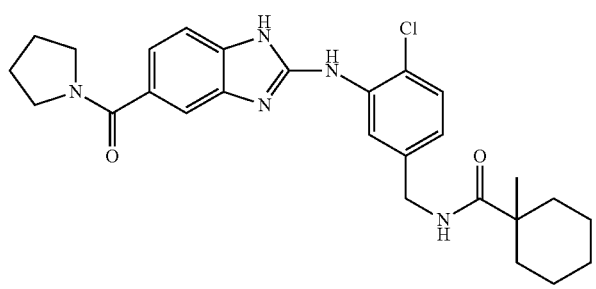 [SMILES: CC1(C(=O)NCc2ccc(Cl)c(Nc3nc4cc(C(=O)N5CCCC5)ccc4[nH]3)c2)CCCCC1] |
| 5 | 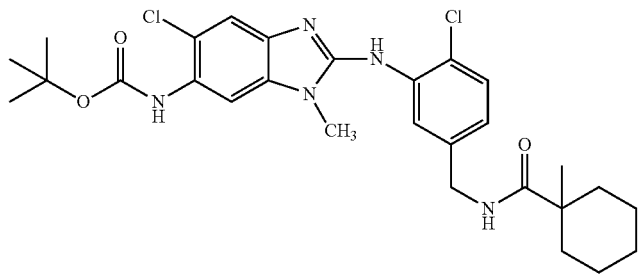 [SMILES: Cn1c(Nc2cc(CNC(=O)C3(C)CCCCC3)ccc2Cl)nc2cc(Cl)c(NC(=O)OC(C)(C)C)cc21] |
| 6 | 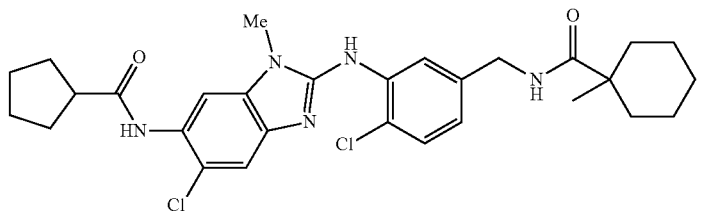 [SMILES: Cn1c(Nc2cc(CNC(=O)C3(C)CCCCC3)ccc2Cl)nc2cc(Cl)c(NC(=O)C3CCCC3)cc21] |
| 7 | 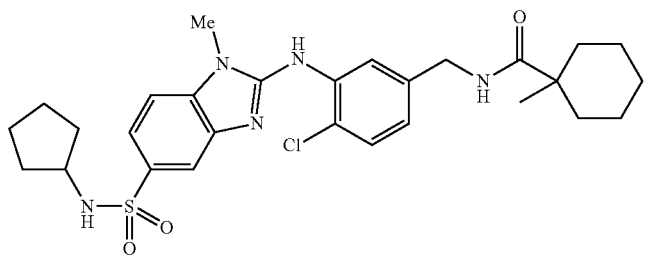 [SMILES: Cn1c(Nc2cc(CNC(=O)C3(C)CCCCC3)ccc2Cl)nc2cc(S(=O)(=O)NC3CCCC3)ccc21] |

-continued
| Example | Structure |
|---|---|
| 8 | 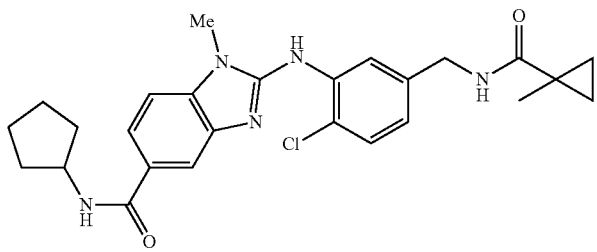 [SMILES: Cn1c(Nc2cc(CNC(=O)C3(C)CC3)ccc2Cl)nc2cc(C(=O)NC3CCCC3)ccc21] |
| 9 | 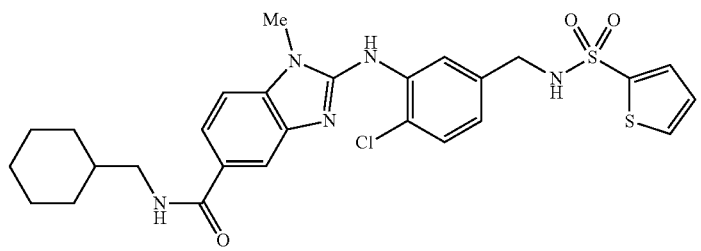 [SMILES: Cn1c(Nc2cc(CNS(=O)(=O)c3cccs3)ccc2Cl)nc2cc(C(=O)NCC3CCCCC3)ccc21] |
| 10 | 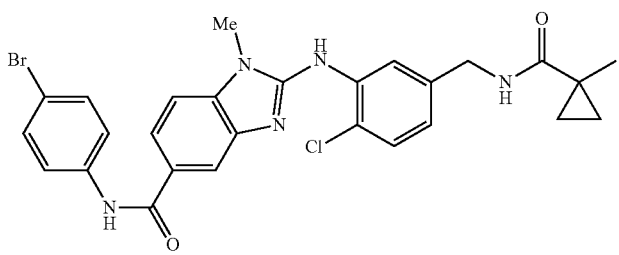 [SMILES: Cn1c(Nc2cc(CNC(=O)C3(C)CC3)ccc2Cl)nc2cc(C(=O)Nc3ccc(Br)cc3)ccc21] |
| 11 | 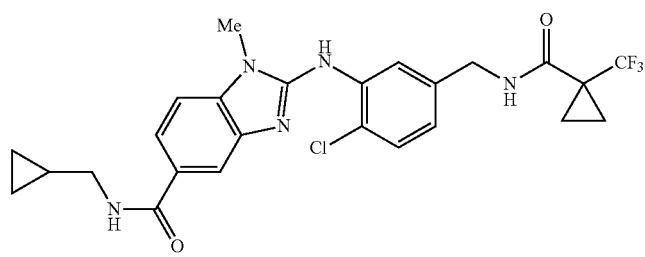 [SMILES: Cn1c(Nc2cc(CNC(=O)C3(C(F)(F)F)CC3)ccc2Cl)nc2cc(C(=O)NCC3CC3)ccc21] |
| 12 | 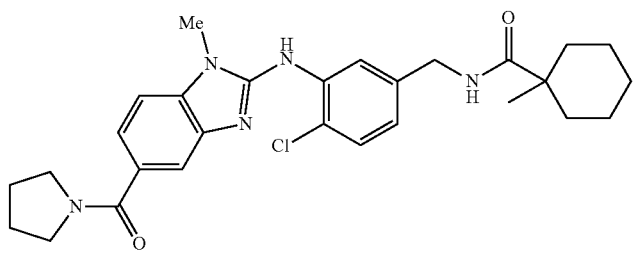 [SMILES: Cn1c(Nc2cc(CNC(=O)C3(C)CCCCC3)ccc2Cl)nc2cc(C(=O)N3CCCC3)ccc21] |
| 13 | 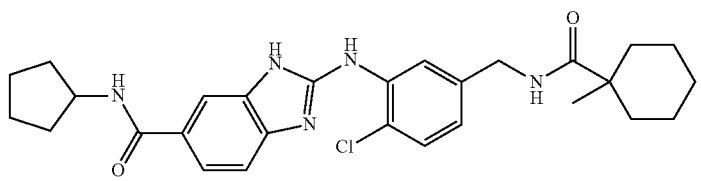 [SMILES: CC1(C(=O)NCc2ccc(Cl)c(Nc3nc4ccc(C(=O)NC5CCCC5)cc4[nH]3)c2)CCCCC1] |

| Example | Structure |
|---|---|
| 14 | 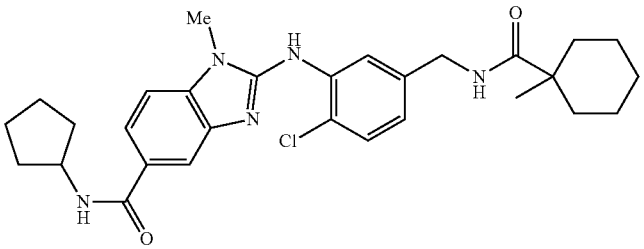 [SMILES: Cn1c(Nc2cc(CNC(=O)C3(C)CCCCC3)ccc2Cl)nc2cc(C(=O)NC3CCCC3)ccc21] |
| 15 | 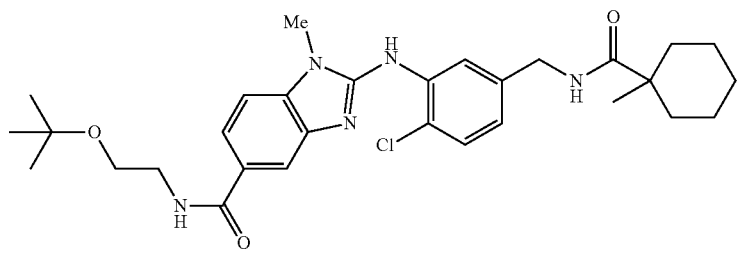 [SMILES: Cn1c(Nc2cc(CNC(=O)C3(C)CCCCC3)ccc2Cl)nc2cc(C(=O)NCCOC(C)(C)C)ccc21] |
| 16 | 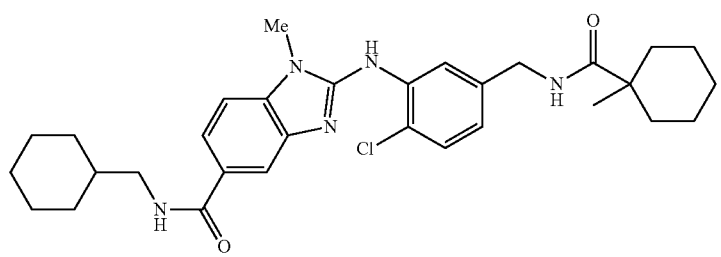 [SMILES: Cn1c(Nc2cc(CNC(=O)C3(C)CCCCC3)ccc2Cl)nc2cc(C(=O)NCC3CCCCC3)ccc21] |
| 17 | 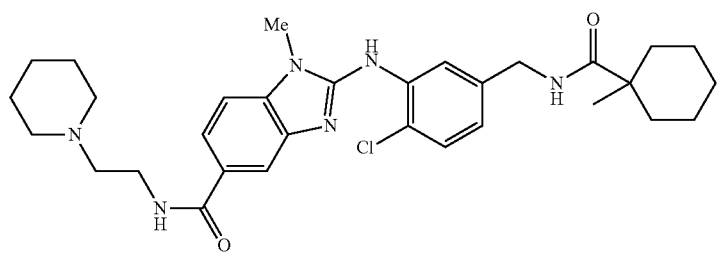 [SMILES: Cn1c(Nc2cc(CNC(=O)C3(C)CCCCC3)ccc2Cl)nc2cc(C(=O)NCCN3CCCCC3)ccc21] |
| 18 | 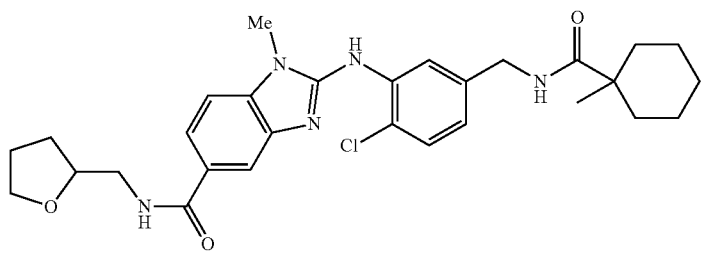 [SMILES: Cn1c(Nc2cc(CNC(=O)C3(C)CCCCC3)ccc2Cl)nc2cc(C(=O)NCC3CCCO3)ccc21] |
| 19 | 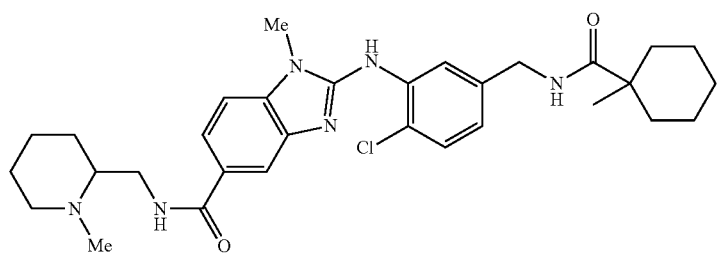 [SMILES: CN1CCCCC1CNC(=O)c1ccc2c(c1)nc(Nc1cc(CNC(=O)C3(C)CCCCC3)ccc1Cl)n2C] |

| Example | Structure |
|---|---|
| 20 | 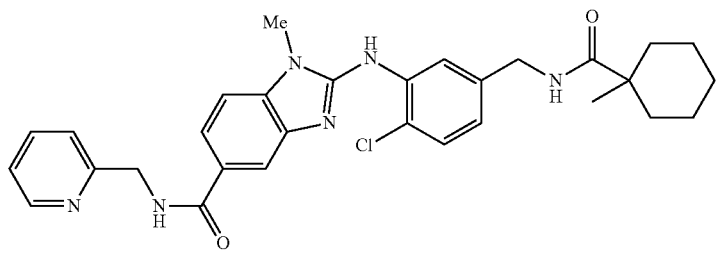 [SMILES: Cn1c(Nc2cc(CNC(=O)C3(C)CCCCC3)ccc2Cl)nc2cc(C(=O)NCc3ccccn3)ccc21] |
| 21 | 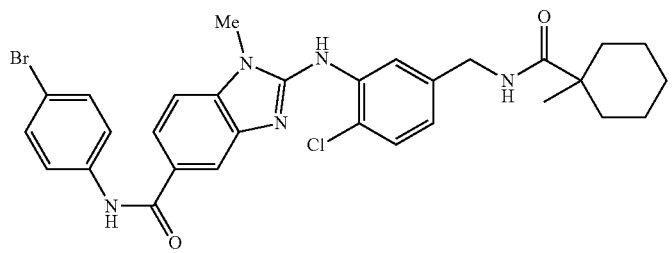 [SMILES: Cn1c(Nc2cc(CNC(=O)C3(C)CCCCC3)ccc2Cl)nc2cc(C(=O)Nc3ccc(Br)cc3)ccc21] |
| 22 | 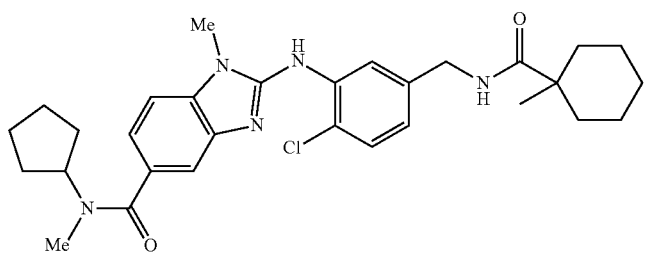 [SMILES: CN(C(=O)c1ccc2c(c1)nc(Nc1cc(CNC(=O)C3(C)CCCCC3)ccc1Cl)n2C)C1CCCC1] |
| 23 | 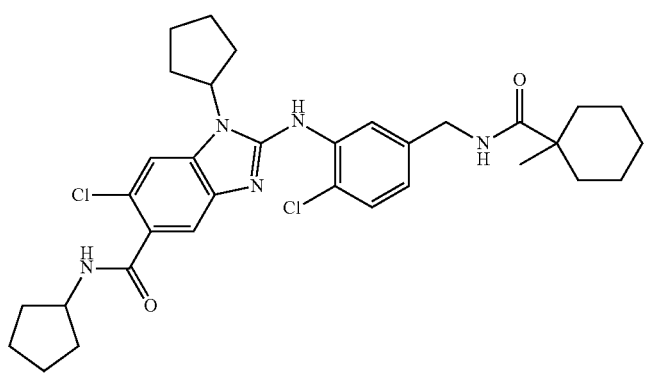 [SMILES: CC1(C(=O)NCc2ccc(Cl)c(Nc3nc4cc(C(=O)NC5CCCC5)c(Cl)cc4n3C3CCCC3)c2)CCCCC1] |
| 24 | 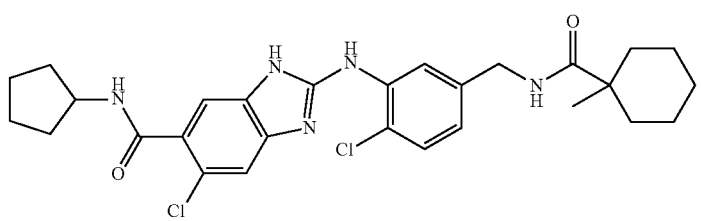 [SMILES: CC1(C(=O)NCc2ccc(Cl)c(Nc3nc4cc(Cl)c(C(=O)NC5CCCC5)cc4[nH]3)c2)CCCCC1] |
| 25 | 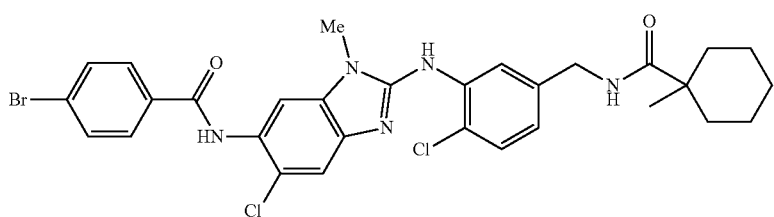 [SMILES: Cn1c(Nc2cc(CNC(=O)C3(C)CCCCC3)ccc2Cl)nc2cc(Cl)c(NC(=O)c3ccc(Br)cc3)cc21] |

-continued
| Example | Structure |
|---|---|
| 26 | 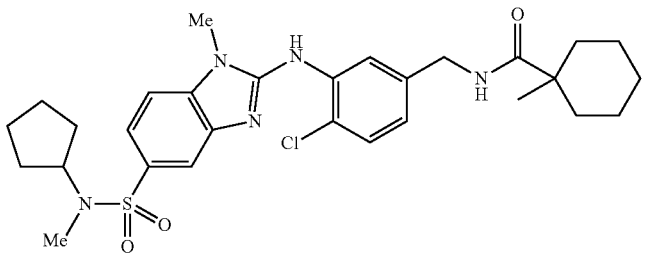 [SMILES: CN(C1CCCC1)S(=O)(=O)c1ccc2c(c1)nc(Nc1cc(CNC(=O)C3(C)CCCCC3)ccc1Cl)n2C] |
| 27 | 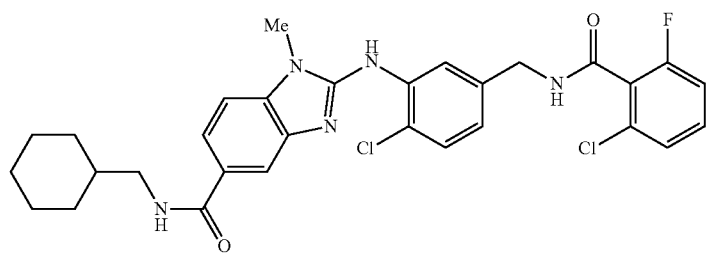 [SMILES: Cn1c(Nc2cc(CNC(=O)c3c(F)cccc3Cl)ccc2Cl)nc2cc(C(=O)NCC3CCCCC3)ccc21] |
| 28 | 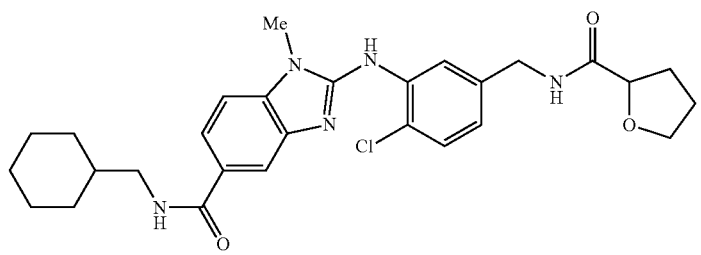 [SMILES: Cn1c(Nc2cc(CNC(=O)C3CCCO3)ccc2Cl)nc2cc(C(=O)NCC3CCCCC3)ccc21] |
| 29 | 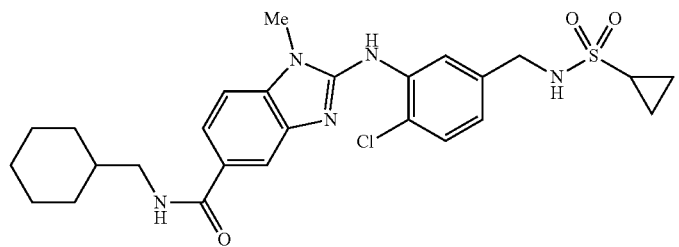 |
| 30 | 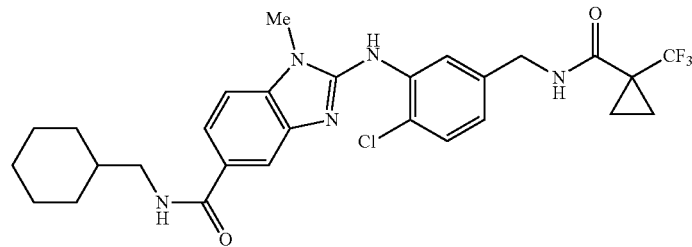 [SMILES: Cn1c(Nc2cc(CNC(=O)C3(C(F)(F)F)CC3)ccc2Cl)nc2cc(C(=O)NCC3CCCCC3)ccc21] |
| 31 | 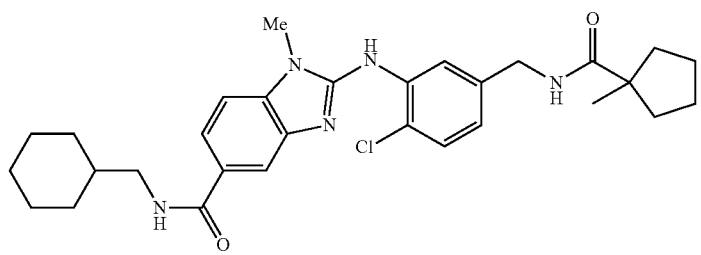 [SMILES: Cn1c(Nc2cc(CNC(=O)C3(C)CCCC3)ccc2Cl)nc2cc(C(=O)NCC3CCCCC3)ccc21] |

-continued
| Example | Structure |
|---|---|
| 32 | 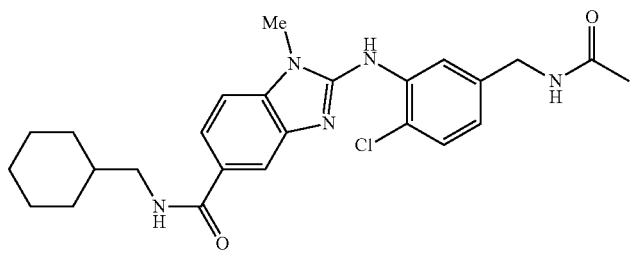 [SMILES: CC(=O)NCc1ccc(Cl)c(Nc2nc3cc(C(=O)NCC4CCCCC4)ccc3n2C)c1] |
| 33 | 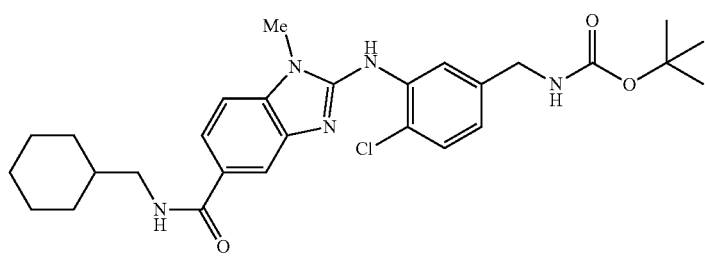 [SMILES: Cn1c(Nc2cc(CNC(=O)OC(C)(C)C)ccc2Cl)nc2cc(C(=O)NCC3CCCCC3)ccc21] |
| 34 | 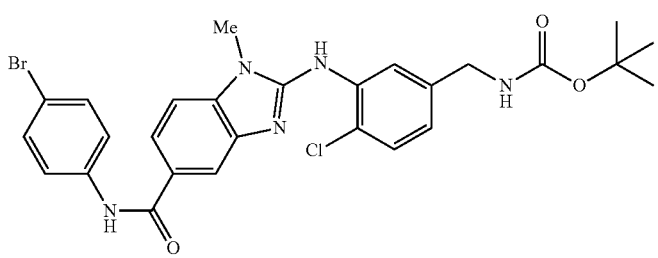 [SMILES: Cn1c(Nc2cc(CNC(=O)OC(C)(C)C)ccc2Cl)nc2cc(C(=O)Nc3ccc(Br)cc3)ccc21] |
| 35 | 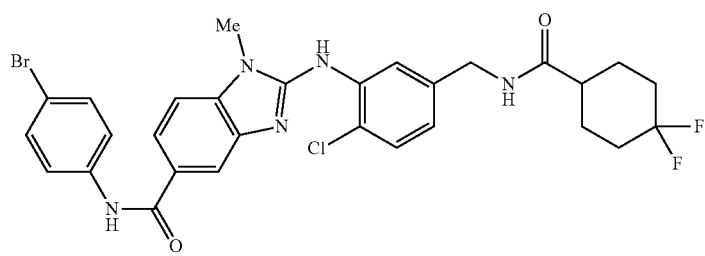 [SMILES: Cn1c(Nc2cc(CNC(=O)C3CCC(F)(F)CC3)ccc2Cl)nc2cc(C(=O)Nc3ccc(Br)cc3)ccc21] |
| 36 | 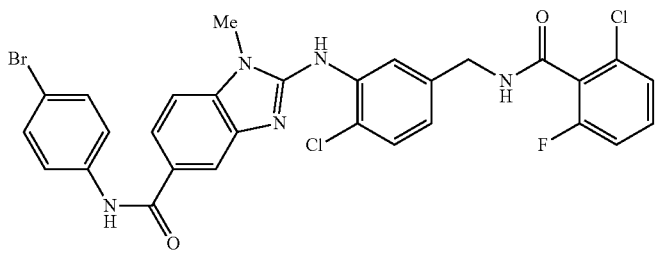 [SMILES: Cn1c(Nc2cc(CNC(=O)c3c(F)cccc3Cl)ccc2Cl)nc2cc(C(=O)Nc3ccc(Br)cc3)ccc21] |
| 37 | 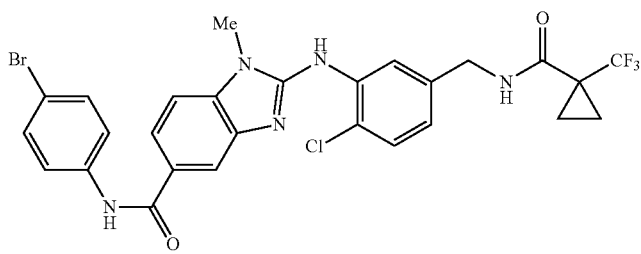 [SMILES: Cn1c(Nc2cc(CNC(=O)C3(C(F)(F)F)CC3)ccc2Cl)nc2cc(C(=O)Nc3ccc(Br)cc3)ccc21] |

-continued
| Example | Structure |
|---|---|
| 38 | 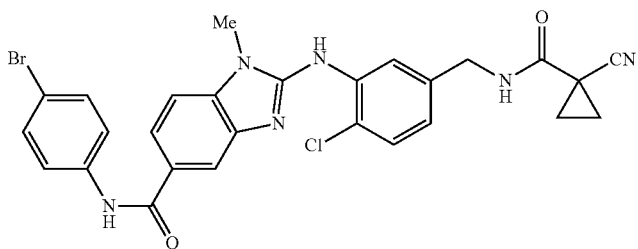 [SMILES: Cn1c(Nc2cc(CNC(=O)C3(C#N)CC3)ccc2Cl)nc2cc(C(=O)Nc3ccc(Br)cc3)ccc21] |
| 39 | 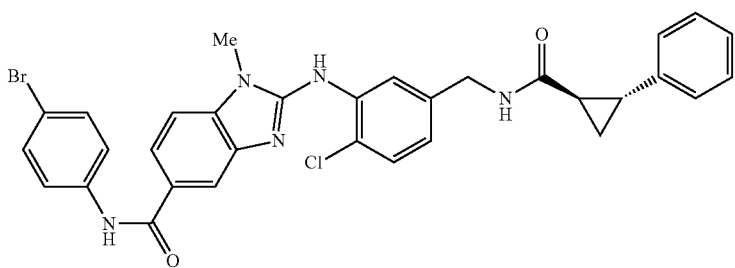 [SMILES: Cn1c(Nc2cc(CNC(=O)[C@@H]3C[C@H]3c3ccccc3)ccc2Cl)nc2cc(C(=O)Nc3ccc(Br)cc3)ccc21] |
| 40 | 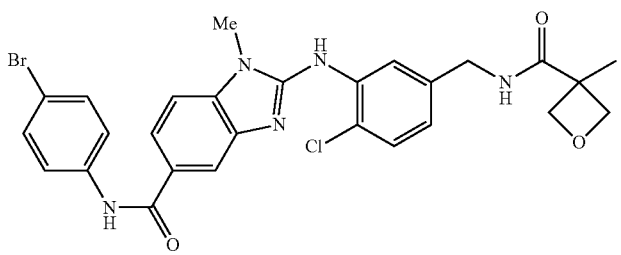 [SMILES: Cn1c(Nc2cc(CNC(=O)C3(C)COC3)ccc2Cl)nc2cc(C(=O)Nc3ccc(Br)cc3)ccc21] |
| 41 | 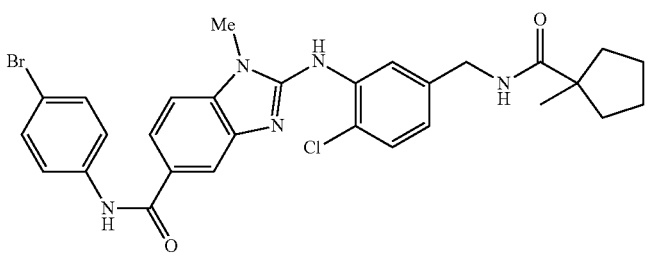 [SMILES: Cn1c(Nc2cc(CNC(=O)C3(C)CCCC3)ccc2Cl)nc2cc(C(=O)Nc3ccc(Br)cc3)ccc21] |
| 42 | 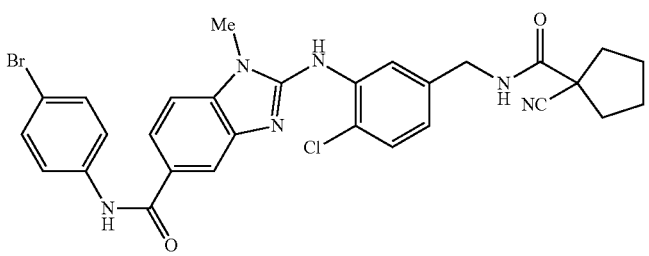 [SMILES: Cn1c(Nc2cc(CNC(=O)C3(C#N)CCCC3)ccc2Cl)nc2cc(C(=O)Nc3ccc(Br)cc3)ccc21] |
| 43 | 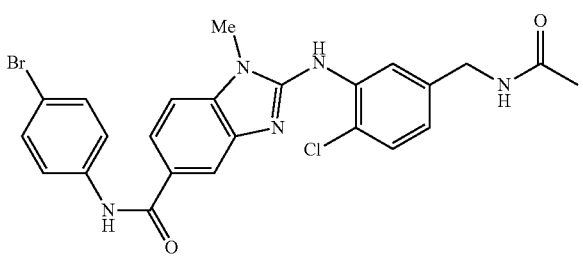 [SMILES: CC(=O)NCc1ccc(Cl)c(Nc2nc3cc(C(=O)Nc4ccc(Br)cc4)ccc3n2C)c1] |

-continued

| Example | Structure |
|---------|-----------|
| 44 | 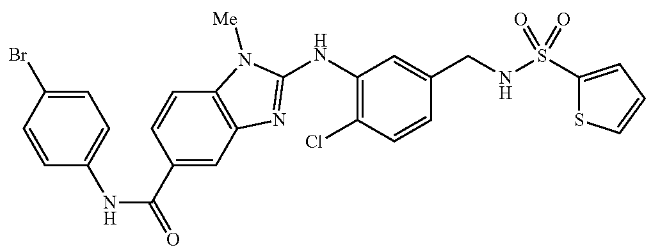 [SMILES: Cn1c(Nc2cc(CNS(=O)(=O)c3cccs3)ccc2Cl)nc2cc(C(=O)Nc3ccc(Br)cc3)ccc21] |
| 45 | 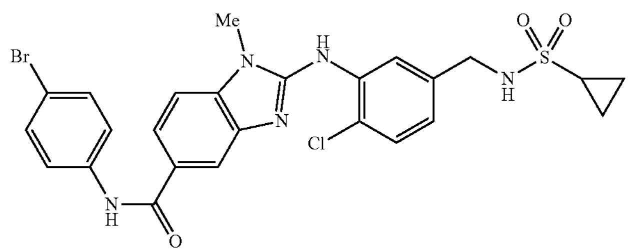 [SMILES: Cn1c(Nc2cc(CNS(=O)(=O)C3CC3)ccc2Cl)nc2cc(C(=O)Nc3ccc(Br)cc3)ccc21] |
| 46 | 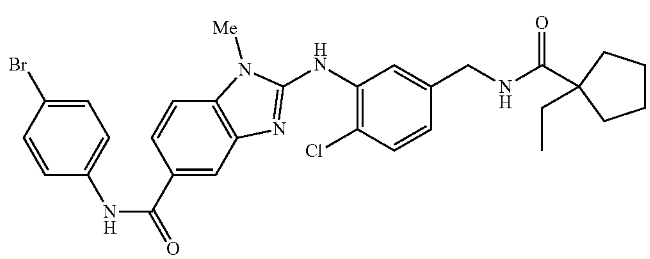 [SMILES: CCC1(C(=O)NCc2ccc(Cl)c(Nc3nc4cc(C(=O)Nc5ccc(Br)cc5)ccc4n3C)c2)CCCC1] |
| 47 | 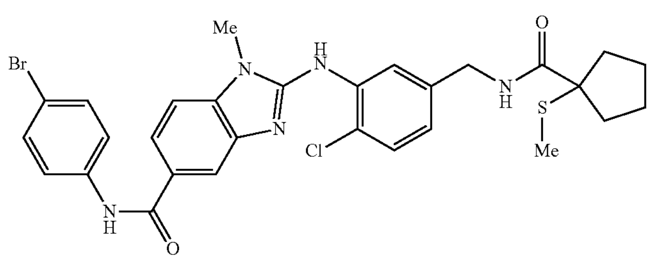 [SMILES: CSC1(C(=O)NCc2ccc(Cl)c(Nc3nc4cc(C(=O)Nc5ccc(Br)cc5)ccc4n3C)c2)CCCC1] |
| 48 | 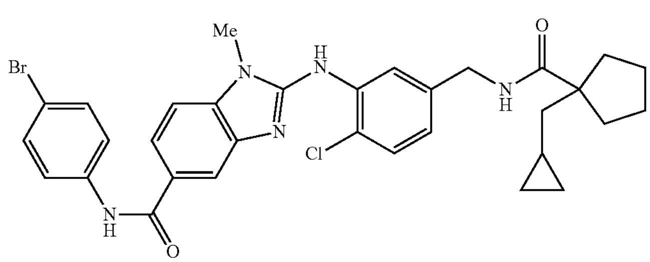 [SMILES: Cn1c(Nc2cc(CNC(=O)C3(CC4CC4)CCCC3)ccc2Cl)nc2cc(C(=O)Nc3ccc(Br)cc3)ccc21] |
| 49 | 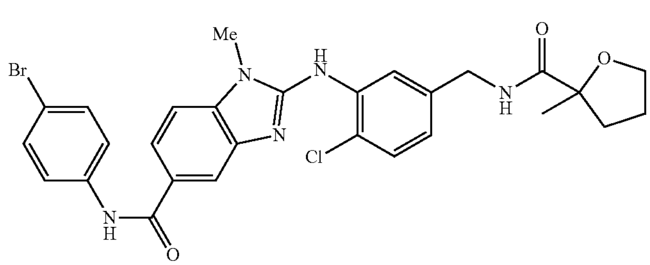 [SMILES: Cn1c(Nc2cc(CNC(=O)C3(C)CCCO3)ccc2Cl)nc2cc(C(=O)Nc3ccc(Br)cc3)ccc21] |

-continued

| Example | Structure |
|---|---|
| 50 | 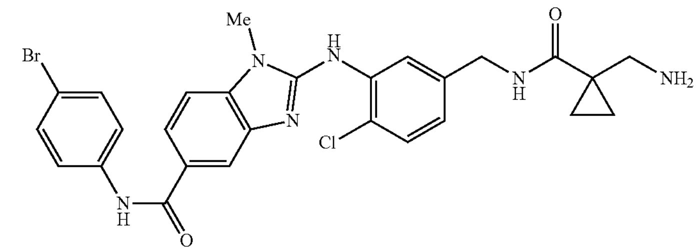 [SMILES: Cn1c(Nc2cc(CNC(=O)C3(CN)CC3)ccc2Cl)nc2cc(C(=O)Nc3ccc(Br)cc3)ccc21] |
| 51 | 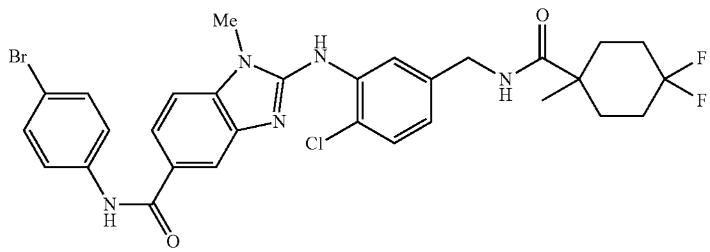 [SMILES: Cn1c(Nc2cc(CNC(=O)C3(C)CCC(F)(F)CC3)ccc2Cl)nc2cc(C(=O)Nc3ccc(Br)cc3)ccc21] |
| 52 | 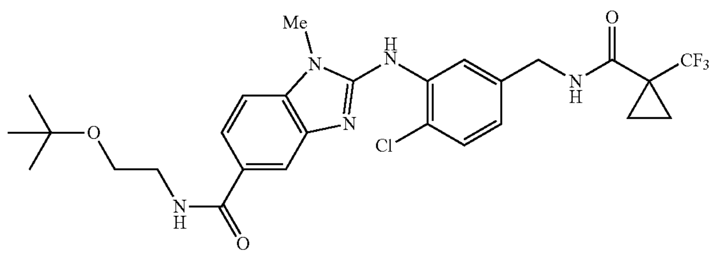 [SMILES: Cn1c(Nc2cc(CNC(=O)C3(C(F)(F)F)CC3)ccc2Cl)nc2cc(C(=O)NCCOC(C)(C)C)ccc21] |
| 53 | 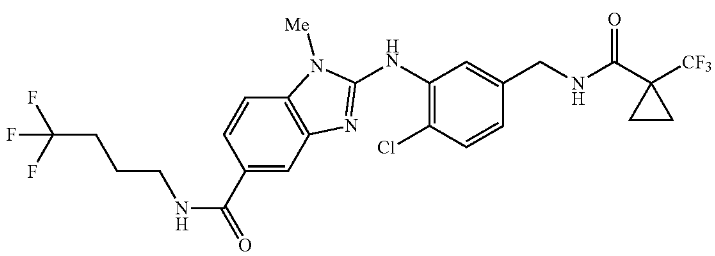 [SMILES: Cn1c(Nc2cc(CNC(=O)C3(C(F)(F)F)CC3)ccc2Cl)nc2cc(C(=O)NCCCC(F)(F)F)ccc21] |
| 54 | 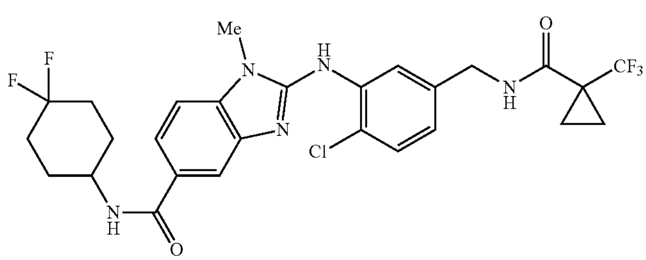 [SMILES: Cn1c(Nc2cc(CNC(=O)C3(C(F)(F)F)CC3)ccc2Cl)nc2cc(C(=O)NC3CCC(F)(F)CC3)ccc21] |
| 55 | 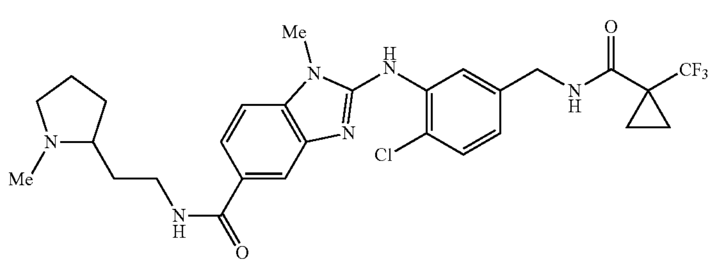 [SMILES: CN1CCCC1CCNC(=O)c1ccc2c(c1)nc(Nc1cc(CNC(=O)C3(C(F)(F)F)CC3)ccc1Cl)n2C] |

| Example | Structure |
|---|---|
| 56 | 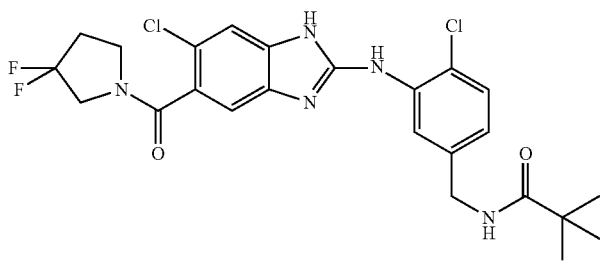 [SMILES: CC(C)(C)C(=O)NCc1ccc(Cl)c(Nc2nc3cc(C(=O)N4CCC(F)(F)C4)c(Cl)cc3[nH]2)c1] |
| 57 | 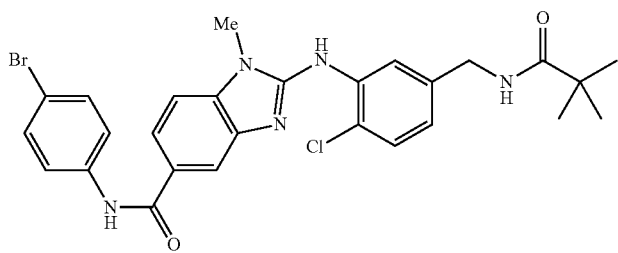 [SMILES: Cn1c(Nc2cc(CNC(=O)C(C)(C)C)ccc2Cl)nc2cc(C(=O)Nc3ccc(Br)cc3)ccc21] |
| 58 | 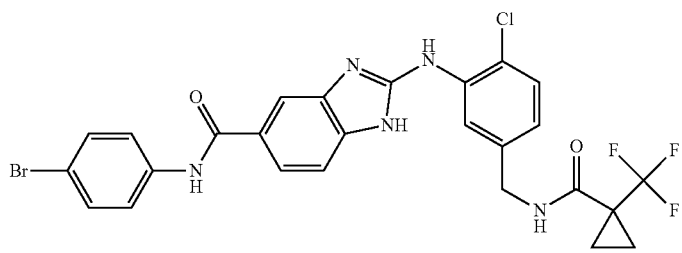 [SMILES: O=C(Nc1ccc(Br)cc1)c1ccc2[nH]c(Nc3cc(CNC(=O)C4(C(F)(F)F)CC4)ccc3Cl)nc2c1] |
| 59 | 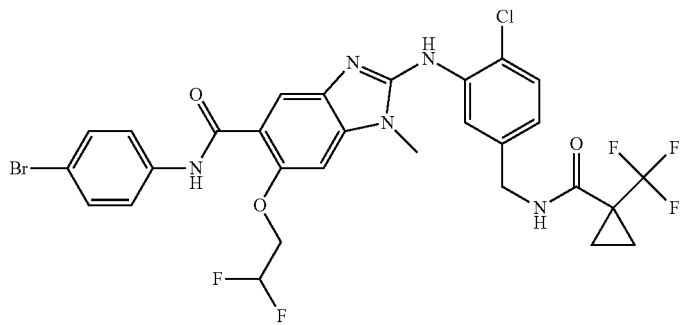 |
| 60 | 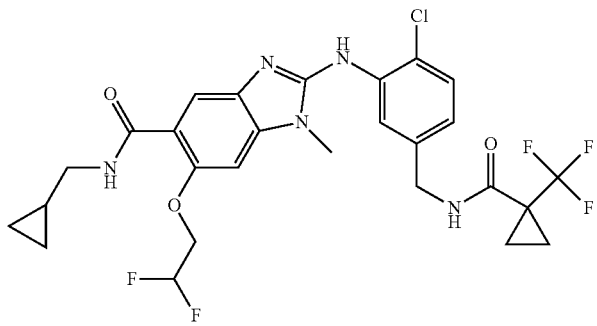 [SMILES: Cn1c(Nc2cc(CNC(=O)C3(C(F)(F)F)CC3)ccc2Cl)nc2cc(C(=O)NCC3CC3)c(OCC(F)F)cc21] |

-continued
| Example | Structure |
|---|---|
| 61 | 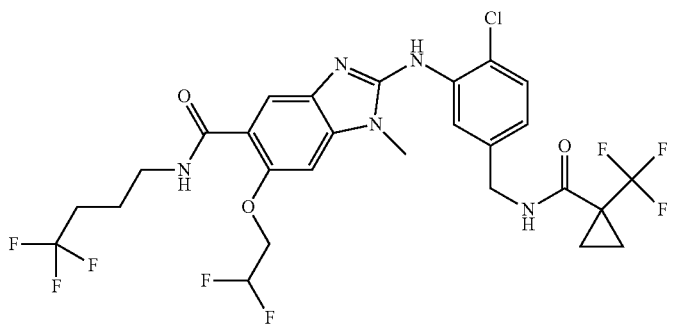 [SMILES: Cn1c(Nc2cc(CNC(=O)C3(C(F)(F)F)CC3)ccc2Cl)nc2cc(C(=O)NCCCC(F)(F)F)c(OCC(F)F)cc21] |
| 62 | 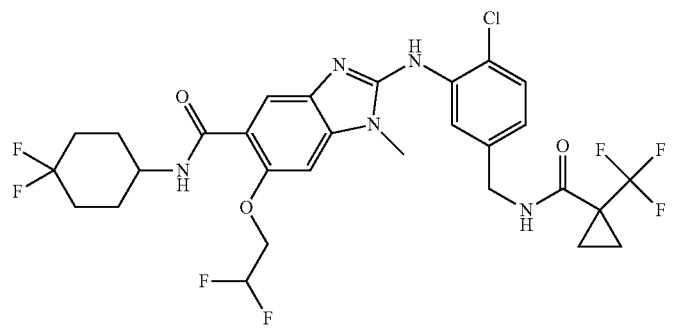 [SMILES: Cn1c(Nc2cc(CNC(=O)C3(C(F)(F)F)CC3)ccc2Cl)nc2cc(C(=O)NC3CCC(F)(F)CC3)c(OCC(F)F)cc21] |
| 63 | 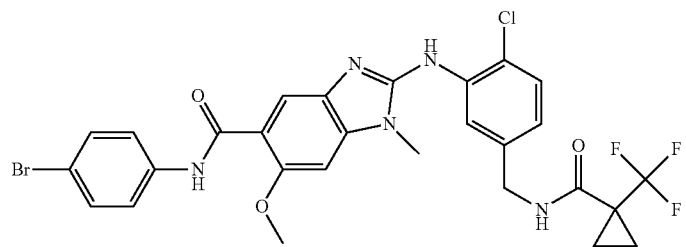 [SMILES: COc1cc2c(cc1C(=O)Nc1ccc(Br)cc1)nc(Nc1cc(CNC(=O)C3(C(F)(F)F)CC3)ccc1Cl)n2C] |
| 64 | 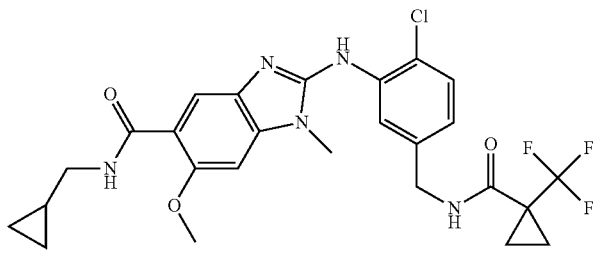 [SMILES: COc1cc2c(cc1C(=O)NCC1CC1)nc(Nc1cc(CNC(=O)C3(C(F)(F)F)CC3)ccc1Cl)n2C] |
| 65 | 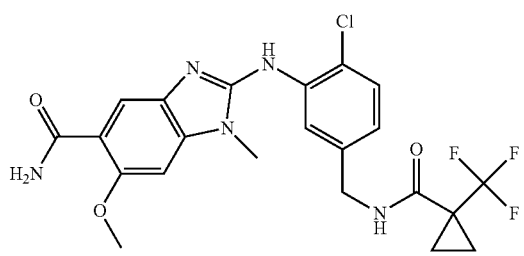 [SMILES: COc1cc2c(cc1C(N)=O)nc(Nc1cc(CNC(=O)C3(C(F)(F)F)CC3)ccc1Cl)n2C] |

| Example | Structure |
|---|---|
| 66 | 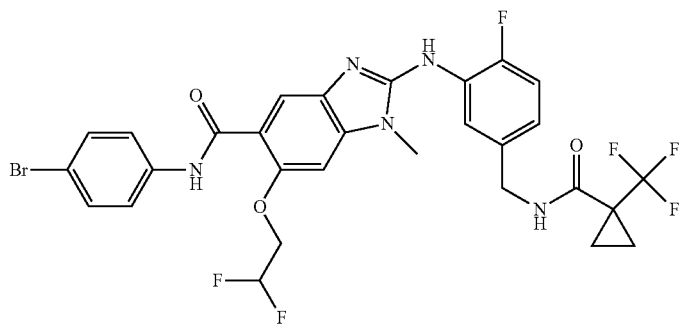 [SMILES: Cn1c(Nc2cc(CNC(=O)C3(C(F)(F)F)CC3)ccc2F)nc2cc(C(=O)Nc3ccc(Br)cc3)c(OCC(F)F)cc21] |
| 67 | 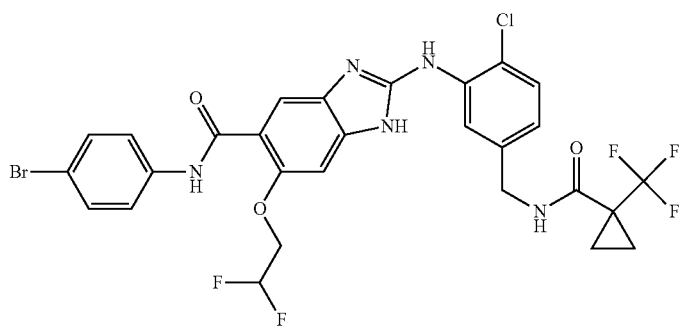 [SMILES: O=C(Nc1ccc(Br)cc1)c1cc2nc(Nc3cc(CNC(=O)C4(C(F)(F)F)CC4)ccc3Cl)[nH]c2cc1OCC(F)F] |
| 68 | 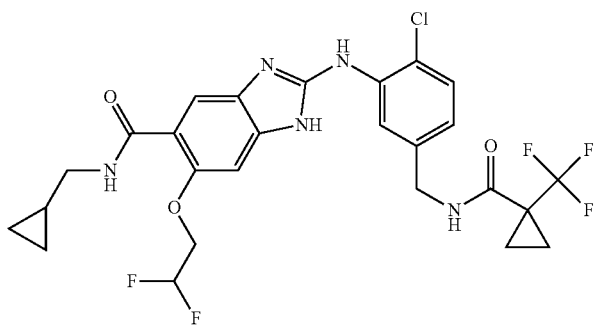 [SMILES: O=C(NCC1CC1)c1cc2nc(Nc3cc(CNC(=O)C4(C(F)(F)F)CC4)ccc3Cl)[nH]c2cc1OCC(F)F] |
| 69 | 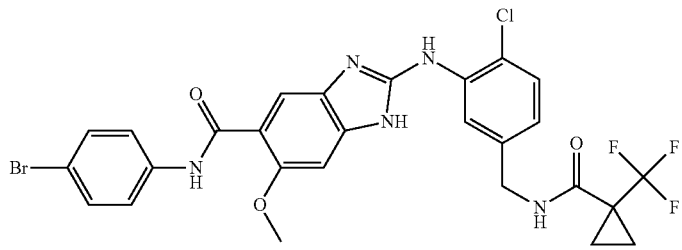 [SMILES: COc1cc2[nH]c(Nc3cc(CNC(=O)C4(C(F)(F)F)CC4)ccc3Cl)nc2cc1C(=O)Nc1ccc(Br)cc1] |
| 70 | 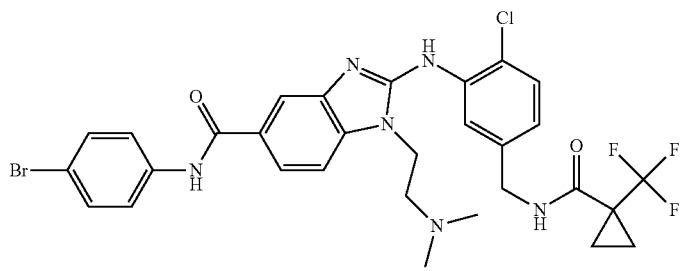 [SMILES: CN(C)CCn1c(Nc2cc(CNC(=O)C3(C(F)(F)F)CC3)ccc2Cl)nc2cc(C(=O)Nc3ccc(Br)cc3)ccc21] |

-continued
| Example | Structure |
|---------|-----------|
| 71 | 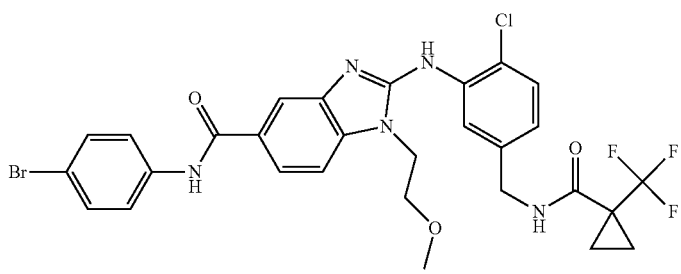 [SMILES: COCCn1c(Nc2cc(CNC(=O)C3(C(F)(F)F)CC3)ccc2Cl)nc2cc(C(=O)Nc3ccc(Br)cc3)ccc21] |
| 72 | 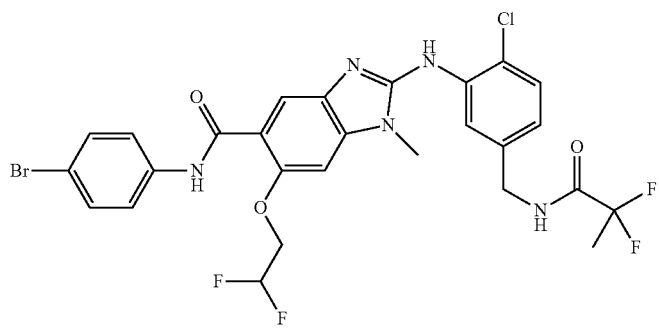 [SMILES: Cn1c(Nc2cc(CNC(=O)C(C)(F)F)ccc2Cl)nc2cc(C(=O)Nc3ccc(Br)cc3)c(OCC(F)F)cc21] |
| 73 | 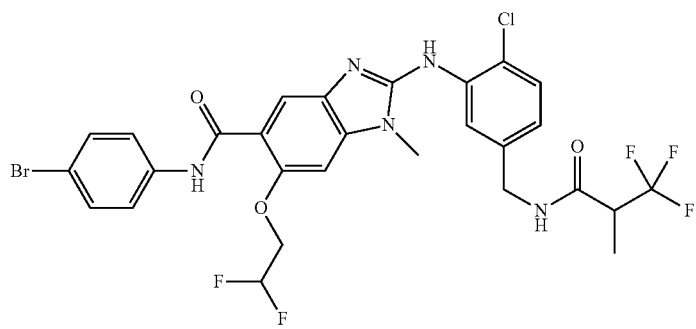 [SMILES: CC(C(=O)NCc1ccc(Cl)c(Nc2nc3cc(C(=O)Nc4ccc(Br)cc4)c(OCC(F)F)cc3n2C)c1)C(F)(F)F] |
| 74 | 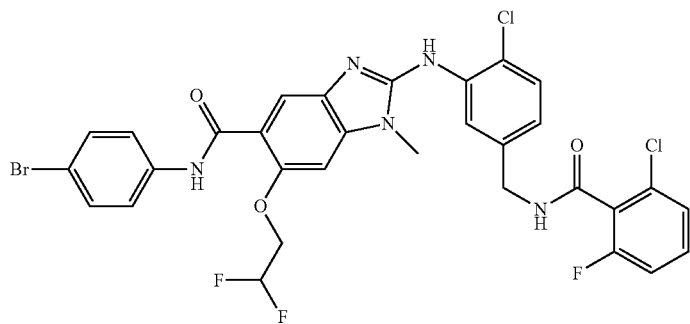 [SMILES: Cn1c(Nc2cc(CNC(=O)c3c(F)cccc3Cl)ccc2Cl)nc2cc(C(=O)Nc3ccc(Br)cc3)c(OCC(F)F)cc21] |
| 75 | 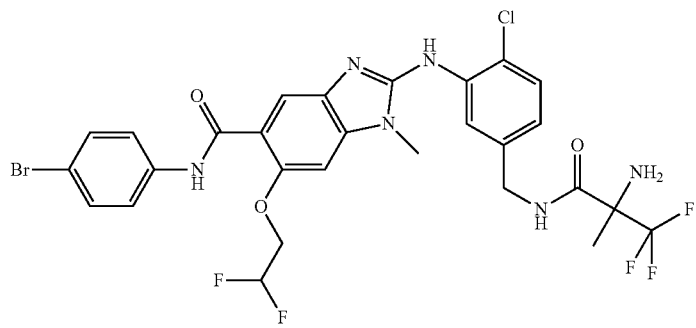 [SMILES: Cn1c(Nc2cc(CNC(=O)C(C)(N)C(F)(F)F)ccc2Cl)nc2cc(C(=O)Nc3ccc(Br)cc3)c(OCC(F)F)cc21] |

-continued
| Example | Structure |
|---|---|
| 76 | 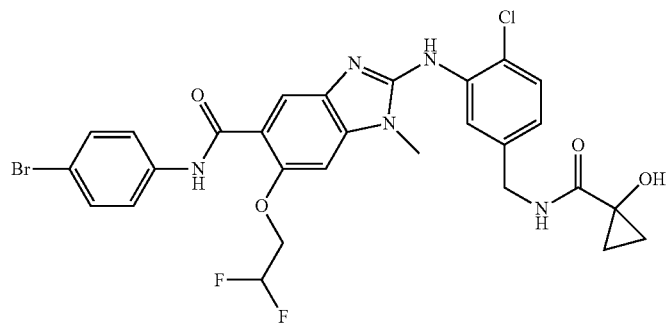 [SMILES: Cn1c(Nc2cc(CNC(=O)C3(O)CC3)ccc2Cl)nc2cc(C(=O)Nc3ccc(Br)cc3)c(OCC(F)F)cc21] |
| 77 | 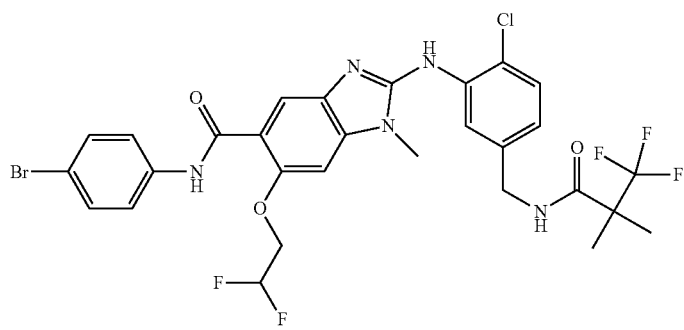 [SMILES: Cn1c(Nc2cc(CNC(=O)C(C)(C)C(F)(F)F)ccc2Cl)nc2cc(C(=O)Nc3ccc(Br)cc3)c(OCC(F)F)cc21] |
| 78 | 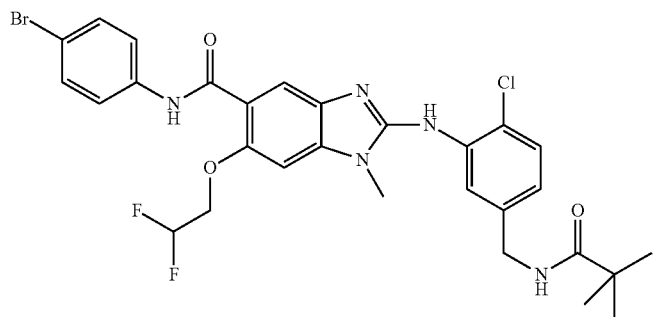 [SMILES: Cn1c(Nc2cc(CNC(=O)C(C)(C)C)ccc2Cl)nc2cc(C(=O)Nc3ccc(Br)cc3)c(OCC(F)F)cc21] |
| 79 | 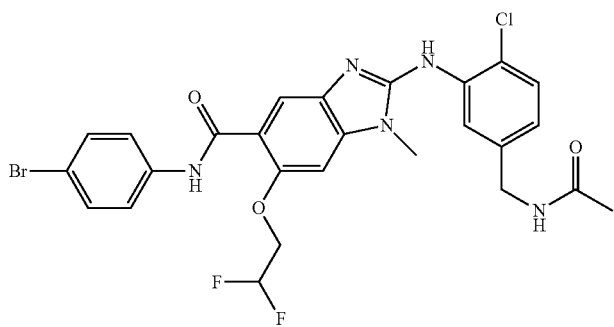 [SMILES: CC(=O)NCc1ccc(Cl)c(Nc2nc3cc(C(=O)Nc4ccc(Br)cc4)c(OCC(F)F)cc3n2C)c1] |

-continued
| Example | Structure |
|---|---|
| 80 | 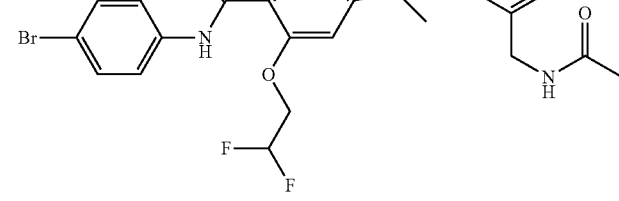 |
| 81 | 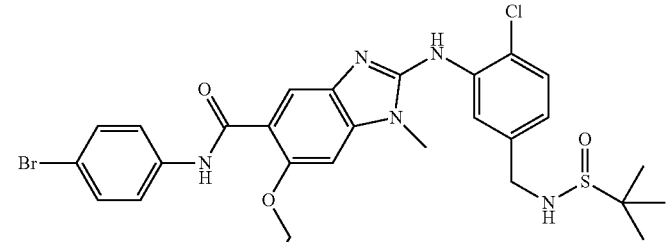 |
| 82 | 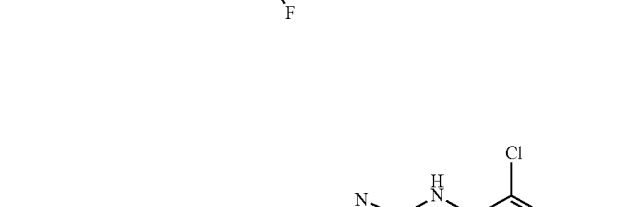 |
| 83 | 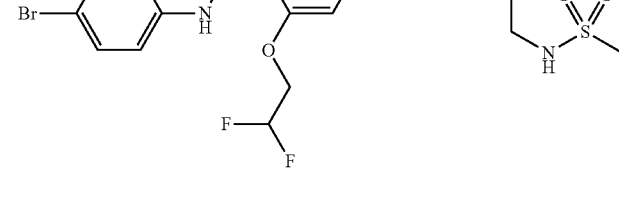 |

| Example | Structure |
|---|---|
| 86 | 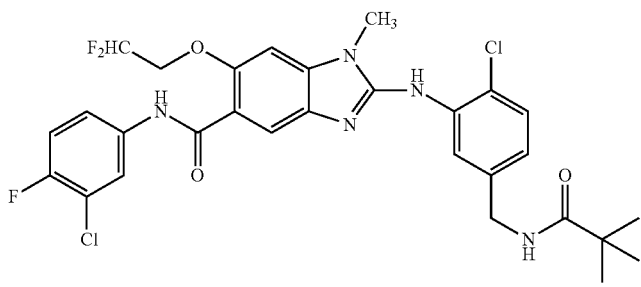 [SMILES: Cn1c(Nc2cc(CNC(=O)C(C)(C)C)ccc2Cl)nc2cc(C(=O)Nc3ccc(F)c(Cl)c3)c(OCC(F)F)cc21] |
| 87 | 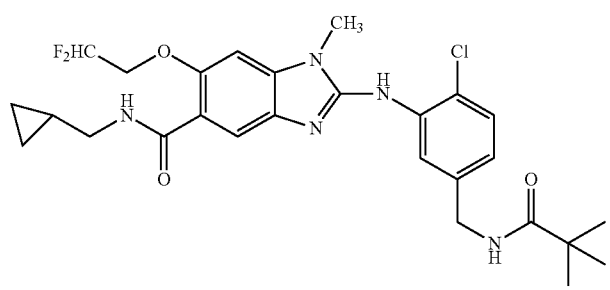 [SMILES: Cn1c(Nc2cc(CNC(=O)C(C)(C)C)ccc2Cl)nc2cc(C(=O)NCC3CC3)c(OCC(F)F)cc21] |
| 88 | 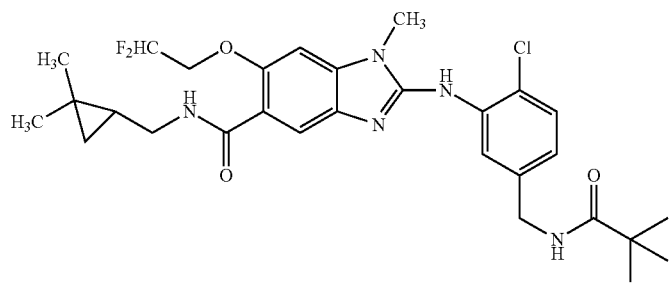 [SMILES: Cn1c(Nc2cc(CNC(=O)C(C)(C)C)ccc2Cl)nc2cc(C(=O)NCC3CC3(C)C)c(OCC(F)F)cc21] |
| 89 | 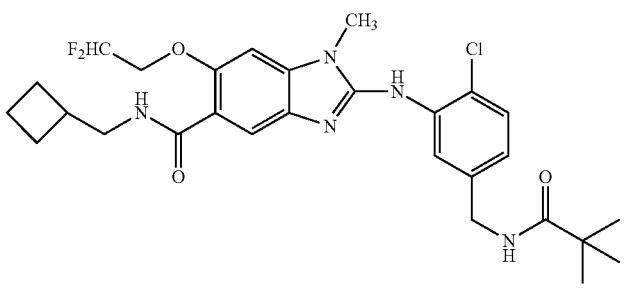 [SMILES: Cn1c(Nc2cc(CNC(=O)C(C)(C)C)ccc2Cl)nc2cc(C(=O)NCC3CCC3)c(OCC(F)F)cc21] |
| 90 | 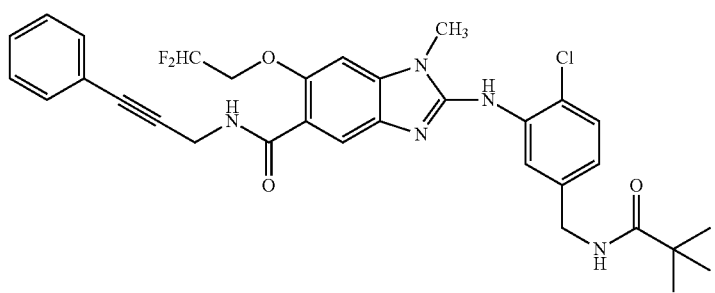 [SMILES: Cn1c(Nc2cc(CNC(=O)C(C)(C)C)ccc2Cl)nc2cc(C(=O)NCC#Cc3ccccc3)c(OCC(F)F)cc21] |

-continued
| Example | Structure |
|---|---|
| 91 | 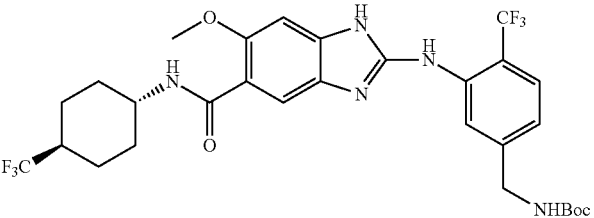 [SMILES: COc1cc2[nH]c(Nc3cc(CNC(=O)OC(C)(C)C)ccc3C(F)(F)F)nc2cc1C(=O)N[C@H]1CC[C@H](C(F)(F)F)CC1] |
| 92 | 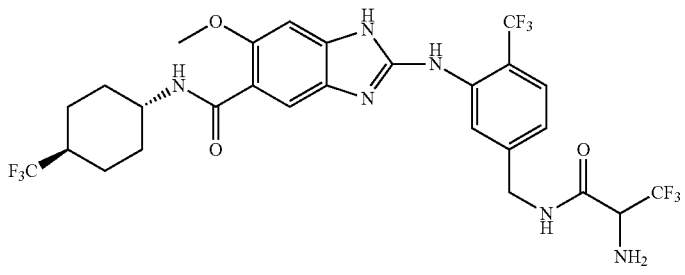 [SMILES: COc1cc2[nH]c(Nc3cc(CNC(=O)C(N)C(F)(F)F)ccc3C(F)(F)F)nc2cc1C(=O)N[C@H]1CC[C@H](C(F)(F)F)CC1] |
| 93 | 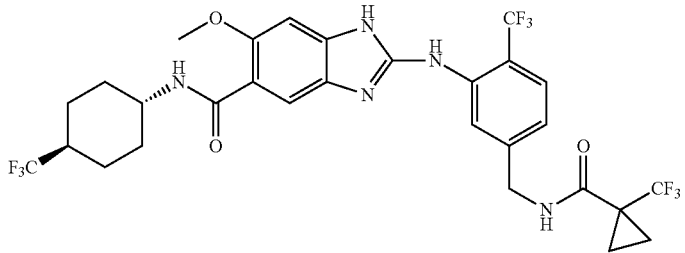 |
| 94 | 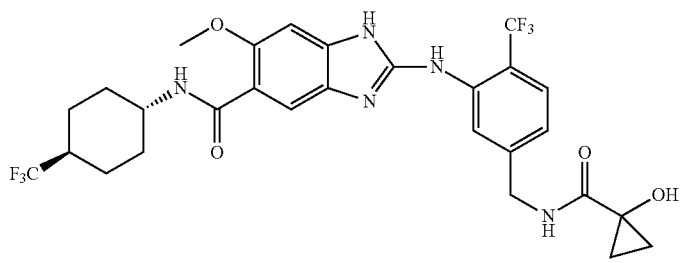 [SMILES: COc1cc2[nH]c(Nc3cc(CNC(=O)C4(C(F)(F)F)CC4)ccc3C(F)(F)F)nc2cc1C(=O)N[C@H]1CC[C@H](C(F)(F)F)CC1] |
| 95 | 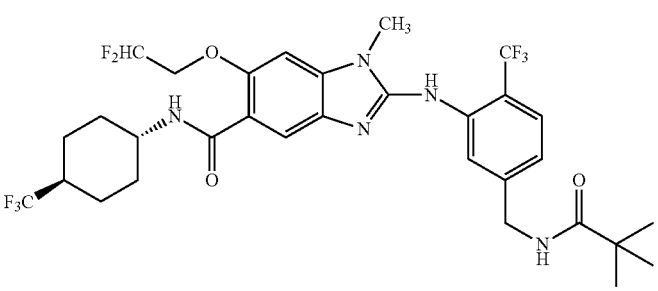 [SMILES: Cn1c(Nc2cc(CNC(=O)C(C)(C)C)ccc2C(F)(F)F)nc2cc(C(=O)N[C@H]3CC[C@H](C(F)(F)F)CC3)c(OCC(F)F)cc21] |
| 96 | 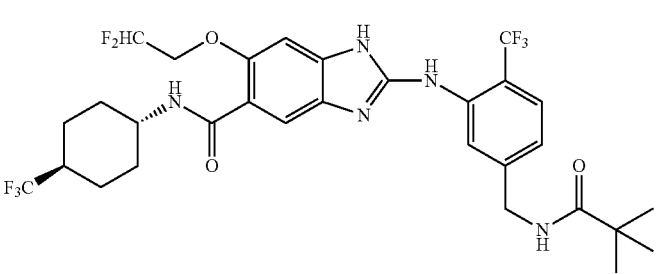 [SMILES: CC(C)(C)C(=O)NCc1ccc(C(F)(F)F)c(Nc2nc3cc(C(=O)N[C@H]4CC[C@H](C(F)(F)F)CC4)c(OCC(F)F)cc3[nH]2)c1] |

| Example | Structure |
|---|---|
| 97 | 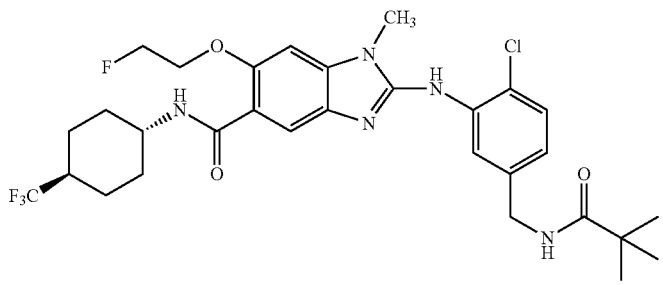 [SMILES: Cn1c(Nc2cc(CNC(=O)C(C)(C)C)ccc2Cl)nc2cc(C(=O)N[C@H]3CC[C@H](C(F)(F)F)CC3)c(OCCF)cc21] |
| 98 | 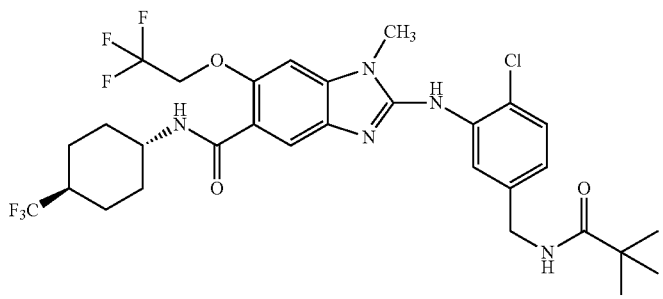 [SMILES: Cn1c(Nc2cc(CNC(=O)C(C)(C)C)ccc2Cl)nc2cc(C(=O)N[C@H]3CC[C@H](C(F)(F)F)CC3)c(OCC(F)(F)F)cc21] |
| 99 | 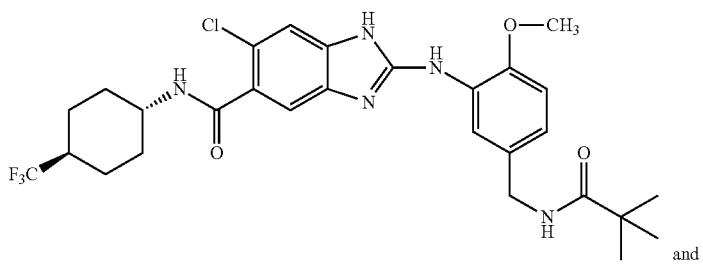 [SMILES: COc1ccc(CNC(=O)C(C)(C)C)cc1Nc1nc2cc(C(=O)N[C@H]3CC[C@H](C(F)(F)F)CC3)c(Cl)cc2[nH]1] and |
| 100 | 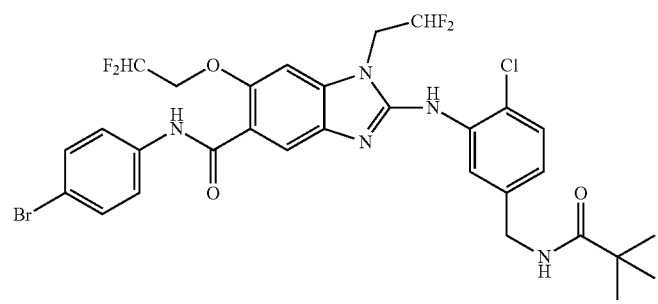 [SMILES: CC(C)(C)C(=O)NCc1ccc(Cl)c(Nc2nc3cc(C(=O)Nc4ccc(Br)cc4)c(OCC(F)F)cc3n2CC(F)F)c1] | or a pharmaceutically acceptable salt of any of the above Examples 1 to 83 or 86-100.

16. A pharmaceutical composition comprising at least one compound according to claim 1 and a pharmaceutically acceptable adjuvant, diluent or carrier.

17. A method for treating pain or inflammation in a patient comprising administering to said patient a therapeutically effective amount of a compound according to claim 1 or a pharmaceutically acceptable salt thereof.

18. A method according to claim 17, wherein the condition to be treated is pain.

* * * * *